United States Patent
Cho et al.

(10) Patent No.: US 11,053,225 B2
(45) Date of Patent: Jul. 6, 2021

(54) PYRIMIDINE DERIVATIVE COMPOUND, OPTICAL ISOMER THEREOF, OR PHARMACEUTICALLY ACCEPTABLE SALT THEREOF, AND COMPOSITION FOR PREVENTING OR TREATING TYRO 3 RELATED DISEASE COMPRISING SAME AS ACTIVE INGREDIENT

(71) Applicant: KOREA RESEARCH INSTITUTE OF CHEMICAL TECHNOLOGY, Daejeon (KR)

(72) Inventors: Sung Yun Cho, Daejeon (KR); Chang Hoon Lee, Daejeon (KR); Yong Ki Min, Daejeon (KR); Jong Yeon Hwang, Jeollabuk-do (KR)

(73) Assignee: KOREA RESEARCH INSTITUTE OF CHEMICAL TECHNOLOGY, Daejeon (KR)

(*) Notice: Subject to any disclaimer, the term of this patent is extended or adjusted under 35 U.S.C. 154(b) by 0 days.

(21) Appl. No.: 16/610,327

(22) PCT Filed: May 2, 2018

(86) PCT No.: PCT/KR2018/005162
§ 371 (c)(1),
(2) Date: Nov. 1, 2019

(87) PCT Pub. No.: WO2018/203691
PCT Pub. Date: Nov. 8, 2018

(65) Prior Publication Data
US 2020/0087286 A1 Mar. 19, 2020

(30) Foreign Application Priority Data

May 2, 2017 (KR) .................. 10-2017-0056002
Sep. 7, 2017 (KR) .................. 10-2017-0114317
Sep. 7, 2017 (KR) .................. 10-2017-0114322

(51) Int. Cl.
| | |
|---|---|
| C07D 401/14 | (2006.01) |
| C07D 403/04 | (2006.01) |
| A61K 31/506 | (2006.01) |
| C07D 403/14 | (2006.01) |
| C07D 239/48 | (2006.01) |
| C07D 405/04 | (2006.01) |
| C07D 405/14 | (2006.01) |
| C07D 409/14 | (2006.01) |
| C07D 413/14 | (2006.01) |
| C07D 417/14 | (2006.01) |

(52) U.S. Cl.
CPC ........ C07D 403/14 (2013.01); C07D 239/48 (2013.01); C07D 403/04 (2013.01); C07D 405/04 (2013.01); C07D 405/14 (2013.01); C07D 409/14 (2013.01); C07D 413/14 (2013.01); C07D 417/14 (2013.01)

(58) Field of Classification Search
CPC ........................ C07D 401/14; C07D 403/04
See application file for complete search history.

(56) References Cited

U.S. PATENT DOCUMENTS

2010/0113445 A1  5/2010  Deanda, Jr. et al.
2016/0145252 A1* 5/2016  Jorand-Lebrun ......... A61P 7/00
                                            514/210.2

FOREIGN PATENT DOCUMENTS

| CN | 106588884 A | 4/2017 |
|---|---|---|
| CN | 106588885 A | 4/2017 |
| EP | 3530656 A1 | 8/2019 |
| EP | 3530657 A1 | 8/2019 |
| JP | 2010-522188 A | 7/2013 |
| KR | 10-2009-0121399 A | 11/2009 |
| WO | 2003-106451 A | 12/2003 |
| WO | 2004-043936 A1 | 5/2004 |
| WO | 2007-032445 A1 | 3/2007 |

(Continued)

OTHER PUBLICATIONS

Liu et al. Chemical Abstract vol. 166,No. 515804 (Abstract for CN 106588885 (Apr. 26, 2017) . (Year: 2017).*
Machine Translation for CN 106588885 (Apr. 26, 2017).*
International Search Report issued for PCT Application No. PCT/KR2018/005162 dated Aug. 16, 2018, 2 pages.
Zhou, S. et al., "Pharmacophore-based 3D-QSAR modeling, virtual screening and molecular docking analysis for the Detection of MERTK inhibitors with novel scaffold", Combinatorial Chemistry & High Throughput Screening, 2016, vol. 19, No. 1, pp. 73-96.

(Continued)

*Primary Examiner* — Emily A Bernhardt
(74) *Attorney, Agent, or Firm* — Rothwell, Figg, Ernst & Manbeck, P.C.

(57) ABSTRACT

A pyrimidine derivative compound of Chemical Formula 1, an optical isomer thereof, or a pharmaceutically acceptable salt thereof, and a composition for preventing or treating cancer comprising the same as an active ingredient. The pyrimidine derivative compound of Chemical Formula 1, the optical isomer thereof, or the pharmaceutically acceptable salt thereof has an excellent selective inhibitory effect especially against TYRO 3 among TAM receptor inhibitory effects, and thus can be used as an excellent composition of preventing or treating cancer without adverse effects resulting from the inhibition of Axl and Mer.

[Chemical Formula 1]

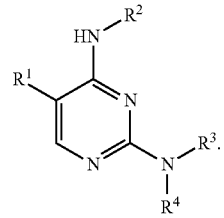

10 Claims, No Drawings

(56) References Cited

FOREIGN PATENT DOCUMENTS

| WO | 2010-038081 | A2 | 4/2010 |
| WO | 2013-177168 | A1 | 11/2013 |
| WO | 2015-157127 | A1 | 10/2015 |
| WO | 2017-059280 | A1 | 4/2017 |

OTHER PUBLICATIONS

Li, Z. et al., "Discovery of AM 925, a FLT3 and CDK4 dual kinase inhibitor with preferential affinity for the activated state of FLT3," Journal of Medicinal Chemistry, 2014, 57(8), 3430-3449.
Powell, N. A., et al., "Optimization of highly selective 2,4-diaminopyrimidine-5-carbox-amide inhibitors of Sky kinase," Bioorganic & Medicinal Chemistry Letters, 2013, 23(4), 1051-1055.
Mollard, A. et al., "Design, synthesis, and biological evaluation of a series of novel AXL kinase inhibitors," ACS Medicinal Chemistry Letters, 2011, 2(12), 907-912.
Extended European Search Report dated Dec. 8, 2020 in European patent application No. 18794872.4, 12 pages.

\* cited by examiner

PYRIMIDINE DERIVATIVE COMPOUND, OPTICAL ISOMER THEREOF, OR PHARMACEUTICALLY ACCEPTABLE SALT THEREOF, AND COMPOSITION FOR PREVENTING OR TREATING TYRO 3 RELATED DISEASE COMPRISING SAME AS ACTIVE INGREDIENT

CROSS-REFERENCE TO RELATED APPLICATIONS

This application is a 35 U.S.C. 371 National Phase Entry Application from PCT/KR2018/005162, filed on May 2, 2018, which claims the benefit of priority from Korean Patent Application No. 10-2017-0056002 filed on May 2, 2017; Korean Patent Application No. 10-2017-0114317 filed on Sep. 7, 2017; and Korean Patent Application No. 10-2017-0114322 filed on Sep. 7, 2017, with the Korean Intellectual Property Office, the disclosures of which are incorporated herein by reference in their entirety.

TECHNICAL FIELD

The present invention relates to a pyrimidine derivative compound, an optical isomer thereof, or a pharmaceutically acceptable salt thereof, and to a composition containing the same as an active ingredient for prevention or treatment of a Tyro 3-related disease.

BACKGROUND ART

TAM receptors are called the TAM family and are receptor tyrosine kinases (RTKs) collectively referring to three receptors Tyro 3, Axl, and Mer (Mertk). The TAM receptors, which are proteins present in the cell membrane and bind to signal substances outside the cell to transmit signals to the inside of the cell, operate kinases inside the cell to transmit the signals to the inside of the cell (Lemke, G., 2013).

Typical ligands for TAM receptors include growth arrest-specific gene 6 (Gas6) and Protein S (Pros1). The two ligands, which are soluble circulating proteins, have unique specificity to the TAM receptors even if they have 42% protein identity (Lew, E. D., et al., 2014).

The TAM ligands have a γ-carboxyglutamic acid-rich (Gla) domain. The vitamin K-dependent-carboxylation of glutamate residues in the Gla domain is necessary to bind, through $Ca^{2+}$, the TAM receptors to phosphatidylserine (PtdSer), which is a phospholipid exposed to the cell membrane of apoptotic cells, activated platelets, enveloped viruses, and activated T cells. Importantly, only the carboxylated ligands binding to PtdSer can significantly activate TAM signaling (Lew, E. D., et al., 2014; Tsou, W. I., et al., 2014).

The signal transition of TAM receptors is involved in platelet aggregation, thrombus formation, erythropoiesis, and homeostasis regulation of endothelial cells and vascular smooth muscles. In addition, TAM-dependent pathways are known to be involved in spermatogenesis, functioning of retina and lactating mammary glands, bone physiology, atherosclerosis, nervous system biology, and permeability of blood-brain barriers (Linger, R. M. A., et al., 2008; Paolino M., et al., 2016).

As for the phenotypes by animal models in which the genes of the TAM receptors Tyro 3, Axl, and Mer have been knocked out, the knockout of Tyro 3, Axl, and Mer alone was observed to commonly show hyperactivity of antigen-presenting cell (APC) and autoantibody production and prevent thrombosis. Meanwhile, the knockout of Mer causes excretory dysfunction of apoptotic cells, retinitis pigmentosa, increased inflammation, and the like. In addition, the knockout of Axl is known to cause side effects, such as severe autoimmune encephalomyelitis, increased demyelination, excretory dysfunction of apoptotic cells, and the like. The knockout of Tyro 3 was observed to cause no specific problems. Therefore, the development of selective inhibitors on TAM receptors, especially, Tyro 3, has been noted as a measure to overcome side effects by the inhibition of TAM receptors.

To date, most studies on TAM receptors have been directed to the roles of TAM receptors in two procedures, cancer development and immunoregulation. Regarding the cancer development of TAM receptors, a Tyro 3-targeted inhibitor has been recently proposed as a drug target for a breast cancer medicine, and study results have been reported that Tyro 3 was strongly expressed by 2 times or more in liver cancer patients compared with normal tissue and was significantly involved in cancer growth, liver destruction, and the like. Accordingly, the regulation of Tyro 3 inhibition or overexpression may be an important target in the development of liver cancer medicines (Duan, Y., et al., 2016).

The cases diagnosed with stage 3 ovarian cancer have a low survival rate of 5 years or shorter. It has been reported that the RNA expression of Tyro3 was increased and the RNA expression of Axl and Mer was decreased in the ovarian cell line, SKOV3/TR, which was resistant to Taxol known as an anticancer drug. The increased expression of Tyro 3 extends the survival of cancer cells and allows drug resistance to Taxol in SKOV3/TR (Lee, C., 2015). In addition, the expression of Tyro 3 was known to increase in skin cancer, and it was revealed that the knockdown of Tyro 3 inhibited cell proliferation and colony formation in melanoma cells.

Therefore, the development of Tyro 3-selective inhibitors makes it possible to expect the development of cancer medicines having excellent cancer treatment effects while minimizing side effects and capable of overcoming anticancer drug resistance.

While studying TAM receptor inhibiting compounds, the present inventors found a novel TAM receptor inhibiting compound and especially verified that the novel TAM receptor inhibiting compound had an excellent selective inhibition effect on Tyro 3 among TAM receptors, and thus the present inventors could completed the present invention.

DETAILED DESCRIPTION OF THE INVENTION

Technical Problem

An aspect of the present invention is to provide a pyrimidine derivative compound, an optical isomer thereof, or a pharmaceutically acceptable salt thereof, and a composition containing the same as an active ingredient for prevention or treatment of a Tyro 3-related disease.

Technical Solution

In accordance with an aspect of the present invention, there is provided a pyrimidine derivative compound represented by Chemical Formula 1 below, an optical isomer thereof, or a pharmaceutically acceptable salt thereof.

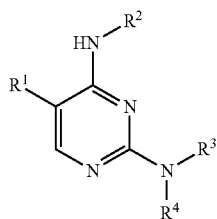

[Chemical Formula 1]

In Chemical Formula 1:

$R^1$ is hydrogen, halogen, substituted or unsubstituted $C_1$-$C_{10}$ alkyl, substituted or unsubstituted $C_1$-$C_{10}$ alkoxy, substituted or unsubstituted $C_{4-10}$ aryl, or substituted or unsubstituted $C_{4-10}$ heteroaryl, wherein the substituted alkyl, substituted alkoxy, substituted aryl, or substituted heteroaryl is substituted with at least one substituent selected from the group consisting of halogen, hydroxy, cyano, amino, nitro, substituted or unsubstituted $C_1$-$C_{10}$ alkyl, substituted or unsubstituted $C_1$-$C_{10}$ alkoxy, or substituted or unsubstituted piperidinyl, where the substituted alkyl, substituted alkoxy, or substituted piperidinyl is substituted with at least one substituent selected from the group consisting of halogen, $C_1$-$C_{10}$ haloalkyl, oxo (=O), hydroxy, cyano, nitro, amino, acetamino, trihalogen acetamino, trihalogen acetyl, $C_1$-$C_{10}$ alkyl, $C_1$-$C_{10}$ alkoxy, $C_4$-$C_{10}$ cycloalkyl, $C_4$-$C_{10}$ heterocycloalkyl, $C_4$-$C_{10}$ aryl, or $C_4$-$C_{10}$ heteroaryl;

$R^2$ is substituted or unsubstituted $C_4$-$C_{10}$ cycloalkyl, substituted or unsubstituted $C_4$-$C_8$ heterocycloalkyl, substituted or unsubstituted $C_4$-$C_{10}$ aryl, substituted or unsubstituted $C_4$-$C_{10}$ heteroaryl, or a substituted or unsubstituted fused ring in which $C_4$-$C_{10}$ aryl is fused with $C_4$-$C_8$ heterocycloalkyl, wherein the substituted cycloalkyl, substituted heterocycloalkyl, substituted aryl, substituted heteroaryl, or fused ring is substituted with at least one substituent selected from the group consisting of halogen, $C_1$-$C_{10}$ haloalkyl, oxo (=O), hydroxy, cyano, nitro, acetamino, trihalogen acetamino, trihalogen acetyl, $C_4$-$C_{10}$ cycloalkyl, $C_4$-$C_8$ heterocycloalkyl, $C_4$-$C_{10}$ aryl, $C_4$-$C_{10}$ heteroaryl, substituted or unsubstituted amino, substituted or unsubstituted $C_1$-$C_{10}$ alkyl, substituted or unsubstituted $C_1$-$C_{10}$ alkoxy, or substituted or unsubstituted $C_{4-10}$ aryl $C_{1-10}$ alkyl, where the substituted amino, substituted alkyl, substituted alkoxy, or substituted arylalkyl is substituted with at least one substituent selected from the group consisting of halogen, oxo (=O), or substituted or unsubstituted $C_1$-$C_{10}$ alkyl, where the substituted alkyl is substituted with at least one substituent selected from halogen or oxo (=O); and $R^3$ and $R^4$ each are independently hydrogen, halogen, substituted or unsubstituted $C_4$-$C_{10}$ cycloalkyl, substituted or unsubstituted $C_4$-$C_8$ heterocycloalkyl, substituted or unsubstituted $C_4$-$C_{10}$ aryl, substituted or unsubstituted $C_4$-$C_{10}$ heteroaryl, substituted or unsubstituted $C_{4-10}$ aryl $C_{1-10}$ alkyl, substituted or unsubstituted $C_4$-$C_{10}$ heteroaryl $C_{1-10}$ alkyl, or a substituted or unsubstituted fused ring in which $C_4$-$C_{10}$ aryl is fused with $C_4$-$C_{10}$ cycloalkyl or $C_4$-$C_8$ heterocycloalkyl, wherein the substituted cycloalkyl, substituted heterocycloalkyl, substituted aryl, substituted heteroaryl, substituted arylalkyl, substituted heteroarylalkyl, or substituted fused ring is substituted with at least one substituent selected from the group consisting of halogen, $C_1$-$C_{10}$ haloalkyl, hydroxy, cyano, nitro, amino, acetamino, trihalogen acetamino, trihalogen acetyl, oxo (=O), $C_4$-$C_{10}$ cycloalkyl, $C_4$-$C_8$ heterocycloalkyl, $C_4$-$C_{10}$ heteroaryl, substituted or unsubstituted $C_1$-$C_{10}$ alkyl, substituted or unsubstituted $C_1$-$C_{10}$ alkoxy, or substituted or unsubstituted $C_4$-$C_{10}$ aryl, where the substituted alkyl, substituted alkoxy, or substituted aryl is substituted with at least one substituent selected from the group consisting of halogen, oxo (=O), or substituted or unsubstituted $C_1$-$C_{10}$ alkyl, where the substituted alkyl is substituted with at least one substituent selected from halogen or oxo (=O), or when $R^3$ and $R^4$, together with a nitrogen atom to which they are bonded, form substituted or unsubstituted $C_4$-$C_8$ heterocycloalkyl, the substituted heterocycloalkyl is substituted with at least one substituent selected from the group consisting of halogen, hydroxy, amino, cyano, nitro, substituted or unsubstituted $C_{4-10}$ aryl $C_{1-10}$ alkyl, or $C_4$-$C_{10}$ heteroaryl $C_{1-10}$ alkyl, where the substituted arylalkyl or the heteroarylalkyl is substituted with at least one substituent selected from halogen or oxo (=O).

The term "alkyl" refers to a single-bonded, straight- or branched-chain hydrocarbon group, and examples thereof include methyl, ethyl, propyl, n-butyl, isobutyl, tert-butyl, 1-methylproyl, and the like.

The term "alkoxy" refers to a single-bonded, straight- or branched-chain hydrocarbon group bonded to oxygen, and examples thereof include methoxy, ethoxy, propoxy, n-butoxy, tert-butoxy, 1-methylpropoxy, and the like.

The term "cycloalkyl" refers to a cyclic, single-bonded, saturated hydrocarbon group, and examples thereof include cyclobutyl, cyclopentyl, cyclohexyl, and the like, depending on the number of carbon atoms.

The term "heterocycloalkyl" refers to a cyclic, single-bonded, saturated hydrocarbon group containing at least one heteroatom, such as N, O, or S, and examples thereof include aziridine, pyrrolidine, piperidine, piperazine, morpholine, tetrahydrofuran, tetrahydropyran, and the like, depending on the number and kind of heteroatoms and the number of carbon atoms included in the ring.

The term "aryl" refers to an aromatic substituent having at least one ring having a covalent pi electron system.

The term "heteroaryl" refers to an aromatic, cyclic compound containing at least one heteroatom, such as N, O, or S, and examples thereof include pyridine, indole, isoindole, and the like, depending on the number and kind of heteroatoms and the number of carbon atoms included in the ring.

Examples of the aryl or heteroaryl may include phenyl, furan, pyran, pyridyl, pyrimidyl, triazyl, and the like, but are not limited thereto.

More specifically, the examples of the compound of Chemical Formula 1 of the present invention include at least one selected from the group consisting of:

5-bromo-N4-cyclohexyl-N2-(p-tolyl)pyrimidine-2,4-diamine (Compound 1);

N4-cyclohexyl-N2,5-di-(p-tolyl)pyrimidine-2,4-diamine (Compound 2);

5-bromo-N4-cyclohexyl-N2-(3,5-dichlorophenyl)pyrimidine-2,4-diamine (Compound 3);

2-chloro-N4-cyclohexyl-5-(1-methyl-1H-pyrazol-4-yl)pyrimidine-4-amine (Compound 4);

N4-cyclohexyl-N2-(3,5-dichlorophenyl)-5-(1-methyl-1H-pyrazol-4-yl)pyrimidine-2,4-diamine (Compound 5);

N4-cyclohexyl-5-(1-methyl-1H-pyrazol-4-yl)-N2-phenylpyrimidine-2,4-diamine (Compound 6);

N2-(3-chlorophenyl)-N4-cyclohexyl-5-(1-methyl-1H-pyrazol-4-yl)pyrimidine-2,4-diamine (Compound 7);

N4-cyclohexyl-5-(1-methyl-1H-pyrazol-4-yl)-N2-(3-(trifluoromethyl)benzyl)pyrimidine-2,4-diamine (Compound 8);
N2-(3-chloro-4-methoxyphenyl)-N4-cyclohexyl-5-(1-methyl-1H-pyrazol-4-yl)pyrimidine-2,4-diamine (Compound 9);
N4-cyclohexyl-5-(1-methyl-1H-pyrazol-4-yl)-N2-(o-tolyl)pyrimidine-2,4-diamine (Compound 10);
N4-cyclohexyl-5-(1-methyl-1H-pyrazol-4-yl)-N2-(5-methylisoxazol-3-yl)pyrimidine-2,4-diamine (Compound 11);
N2-(5-tert-butylisoxazol-3-yl)-N4-cyclohexyl-5-(1-methyl-1H-pyrazol-4-yl)pyrimidine-2,4-diamine (Compound 12);
N4-cyclohexyl-N2-(2-isopropylphenyl)-5-(1-methyl-1H-pyrazol-4-yl)pyrimidine-2,4-diamine (Compound 13);
N4-cyclohexyl-5-(furan-3-yl)-N2-(p-tolyl)pyrimidine-2,4-diamine (Compound 14);
N4-cyclohexyl-N2-(3,5-dichlorophenyl)-5-(furan-3-yl)pyrimidine-2,4-diamine (Compound 15);
N4-cyclohexyl-N2-(2,2-difluoro-2-(4-methoxyphenyl)ethyl)-5-(1-methyl-1H-pyrazol-4-yl)pyrimidine-2,4-diamine (Compound 16);
N4-cyclohexyl-5-(1-methyl-1H-pyrazol-4-yl)-N2-(2-(pyridin-4-yl)ethyl)pyrimidine-2,4-diamine (Compound 17);
(4-(4-(cyclohexylamino)-5-(1-methyl-1H-pyrazol-4-yl)pyrimidin-2-yl)piperazin-1-yl)(thiophen-2-yl)methanone (Compound 18);
4-(4-(cyclohexylamino)-5-(1-methyl-1H-pyrazol-4-yl)pyrimidin-2-ylamino)-1,5-dimethyl-2-phenyl-1,2-dihydropyrazol-3-one (Compound 19);
N4-cyclohexyl-5-(1-methyl-1H-pyrazol-4-yl)-N2-(3-methylisoxazol-5-yl)pyrimidine-2,4-diamine (Compound 20);
N4-cyclohexyl-N2-(5-ethyl-1,3,4-thiadiazol-2-yl)-5-(1-methyl-1H-pyrazol-4-yl)pyrimidine-2,4-diamine (Compound 21);
N4-cyclohexyl-5-(1-methyl-1H-pyrazol-4-yl)-N2-(thiazol-2-yl)pyrimidine-2,4-diamine (Compound 22);
N4-cyclohexyl-N2-adamantyl-5-(1-methyl-1H-pyrazol-4-yl)pyrimidine-2,4-diamine (Compound 23);
N4-cyclohexyl-N2-(2-methoxyphenyl)-5-(1-methyl-1H-pyrazol-4-yl)pyrimidine-2,4-diamine (Compound 24);
N4-cyclohexyl-5-(1-methyl-1H-pyrazol-4-yl)-N2-(m-tolyl)pyrimidine-2,4-diamine (Compound 25);
N-((1s,4s)-4-(2-(3,5-dichlorophenylamino)-5-(1-methyl-1H-pyrazol-4-yl)pyrimidin-4-ylamino)cyclohexyl)-2,2,2-trifluoroacetamide (Compound 26);
1-(4-(2-(3,5-dichlorophenylamino)-5-(1-methyl-1H-pyrazol-4-yl)pyrimidin-4-ylamino)piperidin-1-yl)-2,2,2-trifluoroethanone (Compound 27);
N4-((1s,4s)-4-aminocyclohexyl)-N2-(3,5-dichlorophenyl)-5-(1-methyl-1H-pyrazol-4-yl)pyrimidine-2,4-diamine (Compound 28);
N2-(3,5-dichlorophenyl)-5-(1-methyl-1H-pyrazol-4-yl)-N4-(piperidin-4-yl)pyrimidine-2,4-diamine (Compound 29);
N2-(3,5-dichlorophenyl)-N4-((1s,4s)-4-(dimethylamino)cyclohexyl)-5-(1-methyl-1H-pyrazol-4-yl)pyrimidine-2,4-diamine (Compound 30);
N-((1s,4s)-4-(2-(3,5-dichlorophenylamino)-5-(1-methyl-1H-pyrazol-4-yl)pyrimidin-4-ylamino)cyclohexyl)-acetamide (Compound 31);
N2-(3,5-dichlorophenyl)-5-(1-methyl-1H-pyrazol-4-yl)-N4-(1-methylpiperidin-4-yl)pyrimidine-2,4-diamine (Compound 32);
1-(4-(2-(3,5-dichlorophenylamino)-5-(1-methyl-1H-pyrazol-4-yl)pyrimidin-4-ylamino)piperidin-1-yl)ethanone (Compound 33);
1-(4-(5-(1-methyl-1H-pyrazol-4-yl)-2-(phenylamino)pyrimidin-4-ylamino)piperidin-1-yl)-2,2,2-trifluoroethanone (Compound 34);
1-(4-(2-(3-chlorophenylamino)-5-(1-methyl-1H-pyrazol-4-yl)pyrimidin-4-ylamino)piperidin-1-yl)-2,2,2-trifluoroethanone (Compound 35);
N2-(3-chlorophenyl)-5-(1-methyl-1H-pyrazol-4-yl)-N4-(piperidin-4-yl)pyrimidine-2,4-diamine (Compound 36);
1-(4-(2-(4-chlorophenylamino)-5-(1-methyl-1H-pyrazol-4-yl)pyrimidin-4-ylamino)piperidin-1-yl)-2,2,2-trifluoroethanone (Compound 37);
N4-(1-benzylpiperidin-4-yl)-N2-(3,5-dichlorophenyl)-5-(1-methyl-1H-pyrazol-4-yl)pyrimidine-2,4-diamine (Compound 38);
1-(4-(2-(3-fluorophenylamino)-5-(1-methyl-1H-pyrazol-4-yl)pyrimidin-4-ylamino)piperidin-1-yl)-2,2,2-trifluoroethanone (Compound 39);
N2-(4-chlorophenyl)-5-(1-methyl-1H-pyrazol-4-yl)-N4-(piperidin-4-yl)pyrimidine-2,4-diamine (Compound 40);
N2-(3-fluorophenyl)-5-(1-methyl-1H-pyrazol-4-yl)-N4-(piperidin-4-yl)pyrimidine-2,4-diamine (Compound 41);
5-(1-methyl-1H-pyrazol-4-yl)-N2-phenyl-N4-(piperidin-4-yl)pyrimidine-2,4-diamine (Compound 42);
1-(4-(2-(3-methyl-4-chlorophenylamino)-5-(1-methyl-1H-pyrazol-4-yl)pyrimidin-4-ylamino)piperidin-1-yl)-2,2,2-trifluoroethanone (Compound 43);
1-(4-(2-(4-methoxyphenylamino)-5-(1-methyl-1H-pyrazol-4-yl)pyrimidin-4-ylamino)piperidin-1-yl)-2,2,2-trifluoroethanone (Compound 44);
1-(4-(2-(3-chloro-4-methoxyphenylamino)-5-(1-methyl-1H-pyrazol-4-yl)pyrimidin-4-ylamino)piperidin-1-yl)-2,2,2-trifluoroethanone (Compound 45);
N2-(3-methyl-4-chlorophenyl)-5-(1-methyl-1H-pyrazol-4-yl)-N4-(piperidin-4-yl)pyrimidine-2,4-diamine (Compound 46);
N2-(4-methoxyphenyl)-5-(1-methyl-1H-pyrazol-4-yl)-N4-(piperidin-4-yl)pyrimidine-2,4-diamine (Compound 47);
N2-(3-chloro-4-methoxyphenyl)-5-(1-methyl-1H-pyrazol-4-yl)-N4-(piperidin-4-yl)pyrimidine-2,4-diamine (Compound 48); 1-(4-(2-(p-toluidino)-5-(furan-3-yl)pyrimidin-4-ylamino)piperidin-1-yl)-2,2,2-trifluoroethanone (Compound 49);
1-(4-(2-(m-toluidino)-5-(furan-3-yl)pyrimidin-4-ylamino)piperidin-1-yl)-2,2,2-trifluoroethanone (Compound 50);
5-(furan-3-yl)-N4-(piperidin-4-yl)-N2-(p-tolyl)pyrimidine-2,4-diamine (Compound 51);
5-(furan-3-yl)-N4-(piperidin-4-yl)-N2-(m-tolyl)pyrimidine-2,4-diamine (Compound 52);
1-(4-(2-(3-chlorophenylamino)-5-(furan-3-yl)pyrimidin-4-ylamino)piperidin-1-yl)-2,2,2-trifluoroethanone (Compound 53);
1-(4-(2-(3-fluorophenylamino)-5-(furan-3-yl)pyrimidin-4-ylamino)piperidin-1-yl)-2,2,2-trifluoroethanone (Compound 54);
N2-(3-fluorophenyl)-5-(furan-3-yl)-N4-(piperidin-4-yl)pyrimidine-2,4-diamine (Compound 55);
N2-(3-chlorophenyl)-5-(furan-3-yl)-N4-(piperidin-4-yl)pyrimidine-2,4-diamine (Compound 56);
1-(4-(2-(3,5-dichlorophenylamino)-5-phenylpyrimidin-4-ylamino)piperidin-1-yl)-2,2,2-trifluoroethanone (Compound 57);
N2-(3,5-dichlorophenyl)-5-phenyl-N4-(piperidin-4-yl)pyrimidine-2,4-diamine (Compound 58);
1-(4-(2-(3,5-dichlorophenylamino)-5-(3-methoxyphenyl)pyrimidin-4-ylamino)piperidin-1-yl)-2,2,2-trifluoroethanone (Compound 59);

N2-(3,5-dichlorophenyl)-5-(3-methoxyphenyl)-N4-(piperidin-4-yl)pyrimidine-2,4-diamine (Compound 60);

1-(4-(2-(3,5-dichlorophenylamino)-5-(3,4-dimethoxyphenyl)pyrimidin-4-ylamino)piperidin-1-yl)-2,2,2-trifluoroethanone (Compound 61);

N2-(3,5-dichlorophenyl)-5-(3,4-dimethoxyphenyl)-N4-(piperidin-4-yl)pyrimidine-2,4-diamine (Compound 62);

1-(4-(2-(3-methyl-4-chlorophenylamino)-5-(3,4-dimethoxyphenyl)pyrimidin-4-ylamino)piperidin-1-yl)-2,2,2-trifluoroethanone (Compound 63);

1-(4-(5-(3,4-dimethoxyphenyl)-2-(4-methoxyphenylamino)pyrimidin-4-ylamino)piperidin-1-yl)-2,2,2-trifluoroethanone (Compound 64);

1-(4-(5-(3,4-dimethoxyphenyl)-2-(2-methoxyphenylamino)pyrimidin-4-ylamino)piperidin-1-yl)-2,2,2-trifluoroethanone (Compound 65);

N2-(3-methyl-4-chlorophenyl)-5-(3,4-dimethoxyphenyl)-N4-(piperidin-4-yl)pyrimidine-2,4-diamine (Compound 66);

5-(3,4-dimethoxyphenyl)-N2-(4-methoxyphenyl)-N4-(piperidin-4-yl)pyrimidine-2,4-diamine (Compound 67);

5-(3,4-dimethoxyphenyl)-N2-(2-methoxyphenyl)-N4-(piperidin-4-yl)pyrimidine-2,4-diamine (Compound 68);

1-(4-(2-(3-chlorophenylamino)-5-(3,4-dimethoxyphenyl)pyrimidin-4-ylamino)piperidin-1-yl)-2,2,2-trifluoroethanone (Compound 69);

1-(4-(5-(1-methyl-1H-pyrazol-4-yl)-2-(2-(2,2,2-trifluoroacetyl)-1,2,3,4-tetrahydroisoquinolin-7-ylamino)pyrimidin-4-ylamino)piperidin-1-yl)-2,2,2-trifluoroethanone (Compound 70);

1-(4-(2-(3,5-dichlorophenylamino)-5-(1-(2-hydroxyethyl)-1H-pyrazol-4-yl)pyrimidin-4-ylamino)piperidin-1-yl)-2,2,2-trifluoroethanone (Compound 71);

5-(1-methyl-1H-pyrazol-4-yl)-N4-(piperidin-4-yl)-N2-(1,2,3,4-tetrahydroisoquinolin-7-yl)pyrimidine-2,4-diamine (Compound 72);

N2-(3,5-dichlorophenyl)-N4-(piperidin-4-yl)-5-(1-(piperidin-4-yl)-1H-pyrazol-4-yl)pyrimidine-2,4-diamine (Compound 73);

N2-(3-chlorophenyl)-5-(3,4-dimethoxyphenyl)-N4-(piperidin-4-yl)pyrimidine-2,4-diamine (Compound 74);

2-(4-(2-(3,5-dichlorophenylamino)-4-(piperidin-4-ylamino)pyrimidin-5-yl)-1H-pyrazol-1-yl)ethanol (Compound 75);

1-(4-(5-(1-(2-hydroxyethyl)-1H-pyrazol-4-yl)-2-(2-(2,2,2-trifluoroacetyl)-1,2,3,4-tetrahydroisoquinolin-7-ylamino)pyrimidin-4-ylamino)piperidin-1-yl)-2,2,2-trifluoroethanone (Compound 76);

1-(4-(2-(3-methyl-4-chlorophenylamino)-5-(1-(2-hydroxyethyl)-1H-pyrazol-4-yl)pyrimidin-4-ylamino)piperidin-1-yl)-2,2,2-trifluoroethanone (Compound 77);

1-(4-(5-(1-(2-hydroxyethyl)-1H-pyrazol-4-yl)-2-(4-methoxyphenylamino)pyrimidin-4-ylamino)piperidin-1-yl)-2,2,2-trifluoroethanone (Compound 78);

2-(4-(4-(piperidin-4-ylamino)-2-(1,2,3,4-tetrahydroisoquinolin-7-ylamino)pyrimidin-5-yl)-1H-pyrazol-1-yl)ethanol (Compound 79);

2-(4-(2-(3-methyl-4-chlorophenylamino)-4-(piperidin-4-ylamino)pyrimidin-5-yl)-1H-pyrazol-1-yl)ethanol (Compound 80);

2-(4-(2-(4-methoxyphenylamino)-4-(piperidin-4-ylamino)pyrimidin-5-yl)-1H-pyrazol-1-yl)ethanol (Compound 81);

1-(7-(2-(3,5-dichlorophenylamino)-5-(1-methyl-1H-pyrazol-4-yl)pyrimidin-4-ylamino)-3,4-dihydroisoquinolin-2(1H)-yl)-2,2,2-trifluoroethanone (Compound 82);

1-(7-(2-(3-methyl-4-chlorophenylamino)-5-(1-methyl-1H-pyrazol-4-yl)pyrimidin-4-ylamino)-3,4-dihydroisoquinolin-2(1H)-yl)-2,2,2-trifluoroethanone (Compound 83);

N2-(3,5-dichlorophenyl)-5-(1-methyl-1H-pyrazol-4-yl)-N4-(1,2,3,4-tetrahydroisoquinolin-7-yl)pyrimidine-2,4-diamine (Compound 84);

N2-(3-methyl-4-chlorophenyl)-5-(1-methyl-1H-pyrazol-4-yl)-N4-(1,2,3,4-tetrahydroisoquinolin-7-yl)pyrimidine-2,4-diamine (Compound 85);

N-((1s,4s)-4-(5-(1-methyl-1H-pyrazol-4-yl)-2-(2-(2,2,2-trifluoroacetyl)-1,2,3,4-tetrahydroisoquinolin-7-ylamino)pyrimidin-4-ylamino)cyclohexyl)-2,2,2-trifluoroacetamide (Compound 86);

1-(7-(2-(3,5-dichlorophenylamino)-5-(1-(2-hydroxyethyl)-1H-pyrazol-4-yl)pyrimidin-4-ylamino)-3,4-dihydroisoquinolin-2(1H)-yl)-2,2,2-trifluoroethanone (Compound 87);

N4-((1s,4s)-4-aminocyclohexyl)-5-(1-methyl-1H-pyrazol-4-yl)-N2-(1,2,3,4-tetrahydroisoquinolin-7-yl)pyrimidine-2,4-diamine (Compound 88);

2-(4-(2-(3,5-dichlorophenylamino)-4-(1,2,3,4-tetrahydroisoquinolin-7-ylamino)pyrimidin-5-yl)-1H-pyrazol-1-yl)ethanol (Compound 89);

N-((1s,4s)-4-(2-(3-chlorophenylamino)-5-(1-methyl-1H-pyrazol-4-yl)pyrimidin-4-ylamino)cyclohexyl)-2,2,2-trifluoroacetamide (Compound 90);

N-((1s,4s)-4-(2-(3-acetylphenylamino)-5-(1-methyl-1H-pyrazol-4-yl)pyrimidin-4-ylamino)cyclohexyl)-2,2,2-trifluoroacetamide (Compound 91);

N-((1s,4s)-4-(2-(m-toluidino)-5-(1-methyl-1H-pyrazol-4-yl)pyrimidin-4-ylamino)cyclohexyl)-2,2,2-trifluoroacetamide (Compound 92);

1-(7-(2-(3-chlorophenylamino)-5-(1-(2-hydroxyethyl)-1H-pyrazol-4-yl)pyrimidin-4-ylamino)-3,4-dihydroisoquinolin-2(1H)-yl)-2,2,2-trifluoroethanone (Compound 93);

1-(7-(2-(3-fluorophenylamino)-5-(1-(2-hydroxyethyl)-1H-pyrazol-4-yl)pyrimidin-4-ylamino)-3,4-dihydroisoquinolin-2(1H)-yl)-2,2,2-trifluoroethanone (Compound 94);

N-((1s,4s)-4-(2-(3,5-dichlorophenylamino)-5-(1-(2-hydroxyethyl)-1H-pyrazol-4-yl)pyrimidin-4-ylamino)cyclohexyl)-2,2,2-trifluoroacetamide (Compound 95);

N-((1s,4s)-4-(5-(1-(2-hydroxyethyl)-1H-pyrazol-4-yl)-2-(2-(2,2,2-trifluoroacetyl)-1,2,3,4-tetrahydroisoquinolin-7-ylamino)pyrimidin-4-ylamino)cyclohexyl)-2,2,2-trifluoroacetamide (Compound 96);

N4-((1s,4s)-4-aminocyclohexyl)-N2-(3-chlorophenyl)-5-(1-methyl-1H-pyrazol-4-yl)pyrimidine-2,4-diamine (Compound 97);

N4-((1s,4s)-4-aminocyclohexyl)-N2-(3-acetylphenyl)-5-(1-methyl-1H-pyrazol-4-yl)pyrimidine-2,4-diamine (Compound 98);

N4-((1s,4s)-4-aminocyclohexyl)-5-(1-methyl-1H-pyrazol-4-yl)-N2-(m-tolyl)pyrimidine-2,4-diamine (Compound 99);

N-((1s,4s)-4-(2-(3-chlorophenylamino)-5-(1-(2-hydroxyethyl)-1H-pyrazol-4-yl)pyrimidin-4-ylamino)cyclohexyl)-2,2,2-trifluoroacetamide (Compound 100);

2-(4-(2-(3-chlorophenylamino)-4-(1,2,3,4-tetrahydroisoquinolin-7-ylamino)pyrimidin-5-yl)-1H-pyrazol-1-yl)ethanol (Compound 101);

2-(4-(2-(3-fluorophenylamino)-4-(1,2,3,4-tetrahydroisoquinolin-7-ylamino)pyrimidin-5-yl)-1H-pyrazol-1-yl)ethanol (Compound 102);

2-(4-(4-((1s,4s)-4-aminocyclohexylamino)-2-(3,5-dichlorophenylamino)pyrimidin-5-yl)-1H-pyrazol-1-yl)ethanol (Compound 103);

2-(4-(4-((1s,4s)-4-aminocyclohexylamino)-2-(1,2,3,4-tetrahydroisoquinolin-7-ylamino)pyrimidin-5-yl)-1H-pyrazol-1-yl)ethanol (Compound 104);

2-(4-(4-((1s,4s)-4-aminocyclohexylamino)-2-(3-chlorophenylamino)pyrimidin-5-yl)-1H-pyrazol-1-yl)ethanol (Compound 105);

N-((1s,4s)-4-((2-((4-chloro-3-methylphenyl)amino)-5-(1-(2 hydroxyethyl)-1H-pyrazol-4-yl)pyrimidin-4-yl)amino)cyclohexyl)-2,2,2-trifluoroacetamide (Compound 106);

2-(4-(4-((1s,4s)-4-aminocyclohexylamino)-2-(3-methyl-4-chlorophenylamino)pyrimidin-5-yl)-1H-pyrazol-1-yl)ethanol (Compound 107);

N-((1s,4s)-4-(2-(3,5-dichlorophenylamino)-5-(1-(1-(2,2,2-trifluoroacetyl)piperidin-4-yl)-1H-pyrazol-4-yl)pyrimidin-4-ylamino)cyclohexyl)-2,2,2-trifluoroacetamide (Compound 108);

N-((1r,4r)-4-(2-(3,5-dichlorophenylamino)-5-(1-methyl-1H-pyrazol-4-yl)pyrimidin-4-ylamino)cyclohexyl)-2,2,2-trifluoroacetamide (Compound 109);

N-((1r,4r)-4-(2-(3,5-dichlorophenylamino)-5-(1-(2-hydroxyethyl)-1H-pyrazol-4-yl)pyrimidin-4-ylamino)cyclohexyl)-2,2,2-trifluoroacetamide (Compound 110);

N4-((1s,4s)-4-aminocyclohexyl)-N2-(3,5-dichlorophenyl)-5-(1-(piperidin-4-yl)-1H-pyrazol-4-yl)pyrimidine-2,4-diamine (Compound 111);

N4-((1r,4r)-4-aminocyclohexyl)-N2-(3,5-dichlorophenyl)-5-(1-methyl-1H-pyrazol-4-yl)pyrimidine-2,4-diamine (Compound 112);

2-(4-(4-((1r,4r)-4-aminocyclohexylamino)-2-(3,5-dichlorophenylamino)pyrimidin-5-yl)-1H-pyrazol-1-yl)ethanol (Compound 113);

N-((1r,4r)-4-(2-(3,5-difluorophenylamino)-5-(1-methyl-1H-pyrazol-4-yl)pyrimidin-4-ylamino)cyclohexyl)-2,2,2-trifluoroacetamide (Compound 114);

N-((1r,4r)-4-(2-(3,5-difluorophenylamino)-5-(1-(2-hydroxyethyl)-1H-pyrazol-4-yl)pyrimidin-4-ylamino)cyclohexyl)-2,2,2-trifluoroacetamide (Compound 115);

N4-((1r,4r)-4-aminocyclohexyl)-N2-(3,5-difluorophenyl)-5-(1-methyl-1H-pyrazol-4-yl)pyrimidine-2,4-diamine (Compound 116);

2-(4-(4-((1r,4r)-4-aminocyclohexylamino)-2-(3,5-difluorophenylamino)pyrimidin-5-yl)-1H-pyrazol-1-yl)ethan-1-ol (Compound 117);

N4-((1r,4r)-4-aminocyclohexyl)-N2-(3,5-bis(trifluoromethyl)phenyl)-5-(1-methyl-1H-pyrazol-4-yl)pyrimidine-2,4-diamine (Compound 118);

N-((1r,4r)-4-(2-(3,5-bis(trifluoromethyl)phenylamino)-5-(1-(2-hydroxyethyl)-1H-pyrazol-4-yl)pyrimidin-4-ylamino)cyclohexyl)-2,2,2-trifluoroacetamide (Compound 119);

N4-((1r,4r)-4-aminocyclohexyl)-N2-(3,5-bis(trifluoromethyl)phenyl)-5-(1-methyl-1H-pyrazol-4-yl)pyrimidine-2,4-diamine (Compound 120);

2-(4-(4-((1r,4r)-4-aminocyclohexylamino)-2-(3,5-bis(trifluoromethyl)phenylamino)pyrimidin-5-yl)-1H-pyrazol-1-yl)ethan-1-ol (Compound 121);

1-(4-(2-(3,5-dichlorophenylamino)-5-(1-(piperidin-4-yl)-1H-pyrazol-4-yl)pyrimidin-4-ylamino)cyclohexyl)-2,2,2-trifluoroacetamide (Compound 122);

1-(7-(2-(3,5-difluorophenylamino)-5-(1-(2-hydroxyethyl)-1H-pyrazol-4-yl)pyrimidin-4-ylamino)-3,4-dihydroisoquinolin-2(1H)-yl)-2,2,2-trifluoroethanone (Compound 123);

1-(7-(2-(3,5-bis(trifluoromethyl)phenylamino)-5-(1-(2-hydroxyethyl)-1H-pyrazol-4-yl)pyrimidin-4-ylamino)-3,4-dihydroisoquinolin-2(1H)-yl)-2,2,2-trifluoroethanone (Compound 124);

1-(7-(2-(2,3-dichlorophenylamino)-5-(1-(2-hydroxyethyl)-1H-pyrazol-4-yl)pyrimidin-4-ylamino)-3,4-dihydroisoquinolin-2(1H)-yl)-2,2,2-trifluoroethanone (Compound 125);

1-(7-(2-(2-methyl-3-chlorophenylamino)-5-(1-(2-hydroxyethyl)-1H-pyrazol-4-yl)pyrimidin-4-ylamino)-3,4-dihydroisoquinolin-2(1H)-yl)-2,2,2-trifluoroethanone (Compound 126);

2-(4-(2-(3,5-difluorophenylamino)-4-(1,2,3,4-tetrahydroisoquinolin-7-ylamino)pyrimidin-5-yl)-1H-pyrazol-1-yl)-ethan-1-ol (Compound 127);

2-(4-(2-(3,5-bis(trifluoromethyl)phenylamino)-4-((1,2,3,4-tetrahydroisoquinolin-7-ylamino)pyrimidin-5-yl)-1H-pyrazol-1-yl)-ethan-1-ol (Compound 128);

2-(4-(2-(2,3-dichlorophenylamino)-4-(1,2,3,4-tetrahydroisoquinolin-7-ylamino)pyrimidin-5-yl)-1H-pyrazol-1-yl)-ethan-1-ol (Compound 129);

2-(4-(2-(2-methyl-3-chlorophenylamino)-4-(1,2,3,4-tetrahydroisoquinolin-7-ylamino)pyrimidin-5-yl)-1H-pyrazol-1-yl)-ethan-1-ol (Compound 130);

N2-(3,5-difluorophenyl)-5-(1-(piperidin-4-yl)-1H-pyrazol-4-yl)-N4-(1,2,3,4-tetrahydroisoquinolin-7-yl)pyrimidine-2,4-diamine (Compound 131);

N2-(3,5-dichlorophenyl)-5-(1-(piperidin-4-yl)-1H-pyrazol-4-yl)-N4-(1,2,3,4-tetrahydroisoquinolin-7-yl)pyrimidine-2,4-diamine (Compound 132);

N2-(3,5-bis(trifluoromethyl)phenyl)-N4-(1,2,3,4-tetrahydroisoquinolin-7-yl)-5-(1-(piperidin-4-yl)-1H-pyrazol-4-yl)pyrimidine-2,4-diamine (Compound 133);

N2-(2,3-dichlorophenyl)-5-(1-(piperidin-4-yl)-1H-pyrazol-4-yl)-N4-(1,2,3,4-tetrahydroisoquinolin-7-yl)pyrimidine-2,4-diamine (Compound 134);

N2-(3,5-dimethoxyphenyl)-5-(1-methyl-1H-pyrazol-4-yl)-N4-(1,2,3,4-tetrahydroisoquinolin-7-yl)pyrimidine-2,4-diamine (Compound 135);

N2-(3,5-bis(trifluoromethyl)phenyl)-5-(1-methyl-1H-pyrazol-4-yl)-N4-(1,2,3,4-tetrahydroisoquinolin-7-yl)pyrimidine-2,4-diamine (Compound 136);

N2-(3,5-difluorophenyl)-5-(1-methyl-1H-pyrazol-4-yl)-N4-(1,2,3,4-tetrahydroisoquinolin-7-yl)pyrimidine-2,4-diamine (Compound 137);

1-(7-(2-(3,5-dimethoxyphenylamino)-5-(1-methyl-1H-pyrazol-4-yl)pyrimidin-4-ylamino)-3,4-dihydroisoquinolin-2(1H)-yl)-2,2,2-trifluoroethan-1-one (Compound 138);

1-(7-(2-(3,5-bis(trifluoromethyl)phenylamino)-5-(1-methyl-1H-pyrazol-4-yl)pyrimidin-4-ylamino)-3,4-dihydroisoquinolin-2(1H)-yl)-2,2,2-trifluoroethan-1-one (Compound 139);

1-(7-(2-(3,5-difluorophenylamino)-5-(1-methyl-1H-pyrazol-4-yl)pyrimidin-4-ylamino)-3,4-dihydroisoquinolin-2(1H)-yl)-2,2,2-trifluoroethan-1-one (Compound 140);

N2-(3,5-difluorophenyl)-N4-(2-(2,2,2-trifluoroacetyl)-1,2,3,4-tetrahydroisoquinolin-7-yl)-5-(1-(piperidin-4-yl)-1H-pyrazol-4-yl)pyrimidine-2,4-diamine (Compound 141);

N2-(3,5-dichlorophenyl)-N4-(2-(2,2,2-trifluoroacetyl)-1,2,3,4-tetrahydroisoquinolin-7-yl)-5-(1-(piperidin-4-yl)-1H-pyrazol-4-yl)pyrimidine-2,4-diamine (Compound 142);

N2-(3,5-bis(trifluoromethyl)phenyl)-N4-(2-(2,2,2-trifluoroacetyl)-1,2,3,4-tetrahydroisoquinolin-7-yl)-5-(1-(piperidin-4-yl)-1H-pyrazol-4-yl)pyrimidine-2,4-diamine (Compound 143);

N2-(2,3-dichlorophenyl)-N4-(2-(2,2,2-trifluoroacetyl)-1,2,3,4-tetrahydroisoquinolin-7-yl)-5-(1-(piperidin-4-yl)-1H-pyrazol-4-yl)pyrimidine-2,4-diamine (Compound 144);

N2-(3-chloro-5-fluorophenyl)-5-(1-methyl-1H-pyrazol-4-yl)-N4-(1,2,3,4-tetrahydroisoquinolin-7-yl)pyrimidine-2,4-diamine (Compound 145);

N2-(3-methoxy-5-(trifluoromethyl)phenyl)-5-(1-methyl-1H-pyrazol-4-yl)-N4-(1,2,3,4-tetrahydroisoquinolin-7-yl)pyrimidine-2,4-diamine (Compound 146);

2-(4-(2-(3-chloro-5-fluorophenylamino)-4-(1,2,3,4-tetrahydroisoquinolin-7-ylamino)pyrimidin-5-yl)-1H-pyrazol-1-yl)ethan-1-ol (Compound 147);

2-(4-(2-(3-methoxy-5-(trifluoromethyl)phenylamino)-4-(1,2,3,4-tetrahydroisoquinolin-7-ylamino)pyrimidin-5-yl)-1H-pyrazol-1-yl)ethan-1-ol (Compound 148);

N2-(3-chlorophenyl)-5-(1-methyl-1H-pyrazol-4-yl)-N4-(1,2,3,4-tetrahydroisoquinolin-7-yl)pyrimidine-2,4-diamine (Compound 149);

N2-(3-fluorophenyl)-5-(1-methyl-1H-pyrazol-4-yl)-N4-(1,2,3,4-tetrahydroisoquinolin-7-yl)pyrimidine-2,4-diamine (Compound 150);

5-(1-methyl-1H-pyrazol-4-yl)-N4-(1,2,3,4-tetrahydroisoquinolin-7-yl)-N2-(3-(trifluoromethyl)phenyl)pyrimidine-2,4-diamine (Compound 151);

N2-(3-methoxyphenyl)-5-(1-methyl-1H-pyrazol-4-yl)-N4-(1,2,3,4-tetrahydroisoquinolin-7-yl)pyrimidine-2,4-diamine (Compound 152);

5-(1-methyl-1H-pyrazol-4-yl)-N2-phenyl-N4-(1,2,3,4-tetrahydroisoquinolin-7-yl)pyrimidine-2,4-diamine (Compound 153);

N2-(2-isopropylphenyl)-5-(1-methyl-1H-pyrazol-4-yl)-N4-(1,2,3,4-tetrahydroisoquinolin-7-yl)pyrimidine-2,4-diamine (Compound 154);

5-(1-methyl-1H-pyrazol-4-yl)-N4-(1,2,3,4-tetrahydroisoquinolin-7-yl)-N2-(3-(trifluoromethyl)benzyl)pyrimidine-2,4-diamine (Compound 155);

5-(1-methyl-1H-pyrazol-4-yl)-N4-(1,2,3,4-tetrahydroisoquinolin-7-yl)-N2-(o-tolyl)pyrimidine-2,4-diamine (Compound 156);

N2-(2,6-difluorophenyl)-5-(1-methyl-1H-pyrazol-4-yl)-N4-(1,2,3,4-tetrahydroisoquinolin-7-yl)pyrimidine-2,4-diamine (Compound 157);

5-(1-methyl-1H-pyrazol-4-yl)-N4-(1,2,3,4-tetrahydroisoquinolin-7-yl)-N2-(m-tolyl)pyrimidine-2,4-diamine (Compound 158);

N2-(5-fluoro-2-methylphenyl)-5-(1-methyl-1H-pyrazol-4-yl)-N4-(1,2,3,4-tetrahydroisoquinolin-7-yl)pyrimidine-2,4-diamine (Compound 159);

N2-(3,5-dichlorophenyl)-5-(1-isopropyl-1H-pyrazol-4-yl)-N4-(1,2,3,4-tetrahydroisoquinolin-7-yl)pyrimidine-2,4-diamine (Compound 160);

N2-(3,5-bis(trifluoromethyl)phenyl)-5-(1-isopropyl-1H-pyrazol-4-yl)-N4-(1,2,3,4-tetrahydroisoquinolin-7-yl)pyrimidine-2,4-diamine (Compound 161);

N2-(3,5-difluorophenyl)-5-(1-isopropyl-1H-pyrazol-4-yl)-N4-(1,2,3,4-tetrahydroisoquinolin-7-yl)pyrimidine-2,4-diamine (Compound 162);

N2-(3-chloro-5-fluorophenyl)-5-(1-isopropyl-1H-pyrazol-4-yl)-N4-(1,2,3,4-tetrahydroisoquinolin-7-yl)pyrimidine-2,4-diamine (Compound 163);

5-(1-isopropyl-1H-pyrazol-4-yl)-N2-(3-methoxy-5-(trifluoromethyl)phenyl)-N4-(1,2,3,4-tetrahydroisoquinolin-7-yl)pyrimidine-2,4-diamine (Compound 164);

N2-(3,5-dimethoxyphenyl)-5-(1-isopropyl-1H-pyrazol-4-yl)-N4-(1,2,3,4-tetrahydroisoquinolin-7-yl)pyrimidine-2,4-diamine (Compound 165);

N2-(3,5-dimethylphenyl)-5-(1-isopropyl-1H-pyrazol-4-yl)-N4-(1,2,3,4-tetrahydroisoquinolin-7-yl)pyrimidine-2,4-diamine (Compound 166);

N2-(3-chlorophenyl)-5-(1-isopropyl-1H-pyrazol-4-yl)-N4-(1,2,3,4-tetrahydroisoquinolin-7-yl)pyrimidine-2,4-diamine (Compound 167);

5-(1-isopropyl-1H-pyrazol-4-yl)-N2-(3-methoxyphenyl)-N4-(1,2,3,4-tetrahydroisoquinolin-7-yl)pyrimidine-2,4-diamine (Compound 168);

5-(1-isopropyl-1H-pyrazol-4-yl)-N4-(1,2,3,4-tetrahydroisoquinolin-7-yl)-N2-(m-tolyl)pyrimidine-2,4-diamine (Compound 169);

5-(1-isopropyl-1H-pyrazol-4-yl)-N2-phenyl-N4-(1,2,3,4-tetrahydroisoquinolin-7-yl)pyrimidine-2,4-diamine (Compound 170);

N2-(3,5-dichlorophenyl)-5-(1-propyl-1H-pyrazol-4-yl)-N4-(1,2,3,4-tetrahydroisoquinolin-7-yl)pyrimidine-2,4-diamine (Compound 171);

N2-(3,5-bis(trifluoromethyl)phenyl)-5-(1-propyl-1H-pyrazol-4-yl)-N4-(1,2,3,4-tetrahydroisoquinolin-7-yl)pyrimidine-2,4-diamine (Compound 172);

N2-(3,5-difluorophenyl)-5-(1-propyl-1H-pyrazol-4-yl)-N4-(1,2,3,4-tetrahydroisoquinolin-7-yl)pyrimidine-2,4-diamine (Compound 173);

N2-(3-methoxy-5-(trifluoromethyl)phenyl)-5-(1-propyl-1H-pyrazol-4-yl)-N4-(1,2,3,4-tetrahydroisoquinolin-7-yl)pyrimidine-2,4-diamine (Compound 174);

N2-(3-chloro-5-fluorophenyl)-5-(1-propyl-1H-pyrazol-4-yl)-N4-(1,2,3,4-tetrahydroisoquinolin-7-yl)pyrimidine-2,4-diamine (Compound 175);

N2-(3,5-dimethoxyphenyl)-5-(1-propyl-1H-pyrazol-4-yl)-N4-(1,2,3,4-tetrahydroisoquinolin-7-yl)pyrimidine-2,4-diamine (Compound 176);

N2-(3,5-dimethylphenyl)-5-(1-propyl-1H-pyrazol-4-yl)-N4-(1,2,3,4-tetrahydroisoquinolin-7-yl)pyrimidine-2,4-diamine (Compound 177);

N2-(3-chlorophenyl)-5-(1-propyl-1H-pyrazol-4-yl)-N4-(1,2,3,4-tetrahydroisoquinolin-7-yl)pyrimidine-2,4-diamine (Compound 178);

N2-(3,5-dichlorophenyl)-5-(1-isobutyl-1H-pyrazol-4-yl)-N4-(1,2,3,4-tetrahydroisoquinolin-7-yl)pyrimidine-2,4-diamine (Compound 179);

N2-(3,5-bis(trifluoromethyl)phenyl)-5-(1-isobutyl-1H-pyrazol-4-yl)-N4-(1,2,3,4-tetrahydroisoquinolin-7-yl)pyrimidine-2,4-diamine (Compound 180);

N2-(3,5-difluorophenyl)-5-(1-isobutyl-1H-pyrazol-4-yl)-N4-(1,2,3,4-tetrahydroisoquinolin-7-yl)pyrimidine-2,4-diamine (Compound 181);

N2-(3-chloro-5-fluorophenyl)-5-(1-isobutyl-1H-pyrazol-4-yl)-N4-(1,2,3,4-tetrahydroisoquinolin-7-yl)pyrimidine-2,4-diamine (Compound 182);

5-(1-isobutyl-1H-pyrazol-4-yl)-N2-(3-methoxy-5-(trifluoromethyl)phenyl)-N4-(1,2,3,4-tetrahydroisoquinolin-7-yl)pyrimidine-2,4-diamine (Compound 183);

N2-(3,5-dimethoxyphenyl)-5-(1-isobutyl-1H-pyrazol-4-yl)-N4-(1,2,3,4-tetrahydroisoquinolin-7-yl)pyrimidine-2,4-diamine (Compound 184);

N2-(3,5-dimethylphenyl)-5-(1-isobutyl-1H-pyrazol-4-yl)-N4-(1,2,3,4-tetrahydroisoquinolin-7-yl)pyrimidine-2,4-diamine (Compound 185);

N2-(3-chlorophenyl)-5-(1-isobutyl-1H-pyrazol-4-yl)-N4-(1,2,3,4-tetrahydroisoquinolin-7-yl)pyrimidine-2,4-diamine (Compound 186);

5-(1-isobutyl-1H-pyrazol-4-yl)-N2-(3-methoxyphenyl)-N4-(1,2,3,4-tetrahydroisoquinolin-7-yl)pyrimidine-2,4-diamine (Compound 187);

5-(1-isobutyl-1H-pyrazol-4-yl)-N4-(1,2,3,4-tetrahydroisoquinolin-7-yl)-N2-(m-tolyl)pyrimidine-2,4-diamine (Compound 188);

5-(1-isobutyl-1H-pyrazol-4-yl)-N2-phenyl-N4-(1,2,3,4-tetrahydroisoquinolin-7-yl)pyrimidine-2,4-diamine (Compound 189);

N2-(2,3-dichlorophenyl)-5-(1-isobutyl-1H-pyrazol-4-yl)-N4-(1,2,3,4-tetrahydroisoquinolin-7-yl)pyrimidine-2,4-diamine (Compound 190);

N2-(2,5-difluorophenyl)-5-(1-isobutyl-1H-pyrazol-4-yl)-N4-(1,2,3,4-tetrahydroisoquinolin-7-yl)pyrimidine-2,4-diamine (Compound 191);

5-(1-isobutyl-1H-pyrazol-4-yl)-N2-(2-isopropylphenyl)-N4-(1,2,3,4-tetrahydroisoquinolin-7-yl)pyrimidine-2,4-diamine (Compound 192);

2-(4-(2-(3,5-dimethoxyphenylamino)-4-(1,2,3,4-tetrahydroisoquinolin-7-ylamino)pyrimidin-5-yl)-1H-pyrazol-1-yl)ethan-1-ol (Compound 193);

2-(4-(2-(3,5-dimethylphenylamino)-4-(1,2,3,4-tetrahydroisoquinolin-7-ylamino)pyrimidin-5-yl)-1H-pyrazol-1-yl)ethan-1-ol (Compound 194);

2-(4-(2-(2,3-dimethylphenylamino)-4-(1,2,3,4-tetrahydroisoquinolin-7-ylamino)pyrimidin-5-yl)-1H-pyrazol-1-yl)ethan-1-ol (Compound 195);

2-(4-(2-(3-chlorophenylamino)-4-(1,2,3,4-tetrahydroisoquinolin-7-ylamino)pyrimidin-5-yl)-1H-pyrazol-1-yl)ethan-1-ol (Compound 196);

2-(4-(2-(2,3-dichlorophenylamino)-4-(1,2,3,4-tetrahydroisoquinolin-7-ylamino)pyrimidin-5-yl)-1H-pyrazol-1-yl)ethan-1-ol (Compound 197);

N2-(3,5-difluorophenyl)-5-(1-methyl-1H-pyrazol-4-yl)-N4-(4-(piperidin-4-yl)phenyl)pyrimidine-2,4-diamine (Compound 198);

N2-(3,5-dichlorophenyl)-5-(1-methyl-1H-pyrazol-4-yl)-N4-(4-(piperidin-4-yl)phenyl)pyrimidine-2,4-diamine (Compound 199);

N2-(3-chloro-5-fluorophenyl)-5-(1-methyl-1H-pyrazol-4-yl)-N4-(4-(piperidin-4-yl)phenyl)pyrimidine-2,4-diamine (Compound 200);

2-(4-(2-(3,5-dichlorophenylamino)-4-(4-(piperidin-4-yl)phenylamino)pyrimidin-5-yl)-1H-pyrazol-1-yl)ethan-1-ol (Compound 201);

N2-(3,5-bis(trifluoromethyl)phenyl)-5-(1-methyl-1H-pyrazol-4-yl)-N4-(4-(piperidin-4-yl)phenyl)pyrimidine-2,4-diamine (Compound 202);

N2-(3-methoxy-5-(trifluoromethyl)phenyl)-5-(1-methyl-1H-pyrazol-4-yl)-N4-(4-(piperidin-4-yl)phenyl)pyrimidine-2,4-diamine (Compound 203);

2-(4-(2-(3-chlorophenylamino)-4-(4-(piperidin-4-yl)phenylamino)pyrimidin-5-yl)-1H-pyrazol-1-yl)ethan-1-ol (Compound 204); and 2-(4-(2-(3,5-difluorophenylamino)-4-(4-(piperidin-4-yl)phenylamino)pyrimidin-5-yl)-1H-pyrazol-1-yl)ethan-1-ol (Compound 205).

Furthermore, the present invention is directed to a pyrimidine derivative compound represented by Chemical Formula 2 below, an optical isomer thereof, or a pharmaceutically acceptable salt thereof.

[Chemical Formula 2]

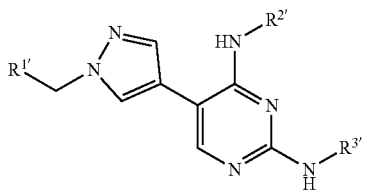

In Chemical Formula 2:

$R^{1'}$ is hydroxy, or substituted or unsubstituted piperidinyl,
wherein the substituted piperidinyl is substituted with at least one substituent selected from the group consisting of halogen, $C_1$-$C_{10}$ haloalkyl, hydroxy, cyano, amino, acetamino, trihalogen acetamino, trihalogen acetyl, nitro, oxo (=O), $C_1$-$C_{10}$ alkyl, $C_1$-$C_{10}$ alkoxy, $C_4$-$C_{10}$ cycloalkyl, $C_4$-$C_{10}$ heterocycloalkyl, $C_4$-$C_{10}$ aryl, or $C_4$-$C_{10}$ heteroaryl;

$R^{2'}$ is substituted or unsubstituted $C_4$-$C_{10}$ cycloalkyl, substituted or unsubstituted $C_4$-$C_8$ heterocycloalkyl, substituted or unsubstituted $C_4$-$C_{10}$ aryl, or substituted or unsubstituted $C_4$-$C_{10}$ heteroaryl,
wherein the substituted cycloalkyl, substituted heterocycloalkyl, substituted aryl, or substituted heteroaryl is substituted with at least one substituent selected from the group consisting of halogen, $C_1$-$C_{10}$ haloalkyl, oxo (=O), hydroxy, cyano, nitro, amino, acetamino, trihalogen acetamino, trihalogen acetyl, $C_1$-$C_{10}$ alkyl, $C_1$-$C_{10}$ alkoxy, $C_4$-$C_{10}$ cycloalkyl, $C_4$-$C_8$ heterocycloalkyl, $C_4$-$C_{10}$ aryl, or $C_4$-$C_{10}$ heteroaryl; and $R^{3'}$ is substituted or unsubstituted $C_4$-$C_{10}$ cycloalkyl, substituted or unsubstituted $C_4$-$C_8$ heterocycloalkyl, substituted or unsubstituted $C_4$-$C_{10}$ aryl, substituted or unsubstituted $C_4$-$C_{10}$ heteroaryl, or substituted or unsubstituted fused ring in which $C_4$-$C_{10}$ aryl is fused with $C_4$-$C_8$ heterocycloalkyl,
wherein the substituted cycloalkyl, substituted heterocycloalkyl, substituted aryl, substituted heteroaryl, or substituted fused ring is substituted with at least one substituent selected from the group consisting of halogen, $C_1$-$C_{10}$ haloalkyl, oxo (=O), hydroxy, cyano, nitro, amino, acetamino, trihalogen acetamino, trihalogen acetyl, $C_1$-$C_{10}$ alkyl, $C_1$-$C_{10}$ alkoxy, $C_4$-$C_{10}$ cycloalkyl, $C_4$-$C_8$ heterocycloalkyl, $C_4$-$C_{10}$ aryl, or $C_4$-$C_{10}$ heteroaryl.

Preferably, in Chemical Formula 2:

$R^{1'}$ is hydroxy, or substituted or unsubstituted piperidin-4-yl,
wherein the substituted piperidin-4-yl is substituted with at least one substituent selected from the group consisting of halogen, $C_1$-$C_{10}$ haloalkyl, oxo (=O), hydroxy, cyano, nitro, amino, acetamino, trihalogen acetamino, trihalogen acetyl, $C_1$-$C_{10}$ alkyl, or $C_1$-$C_{10}$ alkoxy;

$R^{2'}$ is substituted or unsubstituted $C_4$-$C_{10}$ cycloalkyl, or substituted or unsubstituted $C_4$-$C_8$ heterocycloalkyl,
wherein the substituted cycloalkyl or substituted heterocycloalkyl is substituted with at least one substituent selected from the group consisting of halogen, $C_1$-$C_{10}$ haloalkyl, oxo (=O), hydroxy, cyano, nitro, amino, acetamino, trihalogen acetamino, trihalogen acetyl, $C_1$-$C_{10}$ alkyl, or $C_1$-$C_{10}$ alkoxy; and $R^{3'}$ is substituted or unsubstituted $C_4$-$C_{10}$ aryl, or substituted or unsubstituted fused ring in which $C_4$-$C_{10}$ aryl is fused with $C_4$-$C_8$ heterocycloalkyl,
wherein the substituted aryl or substituted fused ring is substituted with at least one substituent selected from the group consisting of halogen, C1-C10 haloalkyl, hydroxy, cyano, nitro, amino, acetamino, trihalogen acetamino, trihalogen acetyl, C1-C10 alkyl, or C1-C10 alkoxy.

More specifically, examples of the compound of Chemical Formula 2 include at least one selected from the group consisting of:

1-(4-(2-(3,5-dichlorophenylamino)-5-(1-(2-hydroxyethyl)-1H-pyrazol-4-yl)pyrimidin-4-ylamino)piperidin-1-yl)-2,2,2-trifluoroethanone (Compound 71);

N2-(3,5-dichlorophenyl)-N4-(piperidin-4-yl)-5-(1-(piperidin-4-yl)-1H-pyrazol-4-yl)pyrimidine-2,4-diamine (Compound 73);

2-(4-(2-(3,5-dichlorophenylamino)-4-(piperidin-4-ylamino) pyrimidin-5-yl)-1H-pyrazol-1-yl)ethanol (Compound 75);

1-(4-(5-(1-(2-hydroxyethyl)-1H-pyrazol-4-yl)-2-(2-(2,2,2-trifluoroacetyl)-1,2,3,4-tetrahydroisoquinolin-7-ylamino) pyrimidin-4-ylamino)piperidin-1-yl)-2,2,2-trifluoroethanone (Compound 76);

1-(4-(2-(3-methyl-4-chlorophenylamino)-5-(1-(2-hydroxyethyl)-1H-pyrazol-4-yl)pyrimidin-4-ylamino)piperidin-1-yl)-2,2,2-trifluoroethanone (Compound 77);

1-(4-(5-(1-(2-hydroxyethyl)-1H-pyrazol-4-yl)-2-(4-methoxyphenylamino)pyrimidin-4-ylamino)piperidin-1-yl)-2,2,2-trifluoroethanone (Compound 78);

2-(4-(4-(piperidin-4-ylamino)-2-(1,2,3,4-tetrahydroisoquinolin-7-ylamino)pyrimidin-5-yl)-1H-pyrazol-1-yl)ethanol (Compound 79);

2-(4-(2-(3-methyl-4-chlorophenylamino)-4-(piperidin-4-ylamino)pyrimidin-5-yl)-1H-pyrazol-1-yl)ethanol (Compound 80);

2-(4-(2-(4-methoxyphenylamino)-4-(piperidin-4-ylamino) pyrimidin-5-yl)-1H-pyrazol-1-yl)ethanol (Compound 81);

N-((1s,4s)-4-(2-(3,5-dichlorophenylamino)-5-(1-(2-hydroxyethyl)-1H-pyrazol-4-yl)pyrimidin-4-ylamino)cyclohexyl)-2,2,2-trifluoroacetamide (Compound 95);

N-((1s,4s)-4-(5-(1-(2-hydroxyethyl)-1H-pyrazol-4-yl)-2-(2-(2,2,2-trifluoroacetyl)-1,2,3,4-tetrahydroisoquinolin-7-ylamino)pyrimidin-4-ylamino)cyclohexyl)-2,2,2-trifluoroacetamide (Compound 96);

N-((1s,4s)-4-(2-(3-chlorophenylamino)-5-(1-(2-hydroxyethyl)-1H-pyrazol-4-yl)pyrimidin-4-ylamino)cyclohexyl)-2,2,2-trifluoroacetamide (Compound 100);

2-(4-(4-((1s,4s)-4-aminocyclohexylamino)-2-(3,5-dichlorophenylamino)pyrimidin-5-yl)-1H-pyrazol-1-yl)ethanol (Compound 103);

2-(4-(4-((1s,4s)-4-aminocyclohexylamino)-2-(1,2,3,4-tetrahydroisoquinolin-7-ylamino)pyrimidin-5-yl)-1H-pyrazol-1-yl)ethanol (Compound 104);

2-(4-(4-((1s,4s)-4-aminocyclohexylamino)-2-(3-chlorophenylamino)pyrimidin-5-yl)-1H-pyrazol-1-yl)ethanol (Compound 105);

N-((1s,4s)-4-((2-((4-chloro-3-methylphenyl)amino)-5-(1-(2-hydroxyethyl)-1H-pyrazol-4-yl)pyrimidin-4-yl) amino)cyclohexyl)-2,2,2-trifluoroacetamide (Compound 106);

2-(4-(4-((1s,4s)-4-aminocyclohexylamino)-2-(3-methyl-4-chlorophenylamino)pyrimidin-5-yl)-1H-pyrazol-1-yl) ethanol (Compound 107);

N-((1s,4s)-4-(2-(3,5-dichlorophenylamino)-5-(1-(1-(2,2,2-trifluoroacetyl)piperidin-4-yl)-1H-pyrazol-4-yl)pyrimidin-4-ylamino)cyclohexyl)-2,2,2-trifluoroacetamide (Compound 108);

N-((1r,4r)-4-(2-(3,5-dichlorophenylamino)-5-(1-(2-hydroxyethyl)-1H-pyrazol-4-yl)pyrimidin-4-ylamino)cyclohexyl)-2,2,2-trifluoroacetamide (Compound 110);

N4-((1s,4s)-4-aminocyclohexyl)-N2-(3,5-dichlorophenyl)-5-(1-(piperidin-4-yl)-1H-pyrazol-4-yl)pyrimidine-2,4-diamine (Compound 111);

2-(4-(4-((1r,4r)-4-aminocyclohexylamino)-2-(3,5-dichlorophenylamino)pyrimidin-5-yl)-1H-pyrazol-1-yl)ethanol (Compound 113);

N-((1r,4r)-4-(2-(3,5-difluorophenylamino)-5-(1-(2-hydroxyethyl)-1H-pyrazol-4-yl)pyrimidin-4-ylamino)cyclohexyl)-2,2,2-trifluoroacetamide (Compound 115);

2-(4-(4-((1r,4r)-4-aminocyclohexylamino)-2-(3,5-difluorophenylamino)pyrimidin-5-yl)-1H-pyrazol-1-yl)ethan-1-ol (Compound 117);

N-((1r,4r)-4-(2-(3,5-bis(trifluoromethyl)phenylamino)-5-(1-(2-hydroxyethyl)-1H-pyrazol-4-yl)pyrimidin-4-ylamino) cyclohexyl)-2,2,2-trifluoroacetamide (Compound 119);

2-(4-(4-((1r,4r)-4-aminocyclohexylamino)-2-(3,5-bis(trifluoromethyl)phenylamino)pyrimidin-5-yl)-1H-pyrazol-1-yl)ethan-1-ol (Compound 121);

1-(4-(2-(3,5-dichlorophenylamino)-5-(1-(piperidin-4-yl)-1H-pyrazol-4-yl)pyrimidin-4-ylamino)cyclohexyl)-2,2,2-trifluoroacetamide (Compound 122);

2-(4-(2-(3,5-dichlorophenylamino)-4-(4-(piperidin-4-yl) phenylamino)pyrimidin-5-yl)-1H-pyrazol-1-yl)ethan-1-ol (Compound 201);

2-(4-(2-(3-chlorophenylamino)-4-(4-(piperidin-4-yl)phenylamino)pyrimidin-5-yl)-1H-pyrazol-1-yl)ethan-1-ol (Compound 204); and 2-(4-(2-(3,5-difluorophenylamino)-4-(4-(piperidin-4-yl) phenylamino)pyrimidin-5-yl)-1H-pyrazol-1-yl)ethan-1-ol (Compound 205).

Furthermore, the present invention is directed to to a pyrimidine derivative compound represented by Chemical Formula below, an optical isomer thereof, or a pharmaceutically acceptable salt thereof.

[Chemical Formula 3]

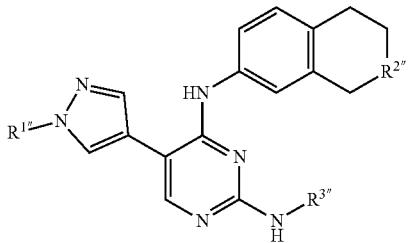

In Chemical Formula 3:
R$^{1''}$ is hydrogen, substituted or unsubstituted C$_1$-C$_{10}$ alkyl, or substituted or unsubstituted piperidinyl,
wherein the substituted alkyl or substituted piperidinyl is substituted with at least one substituent selected from the group consisting of halogen, C$_1$-C$_{10}$ haloalkyl, oxo (=O), hydroxy, cyano, nitro, amino, acetamino, trihalogen acetamino, trihalogen acetyl, C$_1$-C$_{10}$ alkyl, C$_1$-C$_{10}$ alkoxy, C$_4$-C$_{10}$ cycloalkyl, C$_4$-C$_{10}$ heterocycloalkyl, C$_4$-C$_{10}$ aryl, or C$_4$-C$_{10}$ heteroaryl;
R$^{2''}$ is amino, acetamino, or trihalogen acetamino; and
R$^{3''}$ is substituted or unsubstituted C$_4$-C$_{10}$ cycloalkyl, substituted or unsubstituted C$_4$-C$_8$ heterocycloalkyl, substituted or unsubstituted C$_4$-C$_{10}$ aryl, substituted or unsubstituted C$_4$-C$_{10}$ heteroaryl, or substituted or unsubstituted fused ring in which C$_4$-C$_{10}$ aryl is fused with C$_4$-C$_8$ heterocycloalkyl,
wherein the substituted cycloalkyl, substituted heterocycloalkyl, substituted aryl, substituted heteroaryl, or substituted fused ring is substituted with at least one substituent selected from the group consisting of halogen, C$_1$-C$_{10}$ haloalkyl, oxo (=O), hydroxy, cyano, nitro, amino, acetamino, trihalogen acetamino, trihalogen acetyl, C$_1$-C$_{10}$ alkyl, C$_1$-C$_{10}$ alkoxy, C$_4$-C$_{10}$ cycloalkyl, C$_4$-C$_8$ heterocycloalkyl, C$_4$-C$_{10}$ aryl, or C$_4$-C$_{10}$ heteroaryl.

Preferably, in Chemical Formula 3:
R$^{1''}$ is hydrogen, substituted or unsubstituted C$_1$-C$_{10}$ alkyl, or substituted or unsubstituted piperidin-4-yl,
wherein the substituted alkyl or substituted piperidin-4-yl is substituted with at least one substituent selected from the group consisting of halogen, $C_1$-$C_{10}$ haloalkyl, oxo (=O), hydroxy, cyano, nitro, amino, acetamino, trihalogen acetamino, trihalogen acetyl, $C_1$-$C_{10}$ alkyl, or $C_1$-$C_{10}$ alkoxy;

$R^{2''}$ is amino, acetamino, or trihalogen acetamino; and
$R^{3''}$ is substituted or unsubstituted $C_4$-$C_{10}$ aryl,
wherein the substituted aryl is substituted with at least one substituent selected from the group consisting of halogen, C1-C10 haloalkyl, hydroxy, cyano, nitro, amino, acetamino, trihalogen acetamino, trihalogen acetyl, C1-C10 alkyl, or C1-C10 alkoxy.

More specifically, examples of the compound of Chemical Formula 3 includes at least one selected from the group consisting of:

1-(7-(2-(3,5-dichlorophenylamino)-5-(1-methyl-1H-pyrazol-4-yl)pyrimidin-4-ylamino)-3,4-dihydroisoquinolin-2 (1H)-yl)-2,2,2-trifluoroethanone (Compound 82);

1-(7-(2-(3-methyl-4-chlorophenylamino)-5-(1-methyl-1H-pyrazol-4-yl)pyrimidin-4-ylamino)-3,4-dihydroisoquinolin-2(1H)-yl)-2,2,2-trifluoroethanone (Compound 83);

N2-(3,5-dichlorophenyl)-5-(1-methyl-1H-pyrazol-4-yl)-N4-(1,2,3,4-tetrahydroisoquinolin-7-yl)pyrimidine-2,4-diamine (Compound 84);

N2-(3-methyl-4-chlorophenyl)-5-(1-methyl-1H-pyrazol-4-yl)-N4-(1,2,3,4-tetrahydroisoquinolin-7-yl)pyrimidine-2,4-diamine (Compound 85);

1-(7-(2-(3,5-dichlorophenylamino)-5-(1-(2-hydroxyethyl)-1H-pyrazol-4-yl)pyrimidin-4-ylamino)-3,4-dihydroisoquinolin-2(1H)-yl)-2,2,2-trifluoroethanone (Compound 87);

2-(4-(2-(3,5-dichlorophenylamino)-4-(1,2,3,4-tetrahydroisoquinolin-7-ylamino)pyrimidin-5-yl)-1H-pyrazol-1-yl)ethanol (Compound 89);

1-(7-(2-(3-chlorophenylamino)-5-(1-(2-hydroxyethyl)-1H-pyrazol-4-yl)pyrimidin-4-ylamino)-3,4-dihydroisoquinolin-2(1H)-yl)-2,2,2-trifluoroethanone (Compound 93);

1-(7-(2-(3-fluorophenylamino)-5-(1-(2-hydroxyethyl)-1H-pyrazol-4-yl)pyrimidin-4-ylamino)-3,4-dihydroisoquinolin-2(1H)-yl)-2,2,2-trifluoroethanone (Compound 94);

2-(4-(2-(3-chlorophenylamino)-4-(1,2,3,4-tetrahydroisoquinolin-7-ylamino)pyrimidin-5-yl)-1H-pyrazol-1-yl)ethanol (Compound 101);

2-(4-(2-(3-fluorophenylamino)-4-(1,2,3,4-tetrahydroisoquinolin-7-ylamino)pyrimidin-5-yl)-1H-pyrazol-1-yl)ethanol (Compound 102);

1-(7-(2-(3,5-difluorophenylamino)-5-(1-(2-hydroxyethyl)-1H-pyrazol-4-yl)pyrimidin-4-ylamino)-3,4-dihydroisoquinolin-2(1H)-yl)-2,2,2-trifluoroethanone (Compound 123);

1-(7-(2-(3,5-bis(trifluoromethyl)phenylamino)-5-(1-(2-hydroxyethyl)-1H-pyrazol-4-yl)pyrimidin-4-ylamino)-3,4-dihydroisoquinolin-2(1H)-yl)-2,2,2-trifluoroethanone (Compound 124);

1-(7-(2-(2,3-dichlorophenylamino)-5-(1-(2-hydroxyethyl)-1H-pyrazol-4-yl)pyrimidin-4-ylamino)-3,4-dihydroisoquinolin-2(1H)-yl)-2,2,2-trifluoroethanone (Compound 125);

1-(7-(2-(2-methyl-3-chlorophenylamino)-5-(1-(2-hydroxyethyl)-1H-pyrazol-4-yl)pyrimidin-4-ylamino)-3,4-dihydroisoquinolin-2(1H)-yl)-2,2,2-trifluoroethanone (Compound 126);

2-(4-(2-(3,5-difluorophenylamino)-4-(1,2,3,4-tetrahydroisoquinolin-7-ylamino)pyrimidin-5-yl)-1H-pyrazol-1-yl)-ethan-1-ol (Compound 127);

2-(4-(2-(3,5-bis(trifluoromethyl)phenylamino)-4-((1,2,3,4-tetrahydroisoquinolin-7-ylamino)pyrimidin-5-yl)-1H-pyrazol-1-yl)-ethan-1-ol (Compound 128);

2-(4-(2-(2,3-dichlorophenylamino)-4-(1,2,3,4-tetrahydroisoquinolin-7-ylamino)pyrimidin-5-yl)-1H-pyrazol-1-yl)-ethan-1-ol (Compound 129);

2-(4-(2-(2-methyl-3-chlorophenylamino)-4-(1,2,3,4-tetrahydroisoquinolin-7-ylamino)pyrimidin-5-yl)-1H-pyrazol-1-yl)-ethan-1-ol (Compound 130);

N2-(3,5-difluorophenyl)-5-(1-(piperidin-4-yl)-1H-pyrazol-4-yl)-N4-(1,2,3,4-tetrahydroisoquinolin-7-yl)pyrimidine-2,4-diamine (Compound 131);

N2-(3,5-dichlorophenyl)-5-(1-(piperidin-4-yl)-1H-pyrazol-4-yl)-N4-(1,2,3,4-tetrahydroisoquinolin-7-yl)pyrimidine-2,4-diamine (Compound 132);

N2-(3,5-bis(trifluoromethyl)phenyl)-N4-(1,2,3,4-tetrahydroisoquinolin-7-yl)-5-(1-(piperidin-4-yl)-1H-pyrazol-4-yl)pyrimidine-2,4-diamine (Compound 133);

N2-(2,3-dichlorophenyl)-5-(1-(piperidin-4-yl)-1H-pyrazol-4-yl)-N4-(1,2,3,4-tetrahydroisoquinolin-7-yl)pyrimidine-2,4-diamine (Compound 134);

N2-(3,5-dimethoxyphenyl)-5-(1-methyl-1H-pyrazol-4-yl)-N4-(1,2,3,4-tetrahydroisoquinolin-7-yl)pyrimidine-2,4-diamine (Compound 135);

N2-(3,5-bis(trifluoromethyl)phenyl)-5-(1-methyl-1H-pyrazol-4-yl)-N4-(1,2,3,4-tetrahydroisoquinolin-7-yl)pyrimidine-2,4-diamine (Compound 136);

N2-(3,5-difluorophenyl)-5-(1-methyl-1H-pyrazol-4-yl)-N4-(1,2,3,4-tetrahydroisoquinolin-7-yl)pyrimidine-2,4-diamine (Compound 137);

1-(7-(2-(3,5-dimethoxyphenylamino)-5-(1-methyl-1H-pyrazol-4-yl)pyrimidin-4-ylamino)-3,4-dihydroisoquinolin-2(1H)-yl)-2,2,2-trifluoroethan-1-one (Compound 138);

1-(7-(2-(3,5-bis(trifluoromethyl)phenylamino)-5-(1-methyl-1H-pyrazol-4-yl)pyrimidin-4-ylamino)-3,4-dihydroisoquinolin-2(1H)-yl)-2,2,2-trifluoroethan-1-one (Compound 139);

1-(7-(2-(3,5-difluorophenylamino)-5-(1-methyl-1H-pyrazol-4-yl)pyrimidin-4-ylamino)-3,4-dihydroisoquinolin-2 (1H)-yl)-2,2,2-trifluoroethan-1-one (Compound 140);

N2-(3,5-difluorophenyl)-N4-(2-(2,2,2-trifluoroacetyl)-1,2,3,4-tetrahydroisoquinolin-7-yl)-5-(1-(piperidin-4-yl)-1H-pyrazol-4-yl)pyrimidine-2,4-diamine (Compound 141);

N2-(3,5-dichlorophenyl)-N4-(2-(2,2,2-trifluoroacetyl)-1,2,3,4-tetrahydroisoquinolin-7-yl)-5-(1-(piperidin-4-yl)-1H-pyrazol-4-yl)pyrimidine-2,4-diamine (Compound 142);

N2-(3,5-bis(trifluoromethyl)phenyl)-N4-(2-(2,2,2-trifluoroacetyl)-1,2,3,4-tetrahydroisoquinolin-7-yl)-5-(1-(piperidin-4-yl)-1H-pyrazol-4-yl)pyrimidine-2,4-diamine (Compound 143);

N2-(2,3-dichlorophenyl)-N4-(2-(2,2,2-trifluoroacetyl)-1,2,3,4-tetrahydroisoquinolin-7-yl)-5-(1-(piperidin-4-yl)-1H-pyrazol-4-yl)pyrimidine-2,4-diamine (Compound 144);

N2-(3-chloro-5-fluorophenyl)-5-(1-methyl-1H-pyrazol-4-yl)-N4-(1,2,3,4-tetrahydroisoquinolin-7-yl)pyrimidine-2,4-diamine (Compound 145);

N2-(3-methoxy-5-(trifluoromethyl)phenyl)-5-(1-methyl-1H-pyrazol-4-yl)-N4-(1,2,3,4-tetrahydroisoquinolin-7-yl)pyrimidine-2,4-diamine (Compound 146);

2-(4-(2-(3-chloro-5-fluorophenylamino)-4-(1,2,3,4-tetrahydroisoquinolin-7-ylamino)pyrimidin-5-yl)-1H-pyrazol-1-yl)ethan-1-ol (Compound 147);

2-(4-(2-(3-methoxy-5-(trifluoromethyl)phenylamino)-4-(1,2,3,4-tetrahydroisoquinolin-7-ylamino)pyrimidin-5-yl)-1H-pyrazol-1-yl)ethan-1-ol (Compound 148);

N2-(3-chlorophenyl)-5-(1-methyl-1H-pyrazol-4-yl)-N4-(1,2,3,4-tetrahydroisoquinolin-7-yl)pyrimidine-2,4-diamine (Compound 149);

N2-(3-fluorophenyl)-5-(1-methyl-1H-pyrazol-4-yl)-N4-(1,2,3,4-tetrahydroisoquinolin-7-yl)pyrimidine-2,4-diamine (Compound 150);

5-(1-methyl-1H-pyrazol-4-yl)-N4-(1,2,3,4-tetrahydroisoquinolin-7-yl)-N2-(3-(trifluoromethyl)phenyl)pyrimidine-2,4-diamine (Compound 151);

N2-(3-methoxyphenyl)-5-(1-methyl-1H-pyrazol-4-yl)-N4-(1,2,3,4-tetrahydroisoquinolin-7-yl)pyrimidine-2,4-diamine (Compound 152);

5-(1-methyl-1H-pyrazol-4-yl)-N2-phenyl-N4-(1,2,3,4-tetrahydroisoquinolin-7-yl)pyrimidine-2,4-diamine (Compound 153);

N2-(2-isopropylphenyl)-5-(1-methyl-1H-pyrazol-4-yl)-N4-(1,2,3,4-tetrahydroisoquinolin-7-yl)pyrimidine-2,4-diamine (Compound 154);

5-(1-methyl-1H-pyrazol-4-yl)-N4-(1,2,3,4-tetrahydroisoquinolin-7-yl)-N2-(3-(trifluoromethyl)benzyl)pyrimidine-2,4-diamine (Compound 155);

5-(1-methyl-1H-pyrazol-4-yl)-N4-(1,2,3,4-tetrahydroisoquinolin-7-yl)-N2-(o-tolyl)pyrimidine-2,4-diamine (Compound 156);

N2-(2,6-difluorophenyl)-5-(1-methyl-1H-pyrazol-4-yl)-N4-(1,2,3,4-tetrahydroisoquinolin-7-yl)pyrimidine-2,4-diamine (Compound 157);

5-(1-methyl-1H-pyrazol-4-yl)-N4-(1,2,3,4-tetrahydroisoquinolin-7-yl)-N2-(m-tolyl)pyrimidine-2,4-diamine (Compound 158);

N2-(5-fluoro-2-methylphenyl)-5-(1-methyl-1H-pyrazol-4-yl)-N4-(1,2,3,4-tetrahydroisoquinolin-7-yl)pyrimidine-2,4-diamine (Compound 159);

N2-(3,5-dichlorophenyl)-5-(1-isopropyl-1H-pyrazol-4-yl)-N4-(1,2,3,4-tetrahydroisoquinolin-7-yl)pyrimidine-2,4-diamine (Compound 160);

N2-(3,5-bis(trifluoromethyl)phenyl)-5-(1-isopropyl-1H-pyrazol-4-yl)-N4-(1,2,3,4-tetrahydroisoquinolin-7-yl)pyrimidine-2,4-diamine (Compound 161);

N2-(3,5-difluorophenyl)-5-(1-isopropyl-1H-pyrazol-4-yl)-N4-(1,2,3,4-tetrahydroisoquinolin-7-yl)pyrimidine-2,4-diamine (Compound 162);

N2-(3-chloro-5-fluorophenyl)-5-(1-isopropyl-1H-pyrazol-4-yl)-N4-(1,2,3,4-tetrahydroisoquinolin-7-yl)pyrimidine-2,4-diamine (Compound 163);

5-(1-isopropyl-1H-pyrazol-4-yl)-N2-(3-methoxy-5-(trifluoromethyl)phenyl)-N4-(1,2,3,4-tetrahydroisoquinolin-7-yl)pyrimidine-2,4-diamine (Compound 164);

N2-(3,5-dimethoxyphenyl)-5-(1-isopropyl-1H-pyrazol-4-yl)-N4-(1,2,3,4-tetrahydroisoquinolin-7-yl)pyrimidine-2,4-diamine (Compound 165);

N2-(3,5-dimethylphenyl)-5-(1-isopropyl-1H-pyrazol-4-yl)-N4-(1,2,3,4-tetrahydroisoquinolin-7-yl)pyrimidine-2,4-diamine (Compound 166);

N2-(3-chlorophenyl)-5-(1-isopropyl-1H-pyrazol-4-yl)-N4-(1,2,3,4-tetrahydroisoquinolin-7-yl)pyrimidine-2,4-diamine (Compound 167);

5-(1-isopropyl-1H-pyrazol-4-yl)-N2-(3-methoxyphenyl)-N4-(1,2,3,4-tetrahydroisoquinolin-7-yl)pyrimidine-2,4-diamine (Compound 168);

5-(1-isopropyl-1H-pyrazol-4-yl)-N4-(1,2,3,4-tetrahydroisoquinolin-7-yl)-N2-(m-tolyl)pyrimidine-2,4-diamine (Compound 169);

5-(1-isopropyl-1H-pyrazol-4-yl)-N2-phenyl-N4-(1,2,3,4-tetrahydroisoquinolin-7-yl)pyrimidine-2,4-diamine (Compound 170);

N2-(3,5-dichlorophenyl)-5-(1-propyl-1H-pyrazol-4-yl)-N4-(1,2,3,4-tetrahydroisoquinolin-7-yl)pyrimidine-2,4-diamine (Compound 171);

N2-(3,5-bis(trifluoromethyl)phenyl)-5-(1-propyl-1H-pyrazol-4-yl)-N4-(1,2,3,4-tetrahydroisoquinolin-7-yl)pyrimidine-2,4-diamine (Compound 172);

N2-(3,5-difluorophenyl)-5-(1-propyl-1H-pyrazol-4-yl)-N4-(1,2,3,4-tetrahydroisoquinolin-7-yl)pyrimidine-2,4-diamine (Compound 173);

N2-(3-methoxy-5-(trifluoromethyl)phenyl)-5-(1-propyl-1H-pyrazol-4-yl)-N4-(1,2,3,4-tetrahydroisoquinolin-7-yl)pyrimidine-2,4-diamine (Compound 174);

N2-(3-chloro-5-fluorophenyl)-5-(1-propyl-1H-pyrazol-4-yl)-N4-(1,2,3,4-tetrahydroisoquinolin-7-yl)pyrimidine-2,4-diamine (Compound 175);

N2-(3,5-dimethoxyphenyl)-5-(1-propyl-1H-pyrazol-4-yl)-N4-(1,2,3,4-tetrahydroisoquinolin-7-yl)pyrimidine-2,4-diamine (Compound 176);

N2-(3,5-dimethylphenyl)-5-(1-propyl-1H-pyrazol-4-yl)-N4-(1,2,3,4-tetrahydroisoquinolin-7-yl)pyrimidine-2,4-diamine (Compound 177);

N2-(3-chlorophenyl)-5-(1-propyl-1H-pyrazol-4-yl)-N4-(1,2,3,4-tetrahydroisoquinolin-7-yl)pyrimidine-2,4-diamine (Compound 178);

N2-(3,5-dichlorophenyl)-5-(1-isobutyl-1H-pyrazol-4-yl)-N4-(1,2,3,4-tetrahydroisoquinolin-7-yl)pyrimidine-2,4-diamine (Compound 179);

N2-(3,5-bis(trifluoromethyl)phenyl)-5-(1-isobutyl-1H-pyrazol-4-yl)-N4-(1,2,3,4-tetrahydroisoquinolin-7-yl)pyrimidine-2,4-diamine (Compound 180);

N2-(3,5-difluorophenyl)-5-(1-isobutyl-1H-pyrazol-4-yl)-N4-(1,2,3,4-tetrahydroisoquinolin-7-yl)pyrimidine-2,4-diamine (Compound 181);

N2-(3-chloro-5-fluorophenyl)-5-(1-isobutyl-1H-pyrazol-4-yl)-N4-(1,2,3,4-tetrahydroisoquinolin-7-yl)pyrimidine-2,4-diamine (Compound 182);

5-(1-isobutyl-1H-pyrazol-4-yl)-N2-(3-methoxy-5-(trifluoromethyl)phenyl)-N4-(1,2,3,4-tetrahydroisoquinolin-7-yl)pyrimidine-2,4-diamine (Compound 183);

N2-(3,5-dimethoxyphenyl)-5-(1-isobutyl-1H-pyrazol-4-yl)-N4-(1,2,3,4-tetrahydroisoquinolin-7-yl)pyrimidine-2,4-diamine (Compound 184);

N2-(3,5-dimethylphenyl)-5-(1-isobutyl-1H-pyrazol-4-yl)-N4-(1,2,3,4-tetrahydroisoquinolin-7-yl)pyrimidine-2,4-diamine (Compound 185);

N2-(3-chlorophenyl)-5-(1-isobutyl-1H-pyrazol-4-yl)-N4-(1,2,3,4-tetrahydroisoquinolin-7-yl)pyrimidine-2,4-diamine (Compound 186);

5-(1-isobutyl-1H-pyrazol-4-yl)-N2-(3-methoxyphenyl)-N4-(1,2,3,4-tetrahydroisoquinolin-7-yl)pyrimidine-2,4-diamine (Compound 187);

5-(1-isobutyl-1H-pyrazol-4-yl)-N4-(1,2,3,4-tetrahydroisoquinolin-7-yl)-N2-(m-tolyl)pyrimidine-2,4-diamine (Compound 188);

5-(1-isobutyl-1H-pyrazol-4-yl)-N2-phenyl-N4-(1,2,3,4-tetrahydroisoquinolin-7-yl)pyrimidine-2,4-diamine (Compound 189);

N2-(2,3-dichlorophenyl)-5-(1-isobutyl-1H-pyrazol-4-yl)-N4-(1,2,3,4-tetrahydroisoquinolin-7-yl)pyrimidine-2,4-diamine (Compound 190);

N2-(2,5-difluorophenyl)-5-(1-isobutyl-1H-pyrazol-4-yl)-N4-(1,2,3,4-tetrahydroisoquinolin-7-yl)pyrimidine-2,4-diamine (Compound 191);

5-(1-isobutyl-1H-pyrazol-4-yl)-N2-(2-isopropylphenyl)-N4-(1,2,3,4-tetrahydroisoquinolin-7-yl)pyrimidine-2,4-diamine (Compound 192);

2-(4-(2-(3,5-dimethoxyphenylamino)-4-(1,2,3,4-tetrahydroisoquinolin-7-ylamino)pyrimidin-5-yl)-1H-pyrazol-1-yl)ethan-1-ol (Compound 193);

2-(4-(2-(3,5-dimethylphenylamino)-4-(1,2,3,4-tetrahydroisoquinolin-7-ylamino)pyrimidin-5-yl)-1H-pyrazol-1-yl)ethan-1-ol (Compound 194);

2-(4-(2-(2,3-dimethylphenylamino)-4-(1,2,3,4-tetrahydroisoquinolin-7-ylamino)pyrimidin-5-yl)-1H-pyrazol-1-yl)ethan-1-ol (Compound 195);

2-(4-(2-(3-chlorophenylamino)-4-(1,2,3,4-tetrahydroisoquinolin-7-ylamino)pyrimidin-5-yl)-1H-pyrazol-1-yl)ethan-1-ol (Compound 196); and 2-(4-(2-(2,3-dichlorophenylamino)-4-(1,2,3,4-tetrahydroisoquinolin-7-ylamino)pyrimidin-5-yl)-1H-pyrazol-1-yl)ethan-1-ol (Compound 197).

In addition, the compounds represented by Chemical Formulas 1 to 3 of the present invention are prepared by Reaction Scheme 1 below, which is a method disclosed in Korean Patent Application No. 10-2017-0056002.

Provided is a method for preparing the compounds represented by Chemical Formulas 1 to 3 above, the method comprising the steps of:

preparing a compound represented by Compound C by the reaction of a compound represented by Compound B and $NH_2R^2$ (Step 1);

preparing a compound represented by Compound D from the compound represented by Compound C prepared in Step 1 (Step 2); and preparing a compound represented by Compound A from the compound represented by Compound D prepared in Step 2 (Step 3).

[Reaction Scheme 1]

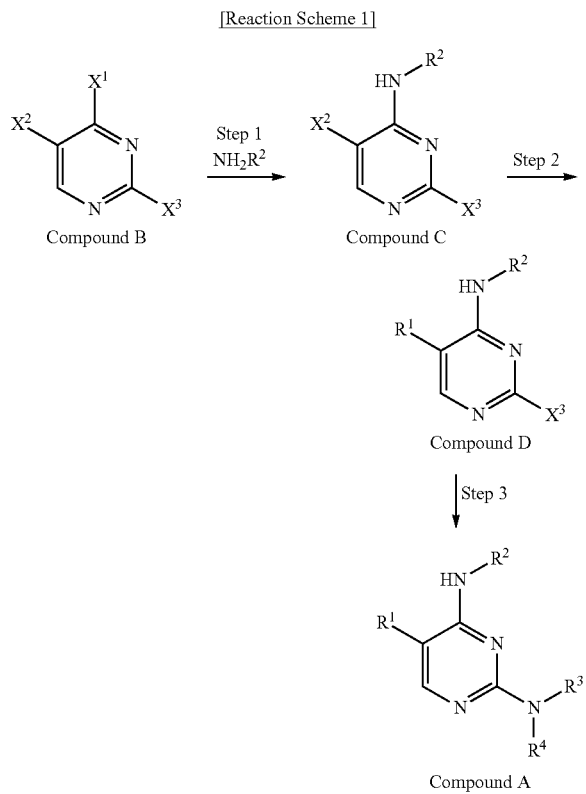

In Reaction Scheme 1:
$R^1$, $R^2$, $R^3$, and $R^4$ are as defined in Chemical Formulas 1 to 3 above; and
$X^1$, $X^2$, and $X^3$ each are a halogen atom.

Hereinafter, the method for preparing the compounds represented by Chemical Formula 1 to 3 (or Compound A) according to the present invention will be described in detail by steps.

In the preparation method for compounds represented by Chemical Formulas 1 to 3 (or Compound A) according to the present invention, Step 1 in Reaction Scheme 1 corresponds to a step of preparing the compound represented by Compound C by the reaction of the compound represented by Compound B and $NH_2R^2$.

Here, Step 1 may be understood as a step in which the substituent —NH—$R^2$ is introduced into the scaffold structure of the compounds of the present invention. Any method is included in the present invention without limitation as long as the compound represented by Compound C can be prepared by introducing the substituent —NH—$R^2$ at the $X^1$ position of the compound represented by Compound B. An exemplary method may be performed by the reaction of 1.4-dioxane with N,N-diisopropylethylamine (DIPEA) and the compound represented by Compound B.

Here, any solvent that can dissolve the compound represented by Compound B and DIPEA therein can be used as a solvent usable in the reaction without limitation. For example, ether solvents including tetrahydrofuran (THF), dioxane, ethylether, 1,2-dimethoxyethane, and the like, lower alcohols including methanol, ethanol, propanol, and butanol, dimethylformamide (DMF), dimethylsulfoxide (DMSO), dichloromethane (DCM), dichloroethane, water, acetonazenesulfonate, toluenesulfonate, chlorobenzenesulfonate, xylenesulfonate, phenylacetate, phenylpropionate, phenylbutyrate, citrate, lactate, β-hydroxybutyrate, glycolate, malate, tartrate, methanesulfonate, propanesulfonate, naphthalene-1-sulfonate, naphthalene-2-sulfonate, mandelate, and a mixture thereof may be used, and 1,4-dioxane may be used.

In addition, the reaction temperature is not particularly limited, but preferably the reaction may be performed at 0-100° C., and for example, the reaction may be performed at room temperature. Furthermore, the reaction time is not particularly limited, but for example, the reaction time may be set to 2-10 hours, and as another example, the reaction may be performed over 20 minutes to 8 hours when the temperature is raised.

In the preparation method for compounds represented by Chemical Formulas 1 to 3 (or Compound A) according to the present invention, Step 2 in Reaction Scheme 1 corresponds to a step of preparing a compound represented by Compound D from the compound represented by Compound C prepared in Step 1 (Step 2).

Here, Step 2 may be understood as a step in which the substituent $R^1$ is introduced into the compound represented by Compound C, and corresponds to a step of preparing a compound represented by Compound D by selectively introducing $R^1$ depending on a target compound.

As an example, but not limited to this, the introduction of $R^1$ may be carried out by the reaction of DMF with $Na_2CO_3$, a compound represented by Compound C, a compound represented by

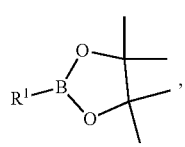

and Pd(dppf)$_2$Cl$_2$, but an equivalent method used as an ordinary technique in the art is included in the present invention without limitation as long as a step of preparing a compound represented by Compound D as shown in Step 2 can be carried out.

Here, any solvent that can be used in the reaction can be used without particular limitation, and for example, dimethylformamide (DMF), dimethylsulfoxide (DMSO), dichloromethane (DCM), dichloroethane, water, acetonazenesulfonate, toluenesulfonate, chlorobenzenesulfonate, xylenesulfonate, phenylacetate, phenylpropionate, phenylbutyrate, citrate, lactate, β-hydroxybutyrate, glycolate, malate, tartrate, methanesulfonate, propanesulfonate, naphthalene-1-sulfonate, naphthalene-2-sulfonate, mandelate, ether solvents including tetrahydrofuran (THF), dioxane, ethyl ether, 1,2-dimethoxyethane, and the like, lower alcohols including methanol, ethanol, propanol, and butanol, and a mixture thereof may be used, and preferably DMF may be used.

The reaction temperature is not particularly limited, but preferably the reaction may be performed at 50-150° C., and for example, the reaction may be performed at 90° C. Furthermore, the reaction time is not particularly limited, but for example, the reaction time may be set to 10-40 hours, and as another example, the reaction may be performed over 20-30 hours.

In the preparation methods for compounds represented by Chemical Formulas 1 to 3 (or Compound A) according to the present invention, Step 3 in Reaction Scheme 1 corresponds to a step of preparing the compounds represented by Chemical Formulas 1 to 3 (or Compound A) from the compound represented by Compound D prepared in Step 2.

Step 3 may be understood as a step in which the substituent —NR$^3$R$^4$ is introduced into the compound represented by Compound D, and corresponds to a step of selectively introducing the substituent —NR$^3$R$^4$ depending on a target compound to prepare the compounds represented by Chemical Formulas 1 to 3 (or Compound A) of the present invention.

As an example, but not limited to this, the introduction of the substituent —NR$^3$R$^4$ may be carried out by the reaction of an acid-treated ethoxy ethanol with the compound represented by Compound D and a compound represented by NHR$^3$R$^4$, and any method that can performed by the step of preparing the compounds represented by Chemical Formulas 1 to 3 (or Compound A) as shown in Step 3 is included in the present invention without limitation.

Any solvent that can be used in the reaction can be used without particular limitation, and for example, dimethylformamide (DMF), dimethylsulfoxide (DMSO), dichloromethane (DCM), dichloroethane, water, acetonazenesulfonate, toluenesulfonate, chlorobenzenesulfonate, xylenesulfonate, phenylacetate, phenylpropionate, phenylbutyrate, citrate, lactate, β-hydroxybutyrate, glycolate, malate, tartrate, methanesulfonate, propanesulfonate, naphthalene-1-sulfonate, naphthalene-2-sulfonate, mandelate, ether solvents including tetrahydrofuran (THF), dioxane, ethyl ether, 1,2-dimethoxyethane, and the like, lower alcohols including methanol, ethanol, propanol, and butanol, and a mixture thereof may be used, and preferably ethoxy ethanol may be used.

The reaction temperature is not particularly limited, but preferably the reaction may be performed at 50-150° C., and for example, the reaction may be performed at 100□. Furthermore, the reaction time is not particularly limited but, for example, the reaction time may be set to 10-40 hours, and as another example, the reaction may be performed over 10-20 hours.

Meanwhile, the preparation method for compounds represented by Chemical Formulas 1 to 3 (or Compound A) according to the present invention may be performed as shown in Reaction Scheme 1, and preferably, for example, Reaction Scheme 2 below.

[Reaction Scheme 2]

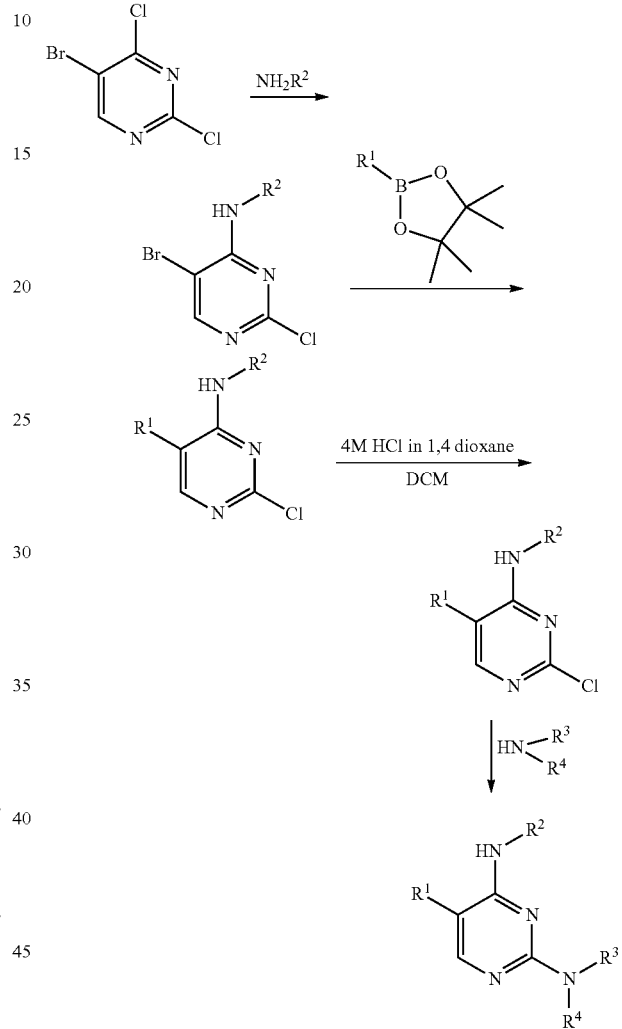

In Reaction Scheme 2,
R$^1$, R$^2$, R$^3$, and R$^4$ are as defined in Chemical Formulas 1 to 3 above.

Furthermore, more preferable examples of the preparation method for the compounds represented by Chemical Formulas 1 to 3 according to the present invention may include preparation methods for exemplary compounds of the present invention. Reaction Scheme 1, Reaction Scheme 2, and the preparation method for the compounds represented by Chemical Formulas 1 to 3 according to the present invention shown in the preparation methods for exemplary compounds of the present invention should be understood as examples of the method for preparing the compounds of the present invention, and any method that can prepare the compounds represented by Chemical Formulas 1 to 3 of the present invention is included in the present invention without limitation. In addition, the methods shown in the present specification and preparation methods that could be easily tried from modification and correction by a person skilled in the art should also be understood to be included in the scope of the present invention and would be obvious to a person skilled in the art.

The compounds represented by Chemical Formula 1 to 3 of the present invention may be used in the form of a pharmaceutically acceptable salt, wherein an acid addition salt formed by a pharmaceutically acceptable free acid is useful as a salt. The acid addition salt is obtained from: inorganic acids, such as hydrochloric acid, nitric acid, phosphoric acid, sulfuric acid, hydrobromic acid, hydriodic acid, nitrous acid, and phosphorous acid; non-toxic organic acids, such as aliphatic mono- and di-carboxylates, phenyl-substituted alkanoates, hydroxy alkanoates and alkandioates, aromatic acids, and aliphatic and aromatic sulfonic acids; and organic acids, such as acetic acid, benzoic acid, citric acid, lactic acid, maleic acid, gluconic acid, methanesulfonic acid, 4-toluenesulfonic acid, tartaric acid, and fumaric acid. Examples of the pharmaceutically non-toxic salts include sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, malate, tartrate, methanesulfonate, propanesulfonate, naphthalene-1-sulfonate, naphthalene-2-sulfonate, and mandelate.

The acid addition salt of the present invention may be prepared by a conventional method, and for example, the acid addition salt may be prepared by dissolving the derivative of Chemical Formulas 1 to 3 in an organic solvent, such as methanol, ethanol, acetone, methylene chloride, or acetonitrile, adding an organic acid or inorganic acid thereto to generate a precipitate, and then filtering and drying the precipitate, or may be prepared by distilling a solvent and an excess acid under reduced pressure, followed by drying and crystallization in an organic solvent.

In addition, a pharmaceutically acceptable metal salt may be prepared by using a base. For example, an alkali metal or alkaline earth metal salt is obtained by dissolving the compound in an excess alkali metal hydroxide or alkaline earth metal hydroxide solution, filtering out a non-solubilized compound salt, and then evaporating and drying the filtrate. Here, the preparation of a sodium, potassium, or calcium salt as the metal salt is pharmaceutically suitable. In addition, the corresponding salt is obtained by the reaction of an alkali metal or alkaline earth metal salt with a suitable silver salt (e.g., silver nitrate).

Furthermore, the present invention includes not only the compounds represented by Chemical Formulas 1 to 3 and the pharmaceutically acceptable salts thereof but also solvates, stereoisomers, hydrates, and the like, which can be prepared therefrom.

In accordance with another aspect of the present invention, there are provided pharmaceutical compositions for prevention or treatment of a tyrosine-protein kinase receptor (Tyro 3)-related disease, the pharmaceutical compositions containing, as an active ingredient, the pyrimidine derivative compounds represented by Chemical Formulas 1 to 3, the optical isomer thereof, or the pharmaceutically acceptable salt thereof.

The pharmaceutical composition exhibits an effect of preventing or treating a Tyro 3-related disease by targeting Tyro 3 to inhibit activity thereof. Examples of the Tyro 3-related disease may include all kinds of diseases that are caused from abnormal actions of Tyro 3 due to abnormal expression of Tyro 3, abnormal activity thereof, and the like. Any disease, of which a condition can be ameliorated or alleviated or which can be prevented or treated through the inhibition of Tyro 3 activity, such as cancer, should be understood as a Tyro 3-related disease on which the pharmaceutical composition of the present invention containing the compounds represented by Chemical Formulas 1 to 3, a stereoisomer thereof, or a pharmaceutically acceptable salt thereof as an active ingredient is used to show useful prevention, alleviation, and treatment effects, and such a disease falls into the scope of the present invention.

In addition, examples of the Tyro 3-related disease include cancer established to be involved in Tyro 3, described in the background of the present invention, for example, known Tyro 3-related diseases, such as breast cancer and ovarian cancer.

The cancer is also called malignant tumor, and is a mass that is abnormally grown by autonomous excessive growth of the body tissue, wherein the mass fast grows while infiltrating into surrounding tissues and causes diffusion or metastasis into each site of the body, thereby threatening life, and the cancer includes carcinoma and sarcoma. More specifically, the cancer may include pseudomyxoma, intrahepatic biliary tract cancer, hepatoblastoma, liver cancer, thyroid cancer, colon cancer, testicular cancer, myelodysplastic syndrome, glioblastoma, oral cancer, cleft lip cancer, mycosis fungoides, acute myeloid leukemia, acute lymphocytic leukemia, basal cell carcinoma, ovarian epithelial cancer, ovarian germ cell cancer, male breast cancer, brain cancer, pituitary adenoma, multiple myeloma, gallbladder cancer, biliary cancer, colorectal cancer, chronic myeloid leukemia, chronic lymphocytic leukemia, retinoblastoma, choroidal melanoma, diffuse giant B cell lymphoma, cancer of the ampulla of vater, bladder cancer, peritoneal cancer, parathyroid cancer, adrenal cancer, paranasal sinus and nasal cavity cancer, non-small cell lung cancer, non-Hodgkin's lymphoma, tongue cancer, astrocytoma, small cell lung cancer, childhood brain cancer, childhood lymphoma, childhood leukemia, small intestine cancer, meningioma, esophageal cancer, glioma, neuroblastoma, renal pelvis cancer, renal cell carcinoma, heart cancer, duodenal cancer, malignant soft tissue cancer, malignant bone cancer, malignant lymphoma, malignant mesothelioma, malignant melanoma, eye cancer, vulvar cancer, ureter cancer, urethral cancer, cancer of unknown primary site, gastric lymphoma, gastric cancer, gastric carcinoid, gastrointestinal stromal tumor, Wilms' cancer, breast cancer, sarcoma, penile cancer, pharyngeal cancer, gestational trophoblastic disease, cervical cancer, endometrial cancer, uterine sarcoma, prostate cancer, metastatic bone cancer, metastatic brain cancer, mediastinal cancer, rectal cancer, rectal carcinoid, vaginal cancer, spinal cord cancer, vestibular schwannoma, pancreatic cancer, salivary gland cancer, Kaposi's sarcoma, Paget's disease, tonsil cancer, squamous cell carcinoma, lung adenocarcinoma, lung cancer, squamous-cell carcinoma of the lung, skin cancer, anal cancer, rhabdomyosarcoma, laryngeal cancer, pleura cancer, and thymic cancer.

The pharmaceutical composition according to the present invention may be formulated into a suitable dosage form together with a pharmaceutically acceptable carrier that is normally used. The term "pharmaceutically acceptable" composition refers to a composition that is physiologically acceptable and does not cause allergic responses, such as gastrointestinal disorder or dizziness, or similar responses, when administered to humans. The composition may be formulated in the form of: an oral formulation, such as powders, granules, a tablet, a capsule, a suspension, an emulsion, syrup, or an aerosol; an externally applied preparation; a suppository; and a sterile injectable solution, according to usual methods, respectively.

Examples of the carrier, excipient, and diluent that may be contained in the composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil, but are not limited thereto. The composition may be formulated by using a diluent or an excipient, such as a filler, stabilizer, binder, disintegrant, or surfactant. A solid preparation for oral administration includes a tablet, a pill, a powder, granules, a capsule, and the like. These solid preparations may be prepared by mixing the compound of the present invention with at least one excipient, for example, starch, microcrystal cellulose, sucrose or lactose, low-substituted hydroxypropyl cellulose, hypromellose, or the like. Alternatively, lubricants, such as magnesium stearate and talc, may be used in addition to the simple excipients. A liquid preparation for oral administration corresponds to a suspension, a liquid for internal use, an emulsion, syrup, and the like, and may include simple diluents that are frequently used, such as water and liquid paraffin, and several types of excipients, such as a wetting agent, a sweetener, an aroma, and a preservative. A preparation for parenteral administration includes a sterile aqueous solution, a non-aqueous solvent, a suspension, an emulsion, a lyophilizer, and a suppository. The non-aqueous solvent and the suspension solvent may include propylene glycol, polyethylene glycol, a vegetable oil such as olive oil, an injectable ester such as ethylolate, and the like. As a substrate for the suppository, Witepsol, Macrogol, Tween 61, cacao butter, laurin butter, glycerol, gelatin, or the like may be used. For the formulation into a dosage form for parenteral administration, the compounds represented by Chemical Formulas 1 to 3 or a pharmaceutically acceptable salt thereof may be sterilized and/or mixed with an adjuvant, such as a preservative, a stabilizer, a hydrator, or an emulsion promoter, a salt for osmotic pressure regulation, and/or a buffer, and other therapeutically useful substances in water to be made into a solution or a suspension, which is then prepared into an ample or a vial unit dosage form.

The pharmaceutical compositions contain the compounds represented by Chemical Formulas 1 to 3 and an excipient. The compound may be added at an amount of preferably 0.001-50 wt %, more preferably 0.001-40 wt %, and most preferably 0.001-30 wt %, relative to a total weight of the entire composition.

The pharmaceutical compositions containing the compounds of Chemical Formulas 1 to 3 as an active ingredient may be administered to mammalian animals, such as mice, livestock, and humans via various routes. All manners of administration may be predicted, and for example, the administration may be carried out through oral, rectal, intravenous, intramuscular, subcutaneous, intrauterine, intracerebroventricular injection. The dose may vary depending on the age, sex, or body weight of a subject to be treated, the particular disease or pathological condition to be treated, the severity of the disease or pathological condition, the time of administration, the route of administration, the absorption, distribution, and excretion rate of a drug, the kind of another drug used, and the determination of a prescriber. The determination of the dose based on these factors is within the level of a person skilled in the art, and the usual dose is in a range of 0.01-2000 mg/kg/day. More preferably, the dose is 1-500 mg/kg/day.

The dose may be administered once a day or divided into multiple doses. The dose is not intended to limit the scope of the present invention in any way.

Advantageous Effects

The present invention relates to a pyrimidine derivative compound, an optical isomer thereof, or a pharmaceutically acceptable salt thereof, and to a composition containing the same as an active ingredient for prevention or treatment of cancer. The pyrimidine derivative compound, optical isomer thereof, or pharmaceutically acceptable salt thereof according to the present invention has excellent inhibitory effects on TAM receptors, especially, an excellent selective inhibitory effect on Tyro 3, and thus can be used as an excellent composition for prevention or treatment of cancer without side effects resulting from the inhibition of Axl and Mer.

MODE FOR CARRYING OUT THE INVENTION

Hereinafter, preferable embodiments of the present invention will be described in detail. However, the present invention is not limited to the embodiments described herein, and thus may be embodied in many different forms. Rather, these embodiments are provided so that this disclosure will be thorough and complete, and will fully convey the scope of the invention to those skilled in the art.

Example 1: Synthesis of Pyrimidine Derivative Compounds and Confirmation of Physicochemical Characteristics Thereof The pyrimidine derivative compounds of the present invention, Compounds 1 to 205, were manufactured with reference to the methods disclosed in Korean Patent Application No. 10-2017-0056002, and structural and physicochemical characteristics thereof are described as below.

Compound 1. 5-bromo-N4-cyclohexyl-N2-(p-tolyl)pyrimidine-2,4-diamine

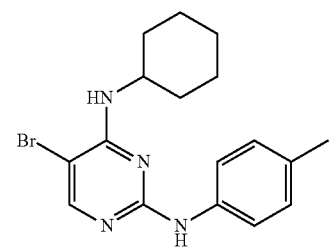 [SMILES: Cc1ccc(Nc2ncc(Br)c(NC3CCCCC3)n2)cc1]

1H NMR (300 MHz, CDCl$_3$) δ 7.98 (s, 1H), 7.50 (d, J=9.0 Hz, 2H), 7.50 (d, J=9.0 Hz, 2H), 6.85 (brS, 1H), 5.16 (m, 1H), 3.98 (m, 1H), 2.34 (s, 3H), 2.13 (m 2H), 1.82 (m, 2H), 1.71 (m, 1H), 1.48 (m, 2H), 1.28 (m, 3H);

LC/MS m/z calcd for $C_{17}H_{21}BrN_4$ (MH$^+$) 361.3, found 362.1.

Compound 2. N4-cyclohexyl-N2,5-di-(p-tolyl)pyrimidine-2,4-diamine

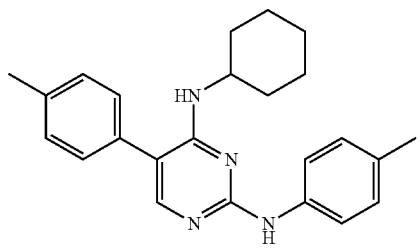

1H NMR (300 MHz, CDCl$_3$) δ 7.85 (m, 2H), 7.51 (m, 6H), 7.21 (d, J=8.1 Hz, 2H), 4.91 (s, 1H), 4.10 (s, 1H), 2.42 (s, 3H), 2.35 (s, 3H), 2.13 (m 2H), 1.82 (m, 2H), 1.71 (m, 1H), 1.48 (m, 2H), 1.28 (m, 3H);

LC/MS m/z calcd for $C_{24}H_{28}N_4$ (MH$^+$) 372.5, found 373.2.

Compound 3. 5-bromo-N4-cyclohexyl-N2-(3,5-dichlorophenyl)pyrimidine-2,4-diamine

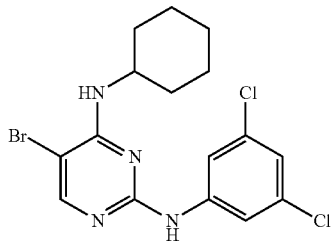 [SMILES: Clc1cc(Cl)cc(Nc2ncc(Br)c(NC3CCCCC3)n2)c1]

1H NMR (300 MHz, CDCl$_3$) δ 8.01 (s, 2H), 7.61 (s, 2H), 7.00 (s, 2H), 5.25 (s, 1H), 4.10 (m, 1H), 2.42 (s, 3H), 2.35 (s, 3H), 2.13 (m 2H), 1.82 (m, 2H), 1.71 (m, 1H), 1.48 (m, 2H), 1.28 (m, 3H).

Compound 4. 2-chloro-N4-cyclohexyl-5-(1-methyl-1H-pyrazol-4-yl)pyrimidine-4-amine

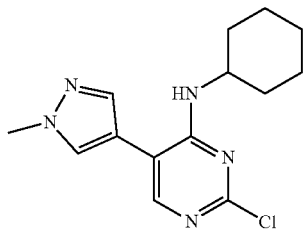 [SMILES: Cn1cc(-c2cnc(Cl)nc2NC2CCCCC2)cn1]

1H NMR (300 MHz, CDCl$_3$) δ 7.86 (s, 2H), 7.59 (s, 1H), 7.49 (s, 1H), 5.12 (s, 1H), 4.10 (s, 1H), 4.01 (s, 3H), 2.02 (s, 2H), 1.71 (m, 3H), 1.48 (m, 2H), 1.19 (m, 3H);

LC/MS m/z calcd for $C_{14}H_{18}ClN_5$ (MH$^+$) 291.7, found 292.2.

Compound 5. N4-cyclohexyl-N2-(3,5-dichlorophenyl)-5-(1-methyl-1H-pyrazol-4-yl)pyrimidine-2,4-diamine

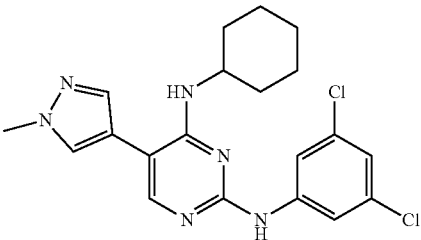 [SMILES: Cn1cc(-c2cnc(Nc3cc(Cl)cc(Cl)c3)nc2NC2CCCCC2)cn1]

1H NMR (300 MHz, CDCl$_3$) δ 7.76 (s, 1H), 7.68 (s, 2H), 7.57 (s, 1H), 7.45 (s, 1H), 7.01 (s, 1H), 5.12 (brs, 1H), 4.10 (s, 1H), 4.01 (s, 3H), 2.02 (m, 2H), 1.71 (m, 3H), 1.48 (m, 2H), 1.19 (m, 3H);

LC/MS m/z calcd for $C_{20}H_{22}Cl_2N_6$ (MH$^+$) 417.4, found 418.2.

Compound 6. N4-cyclohexyl-5-(1-methyl-1H-pyrazol-4-yl)-N2-phenylpyrimidine-2,4-diamine

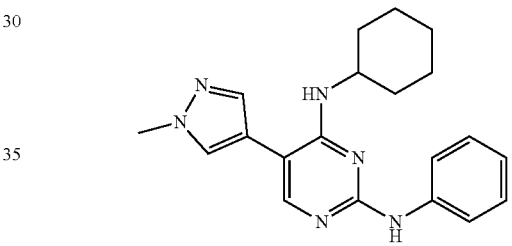

1H NMR (300 MHz, CDCl$_3$) δ 7.81 (s, 1H), 7.70 (d, J=9.0 Hz, 2H), 7.57 (s, 1H), 7.45 (s, 1H), 7.32 (m, 2H), 7.01 (m, 1H), 4.95 (d, J=6.0 Hz, 1H), 4.01 (m, 1H), 3.99 (s, 3H), 2.11 (m, 2H), 1.75 (m, 3H), 1.45 (m, 2H), 1.20 (m, 3H);

LC/MS m/z calcd for $C_{20}H_{24}N_6$ (MH$^+$) 348.20, found 349.1.

Compound 7. N2-(3-chlorophenyl)-N4-cyclohexyl-5-(1-methyl-1H-pyrazol-4-yl)pyrimidine-2,4-diamine

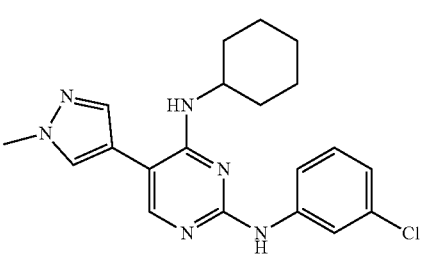 [SMILES: Cn1cc(-c2cnc(Nc3cccc(Cl)c3)nc2NC2CCCCC2)cn1]

1H NMR (300 MHz, CDCl$_3$) δ 8.21 (s, 1H), 7.72 (s, 1H), 7.57 (s, 1H), 7.35 (s, 1H), 7.24 (m, 3H), 6.98 (m, 1H), 4.95 (d, J=6.0 Hz, 1H), 4.01 (m, 1H), 3.99 (s, 3H), 2.11 (m, 2H), 1.75 (m, 3H), 1.45 (m, 2H), 1.20 (m, 3H);

LC/MS m/z calcd for $C_{20}H_{23}ClN_6$ (MH$^+$) 382.17, found 382.2.

Compound 8. N4-cyclohexyl-5-(1-methyl-1H-pyrazol-4-yl)-N2-(3-(trifluoromethyl)benzyl)pyrimidine-2,4-diamine

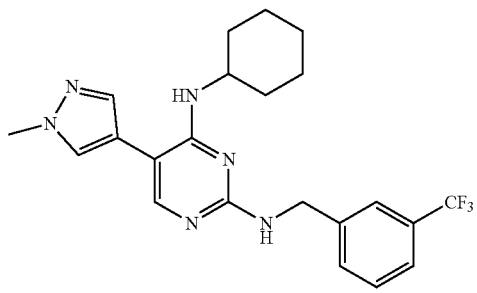 [SMILES: Cn1cc(-c2cnc(NCc3cccc(C(F)(F)F)c3)nc2NC2CCCCC2)cn1]

1H NMR (300 MHz, CDCl$_3$) δ 7.45 (m, 2H), 7.65-7.28 (m, 5H), 5.32 (s, 1H), 4.75 (d, J=9.0 Hz, 1H), 4.72 (d, J=9.0 Hz, 1H), 3.97 (s, 3H), 3.85 (m, 1H), 1.78 (m, 3H), 1.70 (m, 3H), 1.45-1.10 (m, 5H);
LC/MS m/z calcd for $C_{22}H_{25}F_3N_6$ (MH$^+$) 430.21, found 431.1.

Compound 9. N2-(3-chloro-4-methoxyphenyl)-N4-cyclohexyl-5-(1-methyl-1H-pyrazol-4-yl)pyrimidine-2,4-diamine

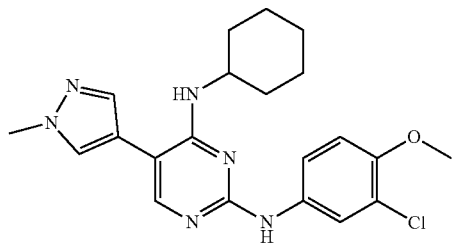

1H NMR (300 MHz, CDCl$_3$) δ 8.02 (s, 1H), 7.79 (s, 1H), 7.56 (s, 1H), 7.42 (m, 2H), 7.28 (m, 2H), 6.90 (m, 1H), 4.96 (d, J=9.0 Hz, 1H), 4.02 (m, 1H), 4.00 (s, 3H), 3.97 (s, 3H), 2.06 (m, 2H), 1.78 (m, 2H), 1.52 (m, 2H), 1.45-1.10 (m, 3H);
LC/MS m/z calcd for $C_{21}H_{25}ClN_6O$ (MH$^+$) 412.18, found 413.0.

Compound 10. N4-cyclohexyl-5-(1-methyl-1H-pyrazol-4-yl)-N2-(o-tolyl)pyrimidine-2,4-diamine

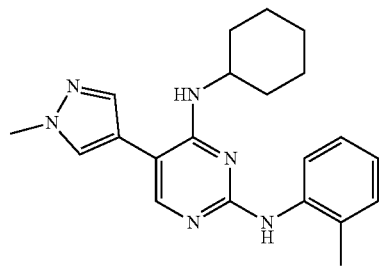 [SMILES: Cc1ccccc1Nc1ncc(-c2cnn(C)c2)c(NC2CCCCC2)n1]

1H NMR (300 MHz, CDCl$_3$) δ 8.21 (d, J=6.0 Hz, 1H), 7.79 (s, 1H), 7.56 (s, 1H), 7.42 (m, 2H), 7.28 (m, 2H), 6.98 (m, 1H), 4.93 (d, J=9.0 Hz, 1H), 4.02 (m, 1H), 4.00 (s, 3H), 2.38 (s, 3H), 2.06 (m, 2H), 1.78 (m, 2H), 1.52 (m, 2H), 1.45-1.10 (m, 3H);
LC/MS m/z calcd for $C_{21}H_{26}N_6$ (MH$^+$) 362.22, found 363.10.

Compound 11. N4-cyclohexyl-5-(1-methyl-1H-pyrazol-4-yl)-N2-(5-methylisoxazol-3-yl)pyrimidine-2,4-diamine

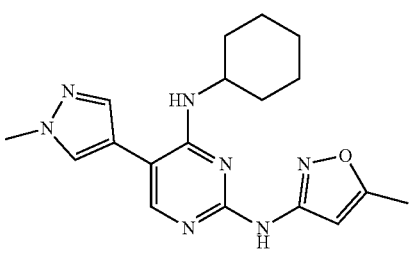

1H NMR (300 MHz, CDCl$_3$) δ 8.38 (brs, 1H), 7.81 (s, 1H), 7.57 (s, 1H), 7.46 (s, 1H), 6.74 (s, 1H), 4.93 (d, J=9.0 Hz, 1H), 4.00 (s, 3H), 3.97 (m, 1H), 2.39 (s, 3H), 2.06 (m, 2H), 1.78 (m, 2H), 1.52 (m, 2H), 1.45-1.10 (m, 3H);
LC/MS m/z calcd for $C_{18}H_{23}N_7O$ (MH$^+$) 353.20, found 354.10.

Compound 12. N2-(5-tert-butylisoxazol-3-yl)-N4-cyclohexyl-5-(1-methyl-1H-pyrazol-4-yl)pyrimidine-2,4-diamine

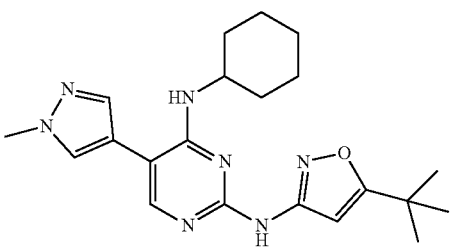 [SMILES: Cn1cc(-c2cnc(Nc3cc(C(C)(C)C)on3)nc2NC2CCCCC2)cn1]

1H NMR (300 MHz, CDCl$_3$) δ 8.65 (brs, 1H), 7.94 (s, 1H), 7.57 (s, 1H), 7.44 (s, 1H), 6.83 (s, 1H), 4.97 (d, J=9.0 Hz, 1H), 4.00 (s, 3H), 4.00 (m, 1H), 2.08 (m, 2H), 1.82-1.60 (m, 3H), 1.47 (s, 3H), 1.49-1.21 (m, 4H);
LC/MS m/z calcd for $C_{21}H_{29}N_7O$ (MH$^+$) 395.2, found 397.2.

Compound 13. N4-cyclohexyl-N2-(2-isopropylphenyl)-5-(1-methyl-1H-pyrazol-4-yl)pyrimidine-2,4-diamine

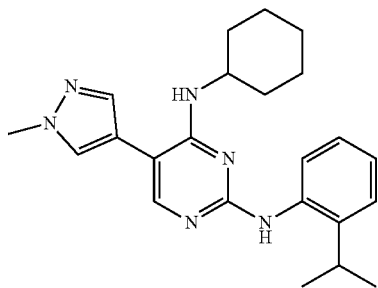 [SMILES: CC(C)c1ccccc1Nc1ncc(-c2cnn(C)c2)c(NC2CCCCC2)n1]

1H NMR (300 MHz, CDCl$_3$) δ 8.06 (d, J=6.0 Hz, 1H), 7.78 (s, 1H), 7.56 (s, 1H), 7.41 (s, 1H), 7.31 (d, J=9.0 Hz, 1H), 7.22 (d, J=6.0 Hz, 1H), 7.07 (d, J=6.0 Hz, 1H), 6.73 (brs, 1H), 4.97 (d, J=9.0 Hz, 1H), 4.00 (s, 3H), 4.00 (m, 1H), 3.22 (m, 1H), 2.08 (m, 2H), 1.82-1.60 (m, 3H), 1.47 (s, 3H), 1.29 (d, J=9.0 Hz, 9H), 1.49-1.21 (m, 4H);

LC/MS m/z calcd for C$_{23}$H$_{30}$N$_6$ (MH$^+$) 390.3, found 391.2.

Compound 14. N4-cyclohexyl-5-(furan-3-yl)-N2-(p-tolyl)pyrimidine-2,4-diamine

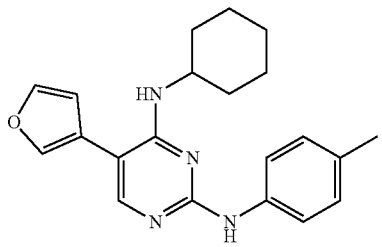 [SMILES: Cc1ccc(Nc2ncc(-c3ccoc3)c(NC3CCCCC3)n2)cc1]

1H NMR (300 MHz, CDCl$_3$) δ 7.85 (s, 1H), 7.56 (m, 4H), 7.15 (d, J=6.0 Hz, 1H), 6.52 (s, 1H), 4.95 (d, J=9.0 Hz, 1H), 4.03 (m, 1H), 2.34 (s, 3H), 2.08 (m, 2H), 1.82-1.63 (m, 3H), 1.47 (s, 3H), 1.49-1.21 (m, 3H);

LC/MS m/z calcd for C$_{21}$H$_{24}$N$_4$O (MH$^+$) 348.4, found 349.3.

Compound 15. N4-cyclohexyl-N2-(3,5-dichlorophenyl)-5-(furan-3-yl)pyrimidine-2,4-diamine

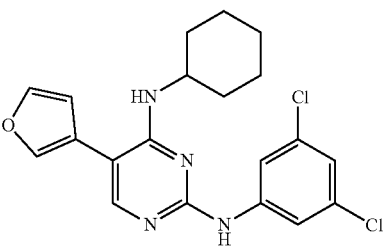 [SMILES: Clc1cc(Cl)cc(Nc2ncc(-c3ccoc3)c(NC3CCCCC3)n2)c1]

1H NMR (300 MHz, CDCl$_3$) δ 7.80 (s, 1H), 7.65 (m, 2H), 7.52 (m, 2H), 6.98 (m, 1H), 6.53 (m, 1H), 5.04 (d, J=9.0 Hz, 1H), 4.03 (m, 1H), 2.09 (m, 2H), 1.82-1.40 (m, 6H), 1.49-1.21 (m, 3H);

LC/MS m/z calcd for C$_{20}$H$_{20}$Cl$_2$N$_4$O (MH$^+$) 403.1, found 403.9.

Compound 16. N4-cyclohexyl-N2-(2,2-difluoro-2-(4-methoxyphenyl)ethyl)-5-(1-methyl-1H-pyrazol-4-yl)pyrimidine-2,4-diamine

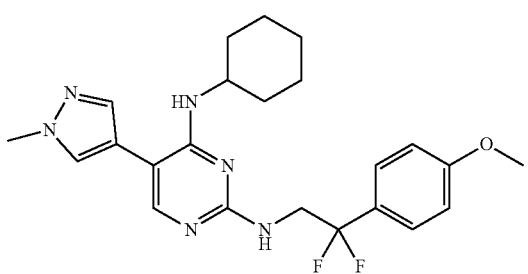

1H NMR (300 MHz, CDCl$_3$) δ 7.80 (s, 1H), 7.76 (s, 1H), 7.55-7.42 (m, 2H), 7.34-7.28 (m, 3H), 7.09-6.99 (m, 2H), 6.91-6.81 (m, 2H), 4.48 (t, J=6.0 Hz, 1H), 3.97 (s, 3H), 3.88-3.78 (m, 5H), 3.51 (s, 3H), 3.7 (s, 1H), 2.00-1.98 (m, 3H);

LC/MS m/z calcd for C$_{23}$H$_{28}$F$_2$N$_6$O (MH$^+$) 442.1, found 443.2.

Compound 17. N4-cyclohexyl-5-(1-methyl-1H-pyrazol-4-yl)-N2-(2-(pyridin-4-yl)ethyl)pyrimidine-2,4-diamine

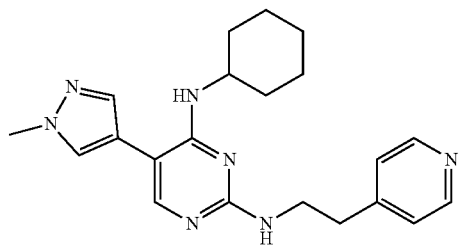 [SMILES: Cn1cc(-c2cnc(NCCc3ccncc3)nc2NC2CCCCC2)cn1]

1H NMR (300 MHz, CDCl$_3$) δ 8.57-8.52 (m, 2H), 7.65 (s, 1H), 7.52 (s, 1H), 7.38 (s, 1H), 7.18-7.15 (m, 2H), 4.89 (d, J=6.0 Hz, 1H), 3.98 (s, 4H), 3.63-3.50 (m, 2H), 2.97-2.86 (m, 2H), 2.06-1.97 (m, 2H), 1.76-1.71 (m, 3H), 1.47-1.33 (m, 2H), 1.30-1.11 (m, 4H);

LC/MS m/z calcd for C$_{21}$H$_{27}$N$_7$ (MH$^+$) 377.2, found 378.2.

Compound 18. (4-(4-(cyclohexylamino)-5-(1-methyl-1H-pyrazol-4-yl)pyrimidin-2-yl)piperazin-1-yl)(thiophen-2-yl)methanone

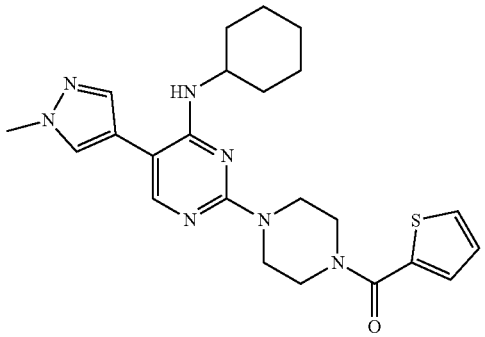 [SMILES: Cn1cc(-c2cnc(N3CCN(C(=O)c4cccs4)CC3)nc2NC2CCCCC2)cn1]

1H NMR (300 MHz, CDCl₃) δ 7.89-7.70 (m, 1H), 7.59-7.45 (m, 2H), 7.45-7.32 (m, 2H), 7.19-6.91 (m, 1H), 4.84 (d, J=7.4 Hz, 1H), 4.03-3.93 (m, 4H), 3.90-3.79 (m, 4H), 2.17-1.86 (m, 3H), 1.83-1.66 (m, 2H), 1.40 (dd, J=24.1, 11.8 Hz, 2H), 1.33-1.08 (m, 4H);
LC/MS m/z calcd for $C_{37}H_{47}ClN_{12}OS$ (MH⁺) 451.6, found 452.2.

Compound 19. 4-(4-(cyclohexylamino)-5-(1-methyl-1H-pyrazol-4-yl)pyrimidin-2-ylamino)-1,5-dimethyl-2-phenyl-1,2-dihydropyrazol-3-one

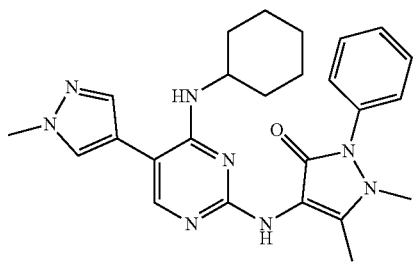 [SMILES: Cc1c(Nc2ncc(-c3cnn(C)c3)c(NC3CCCCC3)n2)c(=O)n(-c2ccccc2)n1C]

1H NMR (300 MHz, CDCl₃) δ 9.51 (s, 1H), 8.21 (s, 1H), 7.96 (m, 2H), 7.59 (m, 3H), 7.35 (m, 3H), 3.92 (s, 3H), 3.11 (s, 3H), 2.65 (m, 1H), 2.15 (s, 3H), 1.82 (m, 2H), 1.45 (m, 3H), 1.21 (m, 5H);
LC/MS m/z calcd for $C_{25}H_{30}N_8O$ (MH⁺) 458.2, found 459.2.

Compound 20. N4-cyclohexyl-5-(1-methyl-1H-pyrazol-4-yl)-N2-(3-methylisoxazol-5-yl)pyrimidine-2,4-diamine

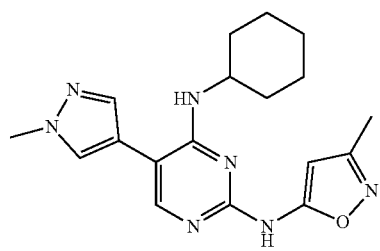

1H NMR (300 MHz, CDCl₃) δ 8.49 (s, 1H), 8.20 (s, 1H), 7.98 (m, 2H), 6.52 (s, 1H), 3.98 (s, 3H), 2.52 (m, 1H), 2.42 (s, 3H), 1.81 (m, 2H), 1.47 (m, 3H), 1.20 (m, 5H);
LC/MS m/z calcd for $C_{18}H_{23}N_7O$ (MH⁺) 352.2, found 353.1.

Compound 21. N4-cyclohexyl-N2-(5-ethyl-1,3,4-thiadiazol-2-yl)-5-(1-methyl-1H-pyrazol-4-yl)pyrimidine-2,4-diamine

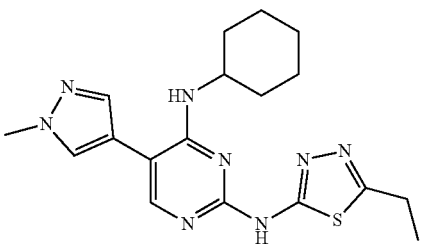 [SMILES: CCc1nnc(Nc2ncc(-c3cnn(C)c3)c(NC3CCCCC3)n2)s1]

1H NMR (300 MHz, CDCl₃) δ 12.10 (s, 1H), 8.24 (s, 1H), 7.92 (m, 2H), 3.93 (s, 3H), 3.11 (t, J=7.2 Hz, 2H), 2.69 (m, 1H), 1.83 (m, 2H), 1.47 (m, 3H), 1.22 (m, 5H); LC/MS m/z calcd for $C_{18}H_{24}N_8S$ (MH⁺) 384.5, found 385.1.

Compound 22. N4-cyclohexyl-5-(1-methyl-1H-pyrazol-4-yl)-N2-(thiazol-2-yl)pyrimidine-2,4-diamine

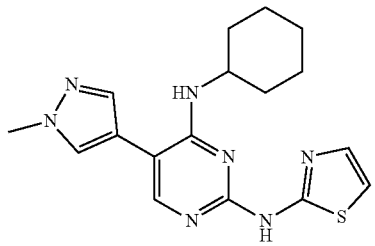 [SMILES: Cn1cc(-c2cnc(Nc3nccs3)nc2NC2CCCCC2)cn1]

1H NMR (300 MHz, CDCl₃) δ 8.21 (s, 1H), 7.95 (m, 2H), 7.21 (d, J=3.5 Hz, 1H), 6.78 (d, J=3.5 Hz, 1H), 3.98 (s, 3H), 1.83 (m, 2H), 1.47 (m, 3H), 1.22 (m, 5H);
LC/MS m/z calcd for $C_{17}H_{21}N_7S$ (MH⁺) 355.5, found 356.1.

Compound 23. N4-cyclohexyl-N2-adamantyl-5-(1-methyl-1H-pyrazol-4-yl)pyrimidine-2,4-diamine

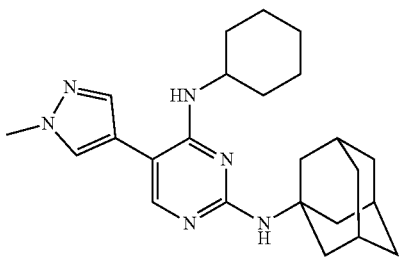 [SMILES: Cn1cc(-c2cnc(NC34CC5CC(CC(C5)C3)C4)nc2NC2CCCCC2)cn1]

1H NMR (300 MHz, CDCl₃) δ 8.20 (s, 1H), 7.94 (m, 2H), 3.98 (s, 3H), 2.67 (m, 1H), 2.28 (m, 2H), 1.98 (m, 2H), 1.78 (m, 2H), 1.75 (m, 3H), 1.68 (m, 3H), 1.42 (m, 5H), 2.21 (m, 9H);

LC/MS m/z calcd for $C_{24}H_{34}N_6$ (MH⁺) 405, found 406.2.

Compound 24. N4-cyclohexyl-N2-(2-methoxyphenyl)-5-(1-methyl-1H-pyrazol-4-yl)pyrimidine-2,4-diamine

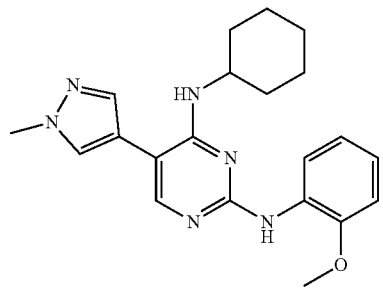 [SMILES: COc1ccccc1Nc1ncc(-c2cnn(C)c2)c(NC2CCCCC2)n1]

1H NMR (300 MHz, CDCl₃) δ 8.20 (s, 1H), 7.89 (m, 2H), 7.35 (m, 2H), 6.97 (m, 2H), 3.97 (s, 3H), 3.83 (s, 3H), 2.62 (m, 1H), 1.75 (m, 3H), 1.45 (m, 3H), 1.21 (m, 4H);

LC/MS m/z calcd for $C_{21}H_{26}N_6O$ (MH⁺) 378.4, found 379.2.

Compound 25. N4-cyclohexyl-5-(1-methyl-1H-pyrazol-4-yl)-N2-(m-tolyl)pyrimidine-2,4-diamine

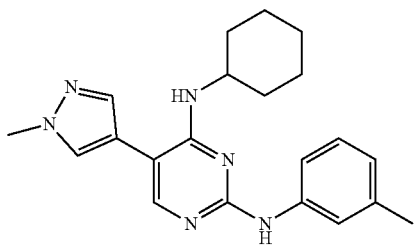

1H NMR (300 MHz, CDCl₃) δ 7.85 (s, 1H), 7.57 (m, 2H), 7.45 (m, 2H), 7.23 (m, 1H), 6.84 (d, J=6.0 Hz, 1H), 4.84 (d, J=7.4 Hz, 1H), 4.03 (m, 1H), 3.98 (s, 3H), 2.38 (s, 3H), 2.18-2.10 (m, 4H), 1.83-1.65 (m, 3H), 1.51-1.28 (m, 2H), 1.28-1.08 (m, 3H);

LC/MS m/z calcd for $C_{21}H_{26}N_6$ (MH⁺) 362.4, found 363.3.

Compound 26. N-((1s,4s)-4-(2-(3,5-dichlorophenylamino)-5-(1-methyl-1H-pyrazol-4-yl)pyrimidin-4-ylamino)cyclohexyl)-2,2,2-trifluoroacetamide

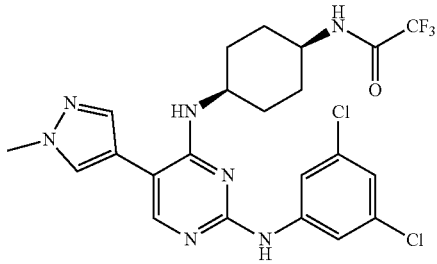 [SMILES: Cn1cc(-c2cnc(Nc3cc(Cl)cc(Cl)c3)nc2N[C@H]2CC[C@@H](NC(=O)C(F)(F)F)CC2)cn1]

1H NMR (300 MHz, Chloroform-d) δ 7.79 (s, 1H), 7.42 (s, 1H), 7.56 (s, 1H), 7.39 (s, 1H), 7.37 (s, 1H), 6.95 (s, 1H), 6.76 (brs, 1H), 5.10 (d, J=9.0 Hz, 1H), 4.23 (m, 1H), 4.10 (m, 1H), 3.98 (s, 3H), 2.19-1.62 (m, 4H), 1.61-1.23 (m, 4H);

LC/MS m/z calcd for $C_{22}H_{22}Cl_2F_3N_7O$ (MH⁺) 527.01, found 528.1.

Compound 27. 1-(4-(2-(3,5-dichlorophenylamino)-5-(1-methyl-1H-pyrazol-4-yl)pyrimidin-4-ylamino)piperidin-1-yl)-2,2,2-trifluoroethanone

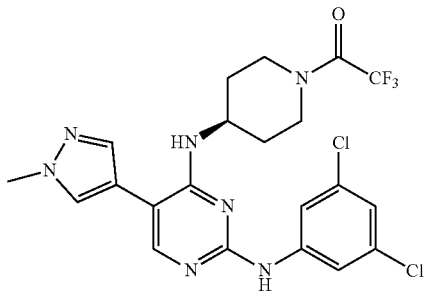

1H NMR (300 MHz, CDCl₃) δ 7.75 (s, 1H), 7.65 (s, 1H), 7.60 (s, 1H), 7.49 (s, 1H), 7.47 (s, 1H), 7.23 (s, 1H), 7.09 (s, 1H), 4.90 (d, J=9.00 Hz, 1H), 4.51 (m, 1H), 4.31 (m, 1H), 4.10 (m, 1H), 4.09 (s, 3H), 3.26 (m, 1H), 2.98 (m, 1H), 2.28 (m, 1H), 1.45 (m, 1H).

Compound 28. N4-((1s,4s)-4-aminocyclohexyl)-N2-(3,5-dichlorophenyl)-5-(1-methyl-1H-pyrazol-4-yl)pyrimidine-2,4-diamine

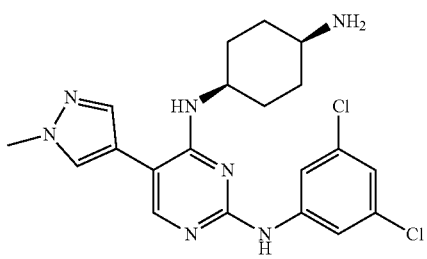 [SMILES: Cn1cc(-c2cnc(Nc3cc(Cl)cc(Cl)c3)nc2N[C@H]2CC[C@@H](N)CC2)cn1]

1H NMR (300 MHz, Chloroform-d) δ 8.12 (s, 1H), 5.49 (d, J=7.6 Hz, 1H), 4.57 (s, 1H), 4.25-4.08 (m, 1H), 3.68 (d, J=8.9 Hz, 1H), 1.85 (ddt, J=12.8, 8.5, 4.0 Hz, 4H), 1.71-1.53 (m, 4H), 1.46 (s, 9H);

LC/MS m/z calcd for $C_{20}H_{23}Cl_2N_7$ (MH$^+$) 432.3, found 433.2.

Compound 29. N2-(3,5-dichlorophenyl)-5-(1-methyl-1H-pyrazol-4-yl)-N4-(piperidin-4-yl)pyrimidine-2,4-diamine

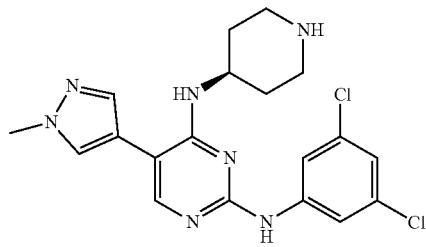

1H NMR (300 MHz, Chloroform-d) δ 7.82 (s, 1H), δ 7.72 (m, 3H), 7.61 (s, 1H), 7.48 (s, 1H), 6.99 (s, 1H), 5.10 (m, 1H), 4.24 (m, 1H), 3.91 (s, 3H), 3.48 (m, 1H), 3.10 (m, 1H), 2.40-1.75 (m, 4H);

LC/MS m/z calcd for $C_{19}H_{21}Cl_2N_7$ (MH$^+$) 418.2, found 419.3.

Compound 30. N2-(3,5-dichlorophenyl)-N4-((1s,4s)-4-(dimethylamino)cyclohexyl)-5-(1-methyl-1H-pyrazol-4-yl)pyrimidine-2,4-diamine

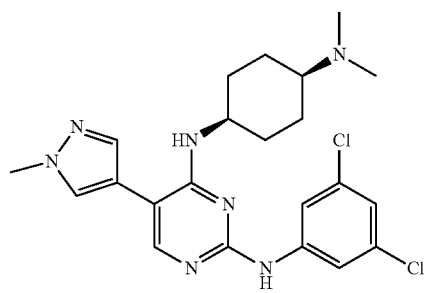 [SMILES: Cn1cc(-c2cnc(Nc3cc(Cl)cc(Cl)c3)nc2N[C@H]2CC[C@@H](N(C)C)CC2)cn1]

1H NMR (300 MHz, CDCl$_3$) δ 8.07 (s, 1H) 7.90-7.83 (m, 1H), 7.66 (d, J=3 Hz, 2H), 7.58-7.53 (m, 2H), 6.946 (t, J=1.8 Hz, 1H), 5.44 (d, J=6 Hz, 1H), 4.30-4.28 (m, 1H), 4.07 (s, 1H), 2.91-2.85 (m, 1H), 2.79 (s, 6H), 2.28-2.22 (m, 2H), 2.05-2.03 (m, 4H), 1.88-1.80 (m, 3H).

Compound 31. N-((1s,4s)-4-(2-(3,5-dichlorophenylamino)-5-(1-methyl-1H-pyrazol-4-yl)pyrimidin-4-ylamino)cyclohexyl)-acetamide

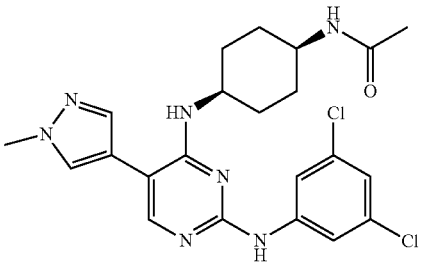 [SMILES: CC(=O)N[C@H]1CC[C@@H](Nc2nc(Nc3cc(Cl)cc(Cl)c3)ncc2-c2cnn(C)c2)CC1]

1H NMR (300 MHz, Chloroform-d) δ 7.81 (s, 1H), 7.64 (d, J=1.8 Hz, 2H), 7.58 (s, 1H), 7.45 (s, 1H), 7.20 (d, J=1.9 Hz, 1H), 6.97 (s, OH), 5.45 (d, J=7.8 Hz, OH), 5.11 (d, J=7.0 Hz, 1H), 4.22-4.10 (m, 1H), 4.00 (s, 3H), 2.04 (d, J=6.4 Hz, 1H), 1.93-1.77 (m, 3H), 1.25 (s, 5H).

Compound 32. N2-(3,5-dichlorophenyl)-5-(1-methyl-1H-pyrazol-4-yl)-N4-(1-methylpiperidin-4-yl)pyrimidine-2,4-diamine

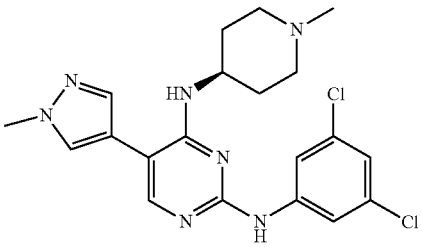

1H NMR (300 MHz, Chloroform-d) δ 7.82-7.78 (m, 1H), 7.63 (d, J=1.8 Hz, 2H), 7.52 (s, 1H), 7.44 (s, 1H), 7.21 (dd, J=2.2, 1.2 Hz, 1H), 6.98 (t, J=1.8 Hz, 1H), 5.12-5.02 (m, 1H), 4.21-4.07 (m, 2H), 4.00 (s, 3H), 3.27-3.15 (m, 2H), 2.57 (s, 3H), 2.22-2.14 (m, 3H), 2.03 (d, J=5.7 Hz, 3H);

LC/MS m/z calcd for $C_{20}H_{23}Cl_2N_7$ (MH$^+$) 432.1, found 433.0.

Compound 33. 1-(4-(2-(3,5-dichlorophenylamino)-5-(1-methyl-1H-pyrazol-4-yl)pyrimidin-4-ylamino)piperidin-1-yl)ethanone

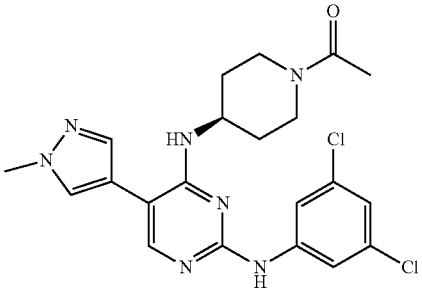

1H NMR (300 MHz, Chloroform-d) δ 7.79 (s, 1H), 7.64 (d, J=1.8 Hz, 2H), 7.53 (s, 1H), 7.42 (s, 1H), 6.98 (t, J=1.8 Hz, 1H), 4.99 (d, J=7.3 Hz, 1H), 4.61 (d, J=13.4 Hz, 2H), 4.24 (dd, J=11.5, 4.0 Hz, 2H), 3.98 (s, 3H), 3.84 (d, J=13.4 Hz, 2H), 3.34 (d, J=11.5 Hz, 2H), 2.87 (d, J=13.6 Hz, 2H), 2.11 (s, 3H).

Compound 34. 1-(4-(5-(1-methyl-1H-pyrazol-4-yl)-2-(phenylamino)pyrimidin-4-ylamino)piperidin-1-yl)-2,2,2-trifluoroethanone

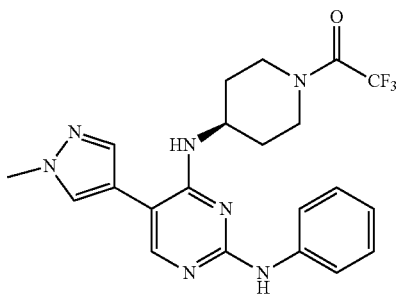

1H NMR (300 MHz, CDCl₃) δ 7.83 (s, 1H), 7.62-7.58 (m, 2H), 7.52 (s, 1H), 7.40 (s, 1H), 7.35-7.28 (m, 2H), 7.05-7.02 (m, 1H), 6.96-6.93 (m, 1H), 4.88-4.85 (m, 1H), 4.55-4.47 (m, 2H), 3.98 (s, 3H), 3.35-3.24 (m, 2H), 3.05-2.95 (m, 2H), 2.27-2.19 (m, 3H);

LC/MS m/z calcd for $C_{21}H_{22}F_3N_7O$ (MH⁺) 445.1, found 446.0.

Compound 35. 1-(4-(2-(3-chlorophenylamino)-5-(1-methyl-1H-pyrazol-4-yl)pyrimidin-4-ylamino)piperidin-1-yl)-2,2,2-trifluoroethanone

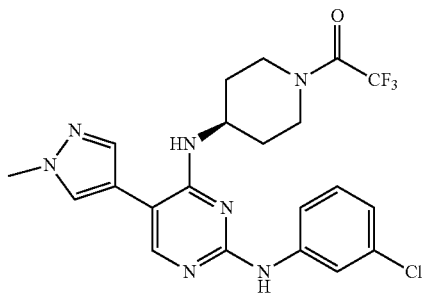

1H NMR (300 MHz, CDCl₃) δ 8.16 (t, J=1.9 Hz, 1H) 7.82 (s, 1H) 7.52 (S, 1H) 7.43 (S, 1H) 7.19 (d, J=9 Hz, 1H) 4.92 (d, J=7.2 Hz, 1H) 4.59-4.57 (m, 1H) 4.54-4.53 (m, 1H) 4.08-4.02 (m, 1H) 3.98 (s, 3H) 3.42-3.33 (m, 1H) 3.10-3.01 (m, 1H) 2.33-2.20 (m, 2H) 1.47-1.42 (m, 2H);

LC/MS m/z calcd for $C_{21}H_{21}ClF_3N_7O$ (MH⁺) 479.1, found 480.0.

Compound 36. N2-(3-chlorophenyl)-5-(1-methyl-1H-pyrazol-4-yl)-N4-(piperidin-4-yl)pyrimidine-2,4-diamine

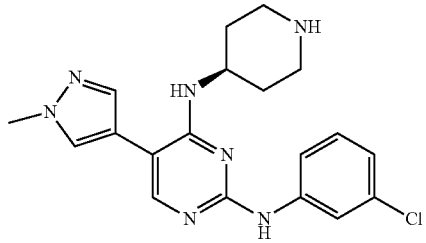

1H NMR (300 MHz, CDCl₃) δ 8.11 (s, 1H), 7.80 (s, 1H), 7.55 (s, 1H), 7.42 (s, 1H), 7.19 (dd, J=4.9, 1.2 Hz, 3H), 7.00-6.91 (m, 1H), 4.97 (d, J=7.5 Hz, 1H), 4.22-4.05 (m, 1H), 3.98 (s, 3H), 3.12 (d, J=12.8 Hz, 2H), 2.85 (dd, J=17.7, 6.3 Hz, 2H), 2.10 (d, J=10.2 Hz, 2H), 1.35 (ddd, J=23.3, 11.4, 3.7 Hz, 3H);

LC/MS m/z calcd for $C_{19}H_{22}ClN_7$ (MH⁺) 383.8, found 384.6.

Compound 37. 1-(4-(2-(4-chlorophenylamino)-5-(1-methyl-1H-pyrazol-4-yl)pyrimidin-4-ylamino)piperidin-1-yl)-2,2,2-trifluoroethanone

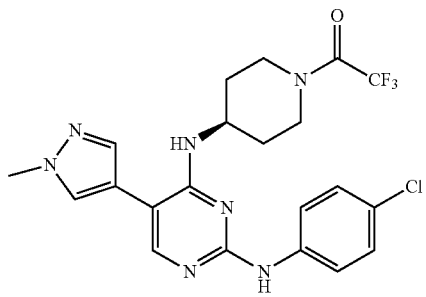

1H NMR (300 MHz, CDCl₃) δ 7.83 (s, 1H) 7.56 (d, J=3 Hz, 1H) 7.54 (d, J=3 Hz, 1H) 7.51 (d, J=3 Hz, 1H) 7.40 (s, 1H) 7.27 (s, 1H) 7.24 (d, J=3 Hz, 1H) 4.88 (d, J=6 Hz, 1H) 4.50 (d, J=15 Hz, 1H) 4.29-4.20 (m, 1H) 4.05-4.01 (m, 1H) 3.34-3.24 (m, 1H) 3.05-2.95 (m, 1H) 2.23-2.04 (m, 2H) 1.47-1.39 (m, 2H);

LC/MS m/z calcd for $C_{21}H_{21}ClF_3N_7O$ (MH⁺) 479.1, found 480.0.

Compound 38. N4-(1-benzylpiperidin-4-yl)-N2-(3,5-dichlorophenyl)-5-(1-methyl-1H-pyrazol-4-yl)pyrimidine-2,4-diamine

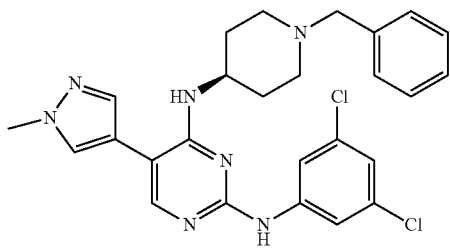

1H NMR (300 MHz, CDCl$_3$) δ 7.83 (s, 1H), 7.56 (d, J=3.0 Hz, 1H), 7.54 (d, J=3.0 Hz, 1H), 7.51 (d, J=3.0 Hz, 1H), 7.40 (s, 1H) 7.27 (s, 1H) 7.24 (d, J=3.0 Hz, 1H), 4.88 (d, J=6.0 Hz, 1H), 4.50 (d, J=15.1 Hz, 1H), 4.29-4.20 (m, 1H), 4.05-4.01 (m, 1H), 3.34-3.24 (m, 1H), 3.05-2.95 (m, 1H), 2.23-2.04 (m, 2H), 1.47-1.39 (m, 2H);
LC/MS m/z calcd for C$_{26}$H$_{27}$Cl$_2$N$_7$ (MH$^+$) 508.5 found 509.2.

Compound 39. 1-(4-(2-(3-fluorophenylamino)-5-(1-methyl-1H-pyrazol-4-yl)pyrimidin-4-ylamino)piperidin-1-yl)-2,2,2-trifluoroethanone

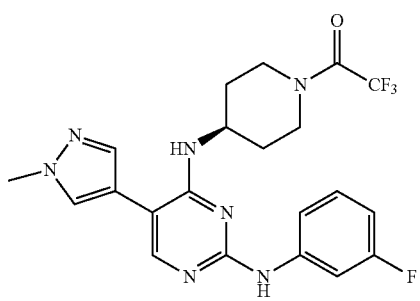

1H NMR (300 MHz, Chloroform-d) δ 7.84 (d, J=11.5 Hz, 1H), 7.72 (s, 1H), 7.55 (s, 1H), 7.47 (s, 1H), 7.32 (d, J=8.2 Hz, 1H), 7.15-7.09 (m, 1H), 6.81 (t, J=8.3 Hz, 1H), 5.37 (d, J=7.5 Hz, 1H), 4.62 (d, J=14.2 Hz, 1H), 4.33 (s, 1H), 4.10 (d, J=14.5 Hz, 1H), 4.02 (s, 3H), 3.34 (t, J=13.0 Hz, 1H), 3.01 (t, J=12.9 Hz, 1H), 2.25 (d, J=14.9 Hz, 2H), 1.51 (d, J=11.6 Hz, 3H).

Compound 40. N2-(4-chlorophenyl)-5-(1-methyl-1H-pyrazol-4-yl)-N4-(piperidin-4-yl)pyrimidine-2,4-diamine

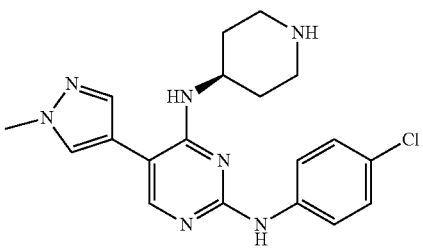

1H NMR (300 MHz, Chloroform-d) δ 7.80 (s, 1H), 7.61 (d, J=2.0 Hz, 1H), 7.58 (d, J=2.1 Hz, 1H), 7.54 (s, 1H), 7.41 (s, 1H), 7.27 (d, J=1.6 Hz, 1H), 7.25-7.19 (m, 2H), 4.94 (d, J=7.4 Hz, 1H), 4.06 (dtd, J=11.0, 7.1, 4.0 Hz, 1H), 3.98 (s, 3H), 3.20-3.06 (m, 2H), 2.84-2.69 (m, 2H), 2.07 (d, J=12.5 Hz, 2H), 1.48-1.27 (m, 3H).

Compound 41. N2-(3-fluorophenyl)-5-(1-methyl-1H-pyrazol-4-yl)-N4-(piperidin-4-yl)pyrimidine-2,4-diamine

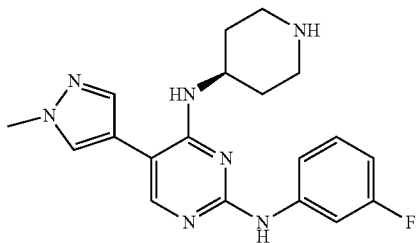

1H NMR (300 MHz, Chloroform-d) δ 7.88 (dt, J=12.1, 2.3 Hz, 1H), 7.81 (s, 1H), 7.55 (s, 1H), 7.42 (s, 1H), 7.25-7.15 (m, 2H), 7.09-7.01 (m, 1H), 6.67 (td, J=8.2, 1.8 Hz, 1H), 4.97 (d, J=7.5 Hz, 1H), 4.19-4.03 (m, 1H), 3.98 (s, 3H), 3.13 (d, J=12.6 Hz, 2H), 2.80 (td, J=12.0, 2.5 Hz, 2H), 2.11 (d, J=12.4 Hz, 2H), 1.46-1.30 (m, 3H).

Compound 42. 5-(1-methyl-1H-pyrazol-4-yl)-N2-phenyl-N4-(piperidin-4-yl)pyrimidine-2,4-diamine

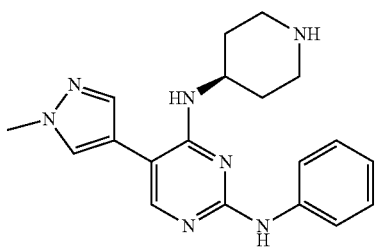

1H NMR (300 MHz, Chloroform-d) δ 7.80 (s, 1H), 7.67-7.60 (m, 2H), 7.54 (s, 1H), 7.41 (s, 1H), 7.32 (d, J=7.5 Hz, 2H), 7.12 (s, 1H), 6.99 (t, J=7.4 Hz, 1H), 4.92 (d, J=7.4 Hz, 1H), 4.10 (ddd, J=10.8, 9.0, 5.4 Hz, 1H), 3.98 (s, 3H), 3.12 (d, J=12.6 Hz, 2H), 2.84-2.70 (m, 2H), 2.09 (d, J=10.2 Hz, 2H), 1.45-1.28 (m, 3H).

Compound 43. 1-(4-(2-(3-methyl-4-chlorophenylamino)-5-(1-methyl-1H-pyrazol-4-yl)pyrimidin-4-ylamino)piperidin-1-yl)-2,2,2-trifluoroethanone

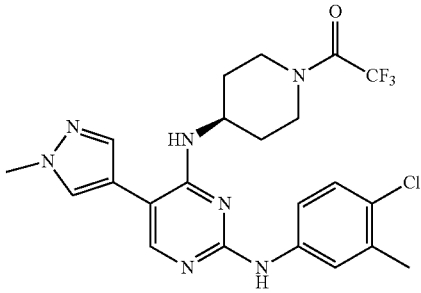

1H NMR (300 MHz, Chloroform-d) δ 7.83 (s, 1H), 7.52 (s, 1H), 7.46 (s, 1H), 7.40 (d, J=3.7 Hz, 2H), 7.23 (s, 1H), 6.93 (s, 1H), 4.87 (d, J=7.4 Hz, 1H), 4.50 (d, J=13.3 Hz, 1H), 4.27 (dd, J=10.8, 4.1 Hz, 2H), 4.05 (s, 1H), 3.97 (s, 3H), 3.29 (t, J=11.6 Hz, 1H), 3.07-2.94 (m, 1H), 2.37 (s, 3H), 2.20 (d, J=9.5 Hz, 2H), 1.52-1.40 (m, 3H).

Compound 44. 1-(4-(2-(4-methoxyphenylamino)-5-(1-methyl-1H-pyrazol-4-yl)pyrimidin-4-ylamino)piperidin-1-yl)-2,2,2-trifluoroethanone

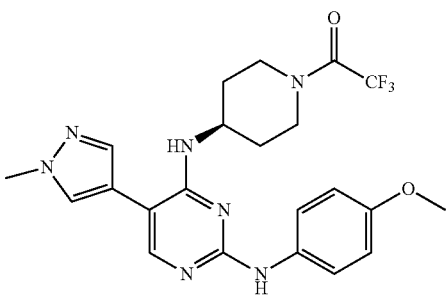

1H NMR (300 MHz, Chloroform-d) δ 7.80 (s, 1H), 7.54-7.43 (m, 3H), 7.39 (s, 1H), 7.00 (s, 1H), 6.90-6.83 (m, 2H), 4.83 (d, J=7.2 Hz, 1H), 4.49 (d, J=13.3 Hz, 1H), 4.28-4.18 (m, 1H), 3.97 (s, 4H), 3.81 (s, 3H), 3.33-3.21 (m, 1H), 2.98 (t, J=11.7 Hz, 1H), 2.19 (d, J=13.5 Hz, 2H), 1.56-1.35 (m, 2H).

Compound 45. 1-(4-(2-(3-chloro-4-methoxyphenylamino)-5-(1-methyl-1H-pyrazol-4-yl)pyrimidin-4-ylamino)piperidin-1-yl)-2,2,2-trifluoroethanone

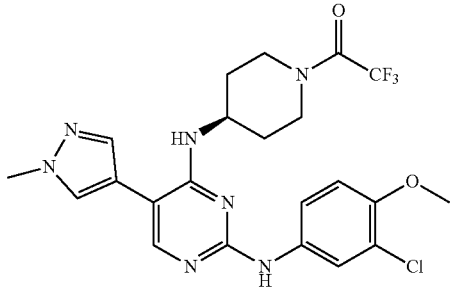

1H NMR (300 MHz, Chloroform-d) δ 8.08 (d, J=2.6 Hz, 1H), 7.81 (s, 1H), 7.52 (s, 1H), 7.40 (d, J=3.7 Hz, 2H), 7.10 (dd, J=8.8, 2.6 Hz, 1H), 6.88 (d, J=8.9 Hz, 1H), 4.90 (d, J=7.4 Hz, 1H), 4.53 (d, J=13.5 Hz, 1H), 4.29 (dt, J=7.4, 4.0 Hz, 1H), 4.03 (d, J=14.2 Hz, 1H), 3.97 (s, 3H), 3.89 (s, 3H), 3.42-3.29 (m, 1H), 3.03 (t, J=11.9 Hz, 1H), 2.23 (t, J=11.0 Hz, 3H), 1.54-1.35 (m, 2H).

Compound 46. N2-(3-methyl-4-chlorophenyl)-5-(1-methyl-1H-pyrazol-4-yl)-N4-(piperidin-4-yl)pyrimidine-2,4-diamine

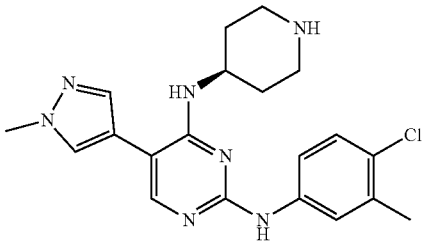

1H NMR (300 MHz, Chloroform-d) δ 7.79 (s, 1H), 7.54 (dd, J=3.2, 1.6 Hz, 2H), 7.45-7.39 (m, 2H), 7.24 (d, J=8.7 Hz, 1H), 6.90 (s, 1H), 4.93 (d, J=7.5 Hz, 1H), 4.08 (d, J=7.5 Hz, 1H), 3.98 (s, 3H), 3.12 (d, J=12.8 Hz, 2H), 2.76 (t, J=10.7 Hz, 2H), 2.38 (s, 3H), 2.07 (d, J=12.8 Hz, 2H), 1.36 (dd, J=18.0, 5.7 Hz, 3H).

Compound 47. N2-(4-methoxyphenyl)-5-(1-methyl-1H-pyrazol-4-yl)-N4-(piperidin-4-yl)pyrimidine-2,4-diamine

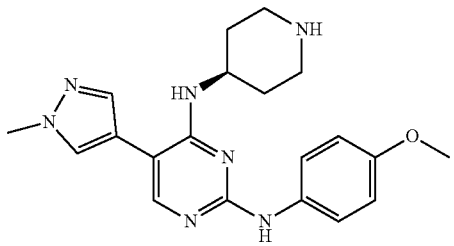

1H NMR (300 MHz, Chloroform-d) δ 7.77 (s, 1H), 7.56-7.51 (m, 2H), 7.50 (d, J=2.2 Hz, 1H), 7.40 (s, 1H), 6.88 (d, J=2.2 Hz, 1H), 6.87-6.81 (m, 2H), 4.88 (d, J=7.5 Hz, 1H), 4.12-4.01 (m, 1H), 3.97 (s, 3H), 3.80 (s, 3H), 3.11 (d, J=12.7 Hz, 2H), 2.81-2.69 (m, 2H), 2.07 (d, J=12.5 Hz, 2H), 1.34 (td, J=11.9, 3.9 Hz, 3H).

Compound 48. N2-(3-chloro-4-methoxyphenyl)-5-(1-methyl-1H-pyrazol-4-yl)-N4-(piperidin-4-yl)pyrimidine-2,4-diamine

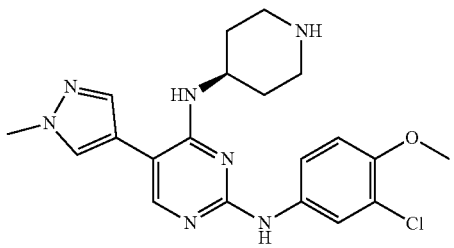

1H NMR (300 MHz, Chloroform-d) δ 8.03 (d, J=2.6 Hz, 1H), 7.78 (s, 1H), 7.56-7.52 (m, 1H), 7.41 (s, 1H), 7.19 (dd, J=8.8, 2.7 Hz, 1H), 7.00 (s, 1H), 6.87 (d, J=8.9 Hz, 1H), 4.93 (d, J=7.7 Hz, 1H), 4.18-4.04 (m, 1H), 3.98 (s, 3H), 3.89 (s, 3H), 3.11 (d, J=12.7 Hz, 2H), 2.88-2.75 (m, 2H), 2.08 (d, J=9.9 Hz, 2H), 1.35 (td, J=11.6, 4.0 Hz, 3H).

Compound 49. 1-(4-(2-(p-toluidino)-5-(furan-3-yl)pyrimidin-4-ylamino)piperidin-1-yl)-2,2,2-trifluoroethanone

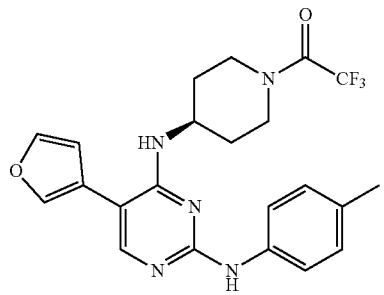

1H NMR (300 MHz, Chloroform-d) δ 7.87 (s, 1H), 7.55 (t, J=1.7 Hz, 1H), 7.50 (dd, J=2.9, 1.6 Hz, 2H), 7.46 (s, 1H), 7.12 (d, J=8.2 Hz, 2H), 7.06 (s, 1H), 6.47 (dd, J=1.8, 0.8 Hz, 1H), 4.87 (d, J=7.1 Hz, 1H), 4.51 (d, J=11.7 Hz, 1H), 4.28 (dt, J=7.5, 3.9 Hz, 1H), 4.03 (d, J=13.9 Hz, 1H), 3.37-3.23 (m, 1H), 3.02 (t, J=11.6 Hz, 1H), 2.33 (s, 3H), 2.22 (d, J=8.1 Hz, 2H), 1.55-1.38 (m, 2H).

Compound 50. 1-(4-(2-(m-toluidino)-5-(furan-3-yl)pyrimidin-4-ylamino)piperidin-1-yl)-2,2,2-trifluoroethanone

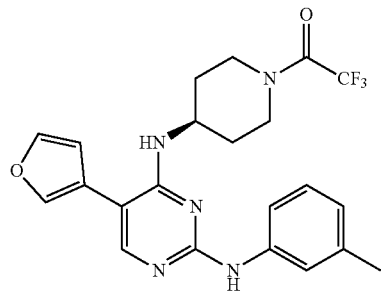

1H NMR (300 MHz, Chloroform-d) δ 7.89 (s, 1H), 7.55 (t, J=1.7 Hz, 1H), 7.53-7.50 (m, 1H), 7.45-7.40 (m, 2H), 7.23-7.16 (m, 1H), 7.04 (s, 1H), 6.85 (d, J=7.4 Hz, 1H), 6.48 (dd, J=1.8, 0.9 Hz, 1H), 4.88 (d, J=7.3 Hz, 1H), 4.50 (d, J=11.4 Hz, 1H), 4.37-4.22 (m, 1H), 4.02 (d, J=14.4 Hz, 1H), 3.39-3.24 (m, 1H), 3.02 (t, J=11.6 Hz, 1H), 2.36 (s, 3H), 2.23 (d, J=10.3 Hz, 2H), 1.57-1.39 (m, 2H).

Compound 51. 5-(furan-3-yl)-N4-(piperidin-4-yl)-N2-(p-tolyl)pyrimidine-2,4-diamine

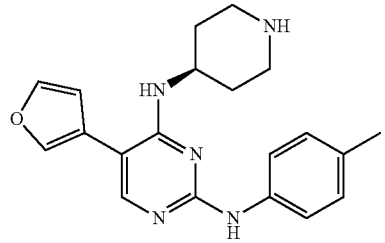

1H NMR (300 MHz, CDCl3) δ 7.85 (s, 1H), 7.60-7.45 (m, 4H), 7.11 (d, J=8.2 Hz, 2H), 6.96 (s, 1H), 6.50 (s, 1H), 4.91 (d, J=7.2 Hz, 1H), 4.12 (dd, J=7.0, 3.7 Hz, 1H), 3.13 (d, J=12.6 Hz, 2H), 2.78 (t, J=10.9 Hz, 2H), 2.32 (s, 3H), 2.08 (t, J=9.7 Hz, 2H), 1.48-1.29 (m, 3H).

Compound 52. 5-(furan-3-yl)-N4-(piperidin-4-yl)-N2-(m-tolyl)pyrimidine-2,4-diamine

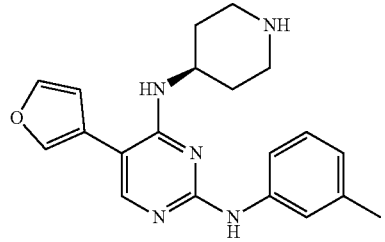

1H NMR (300 MHz, MeOH-d4) δ 7.70 (s, 1H), 7.59 (s, 1H), 7.57-7.53 (m, 1H), 7.35 (s, 1H), 7.32 (s, 1H), 7.07 (t, J=7.7 Hz, 1H), 6.72 (d, J=7.2 Hz, 1H), 6.49 (d, J=1.0 Hz,

1H), 4.17 (t, J=12.9 Hz, 1H), 3.27 (d, J=12.9 Hz, 2H), 2.90 (t, J=11.4 Hz, 2H), 2.24 (s, 4H), 2.13 (d, J=9.8 Hz, 3H), 1.71-1.41 (m, 3H).

Compound 53. 1-(4-(2-(3-chlorophenylamino)-5-(furan-3-yl)pyrimidin-4-ylaminoeridin-1-yl)-2,2,2-trifluoroethanone

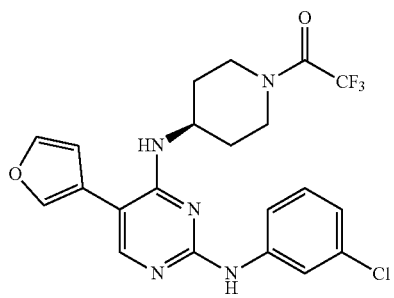

1H NMR (300 MHz, CDCl₃) δ 8.17 (t, J=2.0 Hz, 1H), 7.89 (s, 1H), 7.57 (t, J=1.6 Hz, 1H), 7.53 (s, 1H), 7.30 (s, 1H), 7.22 (t, J=8.0 Hz, 1H), 7.09 (d, J=9.2 Hz, 1H), 6.98 (d, J=7.8 Hz, 1H), 6.48 (d, J=0.9 Hz, 1H), 4.95 (d, J=7.4 Hz, 1H), 4.55 (d, J=13.9 Hz, 1H), 4.42-4.27 (m, 1H), 4.06 (d, J=16.9 Hz, 1H), 3.37 (dd, J=19.1, 7.3 Hz, 1H), 3.07 (t, J=11.9 Hz, 1H), 2.27 (t, J=12.5 Hz, 2H), 1.56-1.40 (m, 2H).

Compound 54. 1-(4-(2-(3-fluorophenylamino)-5-(furan-3-yl)pyrimidin-4-ylamino)piperidin-1-yl)-2,2,2-trifluoroethanone

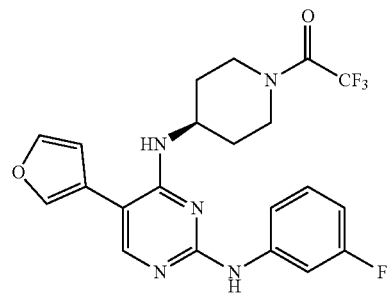

1H NMR (300 MHz, Chloroform-d) δ 7.96-7.89 (m, 2H), 7.59 (t, J=1.6 Hz, 1H), 7.57-7.53 (m, 1H), 7.34 (s, 1H), 7.24 (dd, J=8.1, 6.8 Hz, 1H), 7.06-6.99 (m, 1H), 6.72 (td, J=8.3, 1.9 Hz, 1H), 6.53-6.49 (m, 1H), 4.96 (d, J=7.1 Hz, 1H), 4.58 (d, J=15.2 Hz, 1H), 4.33 (dt, J=7.4, 4.1 Hz, 1H), 4.08 (d, J=15.5 Hz, 1H), 3.44-3.30 (m, 1H), 3.05 (t, J=12.0 Hz, 1H), 2.30 (t, J=13.6 Hz, 2H), 1.50 (d, J=11.9 Hz, 2H).

Compound 55. N2-(3-fluorophenyl)-5-(furan-3-yl)-N4-(piperidin-4-yl)pyrimidine-2,4-diamine

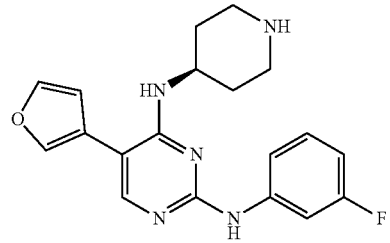

1H NMR (300 MHz, Chloroform-d) δ 7.91-7.84 (m, 2H), 7.59-7.48 (m, 3H), 7.26-7.17 (m, 1H), 7.08-7.03 (m, 1H), 6.68 (td, J=8.2, 2.2 Hz, 1H), 6.50 (dd, J=1.7, 0.8 Hz, 1H), 5.01 (d, J=7.4 Hz, 1H), 3.20 (d, J=12.7 Hz, 3H), 2.92-2.79 (m, 2H), 2.19-2.10 (m, 2H), 1.53-1.43 (m, 2H), 0.95-0.80 (m, 1H).

Compound 56. N2-(3-chlorophenyl)-5-(furan-3-yl)-N4-(piperidin-4-yl)pyrimidine-2,4-diamine

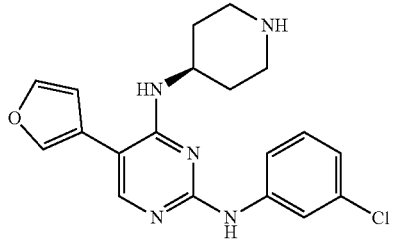

1H NMR (300 MHz, CDCl₃) δ 8.12 (d, J=1.9 Hz, 1H), 7.86 (s, 1H), 7.56 (dd, J=6.2, 4.5 Hz, 2H), 7.29 (s, 1H), 7.25-7.12 (m, 2H), 6.96 (dt, J=7.0, 2.0 Hz, 1H), 6.50 (dd, J=1.7, 0.8 Hz, 1H), 4.99 (d, J=7.6 Hz, 1H), 4.15 (ddd, J=13.8, 7.2, 3.1 Hz, 1H), 3.19 (d, J=12.8 Hz, 2H), 3.00-2.80 (m, 2H), 2.15 (d, J=15.2 Hz, 2H), 1.56-1.35 (m, 3H), 0.92-0.79 (m, 2H).

Compound 57. 1-(4-(2-(3,5-dichlorophenylamino)-5-phenylpyrimidin-4-ylamino)piperidin-1-yl)-2,2,2-trifluoroethanone

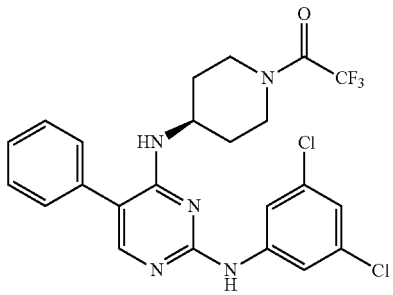

1H NMR (300 MHz, Chloroform-d) δ 7.92 (s, 1H), 7.81 (s, 1H), 7.67 (d, J=1.9 Hz, 2H), 7.51 (d, J=1.6 Hz, 1H), 7.49

(q, J=1.4 Hz, 1H), 7.46-7.42 (m, 1H), 7.38 (d, J=1.7 Hz, 1H), 7.35 (d, J=1.3 Hz, 1H), 7.01 (t, J=1.8 Hz, 1H), 4.99 (d, J=7.5 Hz, 1H), 4.57 (d, J=13.7 Hz, 1H), 4.37 (td, J=7.6, 6.7, 3.1 Hz, 1H), 4.11-4.01 (m, 1H), 3.48-3.34 (m, 1H), 3.07 (t, J=12.4 Hz, 1H), 2.27 (t, J=12.3 Hz, 2H), 1.46 (q, J=12.1 Hz, 2H);

LC/MS m/z calcd for $C_{23}H_{20}Cl_2F_3N_5O$ (MH$^+$) 508.5 found 509.2.

Compound 58. N2-(3,5-dichlorophenyl)-5-phenyl-N4-(piperidin-4-yl)pyrimidine-2,4-diamine

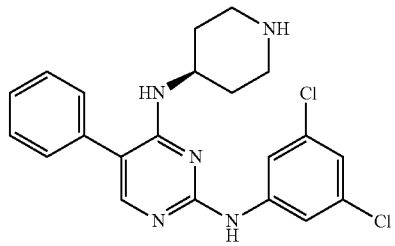

1H NMR (300 MHz, Chloroform-d) δ 7.86 (s, 1H), 7.69 (d, J=1.8 Hz, 2H), 7.62 (d, J=11.3 Hz, 1H), 7.49 (dd, J=7.5, 3.0 Hz, 2H), 7.45-7.35 (m, 3H), 6.98 (s, 1H), 5.03 (d, J=7.6 Hz, 1H), 4.23-4.02 (m, 1H), 3.94-3.75 (m, 1H), 2.96-2.72 (m, 2H), 2.11 (d, J=12.8 Hz, 2H), 1.91 (d, J=11.7 Hz, 2H), 1.43-1.31 (m, 2H);

LC/MS m/z calcd for $C_{21}H_{21}Cl_2N_5$ (MH$^+$) 413.9 found 415.0.

Compound 59. 1-(4-(2-(3,5-dichlorophenylamino)-5-(3-methoxyphenyl)pyrimidin-4-ylamino)piperidin-1-yl)-2,2,2-trifuloroethanone

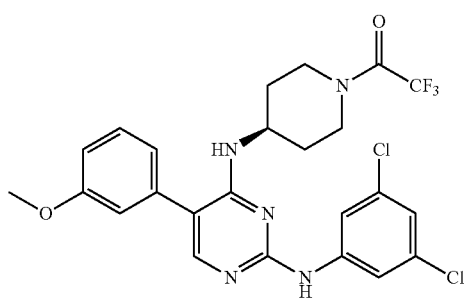

1H NMR (300 MHz, Chloroform-d) δ 7.90 (s, 1H), 7.64 (d, J=1.8 Hz, 2H), 7.58 (s, 1H), 7.40 (t, J=7.9 Hz, 1H), 6.99 (t, J=1.7 Hz, 1H), 6.97-6.89 (m, 2H), 6.88-6.83 (m, 1H), 5.04 (d, J=7.5 Hz, 1H), 4.54 (d, J=13.5 Hz, 1H), 4.40-4.24 (m, 1H), 4.09-3.98 (m, 1H), 3.85 (s, 3H), 3.38 (t, J=12.1 Hz, 1H), 3.05 (t, J=12.0 Hz, 1H), 2.24 (t, J=11.0 Hz, 2H), 1.44 (q, J=12.2 Hz, 2H).

Compound 60. N2-(3,5-dichlorophenyl)-5-(3-methoxyphenyl)-N4-(piperidin-4-yl)pyrimidine-2,4-diamine

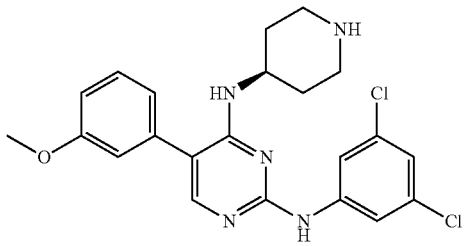

1H NMR (300 MHz, Chloroform-d) δ 7.85 (s, 1H), 7.66 (d, J=1.8 Hz, 2H), 7.47 (s, 1H), 7.39 (t, J=7.9 Hz, 1H), 6.96 (q, J=1.6 Hz, 2H), 6.94-6.91 (m, 1H), 6.89 (t, J=2.0 Hz, 1H), 5.08 (d, J=7.6 Hz, 1H), 4.23-4.07 (m, 1H), 3.85 (s, 3H), 3.11 (d, J=12.7 Hz, 2H), 2.85 (td, J=12.6, 12.1, 2.6 Hz, 2H), 2.10 (d, J=13.3 Hz, 2H), 2.05-1.95 (m, 1H), 1.37 (td, J=11.7, 4.0 Hz, 2H).

Compound 61. 1-(4-(2-(3,5-dichlorophenylamino)-5-(3,4-dimethoxyphenyl)pyrimidin-4-ylamino)piperidin-1-yl)-2,2,2-trifluoroethanone

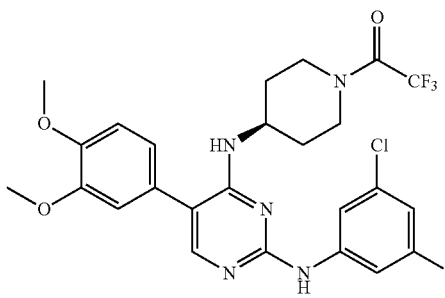

1H NMR (300 MHz, Chloroform-d) δ 8.31 (s, 1H), 7.91 (s, 1H), 7.68 (d, J=1.8 Hz, 2H), 7.02-6.96 (m, 2H), 6.91 (dd, J=8.2, 1.9 Hz, 1H), 6.84 (d, J=1.9 Hz, 1H), 5.04 (d, J=7.5 Hz, 1H), 4.61-4.52 (m, 1H), 4.43-4.27 (m, 1H), 4.06 (d, J=14.3 Hz, 1H), 3.95 (s, 3H), 3.92 (s, 4H), 3.63-3.53 (m, 1H), 3.46-3.33 (m, 1H), 3.07 (t, J=12.9 Hz, 1H), 2.27 (t, J=11.1 Hz, 2H), 1.45 (q, J=12.3, 11.8 Hz, 2H).

Compound 62. N2-(3,5-dichlorophenyl)-5-(3,4-dimethoxyphenyl)-N4-(piperidin-4-yl)pyrimidine-2,4-diamine

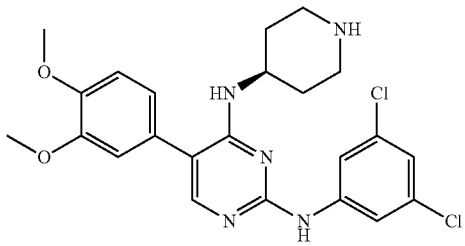

1H NMR (300 MHz, Chloroform-d) δ 7.84 (s, 1H), 7.66 (d, J=1.8 Hz, 2H), 7.45 (s, 1H), 6.98-6.94 (m, 2H), 6.91 (dd, J=8.2, 2.0 Hz, 1H), 6.85 (d, J=1.9 Hz, 1H), 5.03 (d, J=7.6 Hz, 1H), 4.19-4.04 (m, 1H), 3.94 (s, 3H), 3.90 (s, 3H), 3.10 (d, J=12.7 Hz, 2H), 2.91-2.79 (m, 2H), 2.09 (d, J=12.5 Hz, 2H), 1.80 (s, 1H), 1.35 (td, J=11.7, 4.0 Hz, 2H).

Compound 63. 1-(4-(2-(3-methyl-4-chlorophenylamino)-5-(3,4-dimethoxyphenyl)pyrimidin-4-ylamino)piperidin-1-yl)-2,2,2-trifloroethanone

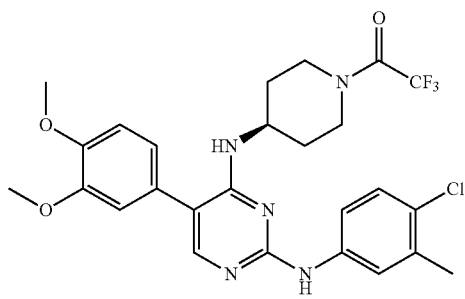

1H NMR (300 MHz, Chloroform-d) δ 7.85 (s, 1H), 7.48 (d, J=2.7 Hz, 1H), 7.44 (dd, J=8.6, 2.7 Hz, 1H), 7.24 (s, 1H), 6.97 (d, J=2.8 Hz, 1H), 6.94 (s, 1H), 6.87 (dd, J=8.2, 2.0 Hz, 1H), 6.80 (d, J=2.0 Hz, 1H), 4.90 (d, J=7.3 Hz, 1H), 4.47 (d, J=13.7 Hz, 1H), 4.27 (ddt, J=15.1, 11.0, 5.6 Hz, 1H), 4.02 (s, 1H), 3.93 (s, 3H), 3.89 (s, 3H), 3.29 (t, J=11.8 Hz, 1H), 3.01 (t, J=12.1 Hz, 1H), 2.38 (s, 3H), 2.20 (d, J=13.0 Hz, 2H), 1.70 (s, 1H), 1.47-1.37 (m, 2H).

Compound 64. 1-(4-(5-(3,4-dimethoxyphenyl)-2-(4-methoxyphenylamino)pyrimidin-4-ylamino)piperidin-1-yl)-2,2,2-trifluoroethanone

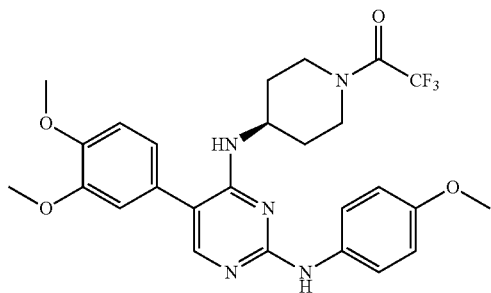

1H NMR (300 MHz, Chloroform-d) δ 7.83 (s, 1H), 7.50 (d, J=2.2 Hz, 1H), 7.48 (d, J=2.2 Hz, 1H), 6.93 (t, J=7.8 Hz, 2H), 6.90-6.87 (m, 2H), 6.85 (d, J=2.2 Hz, 1H), 6.80 (d, J=2.0 Hz, 1H), 4.86 (d, J=7.3 Hz, 1H), 4.46 (d, J=13.7 Hz, 1H), 4.31-4.16 (m, 1H), 3.99 (d, J=14.5 Hz, 1H), 3.92 (s, 3H), 3.89 (s, 3H), 3.81 (s, 3H), 3.33-3.22 (m, 1H), 2.99 (t, J=12.4 Hz, 1H), 2.19 (d, J=13.5 Hz, 2H), 1.75 (s, 1H), 1.42 (q, J=11.8 Hz, 2H).

Compound 65. 1-(4-(5-(3,4-dimethoxyphenyl)-2-(2-methoxyphenylamino)pyrimidin-4-ylamino)piperidin-1-yl)-2,2,2-trifluoroethanone

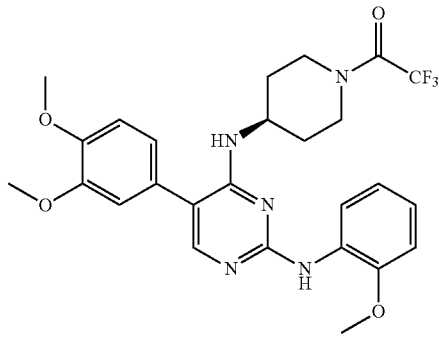

1H NMR (300 MHz, Chloroform-d) δ 8.52-8.45 (m, 1H), 7.88 (s, 1H), 7.57 (s, 1H), 7.00-6.86 (m, 5H), 6.82 (d, J=1.9 Hz, 1H), 4.89 (d, J=7.2 Hz, 1H), 4.49 (d, J=13.7 Hz, 1H), 4.34 (dd, J=10.8, 4.0 Hz, 1H), 4.02 (d, J=14.6 Hz, 1H), 3.92 (d, J=2.0 Hz, 6H), 3.90 (s, 3H), 3.32 (t, J=12.9 Hz, 1H), 3.04 (t, J=12.6 Hz, 1H), 2.22 (d, J=10.8 Hz, 2H), 1.46 (t, J=11.9 Hz, 2H).

Compound 66. N2-(3-methyl-4-chlorophenyl)-5-(3,4-dimethoxyphenyl)-N4-(piperidin-4-yl)pyrimidine-2,4-diamine

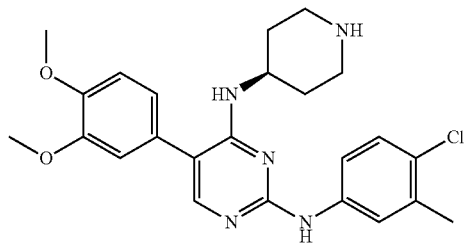

1H NMR (300 MHz, Chloroform-d) δ 7.81 (s, 1H), 7.55 (d, J=2.6 Hz, 1H), 7.44 (dd, J=8.6, 2.7 Hz, 1H), 7.24 (d, J=8.6 Hz, 1H), 7.10 (s, 1H), 6.96 (d, J=8.2 Hz, 1H), 6.90 (dd, J=8.1, 2.0 Hz, 1H), 6.84 (d, J=1.9 Hz, 1H), 4.97 (d, J=7.5 Hz, 1H), 4.19-4.01 (m, 1H), 3.93 (s, 3H), 3.90 (s, 3H), 3.16-3.06 (m, 2H), 2.85-2.72 (m, 2H), 2.38 (s, 3H), 2.08 (d, J=12.0 Hz, 2H), 1.42-1.31 (m, 2H).

Compound 67. 5-(3,4-dimethoxyphenyl)-N2-(4-methoxyphenyl)-N4-(piperidin-4-yl)pyrimidine-2,4-diamine

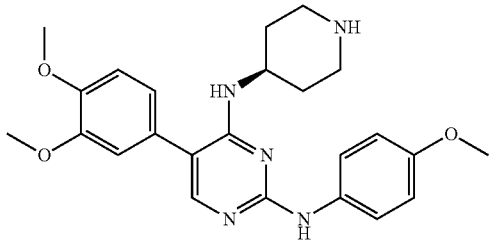

1H NMR (300 MHz, Chloroform-d) δ 7.80 (s, 1H), 7.54 (d, J=2.3 Hz, 1H), 7.52 (d, J=2.1 Hz, 1H), 6.95 (d, J=8.2 Hz, 1H), 6.90 (t, J=1.7 Hz, 1H), 6.88 (d, J=2.1 Hz, 2H), 6.86 (d, J=2.2 Hz, 1H), 6.84 (d, J=1.9 Hz, 1H), 4.92 (d, J=7.5 Hz, 1H), 4.17-3.99 (m, 1H), 3.93 (s, 3H), 3.89 (s, 3H), 3.81 (s, 3H), 3.10 (d, J=12.6 Hz, 2H), 2.82-2.69 (m, 2H), 2.06 (d, J=12.7 Hz, 3H), 1.38-1.28 (m, 2H).

Compound 68. 5-(3,4-dimethoxyphenyl)-N2-(2-methoxyphenyl)-N4-(piperidin-4-yl)pyrimidine-2,4-diamine

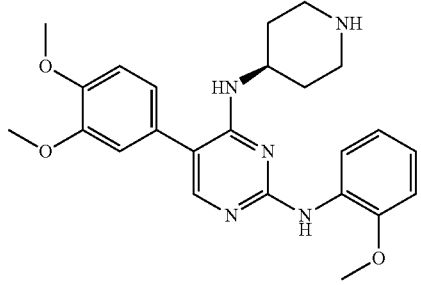

1H NMR (300 MHz, Chloroform-d) δ 8.61-8.51 (m, 1H), 7.85 (s, 1H), 7.57 (s, 1H), 6.97 (dd, J=2.5, 1.7 Hz, 1H), 6.96-6.93 (m, 2H), 6.93-6.91 (m, 1H), 6.89 (q, J=2.7 Hz, 1H), 6.85 (d, J=1.9 Hz, 1H), 4.94 (d, J=7.4 Hz, 1H), 4.26-4.12 (m, 1H), 3.93 (s, 3H), 3.91 (s, 3H), 3.90 (s, 3H), 3.16 (d, J=12.5 Hz, 2H), 2.82 (t, J=10.9 Hz, 2H), 2.14 (d, J=13.0 Hz, 2H), 1.46-1.31 (m, 2H).

Compound 69. 1-(4-(2-(3-chlorophenylamino)-5-(3,4-dimethoxyphenyl)pyrimidin-4-ylamino)piperidin-1-yl)-2,2,2-trifluoroethanone

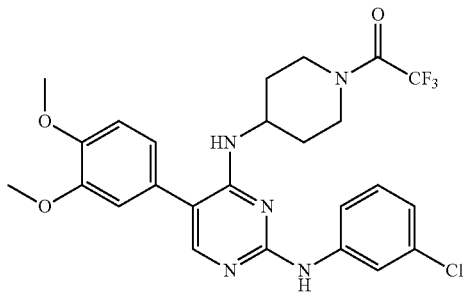 [SMILES: COc1ccc(-c2cnc(Nc3cccc(Cl)c3)nc2NC2CCN(C(=O)C(F)(F)F)CC2)cc1OC]

1H NMR (300 MHz, Chloroform-d) δ 8.14 (s, 1H), 7.83 (s, 1H), 7.19 (d, J=5.8 Hz, 2H), 7.15 (s, 1H), 6.96 (d, J=8.1 Hz, 2H), 6.91-6.86 (m, 1H), 6.81 (d, J=1.9 Hz, 1H), 5.00 (d, J=7.6 Hz, 1H), 4.23-4.09 (m, 1H), 3.94 (s, 3H), 3.90 (s, 3H), 3.15 (d, J=12.4 Hz, 2H), 2.87 (t, J=11.7 Hz, 2H), 2.12 (d, J=12.9 Hz, 2H), 1.46-1.34 (m, 2H).

Compound 70. 1-(4-(5-(1-methyl-1H-pyrazol-4-yl)-2-(2-(2,2,2-trifluoroacetyl)-1,2,3,4-tetrahydroisoquinolin-7-ylamino)pyrimidin-4-ylamino)piperidin-1-yl)-2,2,2-trifluoroethanone

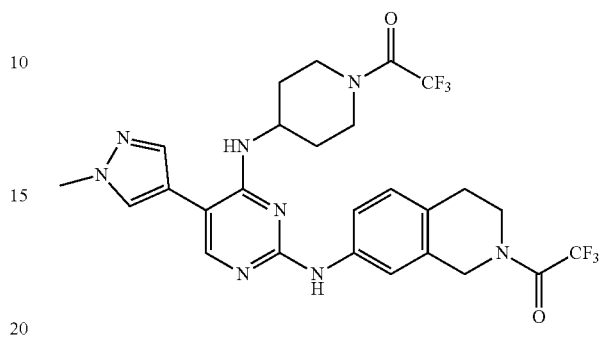

1H NMR (300 MHz, Chloroform-d) δ 7.77 (d, J=7.9 Hz, 1H), 7.57 (s, 2H), 7.51 (s, 1H), 7.45 (d, J=8.7 Hz, 1H), 7.15 (dd, J=9.2, 4.9 Hz, 1H), 6.02 (t, J=8.8 Hz, 1H), 4.75 (d, J=8.6 Hz, 2H), 4.63-4.51 (m, 1H), 4.30 (s, 1H), 4.06 (d, J=15.0 Hz, 1H), 3.99 (s, 3H), 3.89 (q, J=6.3 Hz, 2H), 3.48 (q, J=7.0 Hz, 1H), 3.25 (q, J=11.8, 11.2 Hz, 1H), 3.00-2.89 (m, 3H), 2.36 (s, 1H), 2.17 (d, J=12.7 Hz, 2H).

Compound 71. 1-(4-(2-(3,5-dichlorophenylamino)-5-(1-(2-hydroxyethyl)-1H-pyrazol-4-yl)pyrimidin-4-ylamino)piperidin-1-yl)-2,2,2-trifluoroethanone

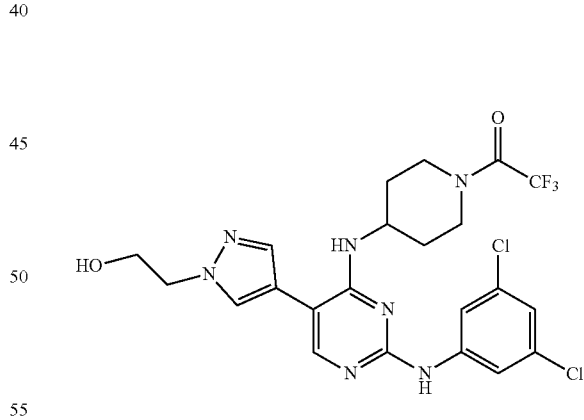

1H NMR (300 MHz, Chloroform-d) δ 7.82 (s, 1H), 7.62 (d, J=1.8 Hz, 2H), 7.58 (s, 1H), 7.53 (s, 1H), 7.45 (s, 1H), 6.99 (t, J=1.9 Hz, 1H), 4.99 (d, J=7.5 Hz, 1H), 4.56 (d, J=13.7 Hz, 1H), 4.37-4.28 (m, 3H), 4.11-4.03 (m, 3H), 3.75 (s, 1H), 3.38 (t, J=13.2 Hz, 1H), 3.05 (t, J=12.8 Hz, 1H), 2.25 (t, J=12.3 Hz, 3H), 1.46 (q, J=12.1 Hz, 2H).

Compound 72. 5-(1-methyl-1H-pyrazol-4-yl)-N4-(piperidin-4-yl)-N2-(1,2,3,4-tetrahydroisoquinolin-7-yl)pyrimidine-2,4-diamine

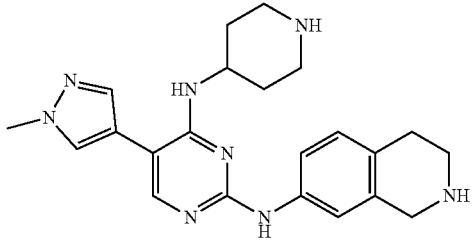 [SMILES: Cn1cc(-c2cnc(Nc3ccc4c(c3)CNCC4)nc2NC2CCNCC2)cn1]

1H NMR (300 MHz, MeOH-d₄) δ 7.79 (s, 1H), 7.76 (s, ¹H), 7.57 (d, J=8.3 Hz, 2H), 7.51 (s, 1H), 7.19 (d, J=8.4 Hz, 1H), 4.32 (s, 2H), 3.97 (s, 3H), 3.47 (d, J=5.9 Hz, 3H), 3.12-3.03 (m, 3H), 2.25 (d, J=14.0 Hz, 2H), 1.94 (d, J=0.7 Hz, 3H), 1.75 (d, J=13.2 Hz, 2H).

Compound 73. N2-(3,5-dichlorophenyl)-N4-(piperidin-4-yl)-5-(1-(piperidin-4-yl)-1H-pyrazol-4-yl)pyrimidine-2,4-diamine

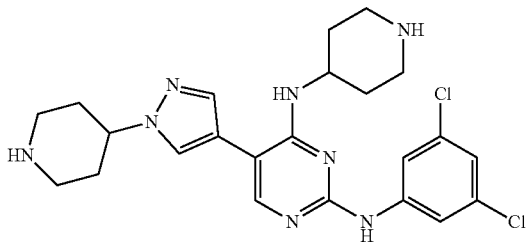 [SMILES: Clc1cc(Cl)cc(Nc2ncc(-c3cnn(C4CCNCC4)c3)c(NC3CCNCC3)n2)c1]

1H NMR (300 MHz, MeOH-d₄) δ 7.85 (s, 1H), 7.80 (s, 1H), 7.79 (s, 1H), 7.79 (s, 1H), 7.63 (s, 1H), 6.97 (d, J=1.9 Hz, 1H), 4.42-4.29 (m, 1H), 4.29-4.09 (m, 1H), 3.19 (dd, J=21.9, 13.0 Hz, 4H), 2.83 (dt, J=22.5, 11.6 Hz, 4H), 2.15 (t, J=13.1 Hz, 3H), 2.09-1.94 (m, 3H), 1.63-1.43 (m, 3H).

Compound 74. N2-(3-chlorophenyl)-5-(3,4-dimethoxyphenyl)-N4-(piperidin-4-yl)pyrimidine-2,4-diamine

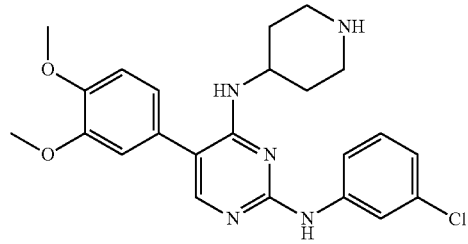 [SMILES: COc1ccc(-c2cnc(Nc3cccc(Cl)c3)nc2NC2CCNCC2)cc1OC]

1H NMR (300 MHz, Chloroform-d) δ 8.13 (s, 1H), 7.82 (s, 1H), 7.20 (d, J=5.8 Hz, 2H), 7.16 (s, 1H), 6.97 (d, J=8.1 Hz, 2H), 6.92-6.88 (m, 1H), 6.84 (d, J=1.9 Hz, 1H), 5.00 (d, J=7.6 Hz, 1H), 4.23-4.09 (m, 1H), 3.94 (s, 3H), 3.90 (s, 3H), 3.15 (d, J=12.4 Hz, 2H), 2.87 (t, J=11.7 Hz, 2H), 2.12 (d, J=12.9 Hz, 2H), 1.46-1.34 (m, 2H).

Compound 75. 2-(4-(2-(3,5-dichlorophenylamino)-4-(piperidin-4-ylamino)pyrimidin-5-yl)-1H-pyrazol-1-yl)ethanol

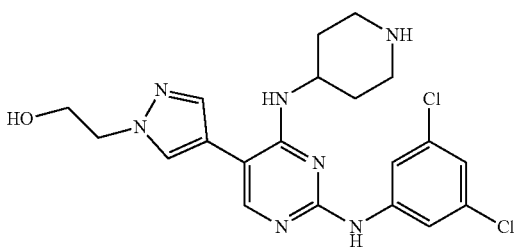 [SMILES: OCCn1cc(-c2cnc(Nc3cc(Cl)cc(Cl)c3)nc2NC2CCNCC2)cn1]

1H NMR (300 MHz, MeOH-d₄) δ 7.81 (t, J=2.2 Hz, 4H), 7.64 (s, 1H), 6.97 (d, J=1.8 Hz, 1H), 4.31 (t, J=5.2 Hz, 2H), 4.19 (d, J=10.9 Hz, 1H), 3.96 (t, J=5.2 Hz, 2H), 3.12 (d, J=12.9 Hz, 2H), 2.84 (dd, J=13.6, 11.0 Hz, 2H), 2.11-1.99 (m, 2H), 1.59-1.40 (m, 3H).

Compound 76. 1-(4-(5-(1-(2-hydroxyethyl)-1H-pyrazol-4-yl)-2-(2-(2,2,2-trifluoroacetyl)-1,2,3,4-tetrahydroisoquinolin-7-ylamino)pyrimidin-4-ylamino)piperidin-1-yl)-2.2.2-trifluoroethanone

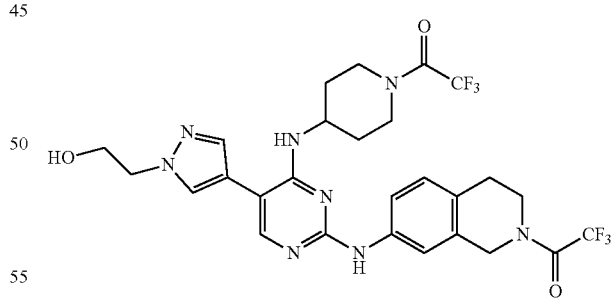

1H NMR (300 MHz, Chloroform-d) δ 7.79 (d, J=2.6 Hz, 1H), 7.56 (s, 1H), 7.53 (s, 1H), 7.50-7.38 (m, 3H), 7.10 (t, J=7.3 Hz, 1H), 4.95 (d, J=7.2 Hz, 1H), 4.76 (d, J=12.4 Hz, 2H), 4.49 (d, J=13.3 Hz, 1H), 4.31 (t, J=4.8 Hz, 3H), 4.06 (t, J=4.7 Hz, 3H), 3.88 (dt, J=11.5, 6.0 Hz, 2H), 3.31 (t, J=12.8 Hz, 1H), 3.03 (d, J=12.5 Hz, 1H), 2.92 (q, J=6.3 Hz, 2H), 2.20 (s, 2H), 1.44 (d, J=21.2 Hz, 3H).

Compound 77. 1-(4-(2-(3-methyl-4-chlorophenylamino)-5-(1-(2-hydroxyethyl)-1H-pyrazol-4-yl)pyrimidin-4-ylamino)piperidin-1-yl)-2,2,2-trifluoroethanone

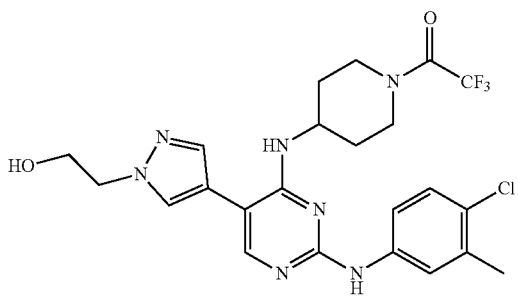 [SMILES: Cc1cc(Nc2ncc(-c3cnn(CCO)c3)c(NC3CCN(C(=O)C(F)(F)F)CC3)n2)ccc1Cl]

1H NMR (300 MHz, Chloroform-d) δ 7.81 (s, 1H), 7.56 (s, 1H), 7.51 (s, 1H), 7.46 (d, J=2.6 Hz, 1H), 7.42 (dd, J=8.5, 2.7 Hz, 1H), 6.97 (s, 1H), 4.88 (d, J=7.3 Hz, 1H), 4.49 (d, J=13.8 Hz, 1H), 4.38-4.27 (m, 2H), 4.25 (d, J=4.1 Hz, 1H), 4.11-4.03 (m, 2H), 4.00 (s, 1H), 3.29 (t, J=13.0 Hz, 1H), 3.00 (t, J=12.8 Hz, 1H), 2.37 (s, 3H), 2.19 (s, 2H), 1.56-1.35 (m, 2H).

Compound 78. 1-(4-(5-(1-(2-hydroxyethyl)-1H-pyrazol-4-yl)-2-(4-methoxyphenylamino)pyrimidin-4-ylamino)piperidin-1-yl)-2,2,2-trifluoroethanone

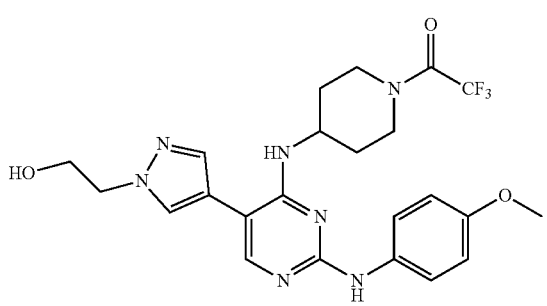 [SMILES: COc1ccc(Nc2ncc(-c3cnn(CCO)c3)c(NC3CCN(C(=O)C(F)(F)F)CC3)n2)cc1]

1H NMR (300 MHz, Chloroform-d) δ 7.73 (s, 1H), 7.54 (s, 1H), 7.50 (s, 1H), 7.47 (d, J=2.2 Hz, 1H), 7.45 (d, J=2.1 Hz, 1H), 7.06 (s, 1H), 6.90-6.83 (m, 2H), 4.87 (d, J=7.2 Hz, 1H), 4.49 (dd, J=11.2, 6.7 Hz, 1H), 4.34-4.27 (m, 2H), 4.21 (dq, J=11.0, 6.8, 5.5 Hz, 1H), 4.09-4.00 (m, 3H), 3.80 (s, 3H), 3.26 (ddd, J=14.4, 11.9, 2.7 Hz, 2H), 2.96 (t, J=12.5 Hz, 1H), 2.27-2.11 (m, 2H), 1.52-1.33 (m, 3H).

Compound 79. 2-(4-(4-(piperidin-4-ylamino)-2-(1,2,3,4-tetrahydroisoquinolin-7-ylamino)pyrimidin-5-yl)-1H-pyrazol-1-yl)ethanol

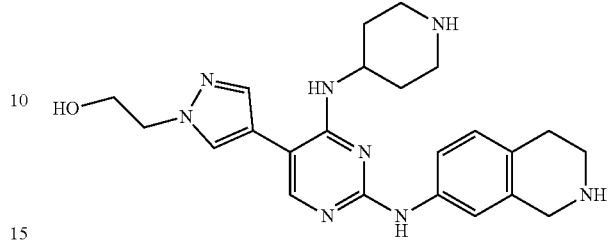

1H NMR (300 MHz, Chloroform-d) δ 7.76 (s, 1H), 7.58 (s, 1H), 7.51 (s, 1H), 7.40 (d, J=2.0 Hz, 1H), 7.32-7.27 (m, 1H), 7.02 (d, J=8.3 Hz, 1H), 6.91 (s, 1H), 4.90 (d, J=7.7 Hz, 1H), 4.30 (t, J=4.7 Hz, 3H), 4.10 (d, J=7.1 Hz, 1H), 4.05 (t, J=4.8 Hz, 3H), 4.01 (s, 2H), 3.19-3.05 (m, 5H), 2.80-2.70 (m, 4H), 2.06 (d, J=12.5 Hz, 3H), 1.41-1.28 (m, 5H).

Compound 80. 2-(4-(2-(3-methyl-4-chlorophenylamino)-4-(piperidin-4-ylamino)pyrimidin-5-yl)-1H-pyrazol-1-yl)ethanol

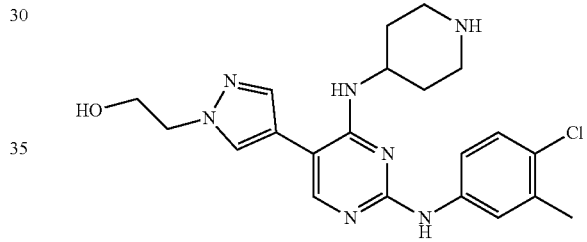

1H NMR (300 MHz, Chloroform-d) δ 7.73 (s, 1H), 7.56 (s, 1H), 7.53 (s, 1H), 7.51 (d, J=2.6 Hz, 1H), 7.41 (dd, J=8.6, 2.6 Hz, 1H), 7.23 (d, J=8.6 Hz, 1H), 7.14 (s, 1H), 4.94 (d, J=7.6 Hz, 1H), 4.30 (dd, J=5.6, 4.0 Hz, 2H), 4.09 (q, J=3.3 Hz, 1H), 4.04 (dd, J=5.6, 4.0 Hz, 2H), 3.08 (dt, J=12.7, 3.7 Hz, 2H), 2.99-2.79 (m, 1H), 2.73 (td, J=12.4, 11.9, 2.6 Hz, 3H), 2.36 (s, 3H), 2.10-1.99 (m, 2H), 1.41-1.26 (m, 3H).

Compound 81. 2-(4-(2-(4-methoxyphenylamino)-4-(piperidin-4-ylamino)pyrimidin-5-yl)-1H-pyrazol-1-yl)ethanol

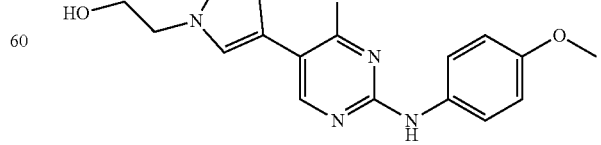

1H NMR (300 MHz, Chloroform-d) δ 7.76 (s, 1H), 7.57 (s, 1H), 7.51 (d, J=2.1 Hz, 2H), 7.49 (d, J=2.1 Hz, 1H), 6.88

(d, J=3.3 Hz, 2H), 6.85 (d, J=2.2 Hz, 1H), 4.89 (d, J=7.5 Hz, 1H), 4.37-4.25 (m, 2H), 4.09 (s, 1H), 4.05 (dd, J=5.5, 4.0 Hz, 2H), 3.80 (s, 3H), 3.12 (d, J=12.8 Hz, 2H), 2.76 (t, J=11.4 Hz, 2H), 2.07 (d, J=13.3 Hz, 3H), 1.43-1.29 (m, 3H).

Compound 82. 1-(7-(2-(3,5-dichlorophenylamino)-5-(1-methyl-1H-pyrazol-4-yl)pyrimidin-4-ylamino)-3,4-dihydroisoquinolin-2(1H)-yl)-2,2,2-trifluoroethanone

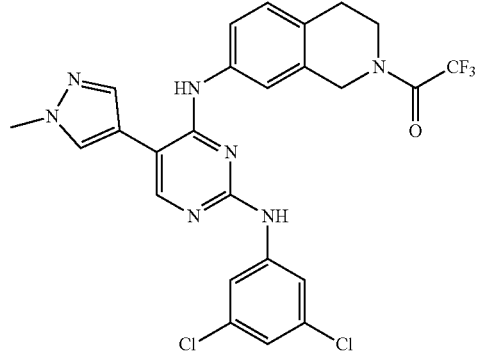 [SMILES: Cn1cc(-c2cnc(Nc3cc(Cl)cc(Cl)c3)nc2Nc2ccc3c(c2)CN(C(=O)C(F)(F)F)CC3)cn1]

1H NMR (300 MHz, Chloroform-d) δ 7.99 (s, 1H), 7.65 (s, 1H), 7.53 (s, 2H), 7.52-7.46 (m, 2H), 7.32 (d, J=8.5 Hz, 1H), 7.28 (s, 1H), 7.23-7.14 (m, 2H), 6.98-6.92 (m, 1H), 6.83 (s, 1H), 4.72 (d, J=14.2 Hz, 2H), 4.02 (s, 3H), 3.87 (dt, J=12.8, 6.0 Hz, 3H), 2.94 (t, J=5.3 Hz, 3H).

Compound 83. 1-(7-(2-(3-methyl-4-chlorophenylamino)-5-(1-methyl-1H-pyrazol-4-yl)pyrimidin-4-ylamino)-3,4-dihydroisoquinolin-2(1H)-yl)-2,2,2-trifluoroethanone

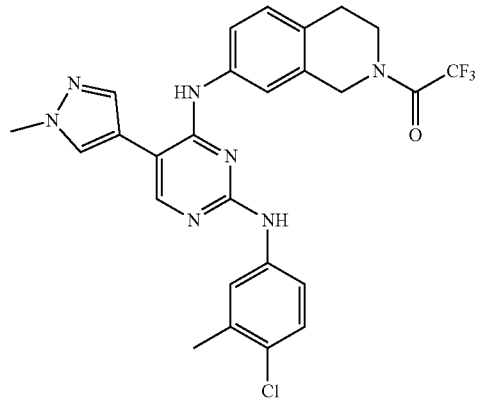 [SMILES: Cc1cc(Nc2ncc(-c3cnn(C)c3)c(Nc3ccc4c(c3)CN(C(=O)C(F)(F)F)CC4)n2)ccc1Cl]

1H NMR (300 MHz, Chloroform-d) δ 7.97 (s, 1H), 7.62 (s, 1H), 7.50 (s, 1H), 7.45-7.34 (m, 3H), 7.33 (s, 1H), 7.23 (d, J=8.4 Hz, 1H), 7.12 (t, J=8.2 Hz, 1H), 7.02 (s, 1H), 6.78 (s, 1H), 4.71 (d, J=20.2 Hz, 2H), 4.01 (s, 3H), 3.88 (dt, J=12.4, 6.0 Hz, 2H), 2.94 (q, J=5.5 Hz, 2H), 2.31 (d, J=2.2 Hz, 3H).

Compound 84. N2-(3,5-dichlorophenyl)-5-(1-methyl-1H-pyrazol-4-yl)-N4-(1,2,3,4-tetrahydroisoquinolin-7-yl)pyrimidine-2,4-diamine

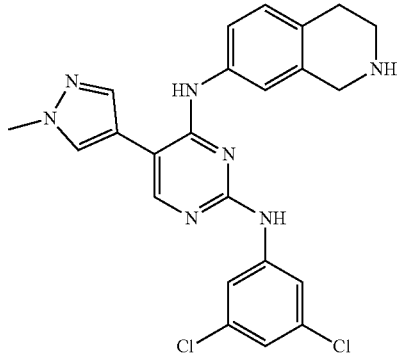 [SMILES: Cn1cc(-c2cnc(Nc3cc(Cl)cc(Cl)c3)nc2Nc2ccc3c(c2)CNCC3)cn1]

1H NMR (300 MHz, Chloroform-d) δ 7.96 (s, 1H), 7.64 (s, 1H), 7.51 (d, J=2.1 Hz, 3H), 7.31 (d, J=2.5 Hz, 1H), 7.28 (d, J=5.9 Hz, 1H), 7.11 (d, J=8.2 Hz, 1H), 7.03 (d, J=2.2 Hz, 1H), 6.94 (t, J=1.9 Hz, 1H), 6.76 (s, 1H), 4.01 (s, 3H), 3.96 (s, 2H), 3.13 (t, J=5.9 Hz, 2H), 2.76 (t, J=6.0 Hz, 2H), 1.73 (s, 1H).

Compound 85. N2-(3-methyl-4-chlorophenyl)-5-(1-methyl-1H-pyrazol-4-yl)-N4-(1,2,3,4-tetrahydroisoquinolin-7-yl)pyrimidine-2,4-diamine

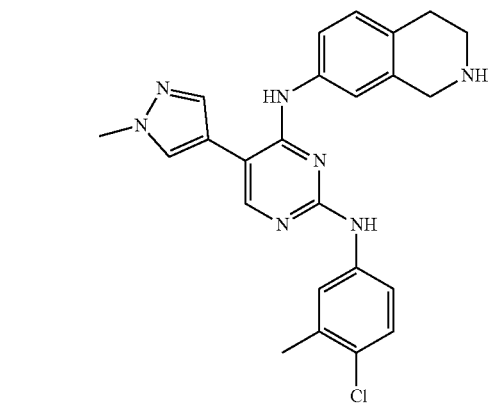 [SMILES: Cc1cc(Nc2ncc(-c3cnn(C)c3)c(Nc3ccc4c(c3)CNCC4)n2)ccc1Cl]

1H NMR (300 MHz, Chloroform-d) δ 7.94 (s, 1H), 7.62 (d, J=0.9 Hz, 1H), 7.50 (s, 1H), 7.43 (d, J=2.7 Hz, 1H), 7.37 (dd, J=8.6, 2.7 Hz, 1H), 7.33-7.28 (m, 1H), 7.21 (d, J=8.6 Hz, 1H), 7.10 (d, J=2.4 Hz, 1H), 7.07 (s, 1H), 7.04 (d, J=4.0 Hz, 1H), 6.73 (s, 1H), 4.01 (s, 3H), 3.95 (s, 2H), 3.15 (t, J=5.9 Hz, 2H), 2.78 (t, J=5.9 Hz, 2H), 2.30 (s, 3H), 1.70 (s, 1H).

Compound 86. N-((1s,4s)-4-(5-(1-methyl-1H-pyrazol-4-yl)-2-(2-(2,2,2-trifluoroacetyl)-1,2,3,4-tetrahydroisoquinolin-7-ylamino)pyrimidin-4-ylamino)cyclohexyl)-2,2,2-trifluoroacetamide

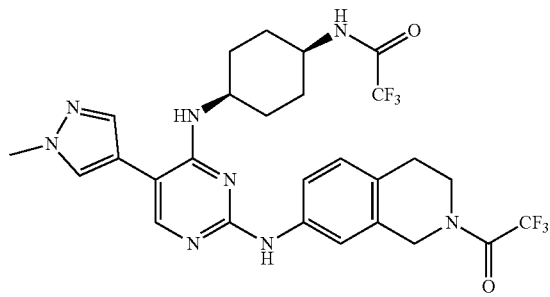 [SMILES: Cn1cc(-c2cnc(Nc3ccc4c(c3)CN(C(=O)C(F)(F)F)CC4)nc2N[C@H]2CC[C@@H](NC(=O)C(F)(F)F)CC2)cn1]

1H NMR (300 MHz, Chloroform-d) δ 7.83 (d, J=2.9 Hz, 1H), 7.57 (s, 1H), 7.56-7.54 (m, 1H), 7.47 (s, 1H), 7.37 (ddd, J=16.1, 8.2, 2.2 Hz, 1H), 7.19 (d, J=21.2 Hz, 1H), 7.09 (t, J=9.1 Hz, 1H), 6.38 (d, J=7.2 Hz, 1H), 5.06 (t, J=7.1 Hz, 1H), 4.75 (d, J=22.2 Hz, 2H), 4.24-4.14 (m, 1H), 4.02-4.00 (m, 1H), 3.99 (s, 4H), 3.89 (t, J=6.1 Hz, 1H), 3.85 (t, J=5.9 Hz, 1H), 2.91 (dt, J=9.8, 6.0 Hz, 2H), 1.96-1.83 (m, 5H), 1.69 (t, J=9.7 Hz, 4H).

Compound 87. 1-(7-(2-(3,5-dichlorophenylamino)-5-(1-(2-hydroxyethyl)-1H-pyrazol-4-yl)pyrimidin-4-ylamino)-3,4-dihydroisoquinolin-2(1H)-yl)-2,2,2-trifluoroethanone

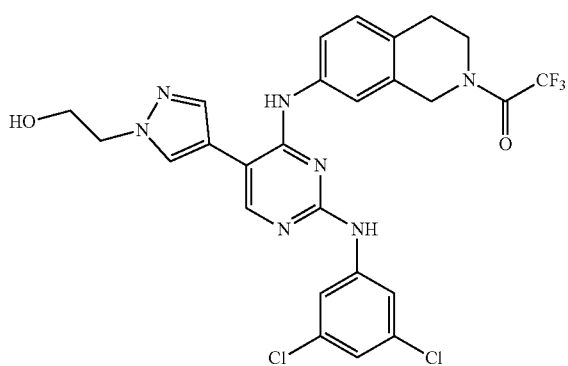 [SMILES: O=C(N1CCc2ccc(Nc3nc(Nc4cc(Cl)cc(Cl)c4)ncc3-c3cnn(CCO)c3)cc2C1)C(F)(F)F]

1H NMR (300 MHz, Chloroform-d) δ 7.96 (s, 1H), 7.68 (s, 1H), 7.65 (s, 1H), 7.52-7.43 (m, 3H), 7.34 (dd, J=19.8, 8.2 Hz, 1H), 7.24 (s, 1H), 7.16 (d, J=9.6 Hz, 2H), 6.94 (s, 1H), 6.85 (s, 1H), 4.71 (d, J=10.5 Hz, 2H), 4.35 (t, J=4.7 Hz, 2H), 4.10 (t, J=4.7 Hz, 2H), 3.85 (q, J=7.1, 5.8 Hz, 2H), 3.41-3.04 (m, 1H), 2.94 (d, J=6.6 Hz, 2H).

Compound 88. N4-((1s,4s)-4-aminocyclohexyl)-5-(1-methyl-1H-pyrazol-4-yl)-N2-(1,2,3,4-tetrahydroisoquinolin-7-yl)pyrimidin-2,4-diamine

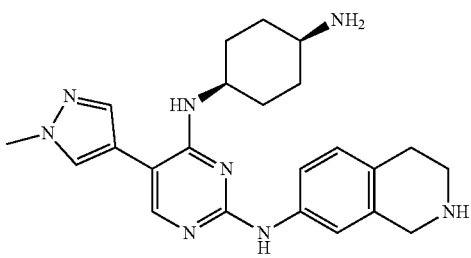 [SMILES: Cn1cc(-c2cnc(Nc3ccc4c(c3)CNCC4)nc2N[C@H]2CC[C@@H](N)CC2)cn1]

1H NMR (300 MHz, Chloroform-d) δ 7.79 (d, J=8.5 Hz, 1H), 7.56 (d, J=4.3 Hz, 1H), 7.48-7.41 (m, 1H), 7.37 (d, J=2.2 Hz, 1H), 7.30 (dd, J=8.2, 2.3 Hz, 1H), 7.03 (d, J=3.1 Hz, 1H), 7.00 (d, J=5.3 Hz, 1H), 6.35 (d, J=7.6 Hz, 1H), 5.01 (d, J=6.9 Hz, 1H), 4.19 (s, 1H), 4.01 (s, 2H), 3.98 (d, J=2.2 Hz, 3H), 3.14 (t, J=5.9 Hz, 2H), 2.75 (t, J=5.8 Hz, 2H), 1.87 (q, J=13.0, 9.3 Hz, 3H), 1.78-1.59 (m, 6H), 1.38 (d, J=5.8 Hz, 1H).

Compound 89. 2-(4-(2-(3,5-dichlorophenylamino)-4-(1,2,3,4-tetrahydroisoquinolin-7-ylamino)pyrimidin-5-yl)-1H-pyrazol-1-yl)ethanol 1H NMR (300 MHz, Chloroform-d) δ 7.92 (s, 1H), 7.66 (s, 1H), 7.57 (s, 1H), 7.50 (d, J=1.8 Hz, 2H), 7.48-7.39 (m, 1H), 7.25 (s, 1H), 7.10 (d, J=8.3 Hz, 1H), 6.99 (s, 1H), 6.93 (t, J=1.8 Hz, 1H), 6.78 (s, 1H), 4.32 (t, J=4.7 Hz, 2H), 4.07 (t, J=4.7 Hz, 2H), 3.91 (s, 2H), 3.12 (t, J=5.9 Hz, 2H), 2.76 (t, J=6.0 Hz, 2H), 1.35-1.28 (m, 1H), 0.87 (d, J=7.3 Hz, 1H).

Compound 90. N-((1s,4s)-4-(2-(3-chlorophenylamino)-5-(1-methyl-1H-pyrazol-4-yl)pyrimidin-4-ylamino)cyclohexyl)-2,2,2-trifluoroacetamide

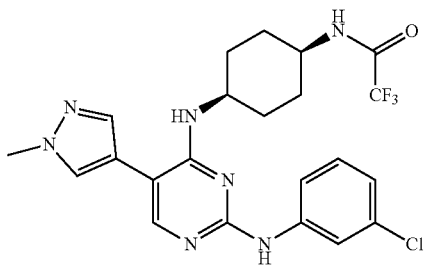 [SMILES: Cn1cc(-c2cnc(Nc3cccc(Cl)c3)nc2N[C@H]2CC[C@@H](NC(=O)C(F)(F)F)CC2)cn1]

1H NMR (300 MHz, Chloroform-d) δ 8.10 (d, J=2.4 Hz, 1H), 7.83 (s, 1H), 7.58 (s, 1H), 7.46 (s, 1H), 7.23 (s, 1H), 7.20 (d, J=4.0 Hz, 1H), 7.18 (s, 1H), 6.96 (dt, J=6.8, 2.2 Hz, 1H), 6.29 (s, 1H), 5.06 (d, J=7.0 Hz, 1H), 4.29-4.15 (m, 1H), 4.04 (s, 1H), 4.00 (s, 3H), 1.94 (tt, J=13.0, 3.9 Hz, 5H), 1.70 (d, J=14.9 Hz, 4H).

Compound 91. N-((1s,4s)-4-(2-(3-acetylphenylamino)-5-(1-methyl-1H-pyrazol-4-yl)pyrimidin-4-ylamino)cyclohexyl)-2,2,2-trifluoroacetamide

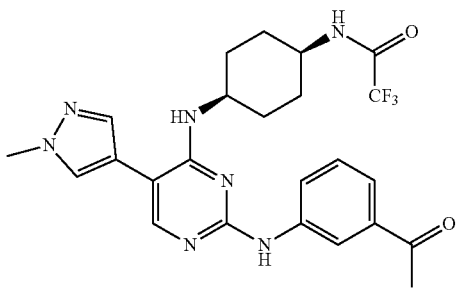 [SMILES: CC(=O)c1cccc(Nc2ncc(-c3cnn(C)c3)c(N[C@H]3CC[C@@H](NC(=O)C(F)(F)F)CC3)n2)c1]

1H NMR (300 MHz, Chloroform-d) δ 8.40 (t, J=1.9 Hz, 1H), 7.86 (s, 1H), 7.75 (d, J=7.8 Hz, 1H), 7.59 (s, 1H), 7.57 (d, J=1.6 Hz, 1H), 7.55 (d, J=1.4 Hz, 1H), 7.50 (s, 1H), 7.38 (t, J=7.9 Hz, 1H), 6.38 (s, 1H), 5.10 (d, J=7.1 Hz, 1H), 4.32 (s, 1H), 4.03 (s, 1H), 3.99 (s, 4H), 2.61 (s, 3H), 1.93 (q, J=4.1 Hz, 4H), 1.77-1.55 (m, 5H).

Compound 92. N-((1s,4s)-4-(2-(m-toluidino)-5-(1-methyl-1H-pyrazol-4-yl)pyrimidin-4-ylamino)cyclohexyl)-2,2,2-trifluoroacetamide

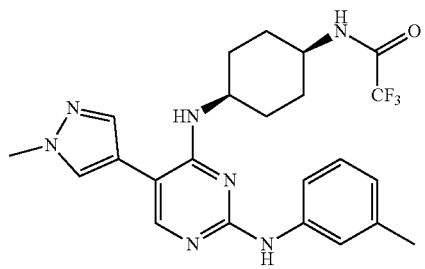 [SMILES: Cc1cccc(Nc2ncc(-c3cnn(C)c3)c(N[C@H]3CC[C@@H](NC(=O)C(F)(F)F)CC3)n2)c1]

1H NMR (300 MHz, Chloroform-d) δ 7.82 (s, 1H), 7.57 (s, 1H), 7.46 (d, J=4.6 Hz, 2H), 7.41 (d, J=8.1 Hz, 1H), 7.19 (t, J=7.8 Hz, 1H), 7.01 (s, 1H), 6.83 (d, J=7.5 Hz, 1H), 6.30 (s, 1H), 5.02 (d, J=6.9 Hz, 1H), 4.21 (s, 1H), 3.99 (s, 3H), 2.36 (s, 3H), 1.90 (td, J=18.2, 15.7, 6.8 Hz, 5H), 1.70 (d, J=9.1 Hz, 4H).

Compound 93. 1-(7-(2-(3-chlorophenylamino)-5-(1-(2-hydroxyethyl)-1H-pyrazol-4-yl)pyrimidin-4-ylamino)-3,4-dihydroisoquinolin-2(1H)-yl)-2,2,2-trifluoroethanone

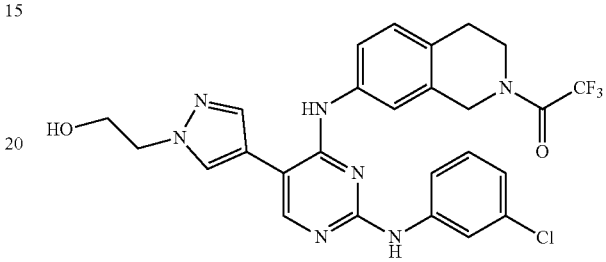

1H NMR (300 MHz, Chloroform-d) δ 7.92 (d, J=0.9 Hz, 1H), 7.76 (t, J=1.9 Hz, 1H), 7.66 (s, 1H), 7.63 (s, 1H), 7.39 (d, J=4.7 Hz, 1H), 7.33 (d, J=2.1 Hz, 1H), 7.29 (d, J=3.3 Hz, 1H), 7.25-7.21 (m, 1H), 7.20-7.16 (m, 1H), 7.13 (d, J=8.8 Hz, 1H), 6.98 (dq, J=7.5, 1.8 Hz, 1H), 6.84 (s, 1H), 4.69 (d, J=10.5 Hz, 2H), 4.37-4.31 (m, 2H), 4.12-4.06 (m, 2H), 3.88 (t, J=6.0 Hz, 1H), 3.83 (t, J=5.9 Hz, 1H), 2.92 (t, J=5.8 Hz, 2H).

Compound 94. 1-(7-(2-(3-fluorophenylamino)-5-(1-(2-hydroxyethyl)-1H-pyrazol-4-yl)pyrimidin-4-ylamino)-3,4-dihydroisoquinolin-2(1H)-yl)-2,2,2-trifluoroethanone

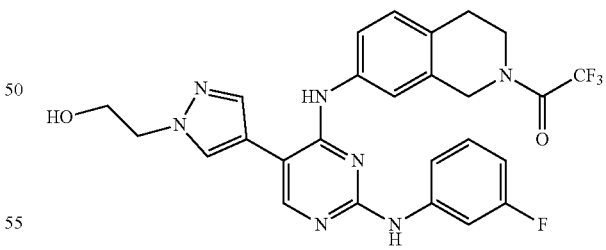

1H NMR (300 MHz, Chloroform-d) δ 7.95 (s, 1H), 7.68 (s, 2H), 7.64 (d, J=2.7 Hz, 2H), 7.39 (t, J=3.3 Hz, 1H), 7.26-7.19 (m, 2H), 7.15 (t, J=8.3 Hz, 1H), 7.00 (t, J=7.3 Hz, 1H), 6.82 (s, 1H), 6.74-6.64 (m, 1H), 4.72 (d, J=12.3 Hz, 2H), 4.39-4.31 (m, 2H), 4.13-4.07 (m, 2H), 3.87 (dd, J=13.6, 7.0 Hz, 2H), 3.31-3.12 (m, 1H), 2.97 (s, 2H).

Compound 95. N-((1s,4s)-4-(2-(3,5-dichlorophenylamino)-5-(1-(2-hydroxyethyl)-1H-pyrazol-4-yl)pyrimidin-4-ylamino)cyclohexyl)-2,2,2-trifluoroacetamide

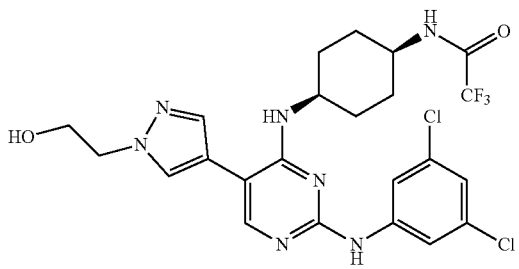 [SMILES: O=C(N[C@H]1CC[C@@H](Nc2nc(Nc3cc(Cl)cc(Cl)c3)ncc2-c2cnn(CCO)c2)CC1)C(F)(F)F]

1H NMR (300 MHz, Chloroform-d) δ 7.82 (s, 1H), 7.66-7.59 (m, 4H), 6.97 (s, 1H), 6.52 (s, 1H), 5.16 (d, J=7.2 Hz, 1H), 4.40-4.31 (m, 2H), 4.24 (s, 1H), 4.08 (t, J=4.7 Hz, 2H), 4.00 (s, 1H), 1.90 (dd, J=10.5, 5.3 Hz, 5H), 1.70 (ddd, J=14.0, 6.8, 4.3 Hz, 5H).

Compound 96. N-((1s,4s)-4-(5-(1-(2-hydroxyethyl)-1H-pyrazol-4-yl)-2-(2-(2,2,2-trifluoroacetyl)-1,2,3,4-tetrahydroisoquinolin-7-ylamino)pyrimidin-4-ylamino)cyclohexyl)-2,2,2-trifluoroacetamide

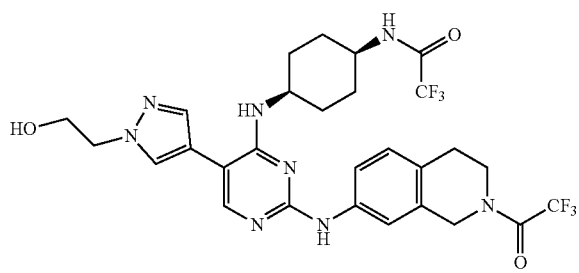 [SMILES: O=C(N[C@H]1CC[C@@H](Nc2nc(Nc3ccc4c(c3)CN(C(=O)C(F)(F)F)CC4)ncc2-c2cnn(CCO)c2)CC1)C(F)(F)F]

1H NMR (300 MHz, Chloroform-d) δ 7.72 (d, J=3.8 Hz, 1H), 7.66 (s, 1H), 7.58 (s, 2H), 7.51 (s, 1H), 7.37 (t, J=9.2 Hz, 1H), 7.09 (t, J=7.3 Hz, 1H), 6.92 (s, 1H), 5.34-5.22 (m, 1H), 4.74 (d, J=11.8 Hz, 2H), 4.41-4.29 (m, 2H), 4.24 (s, 1H), 4.05 (d, J=5.5 Hz, 2H), 3.94 (s, 1H), 3.86 (dt, J=11.3, 6.1 Hz, 2H), 2.92 (t, J=5.9 Hz, 2H), 1.80 (s, 6H), 1.61 (d, J=10.6 Hz, 2H).

Compound 97. N4-((1s,4s)-4-aminocyclohexyl)-N2-(3-chlorophenyl)-5-(1-methyl-1H-pyrazol-4-yl)pyrimidine-2,4-diamine

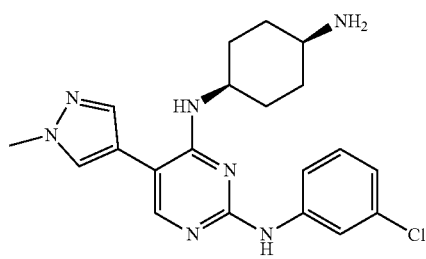 [SMILES: Cn1cc(-c2cnc(Nc3cccc(Cl)c3)nc2N[C@H]2CC[C@@H](N)CC2)cn1]

1H NMR (300 MHz, Chloroform-d) δ 8.09 (d, J=2.5 Hz, 1H), 7.80 (s, 1H), 7.56 (s, 1H), 7.43 (s, 1H), 7.19 (d, J=6.4 Hz, 2H), 7.11 (s, 1H), 6.94 (dt, J=6.2, 2.1 Hz, 1H), 5.14 (d, J=7.3 Hz, 1H), 4.19 (s, 1H), 3.98 (s, 3H), 3.02 (s, 1H), 1.80 (t, J=4.3 Hz, 6H), 1.40 (d, J=10.3 Hz, 4H).

Compound 98. N4-((1s,4s)-4-aminocyclohexyl)-N2-(3-acetylphenyl)-5-(1-methyl-1H-pyrazol-4-yl)pyrimidine-2,4-diamine

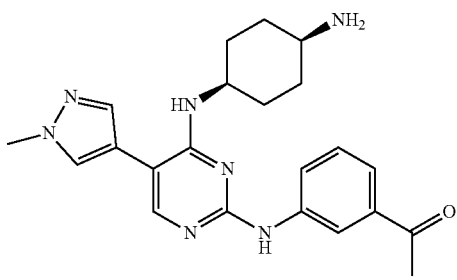 [SMILES: CC(=O)c1cccc(Nc2ncc(-c3cnn(C)c3)c(N[C@H]3CC[C@@H](N)CC3)n2)c1]

1H NMR (300 MHz, Chloroform-d) δ 8.33 (t, J=1.9 Hz, 1H), 7.84 (d, J=3.1 Hz, 1H), 7.82-7.78 (m, 1H), 7.57 (d, J=3.0 Hz, 1H), 7.54 (t, J=1.3 Hz, 1H), 7.46 (s, 2H), 7.38 (t, J=7.9 Hz, 1H), 5.18 (d, J=7.4 Hz, 1H), 4.24 (d, J=14.1 Hz, 1H), 3.99 (s, 3H), 2.98 (d, J=7.6 Hz, 1H), 2.61 (s, 3H), 1.80 (dt, J=8.1, 4.6 Hz, 5H), 1.73 (d, J=5.3 Hz, 2H), 1.54 (s, 3H), 1.35 (t, J=6.9 Hz, 2H).

Compound 99. N4-((1s,4s)-4-aminocyclohexyl)-5-(1-methyl-1H-pyrazol-4-yl)-N2-(m-tolyl)pyrimidine-2,4-diamine

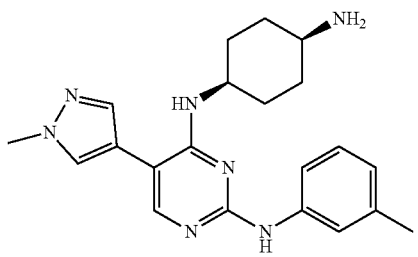

1H NMR (300 MHz, Chloroform-d) δ 7.79 (s, 1H), 7.58-7.54 (m, 1H), 7.52 (s, 1H), 7.42 (s, 1H), 7.40 (d, J=1.8 Hz, 1H), 7.18 (t, J=7.8 Hz, 1H), 7.01 (s, 1H), 6.81 (d, J=7.5 Hz, 1H), 5.10 (d, J=7.2 Hz, 1H), 4.18 (d, J=6.1 Hz, 1H), 3.98 (s, 3H), 3.02-2.89 (m, 1H), 2.35 (s, 3H), 1.80 (dd, J=12.5, 7.7 Hz, 5H), 1.71 (q, J=3.8 Hz, 2H), 1.48 (s, 2H), 1.44-1.30 (m, 3H).

Compound 100. N-((1s,4s)-4-(2-(3-chlorophenylamino)-5-(1-(2-hydroxyethyl)-1H-pyrazol-4-yl)pyrimidin-4-ylamino)cyclohexyl)-2,2,2-trifluoroacetamide

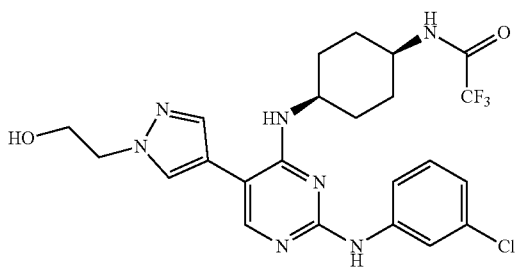 [SMILES: O=C(N[C@H]1CC[C@@H](Nc2nc(Nc3cccc(Cl)c3)ncc2-c2cnn(CCO)c2)CC1)C(F)(F)F]

1H NMR (300 MHz, Chloroform-d) δ 8.06 (s, 1H), 7.77 (s, 1H), 7.63 (s, 1H), 7.60 (s, 1H), 7.39 (s, 1H), 7.20 (dd, J=4.1, 1.9 Hz, 2H), 7.00-6.93 (m, 1H), 6.68 (d, J=7.5 Hz, 1H), 5.19 (d, J=7.2 Hz, 1H), 4.40-4.31 (m, 2H), 4.25 (s, 1H), 4.07 (t, J=4.7 Hz, 2H), 3.99 (s, 1H), 3.36-2.93 (m, 1H), 1.89 (s, 4H), 1.72 (dd, J=14.6, 7.9 Hz, 4H).

Compound 101. 2-(4-(2-(3-chlorophenylamino)-4-(1,2,3,4-tetrahydroisoquinolin-7-ylamino)pyrimidin-5-yl)-1H-pyrazol-1-yl)ethanol

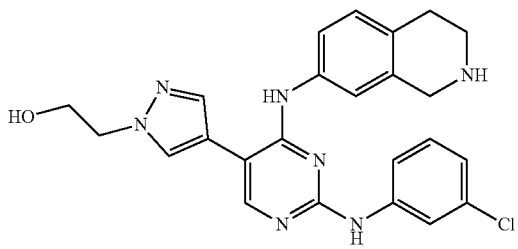 [SMILES: OCCn1cc(-c2cnc(Nc3cccc(Cl)c3)nc2Nc2ccc3c(c2)CNCC3)cn1]

1H NMR (300 MHz, Chloroform-d) δ 7.92 (s, 1H), 7.75 (d, J=2.1 Hz, 1H), 7.65 (s, 1H), 7.56 (s, 1H), 7.32-7.27 (m, 1H), 7.23 (d, J=2.3 Hz, 1H), 7.16 (t, J=8.0 Hz, 1H), 7.10-7.04 (m, 2H), 6.95 (ddd, J=8.0, 2.1, 1.0 Hz, 1H), 6.75 (s, 1H), 4.31 (dd, J=5.4, 4.0 Hz, 2H), 4.06 (t, J=4.8 Hz, 2H), 3.92 (s, 2H), 3.12 (t, J=5.9 Hz, 2H), 2.76 (t, J=5.9 Hz, 2H), 2.49-2.08 (m, 2H).

Compound 102. 2-(4-(2-(3-fluorophenylamino)-4-(1,2,3,4-tetrahydroisoquinolin-7-ylamino)pyrimidin-5-yl)-1H-pyrazol-1-yl)ethanol

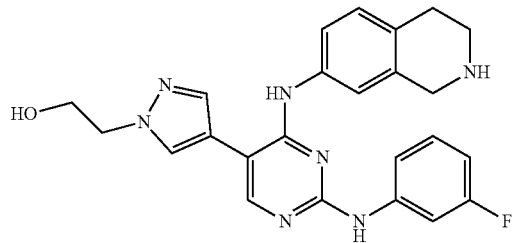 [SMILES: OCCn1cc(-c2cnc(Nc3cccc(F)c3)nc2Nc2ccc3c(c2)CNCC3)cn1]

1H NMR (300 MHz, Chloroform-d) δ 7.95 (s, 1H), 7.68 (s, 1H), 7.64 (s, 1H), 7.60 (s, 1H), 7.20 (d, J=9.0 Hz, 3H), 7.07 (t, J=8.9 Hz, 3H), 6.74 (s, 1H), 6.67 (t, J=7.3 Hz, 1H), 4.37-4.30 (m, 2H), 4.14-4.05 (m, 2H), 3.97 (s, 2H), 3.15 (t, J=6.0 Hz, 2H), 2.79 (t, J=6.0 Hz, 2H).

Compound 103. 2-(4-(4-((1s,4s)-4-aminocyclohexylamino)-2-(3,5-dichlorophenylamino)pyrimidin-5-yl)-1H-pyrazol-1-yl)ethanol

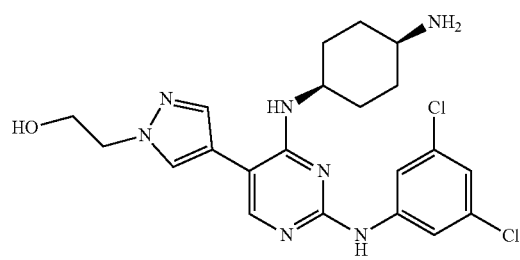 [SMILES: N[C@H]1CC[C@@H](Nc2nc(Nc3cc(Cl)cc(Cl)c3)ncc2-c2cnn(CCO)c2)CC1]

1H NMR (300 MHz, Chloroform-d) δ 7.85 (s, 1H), 7.78 (s, 1H), 7.65 (d, J=1.9 Hz, 2H), 7.55 (d, J=0.9 Hz, 1H), 7.31 (s, 1H), 6.94 (t, J=1.8 Hz, 1H), 5.34-5.28 (m, 1H), 4.37-4.32 (m, 2H), 4.31 (s, 1H), 4.00-3.92 (m, 2H), 2.95 (d, J=9.6 Hz, 1H), 1.88-1.76 (m, 2H), 1.75-1.62 (m, 4H), 1.26 (s, 2H).

Compound 104. 2-(4-(4-((1s,4s)-4-aminocyclohexylamino)-2-(1,2,3,4-tetrahydroisoquinolin-7-ylamino)pyrimidin-5-yl)-1H-pyrazol-1-yl)ethanol

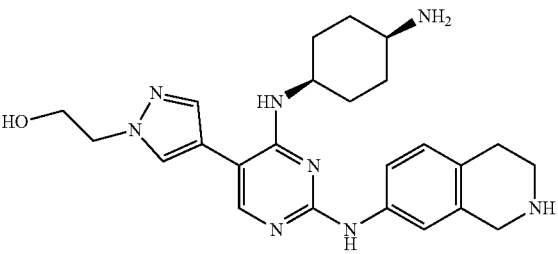 [SMILES: N[C@H]1CC[C@@H](Nc2nc(Nc3ccc4c(c3)CNCC4)ncc2-c2cnn(CCO)c2)CC1]

1H NMR (300 MHz, Chloroform-d) δ 7.82 (d, J=1.0 Hz, 1H), 7.76 (s, 1H), 7.53 (s, 1H), 7.44 (d, J=2.2 Hz, 1H), 7.01 (d, J=8.3 Hz, 1H), 6.89 (s, 1H), 5.23 (d, J=8.2 Hz, 1H), 4.33 (t, J=4.6 Hz, 3H), 4.00 (s, 2H), 3.98-3.91 (m, 2H), 3.13 (t, J=5.9 Hz, 2H), 2.99-2.88 (m, 1H), 2.74 (t, J=6.0 Hz, 2H), 1.80 (d, J=11.4 Hz, 3H), 1.63 (t, J=13.2 Hz, 4H), 1.26 (t, J=11.6 Hz, 3H).

Compound 105. 2-(4-(4-((1s,4s)-4-aminocyclohexylamino)-2-(3-chlorophenylamino)pyrimidin-5-yl)-1H-pyrazol-1-yl)ethanol

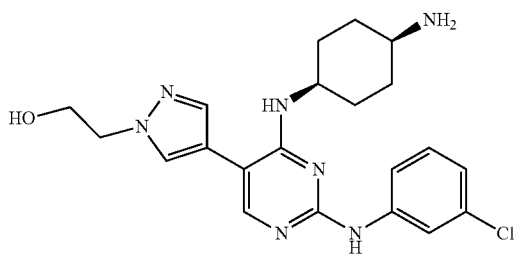 [SMILES: N[C@H]1CC[C@@H](Nc2nc(Nc3cccc(Cl)c3)ncc2-c2cnn(CCO)c2)CC1]

1H NMR (300 MHz, Chloroform-d) δ 8.05 (t, J=2.0 Hz, 1H), 7.84 (s, 1H), 7.77 (s, 1H), 7.55 (d, J=0.9 Hz, 1H), 7.24-7.22 (m, 1H), 7.18 (t, J=7.9 Hz, 1H), 6.94 (dt, J=7.6, 1.6 Hz, 1H), 5.28 (d, J=8.2 Hz, 1H), 4.34 (dd, J=5.3, 3.9 Hz, 2H), 3.96 (dd, J=5.3, 3.9 Hz, 2H), 2.96 (dt, J=9.6, 5.4 Hz, 1H), 2.77-2.50 (m, 2H), 1.89-1.75 (m, 2H), 1.74-1.60 (m, 4H), 1.26 (dd, J=9.0, 4.6 Hz, 3H).

Compound 106. N-((1s,4s)-4-((2-((4-chloro-3-methylphenyl)amino)-5-(1-(2-hydroxyethyl)-1H-pyrazol-4-yl)pyrimidin-4-yl)amino)cyclohexyl)-2,2,2-trifluoroacetamide

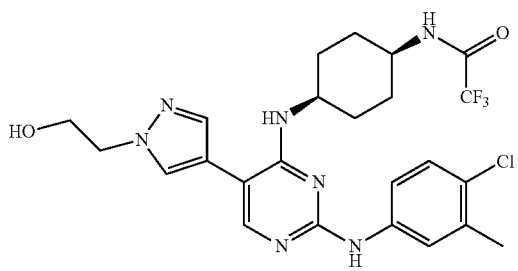 [SMILES: Cc1cc(Nc2ncc(-c3cnn(CCO)c3)c(N[C@H]3CC[C@@H](NC(=O)C(F)(F)F)CC3)n2)ccc1Cl]

1H NMR (300 MHz, Chloroform-d) δ 7.78 (s, 1H), 7.60 (s, 1H), 7.59 (s, 1H), 7.51 (d, J=2.6 Hz, 1H), 7.40 (dd, J=8.7, 2.7 Hz, 1H), 7.25 (s, 1H), 7.06 (s, 1H), 6.67 (d, J=7.7 Hz, 1H), 5.10 (d, J=7.2 Hz, 1H), 4.38-4.30 (m, 2H), 4.23 (d, J=6.6 Hz, 1H), 4.12-4.03 (m, 2H), 3.96 (s, 1H), 2.36 (s, 3H), 1.91-1.79 (m, 4H), 1.76 (d, J=6.8 Hz, 2H), 1.62 (s, 2H).

Compound 107. 2-(4-(4-((1s,4s)-4-aminocyclohexylamino)-2-(3-methyl-4-chlorophenylamino)pyrimidin-5-yl)-1H-pyrazol-1-yl)ethanol

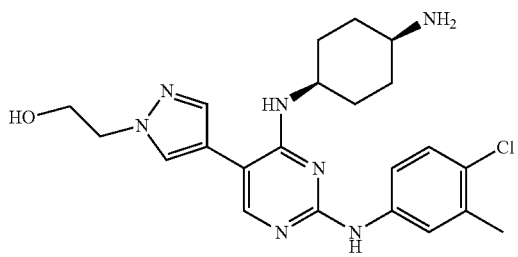 [SMILES: Cc1cc(Nc2ncc(-c3cnn(CCO)c3)c(N[C@H]3CC[C@@H](N)CC3)n2)ccc1Cl]

1H NMR (300 MHz, Chloroform-d) δ 7.84 (s, 1H), 7.77 (s, 1H), 7.55 (d, J=2.7 Hz, 1H), 7.53 (d, J=0.8 Hz, 1H), 7.40 (dd, J=8.6, 2.7 Hz, 1H), 7.23 (d, J=8.6 Hz, 1H), 6.88 (s, 1H), 5.26 (d, J=8.3 Hz, 1H), 4.34 (dd, J=5.3, 3.9 Hz, 2H), 4.31 (s, 1H), 4.00-3.90 (m, 2H), 2.94 (dt, J=10.0, 5.7 Hz, 1H), 2.36 (s, 3H), 1.89-1.76 (m, 3H), 1.64 (t, J=13.4 Hz, 5H), 1.24 (d, J=10.9 Hz, 3H).

Compound 108. N-((1s,4s)-4-(2-(3,5-dichlorophenylamino)-5-(1-(1-(2,2,2-trifluoroacetyl)piperidin-4-yl)-1H-pyrazol-4-yl)pyrimidin-4-ylamino)cyclohexyl)-2,2,2-trifluoroacetamide

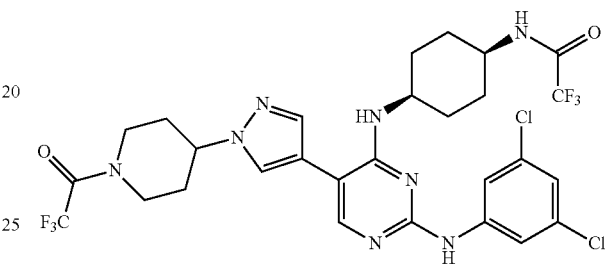

1H NMR (300 MHz, Chloroform-d) δ 7.84 (s, 1H), 7.63 (d, J=1.8 Hz, 3H), 7.58 (s, 1H), 7.29 (s, 1H), 6.98 (t, J=1.8 Hz, 1H), 6.32 (s, 1H), 5.10 (d, J=7.0 Hz, 1H), 4.67 (d, J=13.4 Hz, 1H), 4.59-4.42 (m, 2H), 4.22 (s, 1H), 3.99 (s, 1H), 3.37 (t, J=13.1 Hz, 1H), 3.07 (t, J=12.5 Hz, 1H), 2.34 (d, J=13.0 Hz, 2H), 2.22-2.08 (m, 2H), 2.03-1.86 (m, 5H), 1.82 (s, 2H), 1.67 (s, 2H).

Compound 109. N-((1r,4r)-4-(2-(3,5-dichlorophenylamino)-5-(1-methyl-1H-pyrazol-4-yl)pyrimidin-4-ylamino)cyclohexyl)-2,2,2-trifluoroacetamide

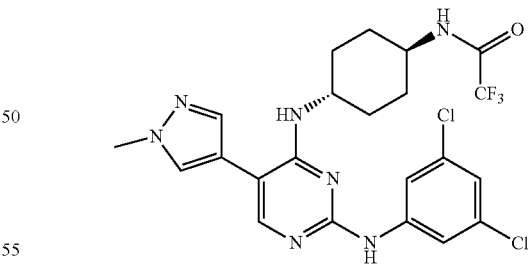

1H NMR (300 MHz, Chloroform-d) δ 7.82 (s, 1H), 7.62 (d, J=1.8 Hz, 2H), 7.54 (s, 1H), 7.42 (s, 1H), 7.22 (s, 1H), 6.97 (d, J=2.2 Hz, 1H), 6.11 (d, J=8.0 Hz, 1H), 4.92 (d, J=7.7 Hz, 1H), 4.03 (d, J=3.9 Hz, 1H), 3.99 (s, 3H), 3.84 (d, J=10.8 Hz, 1H), 2.24 (d, J=12.6 Hz, 2H), 2.13 (d, J=12.6 Hz, 2H), 1.58 (s, 1H), 1.58-1.45 (m, 2H), 1.31 (d, J=12.3 Hz, 2H).

Compound 110. N-((1r,4r)-4-(2-(3,5-dichlorophenylamino)-5-(1-(2-hydroxyethyl)-1H-pyrazol-4-yl)pyrimidin-4-ylamino)cyclohexyl)-2,2,2-trifluoroacetamide

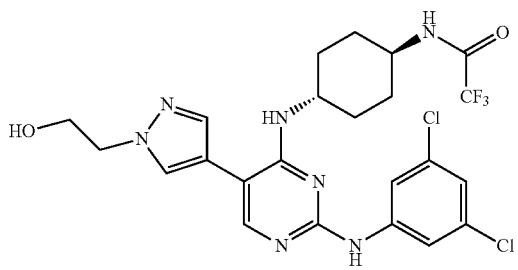 [SMILES: O=C(N[C@H]1CC[C@H](Nc2nc(Nc3cc(Cl)cc(Cl)c3)ncc2-c2cnn(CCO)c2)CC1)C(F)(F)F]

1H NMR (300 MHz, Chloroform-d) δ 7.80 (s, 1H), 7.62 (d, J=1.8 Hz, 2H), 7.58 (d, J=0.8 Hz, 1H), 7.53 (s, 1H), 7.18 (s, 1H), 6.98 (t, J=1.8 Hz, 1H), 6.10 (d, J=8.0 Hz, 1H), 4.93 (d, J=7.6 Hz, 1H), 4.35-4.28 (m, 2H), 4.07 (d, J=4.7 Hz, 2H), 4.05-3.94 (m, 1H), 3.83 (s, 1H), 2.24 (d, J=12.8 Hz, 2H), 2.13 (d, J=12.6 Hz, 2H), 1.78-1.61 (m, 1H), 1.52 (q, J=12.4 Hz, 3H), 1.36 (d, J=12.4 Hz, 2H).

Compound 111. N4-((1s,4s)-4-aminocyclohexyl)-N2-(3,5-dichlorophenyl)-5-(1-(piperidin-4-yl)-1H-pyrazol-4-yl)pyrimidine-2,4-diamine

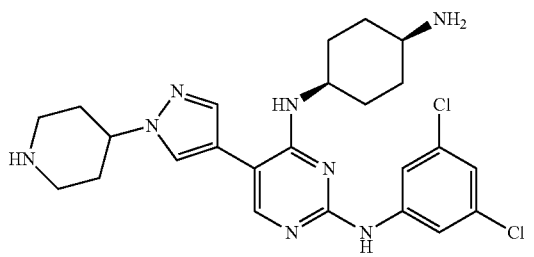 [SMILES: N[C@H]1CC[C@@H](Nc2nc(Nc3cc(Cl)cc(Cl)c3)ncc2-c2cnn(C3CCNCC3)c2)CC1]

1H NMR (300 MHz, Chloroform-d) δ 7.82 (s, 1H), 7.66 (d, J=1.8 Hz, 2H), 7.59 (s, 1H), 7.52 (s, 1H), 7.29 (s, 1H), 6.94 (t, J=1.8 Hz, 1H), 5.19 (d, J=7.3 Hz, 1H), 4.28 (tt, J=11.8, 4.1 Hz, 1H), 4.17 (s, 1H), 3.27 (d, J=12.5 Hz, 2H), 3.03 (s, 1H), 2.86-2.74 (m, 2H), 2.22 (d, J=12.3 Hz, 2H), 1.94 (qd, J=12.1, 4.2 Hz, 3H), 1.80 (d, J=3.6 Hz, 6H), 1.44 (d, J=16.6 Hz, 5H).

Compound 112. N4-((1r,4r)-4-aminocyclohexyl)-N2-(3,5-dichlorophenyl)-5-(1-methyl-1H-pyrazol-4-yl)pyrimidine-2,4-diamine

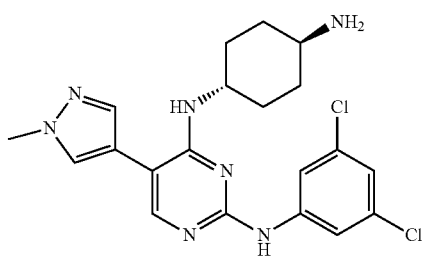 [SMILES: Cn1cc(-c2cnc(Nc3cc(Cl)cc(Cl)c3)nc2N[C@H]2CC[C@H](N)CC2)cn1]

1H NMR (300 MHz, Chloroform-d) δ 7.80 (s, 1H), 7.64 (d, J=1.8 Hz, 2H), 7.54 (s, 1H), 7.41 (s, 1H), 7.37 (s, 1H), 6.96 (t, J=1.8 Hz, 1H), 4.91 (d, J=7.7 Hz, 1H), 3.98 (s, 3H), 3.94 (dd, J=7.5, 3.8 Hz, 1H), 2.67 (td, J=10.9, 5.4 Hz, 1H), 2.15 (d, J=12.2 Hz, 2H), 1.93 (d, J=12.8 Hz, 2H), 1.47 (d, J=12.0 Hz, 3H), 1.42-1.29 (m, 3H).

Compound 113. 2-(4-(4-((1r,4r)-4-aminocyclohexylamino)-2-(3,5-dichlorophenylamino)pyrimidin-5-yl)-1H-pyrazol-1-yl)ethanol

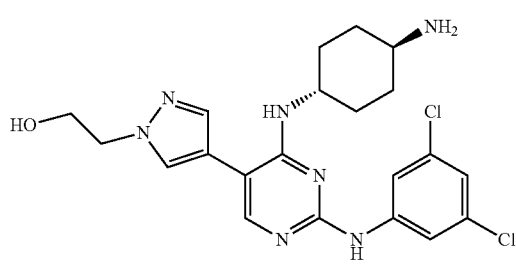 [SMILES: N[C@H]1CC[C@H](Nc2nc(Nc3cc(Cl)cc(Cl)c3)ncc2-c2cnn(CCO)c2)CC1]

1H NMR (300 MHz, Chloroform-d) δ 7.78 (s, 1H), 7.66 (d, J=1.8 Hz, 2H), 7.60 (s, 1H), 7.55 (s, 1H), 7.36 (s, 1H), 6.98 (d, J=1.8 Hz, 1H), 4.93 (d, J=7.7 Hz, 1H), 4.38-4.30 (m, 2H), 4.13-4.07 (m, 2H), 4.06-3.91 (m, 1H), 2.68 (td, J=10.7, 5.3 Hz, 1H), 2.16 (d, J=12.2 Hz, 2H), 1.94 (d, J=13.0 Hz, 2H), 1.39 (q, J=12.1 Hz, 3H), 1.30-1.15 (m, 3H).

Compound 114. N-((1r,4r)-4-(2-(3,5-difluorophenylamino)-5-(1-methyl-1H-pyrazol-4-yl)pyrimidin-4-ylamino)cyclohexyl)-2,2,2-trifluoroacetamide

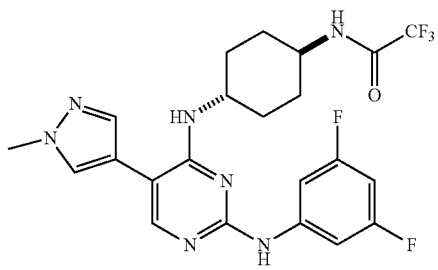

1H NMR (300 MHz, Chloroform-d) δ 7.79 (s, 1H), 7.52 (d, J=0.9 Hz, 1H), 7.40 (s, 1H), 7.29 (d, J=2.2 Hz, 1H), 7.27-7.23 (m, 2H), 6.45-6.34 (m, 1H), 4.90 (d, J=7.5 Hz, 1H), 3.96 (s, 3H), 3.91 (dd, J=7.4, 3.6 Hz, 1H), 2.72-2.60 (m, 1H), 2.14 (d, J=11.9 Hz, 2H), 2.00-1.87 (m, 2H), 1.46-1.13 (m, 6H).

Compound 115. N-((1r,4r)-4-(2-(3,5-difluorophenylamino)-5-(1-(2-hydroxyethyl)-1H-pyrazol-4-yl)pyrimidin-4-ylamino)cyclohexyl)-2,2,2-trifluoroacetamide

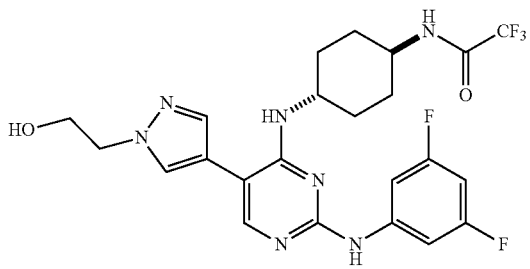

1H NMR (300 MHz, Chloroform-d) δ 7.81 (s, 1H), 7.52 (d, J=0.9 Hz, 1H), 7.42 (s, 1H), 7.30 (d, J=2.2 Hz, 1H), 7.30-7.23 (m, 2H), 6.45-6.35 (m, 1H), 4.91 (d, J=7.5 Hz, 1H), 3.95 (s, 3H), 3.92 (dd, J=7.4, 3.6 Hz, 1H), 2.73-2.60 (m, 1H), 2.14 (d, J=11.9 Hz, 2H), 1.98-1.86 (m, 2H), 1.48-1.13 (m, 6H).

Compound 116. N4-((1r,4r)-4-aminocyclohexyl)-N2-(3,5-difluorophenyl)-5-(1-methyl-1H-pyrazol-4-yl)pyrimidine-2,4-diamine

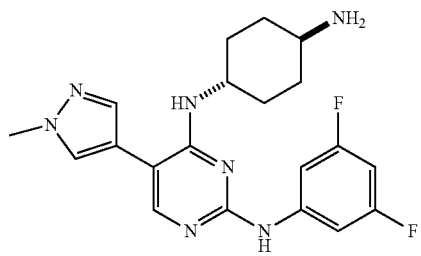

1H NMR (300 MHz, Chloroform-d) δ 7.80 (s, 1H), 7.54 (d, J=0.9 Hz, 1H), 7.42 (s, 1H), 7.31 (d, J=2.2 Hz, 1H), 7.29-7.25 (m, 2H), 6.47-6.36 (m, 1H), 4.92 (d, J=7.5 Hz, 1H), 3.98 (s, 3H), 3.93 (dd, J=7.4, 3.6 Hz, 1H), 2.74-2.62 (m, 1H), 2.16 (d, J=11.9 Hz, 2H), 2.01-1.89 (m, 2H), 1.48-1.13 (m, 6H).

Compound 117. 2-(4-(4-((1r,4r)-4-aminocyclohexylamino)-2-(3,5-difluorophenylamino)pyrimidin-5-yl)-1H-pyrazol-1-yl)ethan-1-ol

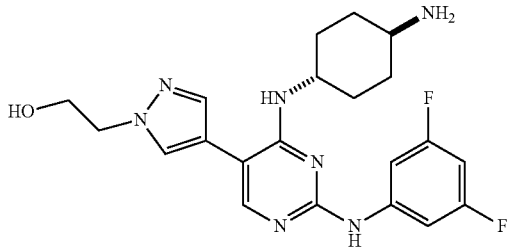

1H NMR (300 MHz, Chloroform-d) δ 7.77 (d, J=1.0 Hz, 1H), 7.59 (d, J=1.0 Hz, 1H), 7.52 (d, J=1.0 Hz, 1H), 7.31 (d, J=2.2 Hz, 1H), 7.28 (s, 1H), 7.25 (s, 1H), 6.46-6.36 (m, 1H), 4.91 (d, J=7.4 Hz, 1H), 4.32 (t, J=4.7 Hz, 2H), 4.07 (dd, J=5.4, 4.0 Hz, 2H), 4.00-3.87 (m, 1H), 2.71-2.60 (m, 1H), 2.16 (d, J=12.2 Hz, 2H), 1.94 (d, J=12.5 Hz, 3H), 1.40-1.13 (m, 6H).

Compound 118. N4-((1r,4r)-4-aminocyclohexyl)-N2-(3,5-bis(trifluoromethyl)phenyl)-5-(1-methyl-1H-pyrazol-4-yl)pyrimidine-2,4-diamine

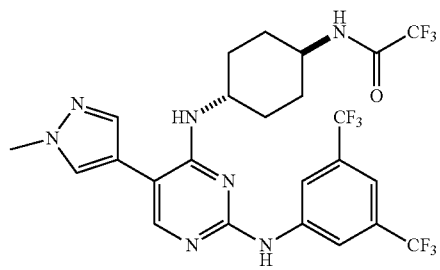

1H NMR (300 MHz, Chloroform-d) δ 8.18 (s 1H), 7.82 (s 1H), 7.71 (s 1H), 7.52 (s 1H), 7.42 (s 1H), 7.40 (s 1H), 7.52 (s 1H), 4.90 (d, J=6.0 Hz), 4.07 (m, 1H), 4.00 (s, 3H), 2.46 (m, 1H), 2.15 (m, 2H), 1.96 (m, 2H), 1.40 (m, 3H).

Compound 119. N-((1r,4r)-4-(2-(3,5-bis(trifluoromethyl)phenylamino)-5-(1-(2-hydroxyethyl)-1H-pyrazol-4-yl)pyrimidin-4-ylamino)cyclohexyl)-2,2,2-trifluoroacetamide

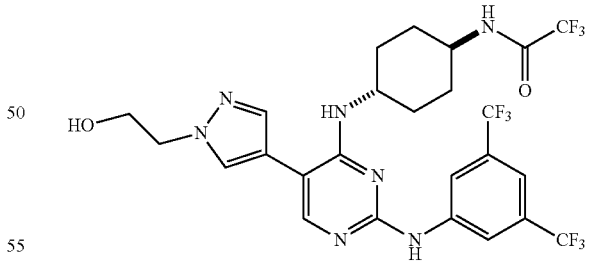

1H NMR (300 MHz, Chloroform-d) δ 8.20 (s 2H), 7.81 (s 1H), 7.60 (s 1H), 7.54 (s 1H), 7.45 (s 1H), 7.41 (s 1H), 4.91 (d, J=6.0 Hz), 4.06 (m, 1H), 4.32 (m, 2H), 4.06 (m, 2H), 4.01 (m, 1H), 2.61 (m, 1H), 2.14 (m, 2H), 1.96 (m, 2H), 1.43 (m, 3H).

Compound 120. N4-((1r,4r)-4-aminocyclohexyl)-N2-(3,5-bis(trifluoromethyl)phenyl)-5-(1-methyl-1H-pyrazol-4-yl)pyrimidine-2,4-diamine

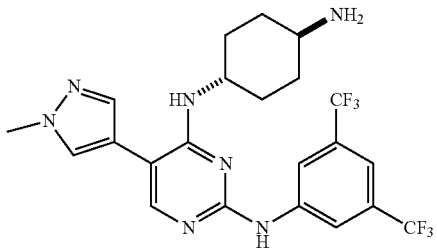

1H NMR (300 MHz, Chloroform-d) δ 8.21 (s 1H), 7.84 (s 1H), 7.75 (s 1H), 7.57 (s 1H), 7.45 (s 1H), 7.42 (s 1H), 7.57 (s 1H), 4.91 (d, J=6.0 Hz), 4.09 (m, 1H), 4.02 (s, 3H), 2.48 (m, 1H), 2.19 (m, 2H), 1.98 (m, 2H), 1.42 (m, 3H).

Compound 121. 2-(4-(4-((1r,4r)-4-aminocyclohexylamino)-2-(3,5-bis(trifluoromethyl)phenylamino)pyrimidin-5-yl)-1H-pyrazol-1-yl)ethan-1-ol

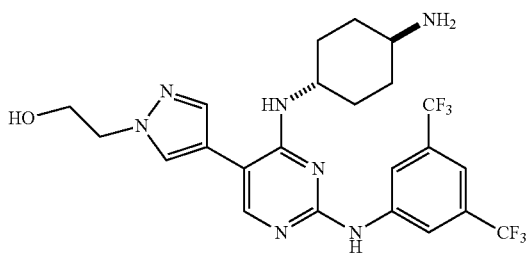

1H NMR (300 MHz, Chloroform-d) δ 8.24 (s 2H), 7.82 (s 1H), 7.61 (s 1H), 7.56 (s 1H), 7.47 (s 1H), 7.42 (s 1H), 4.91 (d, J=6.0 Hz), 4.09 (m, 1H), 4.34 (m, 2H), 4.08 (m, 2H), 4.02 (m, 1H), 2.62 (m, 1H), 2.15 (m, 2H), 1.98 (m, 2H), 1.42 (m, 3H).

Compound 122. 1-(4-(2-(3,5-dichlorophenylamino)-5-(1-(piperidin-4-yl)-1H-pyrazol-4-yl)pyrimidin-4-ylamino)cyclohexyl)-2,2,2-trifluoroacetamide

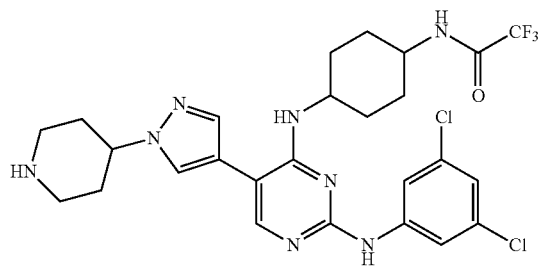 [SMILES: O=C(NC1CCC(Nc2nc(Nc3cc(Cl)cc(Cl)c3)ncc2-c2cnn(C3CCNCC3)c2)CC1)C(F)(F)F]

1H NMR (300 MHz, CDCl₃) δ 7.84 (s, 1H), 7.62 (d, J=1.8 Hz, 2H), 7.58 (s, 1H), 7.48 (s, 1H), 7.35 (s, 1H), 6.99 (t, J=1.8 Hz, 1H), 4.92 (d, J=7.5 Hz, 1H), 4.62 (dd, J=25.6, 13.5 Hz, 2H), 4.46 (dq, J=10.6, 5.4, 4.2 Hz, 1H), 4.32 (dd, J=7.5, 3.9 Hz, 1H), 4.20 (d, J=14.3 Hz, 1H), 4.07 (d, J=14.2 Hz, 1H), 3.38 (t, J=12.9 Hz, 2H), 3.06 (q, J=11.7 Hz, 2H), 2.28 (q, J=12.3, 10.7 Hz, 4H), 2.20-2.06 (m, 2H), 1.47 (t, J=12.4 Hz, 3H).

Compound 123. 1-(7-(2-(3,5-difluorophenylamino)-5-(1-(2-hydroxyethyl)-1H-pyrazol-4-yl)pyrimidin-4-ylamino)-3,4-dihydroisoquinolin-2(1H)-yl)-2,2,2-trifluoroethanone

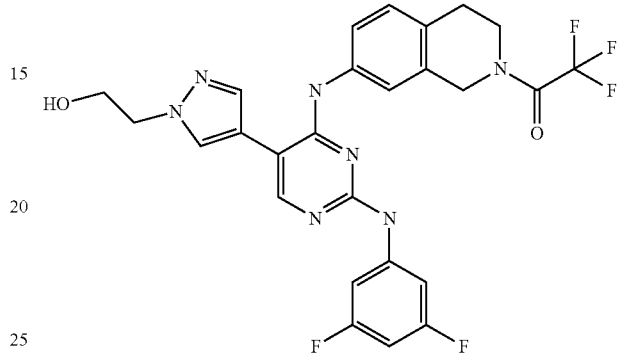

1H NMR (300 MHz, Chloroform-d) δ 7.98 (s, 1H), 7.71 (s, 1H), 7.67 (s, 1H), 7.50 (s, 1H), 7.35 (d, J=2.5 Hz, 1H), 7.26 (dd, J=8.1, 2.2 Hz, 1H), 7.20-7.13 (m, 3H), 6.87 (s, 1H), 6.47-6.39 (m, 1H), 4.75 (d, J=11.2 Hz, 2H), 4.38 (dd, J=5.5, 4.0 Hz, 2H), 4.14-4.09 (m, 2H), 3.90 (dt, J=12.3, 5.9 Hz, 2H), 3.03-2.92 (m, 4H).

Compound 124. 1-(7-(2-(3,5-bis(trifluoromethyl)phenylamino)-5-(1-(2-hydroxyethyl)-1H-pyrazol-4-yl)pyrimidin-4-ylamino)-3,4-dihydroisoquinolin-2(1H)-yl)-2,2,2-trifluoroethanone

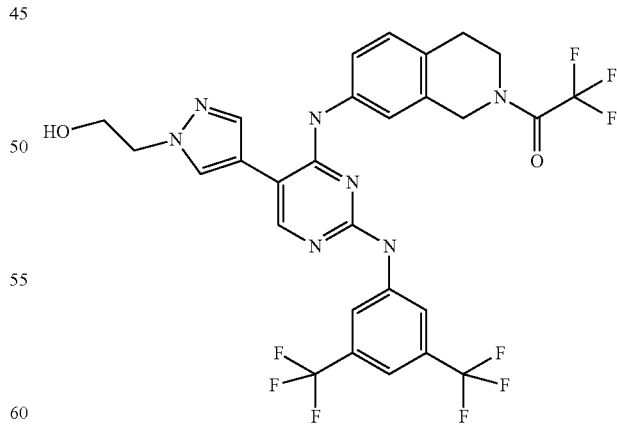

1H NMR (300 MHz, Chloroform-d) δ 8.06 (d, J=3.0 Hz, 2H), 8.03 (s, 1H), 7.81 (d, J=13.9 Hz, 1H), 7.72 (s, 1H), 7.68 (s, 1H), 7.45 (s, 1H), 7.27 (s, 1H), 7.18-7.12 (m, 1H), 6.88 (s, 1H), 4.70 (d, J=15.3 Hz, 2H), 4.43-4.33 (m, 2H), 4.17-4.08 (m, 2H), 3.94-3.82 (m, 2H), 2.95 (t, J=6.0 Hz, 2H).

Compound 125. 1-(7-(2-(2,3-dichlorophenylamino)-5-(1-(2-hydroxyethyl)-1H-pyrazol-4-yl)pyrimidin-4-ylamino)-3,4-dihydroisoquinolin-2(1H)-yl)-2,2,2-trifluoroethanone

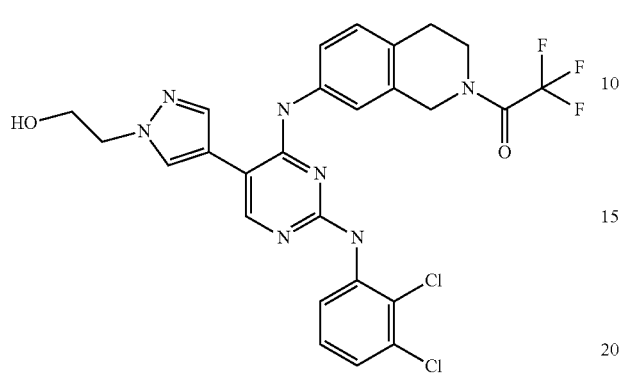

1H NMR (300 MHz, Chloroform-d) δ 8.38-8.30 (m, 1H), 8.01 (d, J=1.8 Hz, 1H), 7.69 (s, 1H), 7.63 (s, 1H), 7.50 (s, 1H), 7.39 (d, J=18.1 Hz, 1H), 7.32 (d, J=7.0 Hz, OH), 7.18-7.15 (m, 1H), 7.14-7.08 (m, 1H), 4.71 (d, J=14.2 Hz, 2H), 4.40-4.33 (m, 2H), 4.14-4.04 (m, 2H), 3.87 (dd, J=13.0, 6.4 Hz, 2H), 2.95 (t, J=5.5 Hz, 2H).

Compound 126. 1-(7-(2-(2-methyl-3-chlorophenylamino)-5-(1-(2-hydroxyethyl)-1H-pyrazol-4-yl)pyrimidin-4-ylamino)-3,4-dihydroisoquinolin-2(1H)-yl)-2,2,2-trifluoroethanone

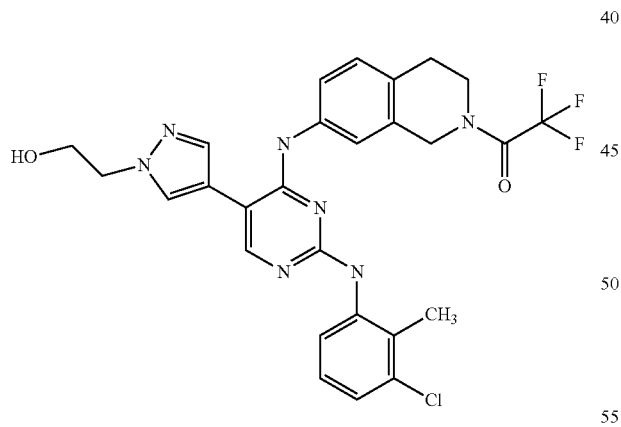

1H NMR (300 MHz, Chloroform-d) δ 7.91 (d, J=1.9 Hz, 1H), 7.69-7.64 (m, 2H), 7.63 (d, J=2.1 Hz, 1H), 7.40 (dd, J=12.5, 2.2 Hz, 1H), 7.34-7.28 (m, 1H), 7.25-7.17 (m, 1H), 7.13 (dd, J=10.9, 2.7 Hz, 1H), 7.04 (t, J=7.9 Hz, 1H), 6.91 (s, 1H), 6.83 (s, 1H), 4.59 (d, J=14.3 Hz, 2H), 4.37 (dd, J=5.6, 4.0 Hz, 2H), 4.15-4.08 (m, 2H), 3.91-3.80 (m, 2H), 2.90 (q, J=5.5 Hz, 2H), 2.37 (s, 3H).

Compound 127. 2-(4-(2-(3,5-difluorophenylamino)-4-(1,2,3,4-tetrahydroisoquinolin-7-ylamino)pyrimidin-5-yl)-1H-pyrazol-1-yl)-ethan-1-ol

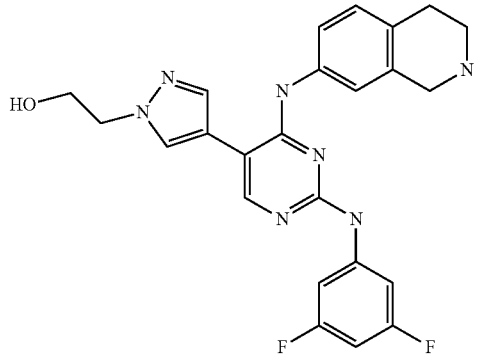 [SMILES: OCCn1cc(-c2cnc(Nc3cc(F)cc(F)c3)nc2Nc2ccc3c(c2)CNCC3)cn1]

1H NMR (300 MHz, Chloroform-d) δ 7.97 (s, 1H), 7.70 (s, 1H), 7.62 (s, 1H), 7.24-7.08 (m, 5H), 6.79 (s, 1H), 6.47-6.36 (m, 1H), 4.39-4.33 (m, 2H), 4.14-4.08 (m, 2H), 3.98 (s, 2H), 3.17 (t, J=5.9 Hz, 2H), 2.81 (t, J=5.9 Hz, 2H).

Compound 128. 2-(4-(2-(3,5-bis(trifluoromethyl)phenylamino)-4-((1,2,3,4-tetrahydroisoquinolin-7-ylamino)pyrimidin-5-yl)-1H-pyrazol-1-yl)-ethan-1-ol

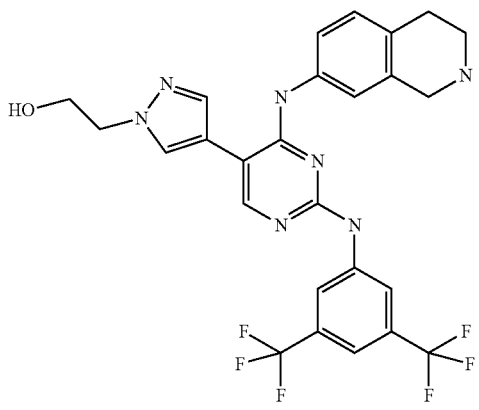 [SMILES: OCCn1cc(-c2cnc(Nc3cc(C(F)(F)F)cc(C(F)(F)F)c3)nc2Nc2ccc3c(c2)CNCC3)cn1]

1H NMR (300 MHz, Chloroform-d) δ 8.05 (d, J=1.5 Hz, 2H), 8.00 (s, 1H), 7.69 (d, J=0.8 Hz, 1H), 7.62 (s, 1H), 7.60 (s, 1H), 7.43 (s, 1H), 7.30 (d, J=2.2 Hz, 1H), 7.05 (d, J=8.3 Hz, 1H), 6.97 (s, 1H), 6.79 (s, 1H), 4.39-4.30 (m, 2H), 4.12-4.05 (m, 2H), 3.92 (s, 2H), 3.13 (t, J=6.0 Hz, 2H), 2.76 (t, J=6.0 Hz, 2H).

Compound 129. 2-(4-(2-(2,3-dichlorophenylamino)-4-(1,2,3,4-tetrahydroisoquinolin-7-ylamino)pyrimidin-5-yl)-1H-pyrazol-1-yl)-ethan-1-ol

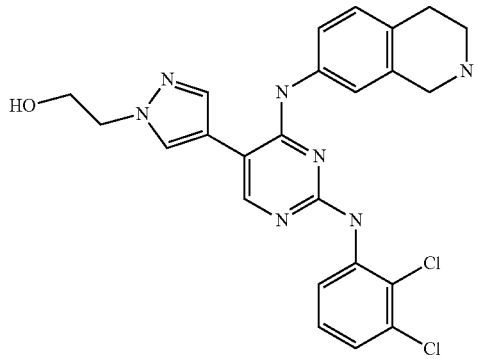 [SMILES: OCCn1cc(-c2cnc(Nc3cccc(Cl)c3Cl)nc2Nc2ccc3c(c2)CNCC3)cn1]

1H NMR (300 MHz, Chloroform-d) δ 8.43-8.35 (m, 1H), 7.96 (s, 1H), 7.67 (d, J=0.8 Hz, 1H), 7.60 (d, J=0.8 Hz, 1H), 7.52 (s, 1H), 7.24-7.16 (m, 2H), 7.14-7.03 (m, 3H), 6.80 (s, 1H), 4.36-4.27 (m, 2H), 4.13-4.03 (m, 2H), 3.95 (s, 2H), 3.15 (t, J=5.9 Hz, 2H), 2.80 (t, J=6.0 Hz, 2H).

Compound 130. 2-(4-(2-(2-methyl-3-chlorophenylamino)-4-(1,2,3,4-tetrahydroisoquinolin-7-ylamino)pyrimidin-5-yl)-1H-pyrazol-1-yl)-ethan-1-ol

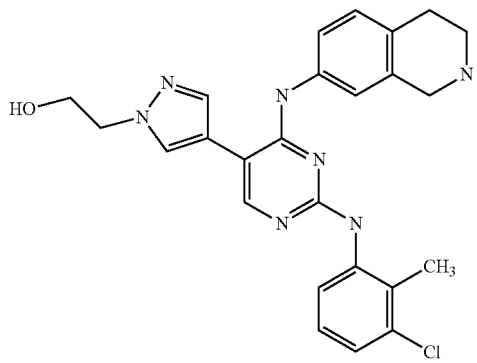 [SMILES: Cc1c(Cl)cccc1Nc1ncc(-c2cnn(CCO)c2)c(Nc2ccc3c(c2)CNCC3)n1]

1H NMR (300 MHz, Chloroform-d) δ 7.88 (s, 1H), 7.71 (d, J=7.8 Hz, 1H), 7.64 (d, J=0.8 Hz, 1H), 7.57 (d, J=0.8 Hz, 1H), 7.21-7.07 (m, 4H), 6.96 (d, J=8.3 Hz, 1H), 6.80 (s, 1H), 6.75 (s, 1H), 4.39-4.26 (m, 2H), 4.09-4.02 (m, 2H), 3.85 (s, 2H), 3.11 (t, J=6.0 Hz, 2H), 2.74 (t, J=5.9 Hz, 2H), 2.35 (s, 3H).

Compound 131. N2-(3,5-difluorophenyl)-5-(1-(piperidin-4-yl)-1H-pyrazol-4-yl)-N4-(1,2,3,4-tetrahydroisoquinolin-7-yl)pyrimidine-2,4-diamine

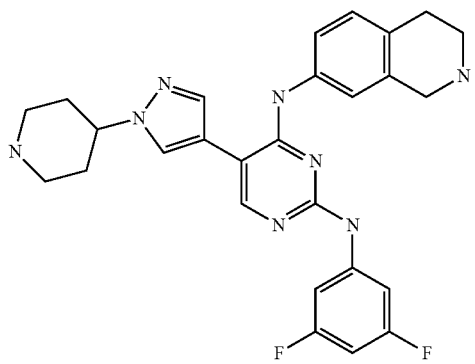 [SMILES: Fc1cc(F)cc(Nc2ncc(-c3cnn(C4CCNCC4)c3)c(Nc3ccc4c(c3)CNCC4)n2)c1]

1H NMR (300 MHz, Chloroform-d) δ 7.99 (s, 1H), 7.70 (s, 1H), 7.61 (s, 1H), 7.24-7.09 (m, 6H), 6.80 (s, 1H), 6.41 (d, J=8.9 Hz, 1H), 4.36-4.27 (m, 1H), 4.02 (s, 2H), 3.35-3.25 (m, 2H), 3.18 (t, J=6.0 Hz, 2H), 2.88-2.78 (m, 4H), 2.29-2.22 (m, 2H), 2.02-1.92 (m, 2H).

Compound 132. N2-(3,5-dichlorophenyl)-5-(1-(piperidin-4-yl)-1H-pyrazol-4-yl)-N4-(1,2,3,4-tetrahydroisoquinolin-7-yl)pyrimidine-2,4-diamine

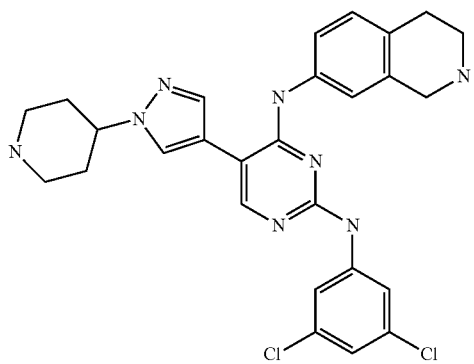 [SMILES: Clc1cc(Cl)cc(Nc2ncc(-c3cnn(C4CCNCC4)c3)c(Nc3ccc4c(c3)CNCC4)n2)c1]

1H NMR (300 MHz, Chloroform-d) δ 7.99 (s, 1H), 7.69 (s, 1H), 7.60 (s, 1H), 7.54 (d, J=1.8 Hz, 2H), 7.31 (d, J=7.8 Hz, 1H), 7.20 (s, 1H), 7.14 (d, J=8.3 Hz, 1H), 7.06 (s, 1H), 6.96 (t, J=1.8 Hz, 1H), 6.81 (s, 1H), 4.39-4.26 (m, 1H), 4.00 (s, 2H), 3.30 (d, J=12.7 Hz, 2H), 3.17 (t, J=6.0 Hz, 2H), 2.87-2.76 (m, 4H), 2.25 (d, J=12.6 Hz, 2H), 2.05-1.92 (m, 2H).

Compound 133. N2-(3,5-bis(trifluoromethyl)phenyl)-N4-(1,2,3,4-tetrahydroisoquinolin-7-yl)-5-(1-(piperidin-4-yl)-1H-pyrazol-4-yl)pyrimidine-2,4-diamine

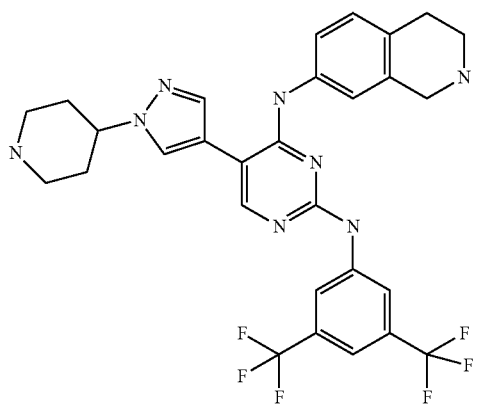 [SMILES: FC(F)(F)c1cc(Nc2ncc(-c3cnn(C4CCNCC4)c3)c(Nc3ccc4c(c3)CNCC4)n2)cc(C(F)(F)F)c1]

1H NMR (300 MHz, Chloroform-d) δ 8.10-8.06 (m, 2H), 8.03 (s, 1H), 7.70 (s, 1H), 7.61 (s, 1H), 7.49 (s, 1H), 7.45 (s, 1H), 7.32 (d, J=6.8 Hz, 1H), 7.09 (d, J=8.3 Hz, 1H), 7.02 (s, 1H), 6.82 (s, 1H), 4.38-4.27 (m, 1H), 3.99 (s, 2H), 3.31 (d, J=12.6 Hz, 2H), 3.18 (t, J=6.0 Hz, 2H), 2.89-2.77 (m, 4H), 2.26 (d, J=12.7 Hz, 2H), 2.07-1.96 (m, 2H).

Compound 134. N2-(2,3-dichlorophenyl)-5-(1-(piperidin-4-yl)-1H-pyrazol-4-yl)-N4-(1,2,3,4-tetrahydroisoquinolin-7-yl)pyrimidine-2,4-diamine

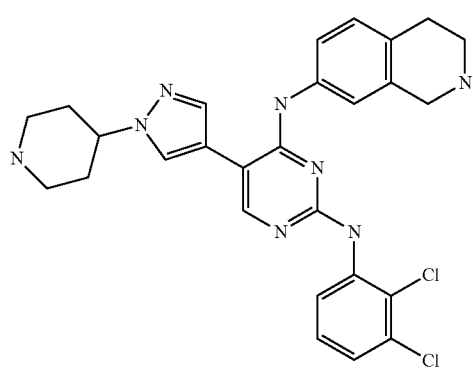 [SMILES: Clc1cccc(Nc2ncc(-c3cnn(C4CCNCC4)c3)c(Nc3ccc4c(c3)CNCC4)n2)c1Cl]

1H NMR (300 MHz, Chloroform-d) δ 8.47-8.40 (m, 1H), 8.02 (s, 1H), 7.69 (s, 1H), 7.61 (s, 1H), 7.55 (s, 1H), 7.28-7.26 (m, 1H), 7.24 (s, 1H), 7.13 (d, J=2.9 Hz, 1H), 7.09 (d, J=10.1 Hz, 2H), 6.83 (s, 1H), 4.40-4.29 (m, 1H), 4.00 (s, 2H), 3.32 (d, J=13.0 Hz, 2H), 3.19 (t, J=6.0 Hz, 2H), 2.92-2.78 (m, 4H), 2.27 (d, J=12.5 Hz, 2H), 2.05-1.97 (m, 2H).

Compound 135. N2-(3,5-dimethoxyphenyl)-5-(1-methyl-1H-pyrazol-4-yl)-N4-(1,2,3,4-tetrahydroisoquinolin-7-yl)pyrimidine-2,4-diamine

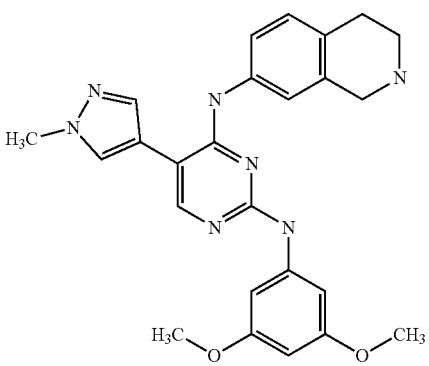

1H NMR (300 MHz, Chloroform-d) δ 7.95 (s, 1H), 7.63 (s, 1H), 7.50 (s, 1H), 7.42 (s, 1H), 7.28 (s, 1H), 7.24-7.18 (m, 1H), 7.03 (d, J=8.1 Hz, 1H), 6.80 (d, J=2.2 Hz, 2H), 6.76 (s, 1H), 6.16 (t, J=2.2 Hz, 1H), 4.00 (s, 3H), 3.94 (s, 2H), 3.69 (s, 6H), 3.14 (t, J=5.9 Hz, 2H), 2.77 (t, J=5.9 Hz, 2H).

Compound 136. N2-(3,5-bis(trifluoromethyl)phenyl)-5-(1-methyl-1H-pyrazol-4-yl)-N4-(1,2,3,4-tetrahydroisoquinolin-7-yl)pyrimidine-2,4-diamine

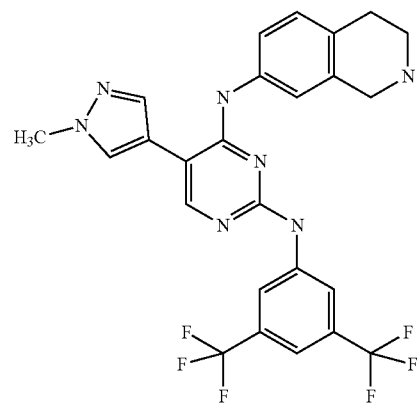 [SMILES: Cn1cc(-c2cnc(Nc3cc(C(F)(F)F)cc(C(F)(F)F)c3)nc2Nc2ccc3c(c2)CNCC3)cn1]

1H NMR (300 MHz, Chloroform-d) δ 8.06 (s, 2H), 8.01 (s, 1H), 7.99 (s, 1H), 7.66 (d, J=0.8 Hz, 1H), 7.55 (s, 1H), 7.43 (s, 1H), 7.26 (d, J=2.3 Hz, 1H), 7.05 (d, J=8.1 Hz, 2H), 6.82 (s, 1H), 4.04 (s, 3H), 3.96 (s, 2H), 3.16 (t, J=6.0 Hz, 2H), 2.80 (t, J=5.9 Hz, 2H).

Compound 137. N2-(3,5-difluorophenyl)-5-(1-methyl-1H-pyrazol-4-yl)-N4-(1,2,3,4-tetrahydroisoquinolin-7-yl)pyrimidine-2,4-diamine

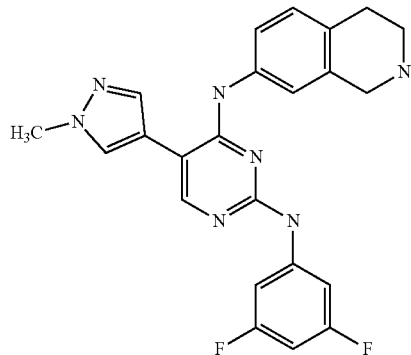 [SMILES: Cn1cc(-c2cnc(Nc3cc(F)cc(F)c3)nc2Nc2ccc3c(c2)CNCC3)cn1]

1H NMR (300 MHz, Chloroform-d) δ 7.96 (s, 1H), 7.64 (s, 1H), 7.52 (s, 1H), 7.37 (s, 1H), 7.22-7.12 (m, 4H), 7.09 (d, J=8.2 Hz, 1H), 6.77 (s, 1H), 6.43-6.34 (m, 1H), 4.01 (s, 3H), 3.98 (s, 2H), 3.15 (t, J=6.0 Hz, 2H), 2.79 (t, J=6.0 Hz, 2H).

Compound 138. 1-(7-(2-(3,5-dimethoxyphenylamino)-5-(1-methyl-1H-pyrazol-4-yl)pyrimidin-4-ylamino)-3,4-dihydroisoquinolin-2(1H)-yl)-2,2,2-trifluoroethan-1-one

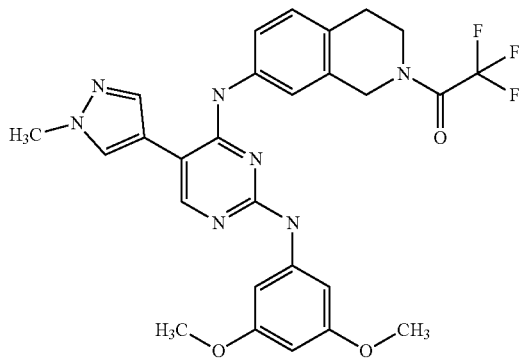 [SMILES: COc1cc(Nc2ncc(-c3cnn(C)c3)c(Nc3ccc4c(c3)CN(C(=O)C(F)(F)F)CC4)n2)cc(OC)c1]

1H NMR (300 MHz, CDCl$_3$) δ 7.99 (s, 1H), 7.65 (d, J=0.8 Hz, 1H), 7.53 (d, J=3.3 Hz, 2H), 7.25 (d, J=8.4 Hz, 1H), 7.17-7.08 (m, 2H), 6.81 (t, J=2.3 Hz, 3H), 6.22-6.15 (m, 1H), 4.73 (d, J=15.1 Hz, 2H), 4.03 (s, 3H), 3.95-3.83 (m, 2H), 3.75 (s, 4H), 3.73 (s, 2H), 2.95 (d, J=6.5 Hz, 2H).

Compound 139. 1-(7-(2-(3,5-bis(trifluoromethyl)phenylamino)-5-(1-methyl-1H-pyrazol-4-yl)pyrimidin-4-ylamino)-3,4-dihydroisoquinolin-2(1H)-yl)-2,2,2-trifluoroethan-1-one

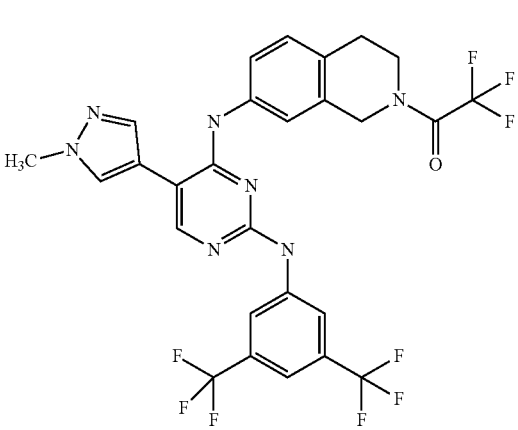 [SMILES: Cn1cc(-c2cnc(Nc3cc(C(F)(F)F)cc(C(F)(F)F)c3)nc2Nc2ccc3c(c2)CN(C(=O)C(F)(F)F)CC3)cn1]

1H NMR (300 MHz, CDCl$_3$) δ 8.15 (d, J=11.8 Hz, 1H), 8.06 (d, J=2.1 Hz, 2H), 8.02 (s, 1H), 7.68 (s, 1H), 7.57 (s, 1H), 7.44 (s, 1H), 7.18-7.15 (m, 1H), 7.13-7.07 (m, 1H), 6.88 (s, 1H), 4.68 (d, J=15.0 Hz, 2H), 4.05 (s, 3H), 3.93-3.79 (m, 2H), 2.94 (t, J=5.9 Hz, 2H).

Compound 140. 1-(7-(2-(3,5-difluorophenylamino)-5-(1-methyl-1H-pyrazol-4-yl)pyrimidin-4-ylamino)-3,4-dihydroisoquinolin-2(1H)-yl)-2,2,2-trifluoroethan-1-one

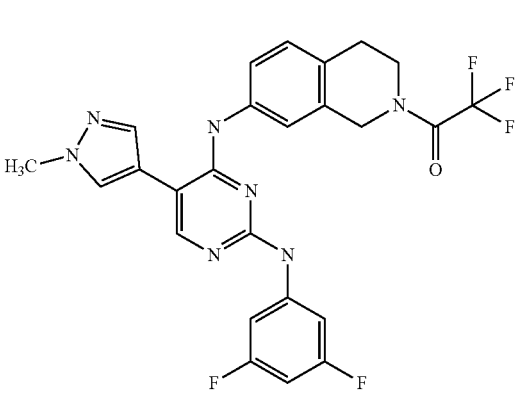 [SMILES: Cn1cc(-c2cnc(Nc3cc(F)cc(F)c3)nc2Nc2ccc3c(c2)CN(C(=O)C(F)(F)F)CC3)cn1]

1H NMR (300 MHz, CDCl$_3$) δ 8.01 (s, 1H), 7.67 (s, 1H), 7.56 (s, 2H), 7.41-7.33 (m, 1H), 7.24 (dd, J=10.0, 7.9 Hz, 1H), 7.19 (s, 1H), 7.15 (s, 1H), 6.85 (d, J=2.7 Hz, 1H), 6.47-6.37 (m, 1H), 4.75 (d, J=13.0 Hz, 2H), 4.04 (s, 3H), 3.95-3.84 (m, 2H), 2.98 (t, J=5.5 Hz, 2H).

Compound 141. N2-(3,5-difluorophenyl)-N4-(2-(2,2,2-trifluoroacetyl)-1,2,3,4-tetrahydroisoquinolin-7-yl)-5-(1-(piperidin-4-yl)-1H-pyrazol-4-yl)pyrimidine-2,4-diamine

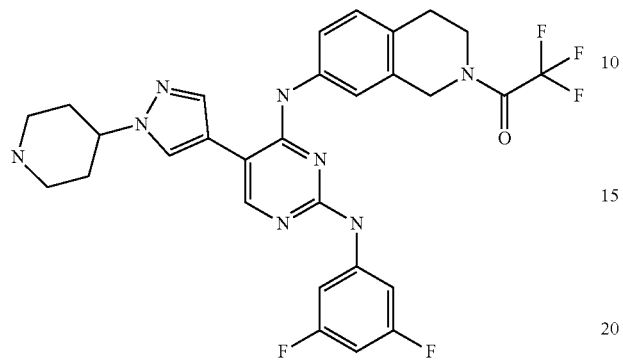

1H NMR (300 MHz, Chloroform-d) δ 8.01 (s, 1H), 7.73 (s, 1H), 7.62 (s, 1H), 7.48 (s, 1H), 7.36 (d, J=8.4 Hz, 1H), 7.28-7.23 (m, 1H), 7.21-7.16 (m, 2H), 7.14 (s, 1H), 6.80 (s, 1H), 6.47-6.38 (m, 1H), 4.75 (d, J=12.5 Hz, 2H), 4.68 (s, 1H), 4.59-4.47 (m, 1H), 4.23 (d, J=14.4 Hz, 1H), 3.96-3.85 (m, 2H), 3.41 (t, J=12.7 Hz, 1H), 3.10 (t, J=12.7 Hz, 1H), 2.98 (t, J=5.4 Hz, 2H), 2.38 (d, J=13.4 Hz, 2H), 2.25-2.11 (m, 2H).

Compound 142. N2-(3,5-dichlorophenyl)-N4-(2-(2,2,2-trifluoroacetyl)-1,2,3,4-tetrahydroisoquinolin-7-yl)-5-(1-(piperidin-4-yl)-1H-pyrazol-4-yl)pyrimidine-2,4-diamine

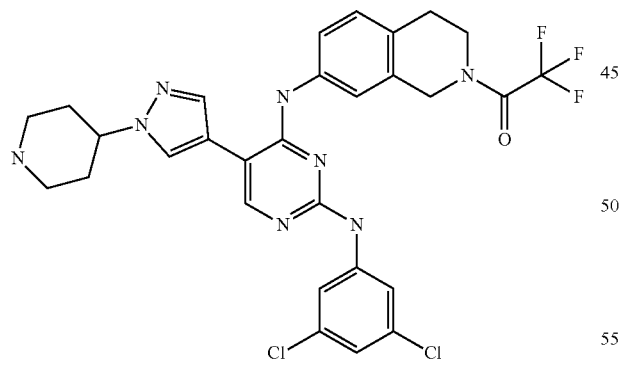

1H NMR (300 MHz, Chloroform-d) δ 8.01 (s, 1H), 7.72 (s, 1H), 7.62 (s, 1H), 7.51 (d, J=5.0 Hz, 3H), 7.41-7.30 (m, 1H), 7.25-7.17 (m, 1H), 6.98 (s, 1H), 6.81 (s, 1H), 4.76 (s, 2H), 4.70 (d, J=12.3 Hz, 1H), 4.60-4.46 (m, 1H), 4.23 (d, J=14.2 Hz, 1H), 3.95-3.83 (m, 2H), 3.41 (t, J=12.5 Hz, 1H), 3.11 (t, J=12.7 Hz, 1H), 2.96 (s, 2H), 2.38 (d, J=13.0 Hz, 2H), 2.26-2.09 (m, 2H).

Compound 143. N2-(3,5-bis(trifluoromethyl)phenyl)-N4-(2-(2,2,2-trifluoroacetyl)-1,2,3,4-tetrahydroisoquinolin-7-yl)-5-(1-(piperidin-4-yl)-1H-pyrazol-4-yl)pyrimidine-2,4-diamine

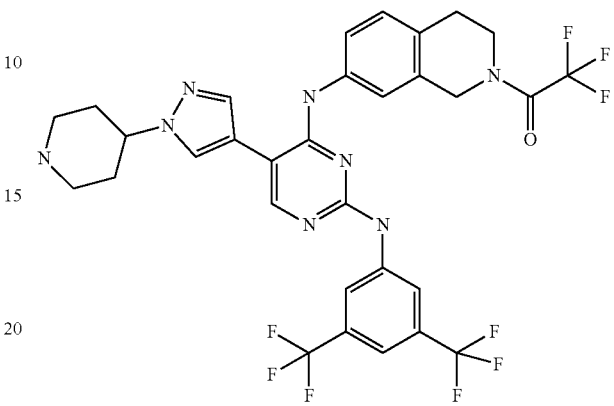

1H NMR (300 MHz, Chloroform-d) δ 8.06 (s, 2H), 8.03 (s, 1H), 7.82 (s, 1H), 7.73 (s, 1H), 7.63 (s, 1H), 7.46 (s, 1H), 7.15 (t, J=10.5 Hz, 1H), 6.81 (s, 1H), 4.73 (s, 2H), 4.68 (s, 1H), 4.60-4.47 (m, 1H), 4.28-4.19 (m, 1H), 3.89 (dt, J=12.2, 5.8 Hz, 2H), 3.42 (t, J=12.9 Hz, 1H), 3.11 (t, J=12.8 Hz, 1H), 2.97 (d, J=6.2 Hz, 2H), 2.39 (d, J=13.0 Hz, 2H), 2.25-2.09 (m, 2H).

Compound 144. N2-(2,3-dichlorophenyl)-N4-(2-(2,2,2-trifluoroacetyl)-1,2,3,4-tetrahydroisoquinolin-7-yl)-5-(1-(piperidin-4-yl)-1H-pyrazol-4-yl)pyrimidine-2,4-diamine

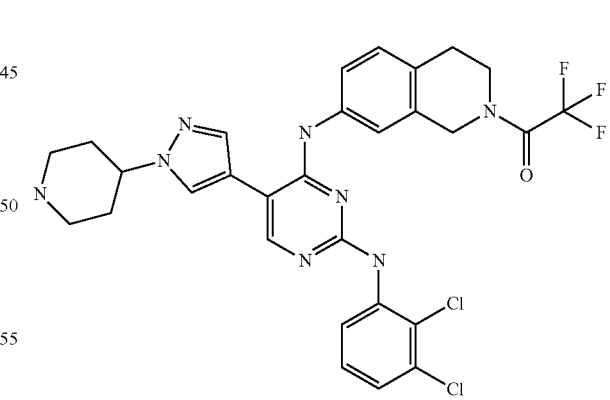

1H NMR (300 MHz, Chloroform-d) δ 8.34 (t, J=5.2 Hz, 1H), 8.03 (d, J=1.3 Hz, 1H), 7.72 (s, 1H), 7.61 (s, 1H), 7.56 (s, 1H), 7.44 (d, J=2.1 Hz, 1H), 7.39-7.30 (m, 1H), 7.20 (s, 1H), 7.18-7.11 (m, 2H), 6.82 (s, 1H), 4.73 (d, J=15.1 Hz, 3H), 4.60-4.47 (m, 1H), 4.24 (d, J=13.6 Hz, 1H), 3.96-3.86 (m, 2H), 3.41 (t, J=13.0 Hz, 1H), 3.11 (t, J=12.8 Hz, 1H), 2.98 (t, J=5.7 Hz, 2H), 2.38 (d, J=12.8 Hz, 2H), 2.24-2.11 (m, 2H).

Compound 145. N2-(3-chloro-5-fluorophenyl)-5-(1-methyl-1H-pyrazol-4-yl)-N4-(1,2,3,4-tetrahydroisoquinolin-7-yl)pyrimidine-2,4-diamine

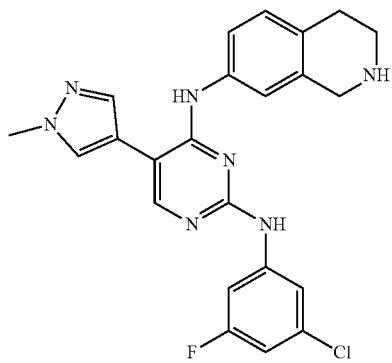 [SMILES: Cn1cc(-c2cnc(Nc3cc(F)cc(Cl)c3)nc2Nc2ccc3c(c2)CNCC3)cn1]

1H NMR (300 MHz, CDCl$_3$) δ 7.98 (s, 1H), 7.66 (d, J=0.8 Hz, 1H), 7.54 (s, 1H), 7.47 (d, J=11.3 Hz, 1H), 7.25 (d, J=8.5 Hz, 2H), 7.13 (d, J=4.6 Hz, 2H), 6.78 (s, 1H), 6.70 (d, J=8.1 Hz, 1H), 4.03 (s, 3H), 4.00 (s, 2H), 3.17 (t, J=6.0 Hz, 2H), 2.81 (t, J=6.0 Hz, 2H).

Compound 146. N2-(3-methoxy-5-(trifluoromethyl)phenyl)-5-(1-methyl-1H-pyrazol-4-yl)-N4-(1,2,3,4-tetrahydroisoquinolin-7-yl)pyrimidine-2,4-diamine

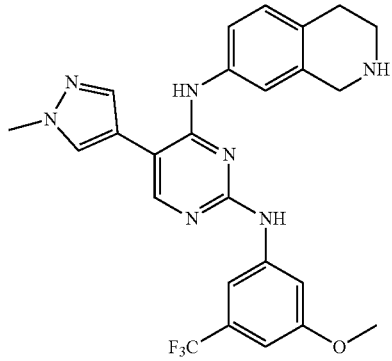

1H NMR (300 MHz, CDCl$_3$) δ 7.99 (s, 1H), 7.65 (s, 1H), 7.53 (s, 2H), 7.31 (s, 1H), 7.26 (d, J=2.3 Hz, 1H), 7.12 (d, J=2.2 Hz, 1H), 7.06 (d, J=8.0 Hz, 1H), 6.80-6.74 (m, 2H), 4.03 (d, J=1.1 Hz, 3H), 3.95 (s, 2H), 3.74 (d, J=2.6 Hz, 3H), 3.20-3.11 (m, 2H), 2.83-2.74 (m, 2H).

Compound 147. 2-(4-(2-(3-chloro-5-fluorophenylamino)-4-(1,2,3,4-tetrahydroisoquinolin-7-ylamino)pyrimidin-5-yl)-1H-pyrazol-1-yl)ethan-1-ol

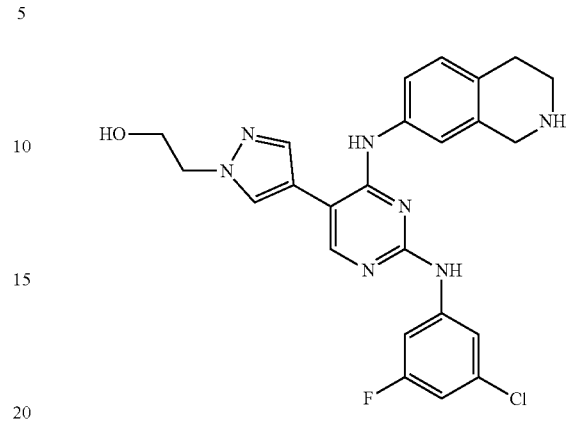

1H NMR (300 MHz, CDCl$_3$) δ 7.98 (s, 1H), 7.71 (d, J=0.8 Hz, 1H), 7.64 (s, 2H), 7.48 (s, 1H), 7.44 (s, 1H), 7.26 (d, J=7.1 Hz, 2H), 7.18 (s, 1H), 7.15 (s, 1H), 7.12 (s, 1H), 6.79 (s, 1H), 6.73-6.67 (m, 1H), 4.40-4.35 (m, 2H), 4.17-4.09 (m, 3H), 4.00 (s, 2H), 3.17 (t, J=6.0 Hz, 2H), 2.81 (t, J=6.0 Hz, 2H).

Compound 148. 2-(4-(2-(3-methoxy-5-(trifluoromethyl)phenylamino)-4-(1,2,3,4-tetrahydroisoquinolin-7-ylamino)pyrimidin-5-yl)-1H-pyrazol-1-yl)ethan-1-ol

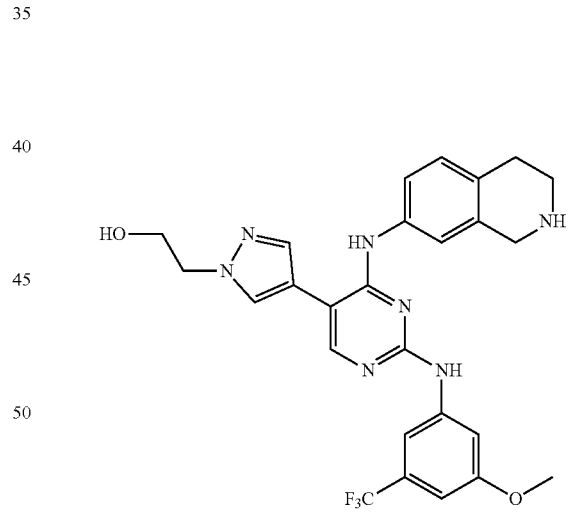

1H NMR (300 MHz, CDCl$_3$) δ 7.97 (d, J=1.5 Hz, 1H), 7.71-7.67 (m, 1H), 7.62 (d, J=0.9 Hz, 1H), 7.52 (d, J=8.6 Hz, 1H), 7.36 (d, J=14.9 Hz, 2H), 7.26 (s, 1H), 7.15-7.04 (m, 2H), 6.78 (d, J=6.4 Hz, 2H), 4.39-4.31 (m, 2H), 4.10 (t, J=4.8 Hz, 2H), 3.95 (s, 1H), 3.75 (s, 3H), 3.72 (s, 1H), 3.68 (d, J=5.5 Hz, 1H), 3.16 (t, J=6.0 Hz, 1H), 2.88 (s, 1H), 2.80 (t, J=6.0 Hz, 2H), 2.06 (d, J=4.4 Hz, 3H).

Compound 149. N2-(3-chlorophenyl)-5-(1-methyl-1H-pyrazol-4-yl)-N4-(1,2,3,4-tetrahydroisoquinolin-7-yl)pyrimidine-2,4-diamine

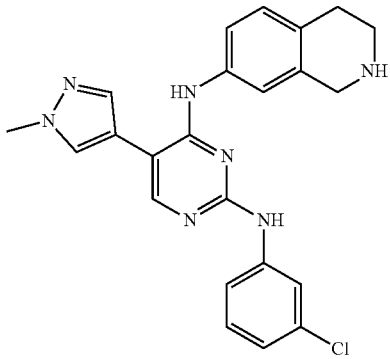 [SMILES: Cn1cc(-c2cnc(Nc3cccc(Cl)c3)nc2Nc2ccc3c(c2)CNCC3)cn1]

1H NMR (300 MHz, CDCl₃) δ 7.97 (s, 1H), 7.79 (t, J=2.1 Hz, 1H), 7.65 (s, 1H), 7.53 (s, 1H), 7.36-7.30 (m, 1H), 7.23 (d, J=6.1 Hz, 1H), 7.19 (s, 1H), 7.17-7.09 (m, 2H), 6.99-6.93 (m, 1H), 6.78 (s, 1H), 4.03 (s, 3H), 3.99 (s, 2H), 3.16 (t, J=6.0 Hz, 2H), 2.80 (t, J=5.9 Hz, 2H).

Compound 150. N2-(3-fluorophenyl)-5-(1-methyl-1H-pyrazol-4-yl)-N4-(1,2,3,4-tetrahydroisoquinolin-7-yl)pyrimidine-2,4-diamine 1H NMR (300 MHz, CDCl₃) δ 7.96 (s, 1H), 7.71 (t, J=2.3 Hz, 1H), 7.68-7.64 (m, 2H), 7.54 (d, J=0.8 Hz, 1H), 7.26-7.19 (m, 3H), 7.09 (t, J=8.5 Hz, 2H), 6.78 (s, 1H), 6.72-6.65 (m, 1H), 4.03 (s, 3H), 4.02 (d, J=3.8 Hz, 2H), 3.19 (t, J=6.0 Hz, 2H), 2.82 (t, J=6.0 Hz, 2H).

Compound 151. 5-(1-methyl-1H-pyrazol-4-yl)-N4-(1,2,3,4-tetrahydroisoquinolin-7-yl)-N2-(3-(trifluoromethyl)phenyl)pyrimidine-2,4-diamine

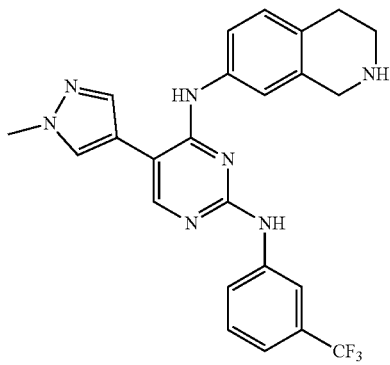 [SMILES: Cn1cc(-c2cnc(Nc3cccc(C(F)(F)F)c3)nc2Nc2ccc3c(c2)CNCC3)cn1]

1H NMR (300 MHz, CDCl₃) δ 7.98 (d, J=3.2 Hz, 1H), 7.84 (s, 1H), 7.81 (d, J=8.4 Hz, 1H), 7.67-7.63 (m, 1H), 7.55-7.51 (m, 1H), 7.42 (d, J=4.7 Hz, 1H), 7.37 (d, J=7.5 Hz, 1H), 7.25 (d, J=7.3 Hz, 2H), 7.12 (d, J=2.2 Hz, 1H), 7.08 (d, J=8.2 Hz, 1H), 6.82-6.76 (m, 1H), 4.03 (d, J=2.7 Hz, 3H), 3.97 (s, 2H), 3.17 (t, J=6.0 Hz, 2H), 2.91 (s, 1H), 2.80 (t, J=5.9 Hz, 1H).

Compound 152. N2-(3-methoxyphenyl)-5-(1-methyl-1H-pyrazol-4-yl)-N4-(1,2,3,4-tetrahydroisoquinolin-7-yl)pyrimidine-2,4-diamine

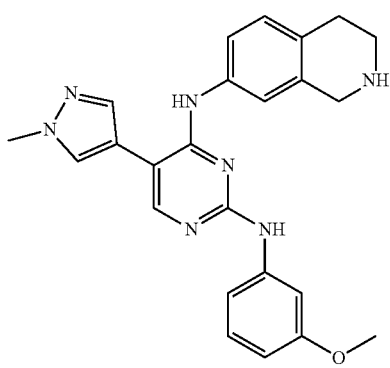

1H NMR (300 MHz, CDCl₃) δ 7.96 (d, J=2.7 Hz, 1H), 7.64 (dd, J=2.3, 0.8 Hz, 1H), 7.55-7.48 (m, 1H), 7.34-7.29 (m, 1H), 7.27 (d, J=2.5 Hz, 1H), 7.25-7.22 (m, 1H), 7.22-7.20 (m, 1H), 7.20-7.14 (m, 2H), 7.14-7.11 (m, 1H), 7.11-7.03 (m, 1H), 6.76 (s, 1H), 6.62-6.56 (m, 1H), 4.02 (d, J=2.7 Hz, 3H), 3.97 (s, 1H), 3.73 (d, J=2.2 Hz, 3H), 3.70 (s, 1H), 3.17 (t, J=6.0 Hz, 1H), 2.90 (s, 2H), 2.80 (t, J=5.9 Hz, 1H).

Compound 153. 5-(1-methyl-1H-pyrazol-4-yl)-N2-phenyl-N4-(1,2,3,4-tetrahydroisoquinolin-7-yl)pyrimidine-2,4-diamine

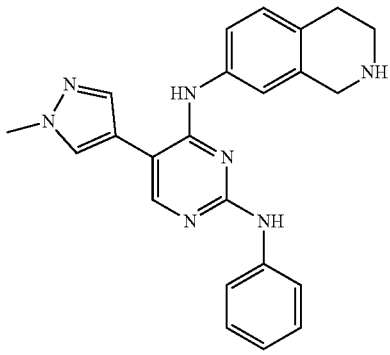 [SMILES: Cn1cc(-c2cnc(Nc3ccccc3)nc2Nc2ccc3c(c2)CNCC3)cn1]

1H NMR (300 MHz, CDCl$_3$) δ 7.96 (s, 1H), 7.65 (d, J=0.8 Hz, 1H), 7.61-7.54 (m, 2H), 7.52 (s, 1H), 7.36-7.30 (m, 1H), 7.25 (dd, J=11.3, 3.2 Hz, 2H), 7.11 (s, 1H), 7.09-7.00 (m, 2H), 6.76 (s, 1H), 4.03 (s, 3H), 3.99 (s, 2H), 3.17 (t, J=6.0 Hz, 2H), 2.80 (t, J=5.9 Hz, 2H).

Compound 154. N2-(2-isopropylphenyl)-5-(1-methyl-1H-pyrazol-4-yl)-N4-(1,2,3,4-tetrahydroisoquinolin-7-yl)pyrimidine-2,4-diamine

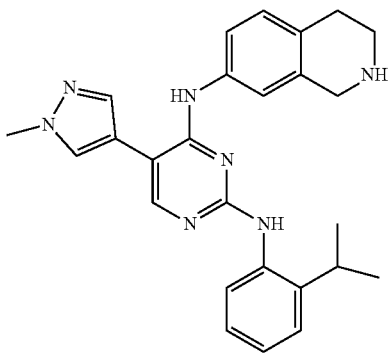 [SMILES: CC(C)c1ccccc1Nc1ncc(-c2cnn(C)c2)c(Nc2ccc3c(c2)CNCC3)n1]

1H NMR (300 MHz, CDCl$_3$) δ 7.91 (d, J=3.2 Hz, 1H), 7.78-7.72 (m, 1H), 7.62 (d, J=0.8 Hz, 1H), 7.51-7.46 (m, 1H), 7.38-7.31 (m, 1H), 7.26 (d, J=2.4 Hz, 1H), 7.24-7.18 (m, 2H), 7.15-7.06 (m, 1H), 6.95 (d, J=8.3 Hz, 1H), 6.76 (d, J=5.2 Hz, 2H), 4.02 (s, 3H), 3.83 (s, 2H), 3.24 (p, J=6.8 Hz, 1H), 3.13 (t, J=5.9 Hz, 2H), 2.75 (t, J=5.8 Hz, 2H), 1.28 (d, J=2.1 Hz, 3H), 1.25 (d, J=1.9 Hz, 3H).

Compound 155. 5-(1-methyl-1H-pyrazol-4-yl)-N4-(1,2,3,4-tetrahydroisoquinolin-7-yl)-N2-(3-(trifluoromethyl)benzyl)pyrimidine-2,4-diamine

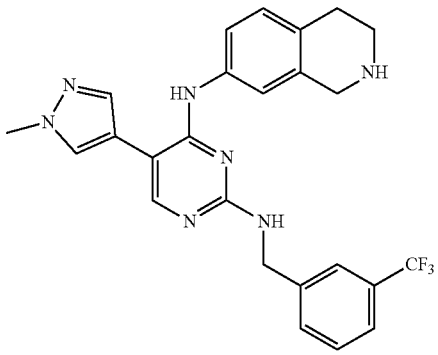 [SMILES: Cn1cc(-c2cnc(NCc3cccc(C(F)(F)F)c3)nc2Nc2ccc3c(c2)CNCC3)cn1]

1H NMR (300 MHz, CDCl$_3$) δ 7.86 (s, 1H), 7.63 (s, 1H), 7.61 (d, J=0.8 Hz, 1H), 7.56 (t, J=8.5 Hz, 2H), 7.50-7.45 (m, 2H), 7.20 (d, J=8.4 Hz, 1H), 7.16 (s, 1H), 6.97 (d, J=8.2 Hz, 1H), 6.69 (s, 1H), 5.56 (s, 1H), 4.71 (d, J=6.2 Hz, 2H), 4.01 (s, 3H), 3.89 (s, 2H), 3.14 (t, J=6.0 Hz, 2H), 2.76 (t, J=6.0 Hz, 2H).

Compound 156. 5-(1-methyl-1H-pyrazol-4-yl)-N4-(1,2,3,4-tetrahydroisoquinolin-7-yl)-N2-(o-tolyl)pyrimidine-2,4-diamine

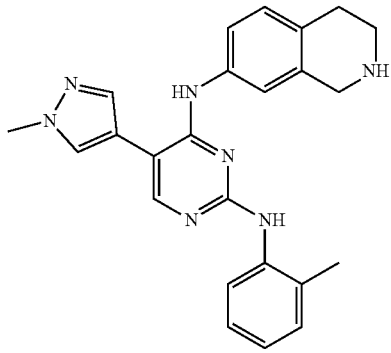 [SMILES: Cc1ccccc1Nc1ncc(-c2cnn(C)c2)c(Nc2ccc3c(c2)CNCC3)n1]

1H NMR (300 MHz, CDCl$_3$) δ 7.91 (d, J=1.9 Hz, 1H), 7.85 (d, J=7.8 Hz, 1H), 7.60 (d, J=2.3 Hz, 1H), 7.48 (s, 1H), 7.34-7.28 (m, 1H), 7.21 (d, J=7.6 Hz, 1H), 7.18-7.01 (m, 3H), 6.97 (d, J=8.4 Hz, 1H), 6.82 (s, 1H), 6.75 (s, 1H), 3.99 (d, J=1.9 Hz, 3H), 3.93 (s, 2H), 2.82 (t, J=5.9 Hz, 4H), 2.36-2.27 (m, 3H).

Compound 157. N2-(2,6-difluorophenyl)-5-(1-methyl-1H-pyrazol-4-yl)-N4-(1,2,3,4-tetrahydroisoquinolin-7-yl)pyrimidine-2,4-diamine

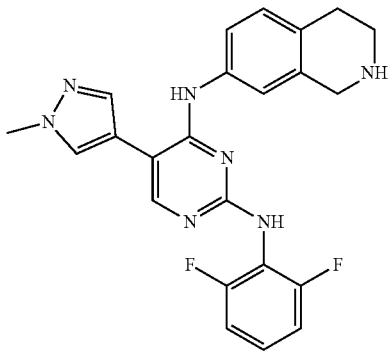 [SMILES: Cn1cc(-c2cnc(Nc3c(F)cccc3F)nc2Nc2ccc3c(c2)CNCC3)cn1]

1H NMR (300 MHz, CDCl₃) δ 7.92 (d, J=2.5 Hz, 1H), 7.62 (d, J=0.8 Hz, 1H), 7.49 (s, 1H), 7.27-7.16 (m, 2H), 7.16-7.08 (m, 1H), 7.01 (t, J=8.0 Hz, 2H), 6.92 (d, J=8.2 Hz, 1H), 6.76 (s, 1H), 4.02 (s, 3H), 3.87 (s, 2H), 3.14 (t, J=6.0 Hz, 2H), 2.75 (t, J=6.0 Hz, 2H).

Compound 158. 5-(1-methyl-1H-pyrazol-4-yl)-N4-(1,2,3,4-tetrahydroisoquinolin-7-yl)-N2-(m-tolyl)pyrimidine-2,4-diamine

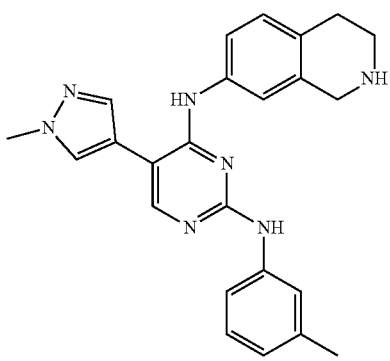 [SMILES: Cc1cccc(Nc2ncc(-c3cnn(C)c3)c(Nc3ccc4c(c3)CNCC4)n2)c1]

1H NMR (300 MHz, CDCl₃) δ 7.95 (d, J=2.0 Hz, 1H), 7.64 (t, J=1.3 Hz, 1H), 7.52 (s, 1H), 7.44 (d, J=8.1 Hz, 1H), 7.34 (d, J=14.4 Hz, 2H), 7.23-7.16 (m, 2H), 7.07 (d, J=7.2 Hz, 2H), 6.85 (d, J=7.9 Hz, 1H), 6.75 (s, 1H), 4.03 (s, 3H), 4.00 (d, J=10.5 Hz, 2H), 3.17 (t, J=6.0 Hz, 1H), 2.89 (d, J=6.1 Hz, 1H), 2.80 (t, J=6.0 Hz, 1H), 2.33 (s, 3H), 2.29 (s, 1H).

Compound 159. N2-(5-fluoro-2-methylphenyl)-5-(1-methyl-1H-pyrazol-4-yl)-N4-(1,2,3,4-tetrahydroisoquinolin-7-yl)pyrimidine-2,4-diamine

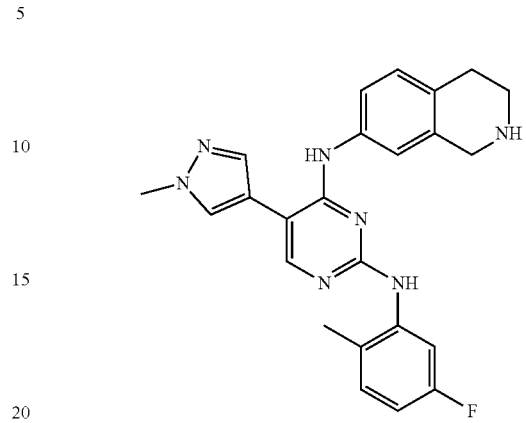

1H NMR (300 MHz, CDCl₃) δ 8.01-7.97 (m, 1H), 7.96 (s, 1H), 7.95 (t, J=2.2 Hz, 1H), 7.67-7.62 (m, 1H), 7.56-7.50 (m, 1H), 7.24 (s, 1H), 7.20 (dd, J=8.0, 2.2 Hz, 1H), 7.14-7.05 (m, 2H), 6.87 (s, 1H), 6.79 (s, 1H), 6.71-6.63 (m, 1H), 4.02 (s, 3H), 4.00 (d, J=8.1 Hz, 2H), 3.19 (t, J=6.0 Hz, 1H), 2.83 (t, J=5.9 Hz, 2H), 2.29 (s, 3H).

Compound 160. N2-(3,5-dichlorophenyl)-5-(1-isopropyl-1H-pyrazol-4-yl)-N4-(1,2,3,4-tetrahydroisoquinolin-7-yl)pyrimidine-2,4-diamine

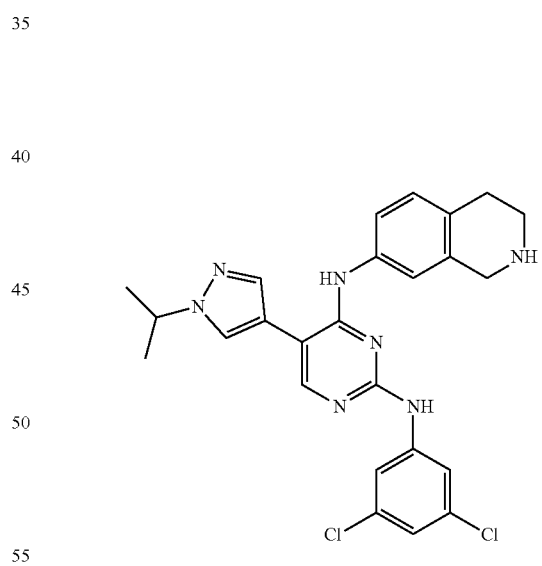

1H NMR (300 MHz, CDCl₃) δ 7.96 (s, 1H), 7.66 (s, 1H), 7.57 (s, 1H), 7.50 (d, J=1.9 Hz, 2H), 7.44 (s, 1H), 7.30-7.26 (m, 1H), 7.11 (d, J=8.2 Hz, 1H), 7.07 (d, J=2.2 Hz, 1H), 6.93 (t, J=1.8 Hz, 1H), 6.81 (s, 1H), 4.66-4.54 (m, 1H), 3.98 (s, 2H), 3.95-3.89 (m, 1H), 3.15 (t, J=6.0 Hz, 2H), 2.78 (t, J=6.0 Hz, 3H), 1.59 (d, J=6.7 Hz, 6H).

Compound 161. N2-(3,5-bis(trifluoromethyl)phenyl)-5-(1-isopropyl-1H-pyrazol-4-yl)-N4-(1,2,3,4-tetrahydroisoquinolin-7-yl)pyrimidine-2,4-diamine

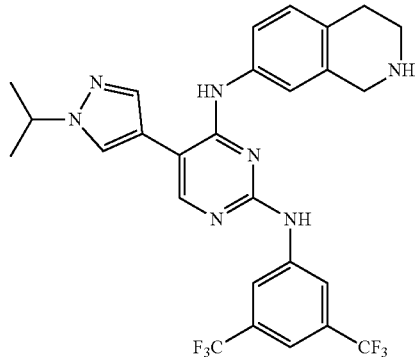 [SMILES: CC(C)n1cc(-c2cnc(Nc3cc(C(F)(F)F)cc(C(F)(F)F)c3)nc2Nc2ccc3c(c2)CNCC3)cn1]

1H NMR (300 MHz, CDCl$_3$) δ 8.19 (d, J=7.8 Hz, 1H), 8.10 (s, 2H), 7.97-7.90 (m, 1H), 7.68-7.62 (m, 1H), 7.58-7.52 (m, 1H), 7.38 (s, 1H), 7.26-7.21 (m, 1H), 7.15-7.04 (m, 1H), 7.00 (d, J=8.6 Hz, 1H), 6.81 (d, J=9.9 Hz, 1H), 4.64-4.50 (m, 1H), 4.09 (s, 2H), 3.19 (d, J=6.3 Hz, 2H), 2.86 (s, 2H), 1.60 (d, J=6.7 Hz, 6H).

Compound 162. N2-(3,5-difluorophenyl)-5-(1-isopropyl-1H-pyrazol-4-yl)-N4-(1,2,3,4-tetrahydroisoquinolin-7-yl)pyrimidine-2,4-diamine

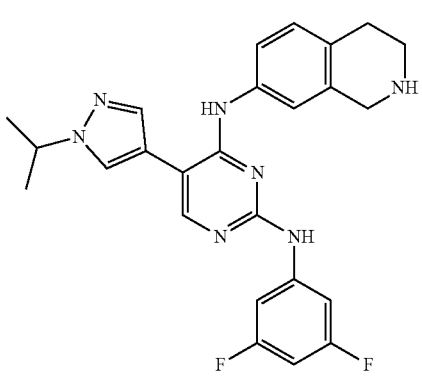

1H NMR (300 MHz, CDCl$_3$) δ 7.93 (s, 1H), 7.65 (s, 1H), 7.58 (s, 1H), 7.53 (d, J=1.8 Hz, 2H), 7.42 (s, 1H), 7.31-7.27 (m, 1H), 7.12 (d, J=8.1 Hz, 1H), 7.08 (d, J=2.1 Hz, 1H), 6.97 (t, J=1.8 Hz, 1H), 6.84 (s, 1H), 4.68-4.56 (m, 1H), 3.99 (s, 2H), 3.96-3.91 (m, 1H), 3.21 (t, J=6.0 Hz, 2H), 2.79 (t, J=6.0 Hz, 3H), 1.61 (d, J=6.7 Hz, 6H);

LC/MS [M+H]$^+$ 462.3.

Compound 163. N2-(3-chloro-5-fluorophenyl)-5-(1-isopropyl-1H-pyrazol-4-yl)-N4-(1,2,3,4-tetrahydroisoquinolin-7-yl)pyrimidine-2,4-diamine

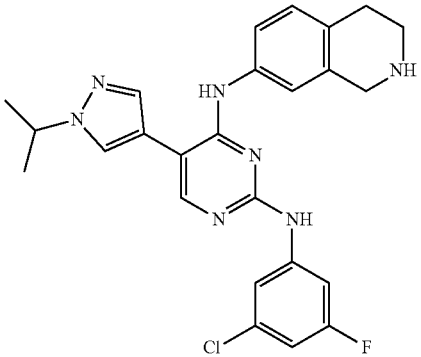 [SMILES: CC(C)n1cc(-c2cnc(Nc3cc(F)cc(Cl)c3)nc2Nc2ccc3c(c2)CNCC3)cn1]

1H NMR (300 MHz, Chloroform-d) δ 7.99-7.87 (m, 1H), 7.75-7.60 (m, 2H), 7.57 (d, J=2.9 Hz, 1H), 7.48-7.39 (m, 1H), 7.31 (d, J=13.3 Hz, 1H), 7.24 (s, 1H), 7.19-7.03 (m, 2H), 6.90-6.79 (m, 1H), 6.72-6.57 (m, 1H), 4.59 (p, J=6.7 Hz, 2H), 4.11 (d, J=11.7 Hz, 1H), 3.32-3.14 (m, 2H), 2.94-2.84 (m, 2H), 1.59 (d, J=6.7 Hz, 6H).

Compound 164. 5-(1-isopropyl-1H-pyrazol-4-yl)-N2-(3-methoxy-5-(trifluoromethyl)phenyl)-N4-(1,2,3,4-tetrahydroisoquinolin-7-yl)pyrimidine-2,4-diamine

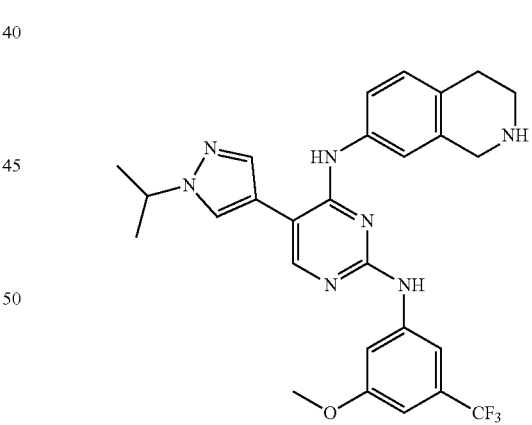

1H NMR (300 MHz, Chloroform-d) δ 8.04-7.94 (m, 1H), 7.65 (d, J=3.3 Hz, 1H), 7.56 (s, 1H), 7.50 (s, 1H), 7.46-7.35 (m, 1H), 7.30 (s, 1H), 7.21 (d, J=13.3 Hz, 2H), 7.05 (t, J=7.9 Hz, 1H), 6.81 (s, 1H), 6.74 (d, J=5.6 Hz, 1H), 4.65-4.53 (m, 1H), 4.03 (s, 1H), 3.73 (s, 2H), 3.71 (s, 2H), 2.87 (d, J=6.6 Hz, 2H), 1.59 (d, J=6.7 Hz, 6H).

Compound 165. N2-(3,5-dimethoxyphenyl)-5-(1-isopropyl-1H-pyrazol-4-yl)-N4-(1,2,3,4-tetrahydroisoquinolin-7-yl)pyrimidine-2,4-diamine

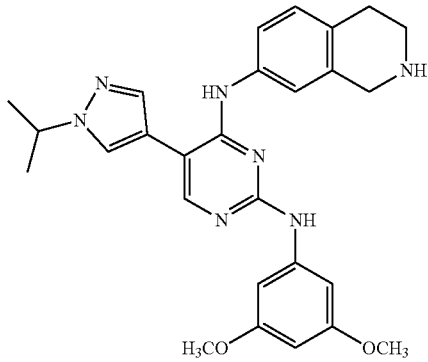 [SMILES: COc1cc(Nc2ncc(-c3cnn(C(C)C)c3)c(Nc3ccc4c(c3)CNCC4)n2)cc(OC)c1]

1H NMR (300 MHz, Chloroform-d) δ 7.94 (d, J=3.3 Hz, 1H), 7.67-7.61 (m, 1H), 7.59-7.52 (m, 1H), 7.46-7.31 (m, 2H), 7.24 (d, J=8.6 Hz, 1H), 7.15 (d, J=7.8 Hz, 1H), 7.05 (d, J=8.1 Hz, 1H), 6.83-6.75 (m, 3H), 6.15 (q, J=2.2 Hz, 1H), 4.58 (p, J=6.6 Hz, 1H), 3.75 (s, 2H), 3.69 (d, J=4.5 Hz, 6H), 2.89 (d, J=10.9 Hz, 2H), 2.08-1.97 (m, 2H), 1.59 (dd, J=6.7, 2.5 Hz, 6H).

Compound 166. N2-(3,5-dimethylphenyl)-5-(1-isopropyl-1H-pyrazol-4-yl)-N4-(1,2,3,4-tetrahydroisoquinolin-7-yl)pyrimidine-2,4-diamine

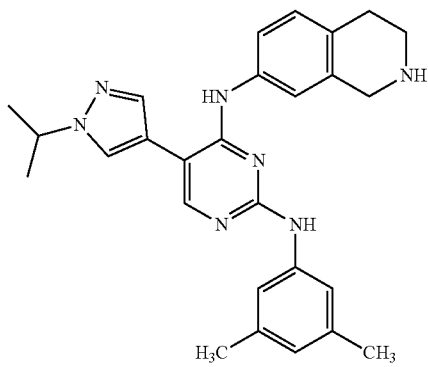 [SMILES: Cc1cc(C)cc(Nc2ncc(-c3cnn(C(C)C)c3)c(Nc3ccc4c(c3)CNCC4)n2)c1]

1H NMR (300 MHz, Chloroform-d) δ 7.92 (d, J=5.4 Hz, 1H), 7.64 (d, J=2.7 Hz, 1H), 7.54 (d, J=1.2 Hz, 1H), 7.39 (d, J=7.5 Hz, 2H), 7.18 (s, 2H), 7.14-7.03 (m, 2H), 6.79 (s, 1H), 6.65 (s, 1H), 4.58 (p, J=6.7 Hz, 1H), 3.97-3.82 (m, 2H), 2.86 (d, J=5.2 Hz, 2H), 2.24 (s, 6H), 1.59 (d, J=6.7 Hz, 6H).

Compound 167. N2-(3-chlorophenyl)-5-(1-isopropyl-1H-pyrazol-4-yl)-N4-(1,2,3,4-tetrahydroisoquinolin-7-yl)pyrimidine-2,4-diamine

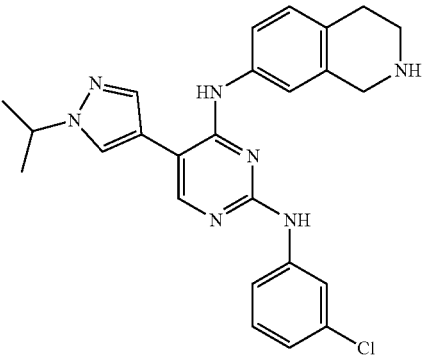 [SMILES: CC(C)n1cc(-c2cnc(Nc3cccc(Cl)c3)nc2Nc2ccc3c(c2)CNCC3)cn1]

1H NMR (300 MHz, Chloroform-d) δ 7.96 (s, 1H), 7.78 (s, 1H), 7.66 (s, 1H), 7.56 (s, 1H), 7.30 (d, J=8.6 Hz, 1H), 7.20 (s, 1H), 7.16 (d, J=7.9 Hz, 2H), 7.11 (d, J=8.1 Hz, 1H), 6.95 (d, J=7.0 Hz, 1H), 6.80 (s, 1H), 4.66-4.51 (m, 1H), 4.02 (s, 1H), 3.19 (t, J=6.1 Hz, 2H), 2.93-2.76 (m, 2H), 1.60 (d, J=6.7 Hz, 6H).

Compound 168. 5-(1-isopropyl-1H-pyrazol-4-yl)-N2-(3-methoxyphenyl)-N4-(1,2,3,4-tetrahydroisoquinolin-7-yl)pyrimidine-2,4-diamine

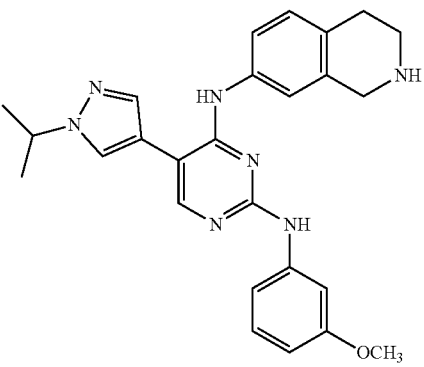 [SMILES: COc1cccc(Nc2ncc(-c3cnn(C(C)C)c3)c(Nc3ccc4c(c3)CNCC4)n2)c1]

1H NMR (300 MHz, Chloroform-d) δ 7.96-7.91 (m, 1H), 7.65 (d, J=0.9 Hz, 1H), 7.55 (d, J=0.9 Hz, 1H), 7.36 (s, 1H), 7.30 (s, 1H), 7.25-6.97 (m, 5H), 6.81 (s, 1H), 6.56 (d, J=7.7 Hz, 1H), 4.58 (p, J=6.7 Hz, 1H), 3.96-3.80 (m, 2H), 3.75-3.63 (m, 3H), 2.88 (s, 2H), 1.59 (d, J=6.7 Hz, 6H).

Compound 169. 5-(1-isopropyl-1H-pyrazol-4-yl)-N4-(1,2,3,4-tetrahydroisoquinolin-7-yl)-N2-(m-tolyl)pyrimidine-2,4-diamine

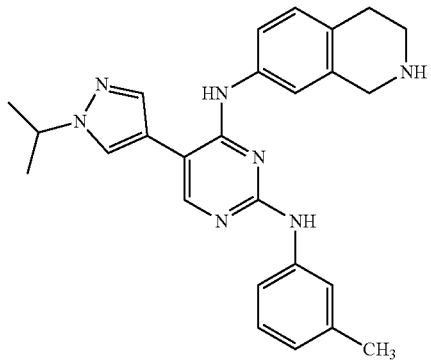 [SMILES: Cc1cccc(Nc2ncc(-c3cnn(C(C)C)c3)c(Nc3ccc4c(c3)CNCC4)n2)c1]

1H NMR (300 MHz, Chloroform-d) δ 7.94 (d, J=2.3 Hz, 1H), 7.65 (s, 1H), 7.54 (d, J=0.8 Hz, 1H), 7.42 (d, J=6.6 Hz, 1H), 7.33 (s, 2H), 7.18 (d, J=7.8 Hz, 2H), 7.13 (d, J=8.1 Hz, 2H), 7.05 (d, J=8.2 Hz, 1H), 6.83 (d, J=7.7 Hz, 1H), 6.77 (s, 1H), 4.58 (p, J=6.8 Hz, 1H), 3.97 (s, 2H), 3.16 (t, J=6.0 Hz, 2H), 2.79 (t, J=5.8 Hz, 2H), 2.30 (s, 3H), 1.59 (d, J=6.7 Hz, 6H).

Compound 170. 5-(1-isopropyl-1H-pyrazol-4-yl)-N2-phenyl-N4-(1,2,3,4-tetrahydroisoquinolin-7-yl)pyrimidine-2,4-diamine

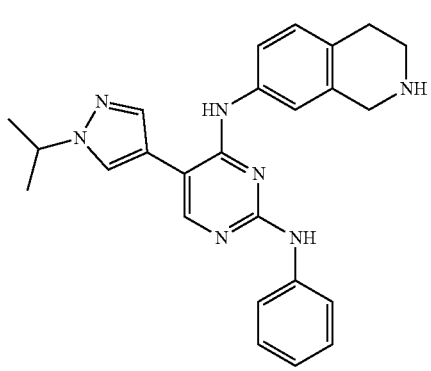 [SMILES: CC(C)n1cc(-c2cnc(Nc3ccccc3)nc2Nc2ccc3c(c2)CNCC3)cn1]

1H NMR (300 MHz, Chloroform-d) δ 7.95 (d, J=2.1 Hz, 1H), 7.67-7.64 (m, 1H), 7.60-7.54 (m, 3H), 7.30 (d, J=7.5 Hz, 3H), 7.18 (d, J=23.3 Hz, 3H), 7.08-7.00 (m, 2H), 6.79 (s, 1H), 4.58 (dt, J=13.5, 6.8 Hz, 1H), 3.98 (s, 2H), 3.16 (t, J=6.0 Hz, 2H), 2.80 (t, J=6.1 Hz, 2H), 1.59 (d, J=6.7 Hz, 6H).

Compound 171. N2-(3,5-dichlorophenyl)-5-(1-propyl-1H-pyrazol-4-yl)-N4-(1,2,3,4-tetrahydroisoquinolin-7-yl)pyrimidine-2,4-diamine

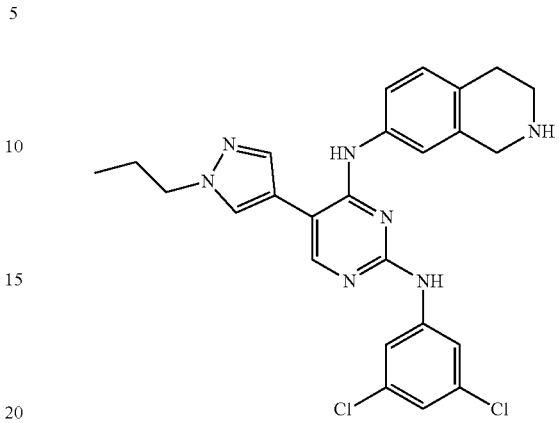

1H NMR (300 MHz, Chloroform-d) δ 7.97 (d, J=3.6 Hz, 1H), 7.65 (s, 1H), 7.57-7.47 (m, 3H), 7.31 (d, J=5.9 Hz, 1H), 7.23 (s, 1H), 7.13 (d, J=8.4 Hz, 1H), 7.07 (s, 1H), 6.93 (t, J=1.7 Hz, 1H), 6.80 (s, 1H), 4.17 (t, J=7.3 Hz, 2H), 3.99-3.78 (m, 2H), 2.87 (d, J=5.1 Hz, 2H), 1.98 (q, J=7.3 Hz, 4H), 0.99 (t, J=7.4 Hz, 3H).

Compound 172. N2-(3,5-bis(trifluoromethyl)phenyl)-5-(1-propyl-1H-pyrazol-4-yl)-N4-(1,2,3,4-tetrahydroisoquinolin-7-yl)pyrimidine-2,4-diamine

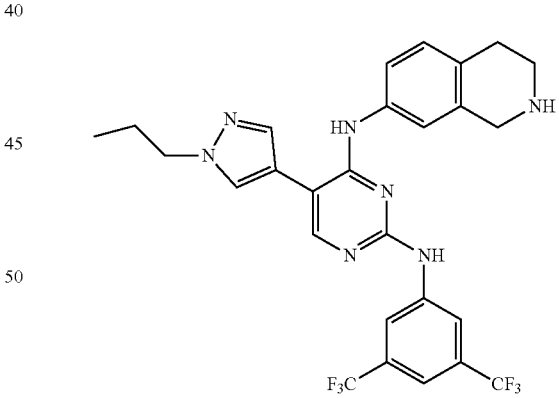

1H NMR (300 MHz, Chloroform-d) δ 8.12-7.98 (m, 2H), 7.72-7.65 (m, 1H), 7.65-7.57 (m, 1H), 7.54 (d, J=2.5 Hz, 1H), 7.40 (d, J=18.9 Hz, 1H), 7.30 (s, 1H), 7.25-7.19 (m, 1H), 7.11-7.01 (m, 1H), 6.96 (s, 1H), 6.84 (d, J=7.8 Hz, 1H), 4.27-4.15 (m, 2H), 3.98-3.75 (m, 2H), 2.88 (s, 2H), 2.10-1.86 (m, 4H), 0.99 (t, J=7.5 Hz, 3H).

Compound 173. N2-(3,5-difluorophenyl)-5-(1-propyl-1H-pyrazol-4-yl)-N4-(1,2,3,4-tetrahydroisoquinolin-7-yl)pyrimidine-2,4-diamine

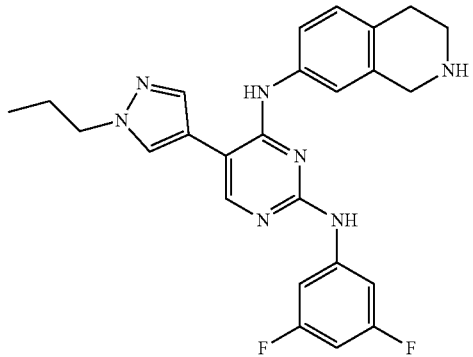 [SMILES: CCCn1cc(-c2cnc(Nc3cc(F)cc(F)c3)nc2Nc2ccc3c(c2)CNCC3)cn1]

1H NMR (300 MHz, Chloroform-d) δ 7.94 (t, J=2.5 Hz, 1H), 7.67-7.62 (m, 1H), 7.55 (d, J=3.3 Hz, 1H), 7.33 (s, 1H), 7.27-7.04 (m, 5H), 6.84 (d, J=11.3 Hz, 1H), 6.46-6.29 (m, 1H), 4.18 (td, J=7.0, 2.7 Hz, 2H), 4.00-3.73 (m, 3H), 2.90 (s, 2H), 1.97 (h, J=7.3 Hz, 4H), 1.04-0.92 (m, 3H).

Compound 174. N2-(3-methoxy-5-(trifluoromethyl)phenyl)-5-(1-propyl-1H-pyrazol-4-yl)-N4-(1,2,3,4-tetrahydroisoquinolin-7-yl)pyrimidine-2,4-diamine

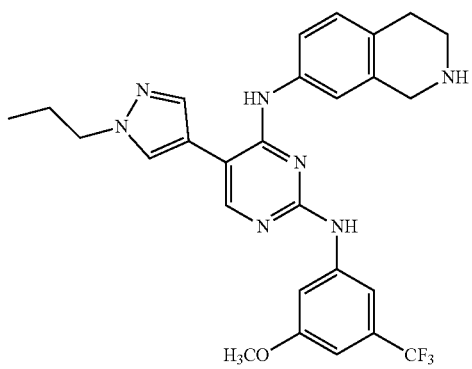 [SMILES: CCCn1cc(-c2cnc(Nc3cc(OC)cc(C(F)(F)F)c3)nc2Nc2ccc3c(c2)CNCC3)cn1]

1H NMR (300 MHz, CDCl₃) δ 7.97 (s, 1H), 7.65 (d, J=0.8 Hz, 1H), 7.54-7.50 (m, 2H), 7.41 (s, 1H), 7.32 (s, 1H), 7.25-7.16 (m, 2H), 7.05 (d, J=8.1 Hz, 1H), 6.76 (d, J=11.0 Hz, 2H), 4.17 (t, J=7.1 Hz, 2H), 3.99 (s, 2H), 3.73 (s, 3H), 3.22-3.14 (m, 2H), 2.85-2.77 (m, 2H), 2.05-1.90 (m, 3H), 0.99 (t, J=7.4 Hz, 3H).

Compound 175. N2-(3-chloro-5-fluorophenyl)-5-(1-propyl-1H-pyrazol-4-yl)-N4-(1,2,3,4-tetrahydroisoquinolin-7-yl)pyrimidine-2,4-diamine

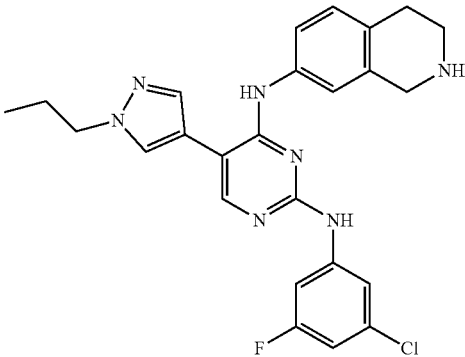 [SMILES: CCCn1cc(-c2cnc(Nc3cc(F)cc(Cl)c3)nc2Nc2ccc3c(c2)CNCC3)cn1]

1H NMR (300 MHz, Chloroform-d) δ 7.95 (s, 1H), 7.64 (d, J=0.8 Hz, 2H), 7.54 (d, J=0.9 Hz, 1H), 7.44 (dt, J=11.4, 2.2 Hz, 1H), 7.25-7.19 (m, 2H), 7.15 (dd, J=8.3, 2.3 Hz, 1H), 7.07 (d, J=8.2 Hz, 1H), 6.80 (s, 1H), 6.66-6.59 (m, 1H), 4.17 (t, J=7.2 Hz, 2H), 4.05 (s, 2H), 3.21 (t, J=6.1 Hz, 2H), 2.85 (t, J=5.8 Hz, 2H), 1.97 (q, J=7.3 Hz, 2H), 0.99 (t, J=7.4 Hz, 3H).

Compound 176. N2-(3,5-dimethoxyphenyl)-5-(1-propyl-1H-pyrazol-4-yl)-N4-(1,2,3,4-tetrahydroisoquinolin-7-yl)pyrimidine-2,4-diamine

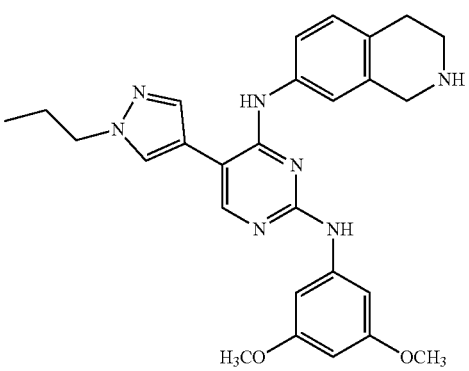 [SMILES: CCCn1cc(-c2cnc(Nc3cc(OC)cc(OC)c3)nc2Nc2ccc3c(c2)CNCC3)cn1]

1H NMR (300 MHz, Chloroform-d) δ 7.94 (s, 1H), 7.63 (d, J=0.8 Hz, 1H), 7.51 (d, J=0.8 Hz, 1H), 7.32 (d, J=2.1 Hz, 1H), 7.21 (d, J=5.6 Hz, 1H), 7.17 (d, J=2.3 Hz, 1H), 7.04 (d, J=8.3 Hz, 1H), 6.79 (d, J=2.2 Hz, 2H), 6.76 (s, 1H), 6.15 (t, J=2.2 Hz, 1H), 4.16 (t, J=7.1 Hz, 2H), 3.99 (s, 2H), 3.69 (s, 6H), 3.19 (t, J=6.0 Hz, 2H), 2.82 (t, J=5.9 Hz, 2H), 2.00-1.93 (m, 2H), 0.99 (t, J=7.4 Hz, 3H).

Compound 177. N2-(3,5-dimethylphenyl)-5-(1-propyl-1H-pyrazol-4-yl)-N4-(1,2,3,4-tetrahydroisoquinolin-7-yl)pyrimidine-2,4-diamine

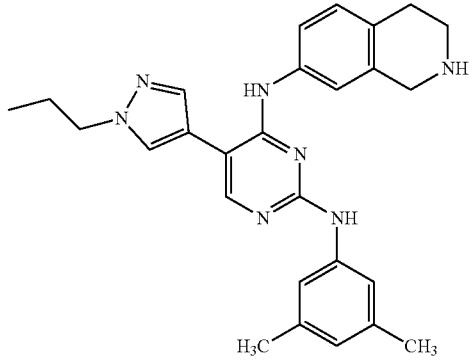 [SMILES: CCCn1cc(-c2cnc(Nc3cc(C)cc(C)c3)nc2Nc2ccc3c(c2)CNCC3)cn1]

1H NMR (300 MHz, Chloroform-d) δ 7.93 (d, J=2.5 Hz, 1H), 7.63 (d, J=0.8 Hz, 1H), 7.51 (s, 1H), 7.40 (dd, J=8.5, 2.4 Hz, 1H), 7.18 (s, 2H), 7.15 (s, 1H), 7.10-7.02 (m, 2H), 6.74 (s, 1H), 6.66 (s, 1H), 4.19-4.13 (m, 2H), 3.96 (s, 2H), 3.16 (t, J=6.1 Hz, 2H), 2.79 (t, J=5.9 Hz, 2H), 2.25 (s, 6H), 1.97 (q, J=7.3 Hz, 2H), 0.99 (t, J=7.4 Hz, 3H).

Compound 178. N2-(3-chlorophenyl)-5-(1-propyl-1H-pyrazol-4-yl)-N4-(1,2,3,4-tetrahydroisoquinolin-7-yl)pyrimidine-2,4-diamine

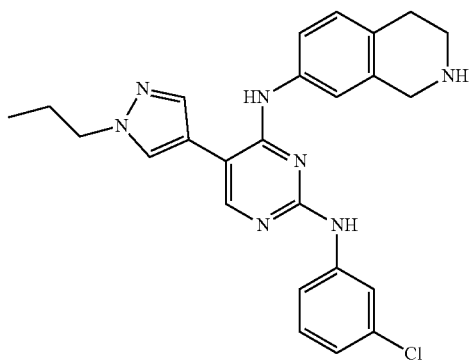 [SMILES: CCCn1cc(-c2cnc(Nc3cccc(Cl)c3)nc2Nc2ccc3c(c2)CNCC3)cn1]

1H NMR (300 MHz, Chloroform-d) δ 7.96 (s, 1H), 7.77 (t, J=2.1 Hz, 1H), 7.65 (d, J=0.9 Hz, 1H), 7.53 (d, J=0.9 Hz, 1H), 7.33-7.27 (m, 2H), 7.19 (d, J=7.9 Hz, 1H), 7.16-7.07 (m, 3H), 6.98-6.93 (m, 1H), 6.77 (s, 1H), 4.17 (t, J=7.2 Hz, 2H), 3.98 (s, 2H), 3.15 (t, J=5.9 Hz, 2H), 2.79 (t, J=5.8 Hz, 2H), 1.98 (q, J=7.4 Hz, 2H), 0.99 (t, J=7.4 Hz, 3H).

Compound 179. N2-(3,5-dichlorophenyl)-5-(1-isobutyl-1H-pyrazol-4-yl)-N4-(1,2,3,4-tetrahydroisoquinolin-7-yl)pyrimidine-2,4-diamine

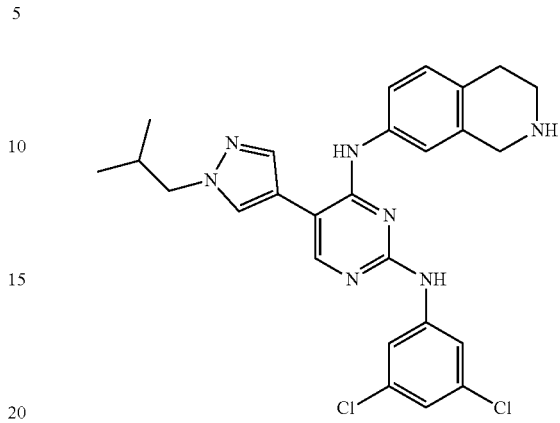

1H NMR (300 MHz, CDCl$_3$) δ 7.97 (s, 1H), 7.66 (s, 1H), 7.56 (s, 1H), 7.54-7.48 (m, 3H), 7.29 (d, J=2.3 Hz, 1H), 7.11 (d, J=8.2 Hz, 1H), 7.06 (d, J=2.2 Hz, 1H), 6.93 (t, J=1.8 Hz, 1H), 6.80 (s, 1H), 4.00 (d, J=7.2 Hz, 2H), 3.97 (s, 2H), 3.15 (t, J=5.9 Hz, 3H), 2.78 (t, J=6.0 Hz, 2H), 2.34-2.23 (m, 1H), 0.97 (d, J=6.7 Hz, 6H);

LC/MS [M+H]$^+$ 509.2.

Compound 180. N2-(3,5-bis(trifluoromethyl)phenyl)-5-(1-isobutyl-1H-pyrazol-4-yl)-N4-(1,2,3,4-tetrahydroisoquinolin-7-yl)pyrimidine-2,4-diamine

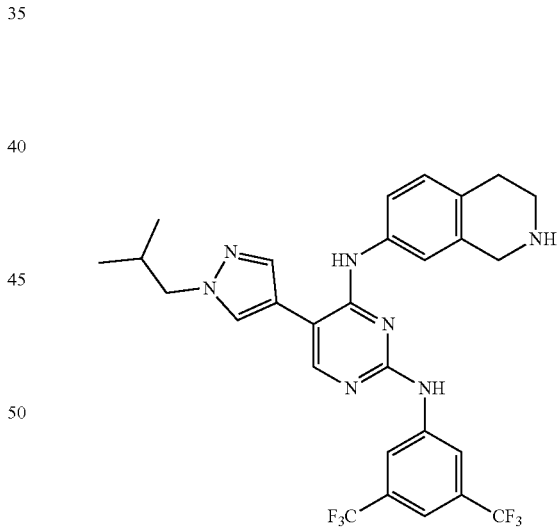

1H NMR (300 MHz, Chloroform-d) δ 8.12 (s, 1H), 8.10-7.99 (m, 2H), 7.96 (s, 1H), 7.65 (d, J=8.0 Hz, 1H), 7.52 (d, J=2.9 Hz, 1H), 7.40 (d, J=16.8 Hz, 2H), 7.1-6.95 (m, 2H), 6.82 (d, J=9.1 Hz, 1H), 4.14 (s, 2H), 4.01 (d, J=7.2 Hz, 2H), 3.21 (s, 2H), 2.88 (s, 2H), 2.33-2.24 (m, 1H), 0.98 (d, J=6.7 Hz, 6H);

LC/MS [M+H]$^+$ 576.3.

Compound 181. N2-(3,5-difluorophenyl)-5-(1-isobutyl-1H-pyrazol-4-yl)-N4-(1,2,3,4-tetrahydroisoquinolin-7-yl)pyrimidine-2,4-diamine

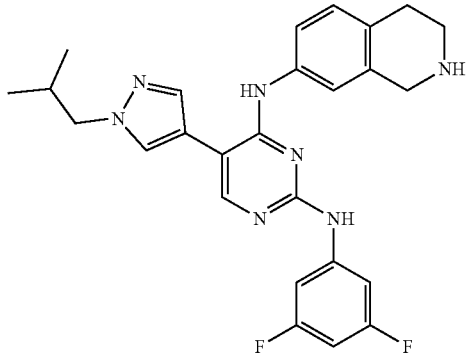 [SMILES: CC(C)Cn1cc(-c2cnc(Nc3cc(F)cc(F)c3)nc2Nc2ccc3c(c2)CNCC3)cn1]

1H NMR (300 MHz, Chloroform-d) δ 7.92 (s, 1H), 7.65-7.59 (m, 1H), 7.51 (d, J=5.6 Hz, 2H), 7.23-7.08 (m, 5H), 7.01 (d, J=8.3 Hz, 1H), 6.91 (d, J=8.4 Hz, 1H), 6.76 (d, J=10.3 Hz, 1H), 6.32 (t, J=9.3 Hz, 1H), 4.25 (s, 2H), 4.01-3.96 (m, 2H), 3.26 (d, J=6.4 Hz, 2H), 2.93 (d, J=6.9 Hz, 2H), 2.31-2.23 (m, 1H), 0.96 (dd, J=6.7, 2.7 Hz, 6H);

LC/MS [M+H]$^+$ 476.1.

Compound 182. N2-(3-chloro-5-fluorophenyl)-5-(1-isobutyl-1H-pyrazol-4-yl)-N4-(1,2,3,4-tetrahydroisoquinolin-7-yl)pyrimidine-2,4-diamine

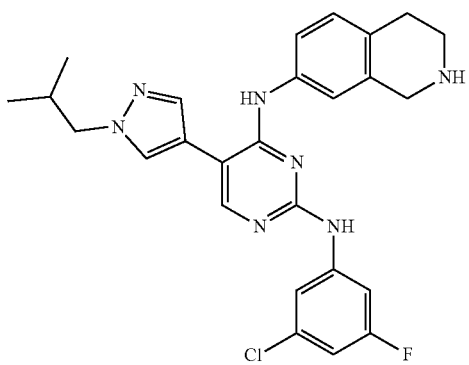 [SMILES: CC(C)Cn1cc(-c2cnc(Nc3cc(F)cc(Cl)c3)nc2Nc2ccc3c(c2)CNCC3)cn1]

1H NMR (300 MHz, Chloroform-d) δ 7.99 (d, J=4.8 Hz, 1H), 7.92 (d, J=7.4 Hz, 2H), 7.63 (d, J=8.6 Hz, 1H), 7.51 (s, 2H), 7.40 (d, J=10.4 Hz, 2H), 7.24-7.09 (m, 3H), 7.04 (s, 1H), 6.80 (s, 1H), 6.65-6.57 (m, 1H), 4.15 (s, 2H), 3.99 (d, J=7.2 Hz, 2H), 3.28 (d, J=6.1 Hz, 2H), 2.92 (d, J=16.4 Hz, 2H), 2.31-2.23 (m, 1H), 0.96 (d, J=6.6 Hz, 6H);

LC/MS [M+H]$^+$ 493.1.

Compound 183. 5-(1-isobutyl-1H-pyrazol-4-yl)-N2-(3-methoxy-5-(trifluoromethyl)phenyl)-N4-(1,2,3,4-tetrahydroisoquinolin-7-yl)pyrimidine-2,4-diamine

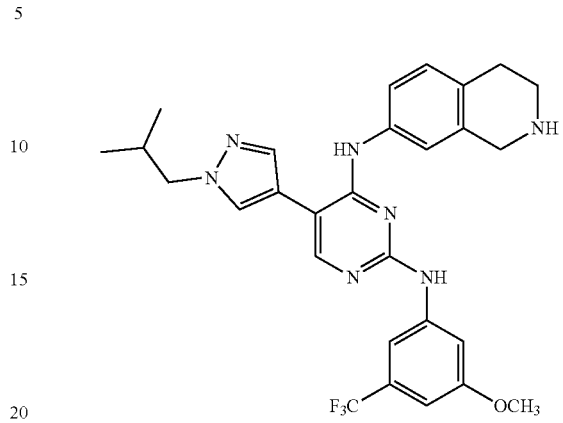

1H NMR (300 MHz, Chloroform-d) δ 7.97 (s, 1H), 7.65 (s, 1H), 7.51 (d, J=2.4 Hz, 3H), 7.31 (s, 1H), 7.20 (d, J=8.3 Hz, 2H), 7.04 (d, J=8.2 Hz, 1H), 6.78 (s, 1H), 6.74 (s, 1H), 4.00 (d, J=7.0 Hz, 4H), 3.72 (d, J=4.5 Hz, 3H), 3.17 (t, J=6.1 Hz, 2H), 2.82 (q, J=6.6, 5.9 Hz, 2H), 2.32-2.24 (m, 1H), 1.00-0.94 (m, 6H);

LC/MS [M+H]$^+$ 538.2.

Compound 184. N2-(3,5-dimethoxyphenyl)-5-(1-isobutyl-1H-pyrazol-4-yl)-N4-(1,2,3,4-tetrahydroisoquinolin-7-yl)pyrimidine-2,4-diamine

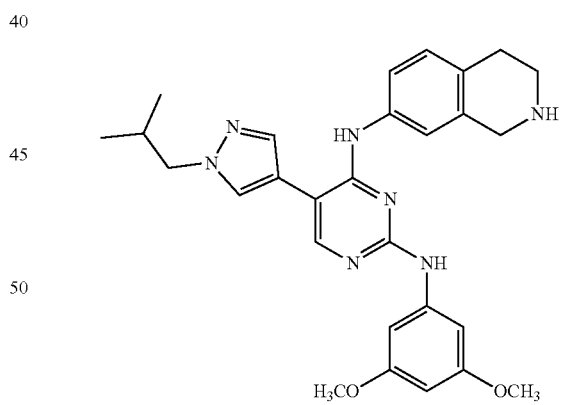

1H NMR (300 MHz, Chloroform-d) δ 7.95 (d, J=1.7 Hz, 1H), 7.63 (s, 1H), 7.49 (s, 1H), 7.30 (d, J=2.1 Hz, 1H), 7.24-7.07 (m, 3H), 7.04 (d, J=8.1 Hz, 1H), 6.83-6.69 (m, 3H), 6.15 (t, J=2.1 Hz, 1H), 4.04-3.95 (m, 4H), 3.69 (s, 6H), 3.18 (t, J=6.0 Hz, 2H), 2.82 (q, J=7.8, 6.1 Hz, 2H), 2.32-2.23 (m, 1H), 0.97 (d, J=6.7 Hz, 6H);

LC/MS [M+H]$^+$ 500.1.

Compound 185. N2-(3,5-dimethylphenyl)-5-(1-isobutyl-1H-pyrazol-4-yl)-N4-(1,2,3,4-tetrahydroisoquinolin-7-yl)pyrimidine-2,4-diamine

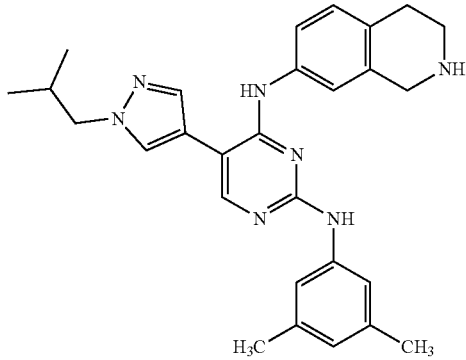 [SMILES: Cc1cc(C)cc(Nc2ncc(-c3cnn(CC(C)C)c3)c(Nc3ccc4c(c3)CNCC4)n2)c1]

1H NMR (300 MHz, Chloroform-d) δ 7.93 (d, J=1.71 Hz, 1H), 7.65 (s, 1H), 7.48 (s, 1H), 7.36 (d, J=2.1 Hz, 1H), 7.26-7.11 (m, 3H), 7.05 (d, J=8.1 Hz, 1H), 6.81-6.64 (m, 3H), 6.14 (t, J=2.1 Hz, 1H), 4.01-3.92 (m, 4H), 3.18 (t, J=6.0 Hz, 2H), 2.82 (q, J=7.8, 6.1 Hz, 2H), 2.32-2.23 (m, 1H), 2.15 (s, 6H), 0.97 (d, J=6.7 Hz, 6H);

LC/MS [M+H]+ 468.1

Compound 186. N2-(3-chlorophenyl)-5-(1-isobutyl-1H-pyrazol-4-yl)-N4-(1,2,3,4-tetrahydroisoquinolin-7-yl)pyrimidine-2,4-diamine

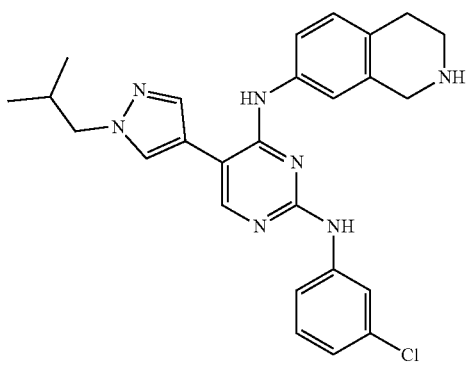 [SMILES: CC(C)Cn1cc(-c2cnc(Nc3cccc(Cl)c3)nc2Nc2ccc3c(c2)CNCC3)cn1]

1H NMR (300 MHz, Chloroform-d) δ 7.96 (d, J=1.6 Hz, 1H), 7.76 (t, J=2.1 Hz, 1H), 7.65 (s, 1H), 7.51 (d, J=0.8 Hz, 1H), 7.33-7.27 (m, 1H), 7.24 (s, 1H), 7.17 (dd, J=9.4, 6.6 Hz, 3H), 7.09 (d, J=8.3 Hz, 1H), 6.98-6.91 (m, 1H), 6.77 (s, 1H), 4.03-3.94 (m, 4H), 3.17 (t, J=5.9 Hz, 2H), 2.80 (t, J=5.9 Hz, 2H), 2.33-2.23 (m, 1H), 0.97 (d, J=6.7 Hz, 6H);

LC/MS [M+H]+ 474.6.

Compound 187. 5-(1-isobutyl-1H-pyrazol-4-yl)-N2-(3-methoxyphenyl)-N4-(1,2,3,4-tetrahydroisoquinolin-7-yl)pyrimidine-2,4-diamine

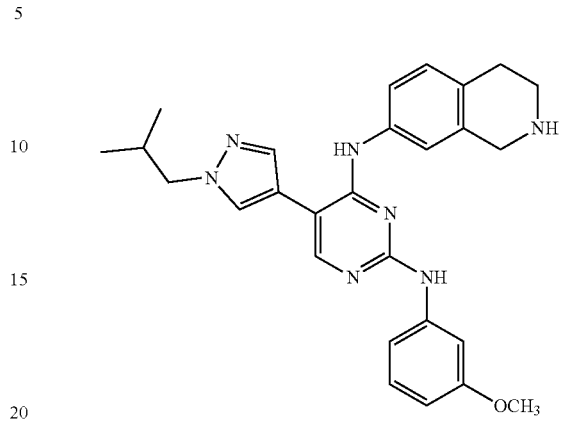

1H NMR (300 MHz, Chloroform-d) δ 7.95 (d, J=2.2 Hz, 1H), 7.64 (s, 1H), 7.49 (s, 1H), 7.33-7.27 (m, 1H), 7.25-7.12 (m, 4H), 7.09-7.01 (m, 2H), 6.76 (s, 1H), 6.56 (d, J=8.0 Hz, 1H), 4.03-3.93 (m, 4H), 3.73-3.66 (m, 3H), 3.17 (t, J=6.1 Hz, 2H), 2.91-2.77 (m, 2H), 2.30-2.23 (m, 1H), 0.97 (d, J=6.7 Hz, 6H);

LC/MS [M+H]+ 467.1.

Compound 188. 5-(1-isobutyl-1H-pyrazol-4-yl)-N4-(1,2,3,4-tetrahydroisoquinolin-7-yl)-N2-(m-tolyl)pyrimidine-2,4-diamine

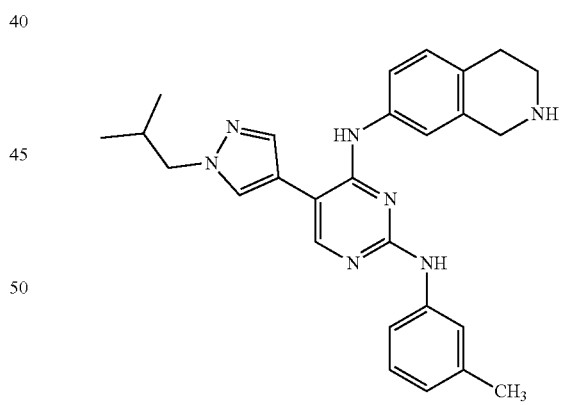

1H NMR (300 MHz, Chloroform-d) δ 7.95 (s, 1H), 7.64 (s, 1H), 7.49 (s, 1H), 7.41 (d, J=8.0 Hz, 1H), 7.33 (s, 2H), 7.18 (d, J=6.1 Hz, 2H), 7.05 (d, J=7.8 Hz, 2H), 6.83 (d, J=7.4 Hz, 1H), 6.75 (s, 1H), 4.02-3.96 (m, 4H), 3.16 (t, J=6.0 Hz, 2H), 2.79 (t, J=6.0 Hz, 2H), 2.30 (s, 3H), 2.26 (d, J=6.4 Hz, 1H), 0.97 (d, J=6.7 Hz, 6H);

LC/MS [M+H]+ 454.7.

Compound 189. 5-(1-isobutyl-1H-pyrazol-4-yl)-N2-phenyl-N4-(1,2,3,4-tetrahydroisoquinolin-7-yl)pyrimidine-2,4-diamine

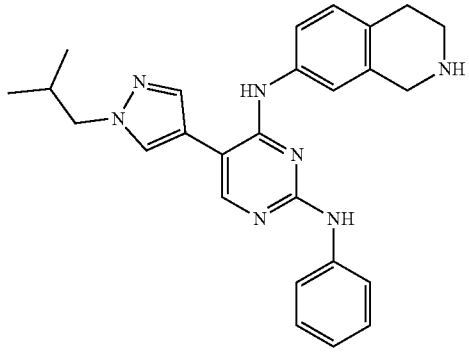 [SMILES: CC(C)Cn1cc(-c2cnc(Nc3ccccc3)nc2Nc2ccc3c(c2)CNCC3)cn1]

1H NMR (300 MHz, Chloroform-d) δ 7.96 (s, 1H), 7.65 (s, 1H), 7.58 (d, J=8.1 Hz, 2H), 7.50 (s, 1H), 7.31 (d, J=7.5 Hz, 3H), 7.21 (d, J=8.2 Hz, 1H), 7.03 (q, J=7.8 Hz, 3H), 6.76 (s, 1H), 4.00 (d, J=7.5 Hz, 4H), 3.16 (t, J=5.9 Hz, 2H), 2.79 (t, J=5.9 Hz, 2H), 2.32-2.24 (m, 1H), 0.98 (d, J=6.7 Hz, 6H); LC/MS [M+H]$^+$ 454.7.

Compound 190. N2-(2,3-dichlorophenyl)-5-(1-isobutyl-1H-pyrazol-4-yl)-N4-(1,2,3,4-tetrahydroisoquinolin-7-yl)pyrimidine-2,4-diamine

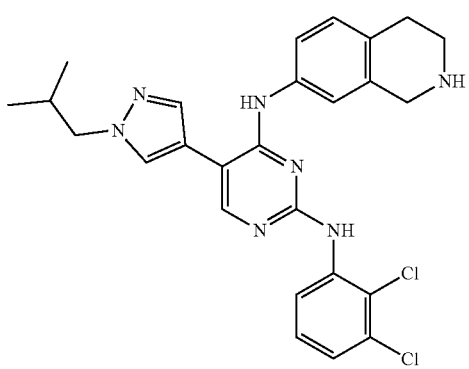 [SMILES: CC(C)Cn1cc(-c2cnc(Nc3cccc(Cl)c3Cl)nc2Nc2ccc3c(c2)CNCC3)cn1]

1H NMR (300 MHz, Chloroform-d) δ 8.42-8.36 (m, 1H), 8.00 (s, 1H), 7.66 (d, J=0.8 Hz, 1H), 7.52 (s, 2H), 7.22 (d, J=2.3 Hz, 1H), 7.18-7.04 (m, 4H), 6.82 (s, 1H), 4.05-3.97 (m, 4H), 3.22 (t, J=6.0 Hz, 2H), 2.87 (t, J=6.0 Hz, 2H), 2.34-2.22 (m, 1H), 0.98 (d, J=6.7 Hz, 6H); LC/MS [M+H]$^+$ 509.1.

Compound 191. N2-(2,5-difluorophenyl)-5-(1-isobutyl-1H-pyrazol-4-yl)-N4-(1,2,3,4-tetrahydroisoquinolin-7-yl)pyrimidine-2,4-diamine

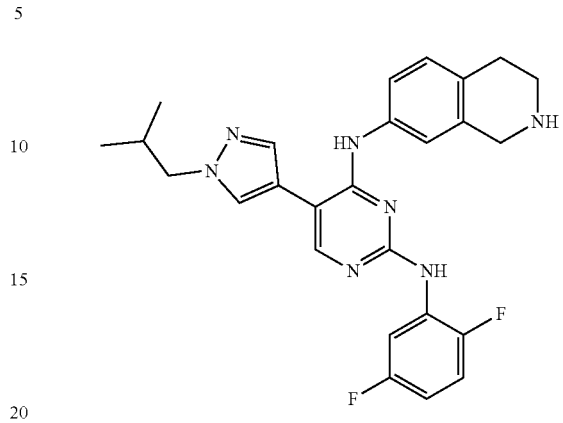

1H NMR (300 MHz, Chloroform-d) δ 8.30-8.14 (m, 1H), 8.00 (d, J=3.4 Hz, 1H), 7.68 (d, J=6.2 Hz, 1H), 7.55 (d, J=10.4 Hz, 1H), 7.26 (d, J=5.3 Hz, 2H), 7.20-7.09 (m, 2H), 7.05-6.92 (m, 1H), 6.80 (s, 1H), 6.56 (t, J=8.3 Hz, 1H), 4.10 (s, 1H), 4.05-3.96 (m, 3H), 3.35-3.20 (m, 2H), 2.96-2.85 (m, 2H), 2.33-2.25 (m, 1H), 0.98 (dd, J=6.7, 1.1 Hz, 6H); LC/MS [M+H]$^+$ 476.1.

Compound 192. 5-(1-isobutyl-1H-pyrazol-4-yl)-N2-(2-isopropylphenyl)-N4-(1,2,3,4-tetrahydroisoquinolin-7-yl)pyrimidine-2,4-diamine

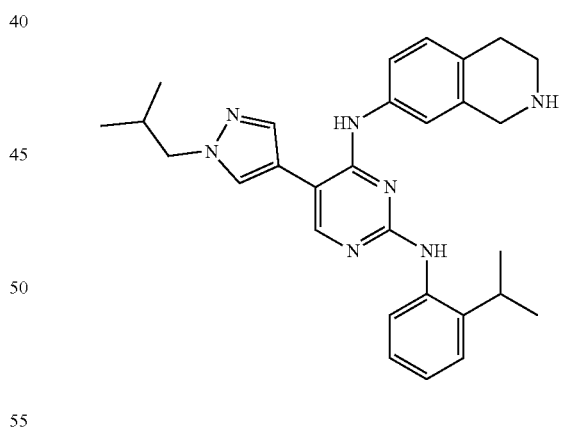

1H NMR (300 MHz, Chloroform-d) δ 7.92 (s, 1H), 7.76-7.70 (m, 1H), 7.62 (s, 1H), 7.48 (s, 1H), 7.37-7.31 (m, 1H), 7.24-7.16 (m, 3H), 7.06 (dd, J=8.3, 2.4 Hz, 1H), 6.93 (d, J=8.3 Hz, 1H), 6.75 (d, J=4.8 Hz, 2H), 4.00 (d, J=7.3 Hz, 3H), 3.82 (s, 2H), 3.21 (q, J=6.9 Hz, 1H), 3.13 (t, J=6.0 Hz, 3H), 2.74 (t, J=5.9 Hz, 2H), 2.32-2.22 (m, 1H), 1.24 (d, J=6.9 Hz, 6H), 0.98 (d, J=6.7 Hz, 6H); LC/MS [M+H]$^+$ 482.5.

Compound 193. 2-(4-(2-(3,5-dimethoxyphenylamino)-4-(1,2,3,4-tetrahydroisoquinolin-7-ylamino)pyrimidin-5-yl)-1H-pyrazol-1-yl)ethan-1-ol

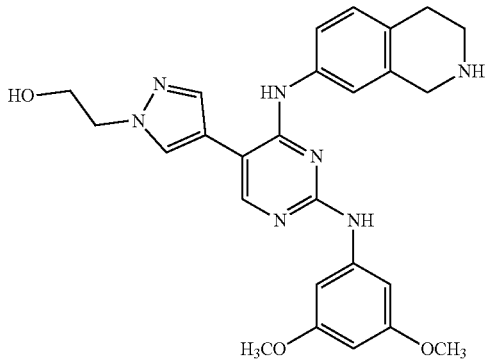 [SMILES: COc1cc(Nc2ncc(-c3cnn(CCO)c3)c(Nc3ccc4c(c3)CNCC4)n2)cc(OC)c1]

1H NMR (300 MHz, Chloroform-d) δ 7.91 (s, 1H), 7.64 (s, 1H), 7.57 (s, 1H), 7.26 (s, 1H), 7.18 (d, J=8.5 Hz, 1H), 7.03 (d, J=8.2 Hz, 1H), 6.80 (d, J=2.2 Hz, 2H), 6.77 (s, 1H), 6.17 (t, J=2.2 Hz, 1H), 4.33 (t, J=4.7 Hz, 2H), 4.08 (t, J=4.7 Hz, 2H), 3.94 (s, 2H), 3.71 (s, 6H), 3.17 (t, J=6.0 Hz, 2H), 3.01 (s, 1H), 2.80 (t, J=5.9 Hz, 2H);

LC/MS [M+H]+ 488.2.

Compound 194. 2-(4-(2-(3,5-dimethylphenylamino)-4-(1,2,3,4-tetrahydroisoquinolin-7-ylamino)pyrimidin-5-yl)-1H-pyrazol-1-yl)ethan-1-ol

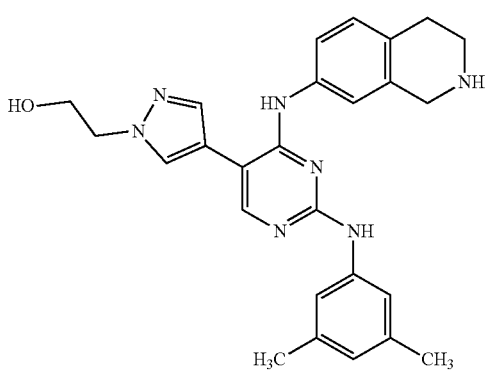 [SMILES: Cc1cc(C)cc(Nc2ncc(-c3cnn(CCO)c3)c(Nc3ccc4c(c3)CNCC4)n2)c1]

1H NMR (300 MHz, Chloroform-d) δ 7.95 (s, 1H), 7.68 (d, J=0.8 Hz, 1H), 7.60 (s, 1H), 7.42 (d, J=8.3 Hz, 1H), 7.20 (d, J=1.5 Hz, 2H), 7.08 (d, J=7.7 Hz, 2H), 6.98 (s, 1H), 6.73 (s, 1H), 6.69 (s, 1H), 4.38-4.31 (m, 2H), 4.13-4.07 (m, 2H), 3.97 (s, 2H), 3.17 (t, J=6.0 Hz, 2H), 2.81 (t, J=5.9 Hz, 2H), 2.28 (s, 6H);

LC/MS [M+H]+ 456.3.

Compound 195. 2-(4-(2-(2,3-dimethylphenylamino)-4-(1,2,3,4-tetrahydroisoquinolin-7-ylamino)pyrimidin-5-yl)-1H-pyrazol-1-yl)ethan-1-ol

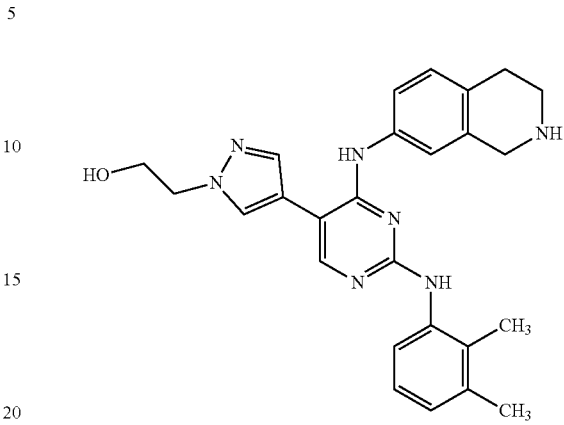

1H NMR (300 MHz, Chloroform-d) δ 7.86 (s, 1H), 7.63 (s, 1H), 7.57 (d, J=5.7 Hz, 2H), 7.22 (d, J=2.2 Hz, 1H), 7.15-7.09 (m, 2H), 7.03 (d, J=7.6 Hz, 1H), 6.94 (d, J=8.3 Hz, 1H), 6.78 (d, J=10.5 Hz, 2H), 4.36-4.31 (m, 2H), 4.11-4.06 (m, 2H), 3.85 (s, 2H), 3.15 (t, J=6.0 Hz, 2H), 2.77 (t, J=6.0 Hz, 2H), 2.34 (s, 3H), 2.22 (s, 3H);

LC/MS [M+H]+ 456.2.

Compound 196. 2-(4-(2-(3-chlorophenylamino)-4-(1,2,3,4-tetrahydroisoquinolin-7-ylamino)pyrimidin-5-yl)-1H-pyrazol-1-yl)ethan-1-ol

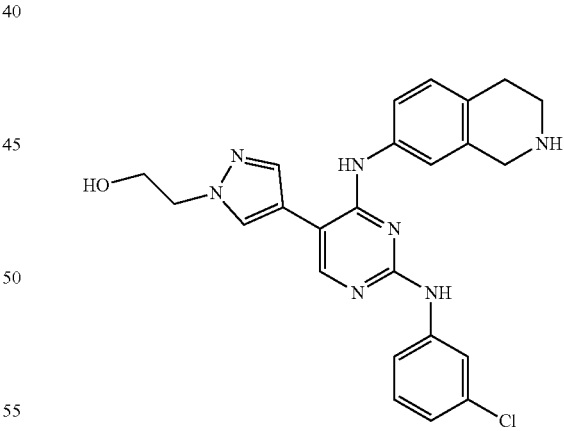

1H NMR (300 MHz, Chloroform-d) δ 7.95 (s, 1H), 7.77 (s, 1H), 7.67 (s, 1H), 7.59 (s, 1H), 7.30 (d, J=8.5 Hz, 1H), 7.18 (t, J=8.0 Hz, 2H), 7.09 (d, J=7.3 Hz, 3H), 6.96 (d, J=7.9 Hz, 1H), 6.75 (s, 1H), 4.38-4.32 (m, 2H), 4.09 (t, J=4.8 Hz, 2H), 3.96 (s, 2H), 3.14 (t, J=5.9 Hz, 2H), 2.78 (t, J=6.0 Hz, 2H).

Compound 197. 2-(4-(2-(2,3-dichlorophenylamino)-4-(1,2,3,4-tetrahydroisoquinolin-7-ylamino)pyrimidin-5-yl)-1H-pyrazol-1-yl)ethan-1-ol

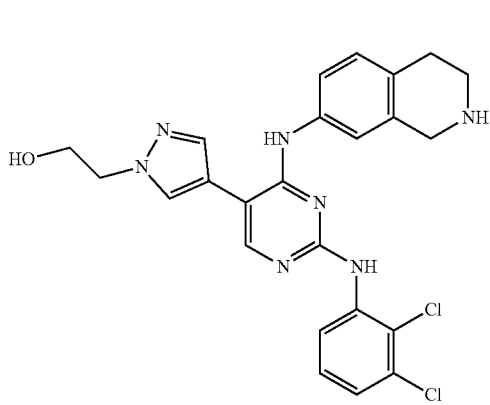 [SMILES: OCCn1cc(-c2cnc(Nc3cccc(Cl)c3Cl)nc2Nc2ccc3c(c2)CNCC3)cn1]

1H NMR (300 MHz, Chloroform-d) δ 7.93 (s, 1H), 7.74 (s, 1H), 7.69 (s, 1H), 7.61 (s, 1H), 7.31 (m, 1H), 7.16 (m, 1H), 7.07 (m, 2H), 6.93 (m, 1H), 6.78 (s, 1H), 4.36 (m, 2H), 4.08 (t, J=4.8 Hz, 2H), 3.95 (s, 2H), 3.15 (t, J=5.9 Hz, 2H), 2.78 (t, J=6.0 Hz, 2H);

LC/MS [M+H]$^+$ 496.51.

Compound 198. N2-(3,5-difluorophenyl)-5-(1-methyl-1H-pyrazol-4-yl)-N4-(4-(piperidin-4-yl)phenyl)pyrimidine-2,4-diamine

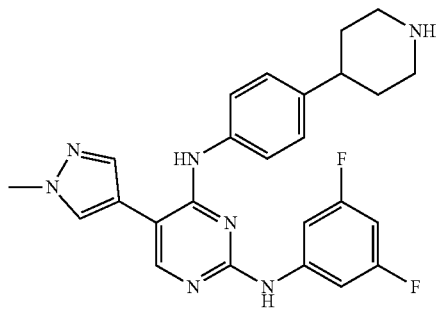 [SMILES: Cn1cc(-c2cnc(Nc3cc(F)cc(F)c3)nc2Nc2ccc(C3CCNCC3)cc2)cn1]

1H NMR (300 MHz, CDCl$_3$) δ 7.97 (s, 1H), 7.65 (s, 1H), 7.53 (s, 1H), 7.43 (s, 1H), 7.40 (s, 1H), 7.24-7.20 (m, 2H), 7.19-7.14 (m, 2H), 6.80 (s, 1H), 6.45-6.36 (m, 1H), 4.01 (s, 3H), 3.25 (d, J=12.2 Hz, 2H), 2.84-2.72 (m, 2H), 2.71-2.58 (m, 1H), 1.88 (d, J=13.0 Hz, 2H), 1.77-1.61 (m, 3H);

LC/MS (ESI) m/z 462.0 [M+H]$^+$.

Compound 199. N2-(3,5-dichlorophenyl)-5-(1-methyl-1H-pyrazol-4-yl)-N4-(4-(piperidin-4-yl)phenyl)pyrimidine-2,4-diamine

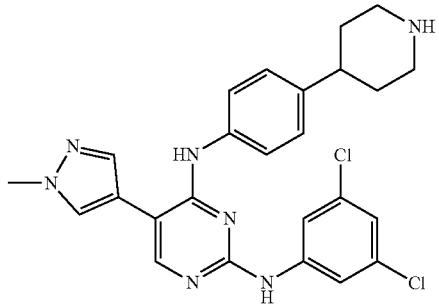 [SMILES: Cn1cc(-c2cnc(Nc3cc(Cl)cc(Cl)c3)nc2Nc2ccc(C3CCNCC3)cc2)cn1]

1H NMR (300 MHz, CDCl$_3$) δ 7.99 (s, 1H), 7.66 (s, 1H), 7.61-7.53 (m, 3H), 7.44 (d, J=8.2 Hz, 2H), 7.24 (d, J=6.1 Hz, 2H), 6.98 (s, 1H), 6.85 (s, 1H), 4.03 (s, 3H), 3.27 (d, J=11.9 Hz, 2H), 2.80 (t, J=12.0 Hz, 2H), 2.65 (t, J=12.0 Hz, 1H), 1.95-1.82 (m, 2H), 1.79-1.58 (m, 3H);

LC/MS (ESI) m/z 495.0 [M+H]$^+$.

Compound 200. N2-(3-chloro-5-fluorophenyl)-5-(1-methyl-1H-pyrazol-4-yl)-N4-(4-(piperidin-4-yl)phenyl)pyrimidine-2,4-diamine

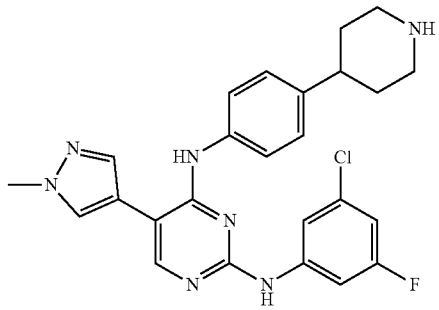 [SMILES: Cn1cc(-c2cnc(Nc3cc(F)cc(Cl)c3)nc2Nc2ccc(C3CCNCC3)cc2)cn1]

1H NMR (300 MHz, CDCl$_3$) δ 7.97 (s, 1H), 7.64 (s, 1H), 7.52 (s, 1H), 7.45 (t, J=2.1 Hz, 1H), 7.43-7.39 (m, 2H), 7.32 (s, 1H), 7.25 (s, 1H), 7.23 (s, 2H), 6.81 (s, 1H), 6.70-6.66 (m, 1H), 4.01 (s, 3H), 3.21 (d, J=11.9 Hz, 2H), 2.83-2.70 (m, 2H), 2.69-2.56 (m, 1H), 1.85 (d, J=12.1 Hz, 2H), 1.70-1.58 (m, 3H);

LC/MS (ESI) m/z 478 [M+H]$^+$.

Compound 201. 2-(4-(2-(3,5-dichlorophenylamino)-4-(4-(piperidin-4-yl)phenylamino)pyrimidin-5-yl)-1H-pyrazol-1-yl)ethan-1-ol

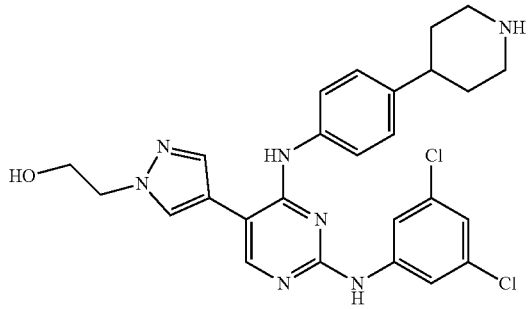 [SMILES: OCCn1cc(-c2cnc(Nc3cc(Cl)cc(Cl)c3)nc2Nc2ccc(C3CCNCC3)cc2)cn1]

1H NMR (300 MHz, MeOH-d$_4$) δ 7.98 (s, 1H), 7.92 (s, 1H), 7.70 (d, J=11.8 Hz, 2H), 7.61-7.45 (m, 3H), 7.44-7.24 (m, 3H), 6.97-6.91 (m, 1H), 4.33 (t, J=5.2 Hz, 2H), 3.99 (t, J=5.3 Hz, 2H), 3.65-3.59 (m, 1H), 3.58-3.54 (m, 1H), 3.09 (s, 1H), 2.18-2.04 (m, 2H), 1.93-1.80 (m, 3H);

LC/MS (ESI) m/z 525.0 [M+H]$^+$.

Compound 202. N2-(3,5-bis(trifluoromethyl)phenyl)-5-(1-methyl-1H-pyrazol-4-yl)-N4-(4-(piperidin-4-yl)phenyl)pyrimidine-2,4-diamine

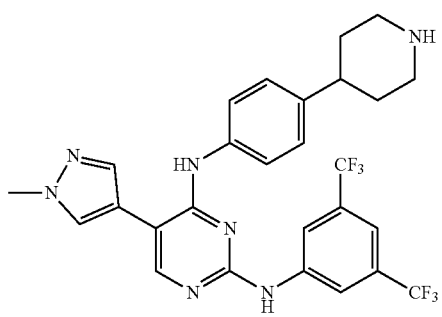 [SMILES: Cn1cc(-c2cnc(Nc3cc(C(F)(F)F)cc(C(F)(F)F)c3)nc2Nc2ccc(C3CCNCC3)cc2)cn1]

1H NMR (300 MHz, CDCl$_3$) δ 8.08 (s, 2H), 8.01 (s, 1H), 7.65 (s, 1H), 7.53 (s, 1H), 7.45 (d, J=6.5 Hz, 2H), 7.40 (d, J=8.3 Hz, 2H), 7.19 (d, J=8.3 Hz, 2H), 6.85 (s, 1H), 4.02 (s, 3H), 3.28 (d, J=12.2 Hz, 2H), 2.81 (t, J=12.1 Hz, 2H), 2.69-2.57 (m, 1H), 1.88 (d, J=12.9 Hz, 2H), 1.79-1.67 (m, 2H);

LC/MS (ESI) m/z 562.0 [M+H]$^+$.

Compound 203. N2-(3-methoxy-5-(trifluoromethyl)phenyl)-5-(1-methyl-1H-pyrazol-4-yl)-N4-(4-(piperidin-4-yl)phenyl)pyrimidine-2,4-diamine

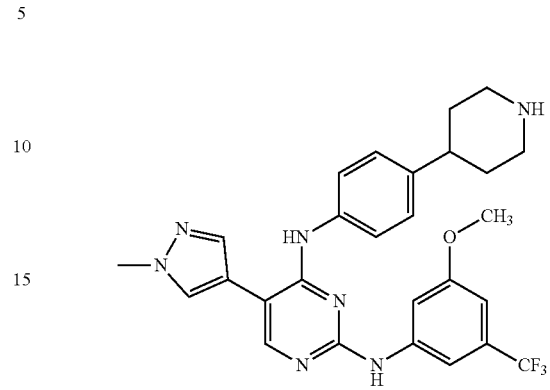

1H NMR (300 MHz, CDCl$_3$) δ 7.95 (s, 1H), 7.71 (s, 1H), 7.63 (s, 1H), 7.51 (s, 1H), 7.48-7.35 (m, 3H), 7.23 (s, 1H), 7.21-7.11 (m, 1H), 6.85 (s, 1H), 6.77 (s, 1H), 4.35 (t, J=7.0 Hz, 1H), 4.01 (s, 3H), 3.87 (t, J=6.0 Hz, 1H), 3.76 (s, 3H), 3.74-3.63 (m, 3H), 2.62-2.46 (m, 4H), 2.28 (q, J=7.4 Hz, 2H).

Compound 204. 2-(4-(2-(3-chlorophenylamino)-4-(4-(piperidin-4-yl)phenylamino)pyrimidin-5-yl)-1H-pyrazol-1-yl)ethan-1-ol

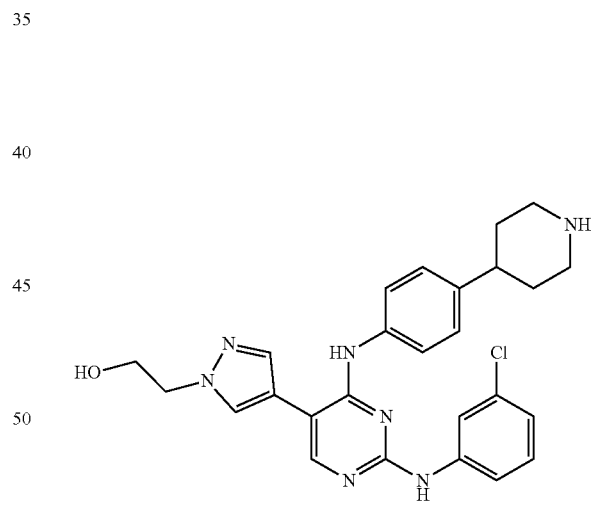

1H NMR (300 MHz, MeOH-d$_4$) δ 7.95 (s, 1H), 7.90 (s, 1H), 7.85 (d, J=2.2 Hz, 1H), 7.71 (s, 1H), 7.58-7.46 (m, 2H), 7.39 (d, J=8.2 Hz, 1H), 7.34-7.22 (m, 2H), 7.17 (t, J=8.1 Hz, 1H), 6.92 (d, J=8.1 Hz, 1H), 4.33 (t, J=5.2 Hz, 2H), 3.99 (t, J=5.2 Hz, 2H), 3.60 (t, J=6.4 Hz, 2H), 3.56-3.47 (m, 2H), 2.38 (t, J=7.5 Hz, 2H), 1.91-1.79 (m, 4H);

LC/MS (ESI) m/z 490.0 [M+H]$^+$.

Compound 205. 2-(4-(2-(3,5-difluorophenylamino)-4-(4-(piperidin-4-yl)phenylamino)pyrimidin-5-yl)-1H-pyrazol-1-yl)ethan-1-ol

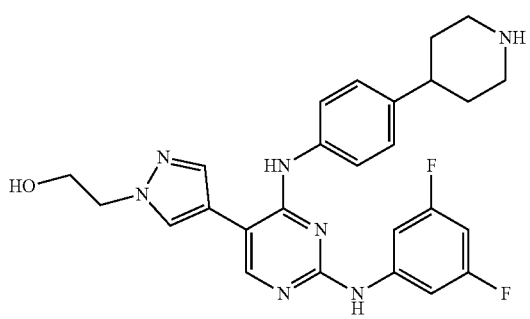 [SMILES: OCCn1cc(-c2cnc(Nc3cc(F)cc(F)c3)nc2Nc2ccc(C3CCNCC3)cc2)cn1]

1H NMR (300 MHz, MeOH-d$_4$) δ 7.97 (s, 1H), 7.92 (s, 1H), 7.72 (s, 1H), 7.56-7.42 (m, 2H), 7.39-7.21 (m, 4H), 6.50-6.35 (m, 1H), 4.33 (t, J=5.2 Hz, 2H), 3.99 (t, J=5.2 Hz, 2H), 3.60 (t, J=6.4 Hz, 2H), 3.51 (q, J=7.0 Hz, 1H), 2.58-2.48 (m, 1H), 2.38 (t, J=7.5 Hz, 2H), 1.88-1.75 (m, 3H);
LC/MS (ESI) m/z 492.0 [M+H]$^+$.

Example 2: Verification on Inhibitory Activities of TAM Receptor Inhibiting Compounds on Tyro 3, Axl, and Mer For evaluation of inhibitory activities of the compounds according to the present invention on Tyro 3, Axl, and Mer, the following test was carried out.

The specific test method followed the method provided by Cisbio. The compounds of the examples were prepared at various concentrations, followed by addition of Tyro 3, Axl, or Mer and substrate peptides, and then ATP was added to initiate a reaction. After 1 hour, the reaction was stopped by addition of a solution containing EDTA. Thereafter, the amount of phosphorylated peptides was measured. Here, the phosphorylated peptides were treated with an europium (Eu)-labeled antibody recognizing phosphorylated peptides, and then after 1 hour, excited by irradiation of the light of a wavelength of 320 or 340 nm using an Envision Reader. The amount of light emitted at 665 nm was measured to investigate the degrees of inhibition of TAM receptors. The TAM receptor inhibitory activities (IC$_{50}$ values) of the respective compounds were analyzed using the GraphPad Prism program, and tabulated in Tables 1 to 3 below. LDC1267 (CAS no. 1361030-48-9, Calbiochem), which is a TAM receptor inhibitor compound, was used as a positive control.

[Chemical Formula 1]

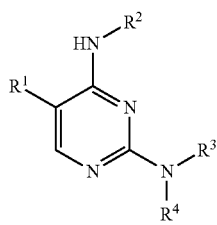

TABLE 1

| Compound number | IC$_{50}$ (μM) | | |
|---|---|---|---|
| | Tyro 3 | Axl | Mer |
| 1 | >10 | >10 | >10 |
| 2 | >10 | >10 | >10 |
| 4 | >10 | 8.5 | >10 |
| 5 | 0.65 | >10 | >2 |
| 6 | 1.46 | >10 | >10 |
| 8 | 0.61 | 0.53 | 0.085 |
| 9 | >10 | >10 | >10 |
| 10 | >10 | 6.3 | 1.2 |
| 11 | >10 | 4.1 | 0.77 |
| 12 | >10 | 2.1 | 0.41 |
| 13 | >10 | 1.8 | >10 |
| 14 | >10 | >10 | >10 |
| 15 | 0.63 | >10 | >10 |
| 16 | 1.03 | 0.51 | >10 |
| 17 | 1.1 | >10 | 0.52 |
| 18 | 1.4 | 4.7 | >10 |
| 19 | 4.5 | 3.8 | >10 |
| 20 | 9.7 | 3.6 | >10 |
| 21 | >10 | 1.1 | >10 |
| 22 | 2.2 | 1.8 | >10 |
| 23 | 0.61 | >10 | 0 |
| 24 | 0.57 | 2.7 | >10 |
| 43 | 1.7 | >10 | >10 |
| 44 | 0.57 | >10 | >10 |
| 47 | 3.5 | >10 | >10 |
| 49 | 4.5 | >10 | 5.4 |
| 50 | 5.3 | >10 | 5.1 |
| 51 | 1.2 | 5.8 | 0.16 |
| 63 | 0.78 | 6.3 | 0.091 |
| 64 | >10 | >10 | >10 |
| 65 | 2.2 | 0.00021 | 0.00082 |
| 67 | 0.84 | 5.04 | >10 |
| 68 | >10 | >10 | 0.015 |
| 69 | 0.55 | >10 | 0.00012 |
| 70 | 1.73 | >10 | 0.84 |
| 72 | 10 | 3.59 | 6.29 |
| 86 | 0.50 | >10 | >10 |
| 88 | 0.87 | >10 | >10 |
| Positive control (LDC1267) | 0.0048 | 0.0049 | 0.068 |

TABLE 2

| Compound number | IC$_{50}$ (μM) | | |
|---|---|---|---|
| | Tyro 3 | Axl | Mer |
| 71 | 0.0035 | >10 | 1.1 |
| 73 | 0.0018 | 4.5 | 0.032 |
| 75 | 0.00006 | 3.6 | 0.03 |
| 76 | 0.045 | 2.4 | >10 |
| 80 | 0.059 | 10.8 | 0.048 |
| 95 | 0.0065 | >10 | >10 |
| 100 | 0.0009 | 0.032 | 0.00091 |
| 103 | 0.00019 | 0.7 | 0.025 |
| 105 | 0.0024 | 0.33 | 0.0033 |
| 107 | 0.013 | 0.2 | 0.0044 |
| 108 | 0.0087 | 0.89 | 0.3 |
| 110 | 0.00028 | 0.92 | 0.028 |
| 111 | 0.00048 | 0.38 | 0.045 |
| 113 | 0.00037 | 0.23 | 0.0069 |
| 115 | 0.052 | 0.19 | 0.0009 |
| 117 | 0.0016 | 0.52 | 0.001 |
| 121 | 0.003 | 0.37 | 0.01 |
| 122 | 0.017 | >10 | >10 |
| 201 | 0.000012 | 0.15 | 0.85 |
| 204 | 0.0013 | 2.35 | 0.15 |
| 205 | 0.00014 | 0.87 | 0.032 |
| Positive control (LDC1267) | 0.0048 | 0.0049 | 0.068 |

TABLE 3

| Compound number | IC$_{50}$ (μM) | | |
|---|---|---|---|
| | Tyro 3 | Axl | Mer |
| 82 | 0.025 | 0.066 | 0.012 |
| 84 | 0.000041 | 0.067 | 0.012 |
| 85 | 0.0023 | 0.044 | 0.0014 |
| 87 | 0.016 | 0.21 | 0.016 |
| 89 | 0.000041 | 0.21 | 0.016 |
| 93 | 0.028 | 1.9 | 0.24 |
| 94 | 0.016 | 0.44 | 0.023 |
| 101 | 0.000012 | 0.73 | 0.026 |
| 102 | 0.00042 | 0.033 | 0.00036 |
| 123 | 0.055 | 3.8 | 0.057 |
| 124 | 0.075 | >10 | >10 |
| 125 | 0.061 | >10 | 1.8 |
| 126 | 0.013 | 5.2 | 1.5 |
| 127 | 0.000052 | 0.082 | >10 |
| 128 | 0.0024 | 7.07 | 0.33 |
| 129 | 0.0035 | 1.15 | 0.0013 |
| 130 | 0.0094 | 1.5 | 0.0019 |
| 131 | 0.00016 | 0.041 | >10 |
| 132 | 0.0002 | 0.27 | 0.0049 |
| 133 | 0.0018 | 4.7 | 0.74 |
| 134 | 0.017 | 0.5 | 0.0043 |
| 135 | 0.004 | 4.5 | 0.35 |
| 136 | 0.017 | >10 | 3.6 |
| 137 | 0.000097 | 0.043 | 0.00078 |
| 138 | 0.05 | >10 | 2.1 |
| 139 | 0.0000062 | >10 | 8 |
| 140 | 0.023 | 2.7 | 0.32 |
| 141 | 0.0091 | 3.6 | 0.091 |
| 142 | 0.008 | 6.2 | 0.033 |
| 143 | 0.052 | 8.2 | >10 |
| 144 | 0.086 | 6.4 | 0.16 |
| 145 | 0.0003 | 1.16 | 0.39 |
| 146 | 0.0018 | 2.15 | 1.25 |
| 147 | 0.00013 | 1.12 | 2.53 |
| 148 | 0.00013 | 0.59 | 2.35 |
| 149 | 0.001 | 2.35 | 5.26 |
| 150 | 0.0023 | 5.67 | 2.35 |
| 151 | 0.0016 | 2.56 | 1.25 |
| 152 | 0.0086 | 8.16 | 5.46 |
| 153 | 0.0097 | 2.56 | 1.25 |
| 155 | 0.064 | 2.57 | 6.54 |
| 156 | 0.00034 | 0.86 | 1.25 |
| 157 | 0.018 | 4.56 | 3.65 |
| 158 | 0.0039 | 1.25 | 0.87 |
| 159 | 0.00017 | 2.35 | 0.23 |
| 160 | 0.00016 | 1.65 | 0.15 |
| 161 | 0.0041 | 4.56 | 0.54 |
| 162 | 0.00014 | 0.99 | 0.13 |
| 163 | 0.00023 | 1.46 | 0.087 |
| 164 | 0.0014 | 3.56 | 0.64 |
| 165 | 0.0083 | 4.87 | 0.58 |
| 166 | 0.00034 | 2.36 | 1.25 |
| 167 | 0.0001 | 5.65 | 3.25 |
| 168 | 0.009 | 4.58 | 0.23 |
| 169 | 0.00017 | 6.59 | 0.19 |
| 170 | 0.0016 | 2.73 | 0.25 |
| 171 | 0.000012 | 0.99 | 0.15 |
| 172 | 0.000012 | 0.9 | 0.33 |
| 173 | 0.00013 | 0.77 | 0.13 |
| 174 | 0.0073 | 4.65 | 0.52 |
| 175 | 0.00032 | 5.78 | 0.47 |
| 176 | 0.0042 | 4.56 | 0.89 |
| 177 | 0.0017 | 1.25 | 0.98 |
| 178 | 0.00027 | 1.11 | 0.96 |
| 179 | 0.00017 | 1.05 | 0.85 |
| 180 | 0.0043 | 2.35 | 0.54 |
| 181 | 0.00016 | 0.96 | 0.85 |
| 182 | 0.00027 | 2.45 | 0.65 |
| 183 | 0.0057 | 1.25 | 0.87 |
| 184 | 0.025 | 5.65 | 0.98 |
| 185 | 0.0028 | 4.89 | 0.32 |
| 186 | 0.0012 | 1.25 | 0.18 |
| 187 | 0.0088 | 1.65 | 0.52 |
| 188 | 0.0094 | 2.36 | 0.68 |
| 189 | 0.013 | 4.65 | 0.56 |
| 191 | 0.019 | 10 | 6.21 |
| 193 | 0.0036 | 2.36 | 0.35 |
| 194 | 0.00058 | 1.58 | 0.15 |
| 196 | 0.0006 | 3.65 | 0.054 |
| 197 | 0.00001 | 1.25 | 0.065 |
| Positive control (LDC1267) | 0.0048 | 0.0049 | 0.068 |

As can be seen from Tables 1 to 3 above, Table 1 shows that the compounds of Chemical Formula 1 in which $R_1$ is a phenyl or furanyl group; $R_2$ is a phenyl, cycloalkyl, or heterocycloalkyl group; and $R_3$ or $R_4$ is substituted with a heteroaryl group containing a heteroatom showed an IC$_{50}$ value of 0.5 μM or more against Tyro 3.

Table 2 showed that the compounds of Chemical Formula 1 in which $R_1$ contains a pyrazole group substituted with a hydroxyalkyl or piperidine group; $R_2$ is a phenyl, cycloalkyl, or heterocycloalkyl group; and $R_3$ or $R_4$ is substituted with a phenyl or tetrahydroisoquinoline group had an IC$_{50}$ value of 0.000012-0.059 μM against Tyro 3, indicating strong activity.

Table 3 showed that the compounds of Chemical Formula 1 in which $R_1$ contains a pyrazole group substituted with an alkyl, hydroxyalkyl or piperidine group; R2 is a tetrahydroisoquinoline group; and $R_3$ or R4 is substituted with a phenyl or tetrahydroisoquinoline group had an IC$_{50}$ value of 0.0000062-0.086 μM against Tyro 3, indicating strong activity.

Accordingly, the compounds listed on Tables 2 and 3 showed an excellent inhibitory activity on Tyro 3 compared with the compounds listed on Table 1 by 10 times or more, indicating that the Tyro 3 inhibitory activity varies greatly depending on the substituents of the pyrimidine derivatives.

It can be especially seen that the compounds of the present invention have an excellent inhibitory effect on Tyro 3 among the TAM receptors, and thus can be advantageously used as a composition for prevention or treatment of cancer without side effects.

Example 3: Verification on hERG Toxicity of TAM Receptor Inhibiting Compounds In the development of medicines, drug toxicity as well as therapeutic effects plays an important role. One of the most commonly used criteria for determining drug toxicity is human ether-a-go-go-related gene (hERG) toxicity. Most pharmaceutical companies determine a drug showing a hERG IC$_{50}$ value of less than 0.1 μM to be highly toxic, and thus stop the development of the drug. Whereas, the companies determine a drug showing a hERG IC$_{50}$ value of 10 μM or more to be non-toxic.

For investigation of the degree of drug toxicity by TAM receptor inhibiting compounds of the present invention, human ether-a-go-go-related gene (hERG) assay was performed on Compounds 29, 60, 73, 75, 84, 89, and 132 on Table 4.

TABLE 4

| Compound number | Structure |
|---|---|
| 29 | (structure) |
| 60 | (structure) |
| 73 | (structure) |
| 75 | (structure) |
| 84 | (structure) |

TABLE 4-continued

| Compound number | Structure |
|---|---|
| 89 | (structure) |
| 132 | (structure) |

As a result of hERG assay, Compounds 29 and 60 on Table 1, which are the compounds in Chemical Formula 1 in which $R_1$ is a methyl group-substituted pyrazole group or a phenyl group, had a hERG $IC_{50}$ value of 1 μM or less, indicating that Compounds 29 and 60 had hERG toxicity.

Whereas, Compounds 73 and 75 on Table 2, which are the compounds in Chemical Formula 1 in which $R_1$ is a pyrazole group substituted with a hydroxyalkyl or piperidine group, had a hERG $IC_{50}$ value of 50 μM or more, indicating that Compounds 73 and 75 had no hERG toxicity.

In addition, Compounds 84, 89, and 132 on Table 3, which are the compounds in Chemical Formula 1 in which $R_1$ is a pyrazole group substituted with an alkyl, hydroxyalkyl, or piperidine group, and $R_2$ is substituted with a tetrahydroisoquinoline group, were confirmed to have no hERG toxicity.

Accordingly, $R_1$ to $R_3$ in the structure of Chemical Formula 1 in the present invention have a great influence on Tyro 3 inhibitory activity and hERG toxicity, and it could be therefore seen that the compounds having particular substituents as shown in Tables 2 and 3 had no toxicity and showed an excellent anticancer effect.

Preparation Example 1: Preparation of Powder Formulation

Compound 139 of the present invention (2 g) and lactose (1 g) were mixed, and filled in airtight sachet to prepare a powder formulation.

Preparation Example 2: Preparation of Tablet Formulation

Compound 139 of the present invention (100 mg), microcrystalline cellulose (100 mg), lactose hydrate (60 mg), low-substituted hydroxypropyl cellulose (20 mg), and magnesium stearate (2 mg) were mixed, and compressed into a tablet according to a general tablet preparation method to prepare a tablet formulation.

Preparation Example 3: Preparation of Capsule Formulation

Compound 139 of the present invention (100 mg), microcrystalline cellulose (100 mg), lactose hydrate (60 mg), low-substituted hydroxypropyl cellulose (20 mg), and magnesium stearate (2 mg) were mixed, and filled in a gelatin capsule according to a general capsule preparation method to prepare a capsule formulation.

Preparation Example 4: Preparation of Pill Formulation

Compound 139 of the present invention (90 mg), glutinous rice starch (5 mg), purified water (5 mg), and a small amount of a hygroscopicity inhibiting additive, such as dextrin, maltodextrin, corn starch, or microcrystalline cellulose (MCC), were mixed, and then made into a pill formulation according to a general method.

Preparation Example 5: Preparation of Injection Formulation

Compound 139 of the present invention (10 mg), sterile distilled water for injection (a suitable amount), and a pH adjuster (a suitable amount) were mixed, and then the above ingredients per ampoule (2 ml) were prepared into an injection formulation according to a general injection preparation method.

The invention claimed is:
1. A pyrimidine derivative compound represented by Chemical Formula 1 below, an optical isomer thereof, or a pharmaceutically acceptable salt thereof:

[Chemical Formula 1]

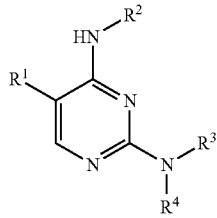

wherein:
$R^1$ is substituted pyrazole-4-yl,
  wherein the substituted pyrazole-4-yl is substituted with hydroxy $C_1$-$C_4$ alkyl or substituted or unsubstituted piperidinyl, and
  wherein the substituted piperidinyl is substituted with at least one substituent selected from the group consisting of halogen, $C_1$-$C_{10}$ haloalkyl, oxo (=O), hydroxy, cyano, nitro, amino, acetamino, trihalogen acetamino, trihalogen acetyl, $C_1$-$C_{10}$ alkyl, $C_1$-$C_{10}$ alkoxy, $C_4$-$C_{10}$ cycloalkyl, $C_4$-$C_{10}$ heterocycloalkyl, $C_4$-$C_{10}$ aryl, or $C_4$-$C_{10}$ heteroaryl;

$R^2$ is substituted or unsubstituted $C_4$-$C_{10}$ cycloalkyl, substituted or unsubstituted $C_4$-$C_8$ heterocycloalkyl, substituted or unsubstituted $C_4$-$C_{10}$ aryl, substituted or unsubstituted $C_4$-$C_{10}$ heteroaryl, or a substituted or unsubstituted fused ring in which $C_4$-$C_{10}$ aryl is fused with $C_4$-$C_8$ heterocycloalkyl,
  wherein the substituted cycloalkyl, substituted heterocycloalkyl, substituted aryl, substituted heteroaryl, or fused ring is substituted with at least one substituent selected from the group consisting of halogen, $C_1$-$C_{10}$ haloalkyl, oxo (=O), hydroxy, cyano, nitro, acetamino, trihalogen acetamino, trihalogen acetyl, $C_4$-$C_{10}$ cycloalkyl, $C_4$-$C_8$ heterocycloalkyl, $C_4$-$C_{10}$ aryl, $C_4$-$C_{10}$ heteroaryl;

$R^3$ is substituted or unsubstituted $C_4$-$C_{10}$ cycloalkyl, substituted or unsubstituted $C_4$-$C_8$ heterocycloalkyl, substituted or unsubstituted $C_4$-$C_{10}$ aryl, substituted or unsubstituted $C_4$-$C_{10}$ heteroaryl, substituted or unsubstituted $C_{4-10}$ aryl $C_{1-10}$ alkyl, substituted or unsubstituted $C_4$-$C_{10}$ heteroaryl $C_{1-10}$ alkyl, or a substituted or unsubstituted fused ring in which $C_4$-$C_{10}$ aryl is fused with $C_4$-$C_{10}$ cycloalkyl or $C_4$-$C_8$ heterocycloalkyl,
  wherein the substituted cycloalkyl, substituted heterocycloalkyl, substituted aryl, substituted heteroaryl, substituted arylalkyl, substituted heteroarylalkyl, or substituted fused ring is substituted with at least one substituent selected from the group consisting of halogen, $C_1$-$C_{10}$ haloalkyl, hydroxy, cyano, nitro, amino, acetamino, trihalogen acetamino, trihalogen acetyl, oxo (=O), $C_4$-$C_{10}$ cycloalkyl, $C_4$-$C_8$ heterocycloalkyl, $C_4$-$C_{10}$ heteroaryl, substituted or unsubstituted $C_1$-$C_{10}$ alkyl, substituted or unsubstituted $C_1$-$C_{10}$ alkoxy, or substituted or unsubstituted $C_4$-$C_{10}$ aryl,
  wherein the substituted alkyl, substituted alkoxy, or substituted aryl is substituted with at least one substituent selected from the group consisting of halogen, oxo (=O), or substituted or unsubstituted $C_1$-$C_{10}$ alkyl, and
  wherein the substituted alkyl is substituted with at least one substituent selected from halogen or oxo (=O); and $R^4$ is hydrogen.

2. The pyrimidine derivative compound, optical isomer thereof, or pharmaceutically acceptable salt thereof of claim 1, wherein the compound of Chemical Formula 1 is selected from the group consisting of:
  1-(4-(2-(3,5-dichlorophenylamino)-5-(1-(2-hydroxyethyl)-1H-pyrazol-4-yl)pyrimidin-4-ylamino)piperidin-1-yl)-2,2,2-trifluoroethanone (Compound 71);
  N2-(3,5-dichlorophenyl)-N4-(piperidin-4-yl)-5-(1-(piperidin-4-yl)-1H-pyrazol-4-yl)pyrimidine-2,4-diamine (Compound 73);
  2-(4-(2-(3,5-dichlorophenylamino)-4-(piperidin-4-ylamino)pyrimidin-5-yl)-1H-pyrazol-1-yl)ethanol (Compound 75);
  1-(4-(5-(1-(2-hydroxyethyl)-1H-pyrazol-4-yl)-2-(2-(2,2,2-trifluoroacetyl)-1,2,3,4-tetrahydroisoquinolin-7-ylamino)pyrimidin-4-ylamino)piperidin-1-yl)-2,2,2-trifluoroethanone (Compound 76);
  1-(4-(2-(3-methyl-4-chlorophenylamino)-5-(1-(2-hydroxyethyl)-1H-pyrazol-4-yl)pyrimidin-4-ylamino)piperidin-1-yl)-2,2,2-trifluoroethanone (Compound 77);
  1-(4-(5-(1-(2-hydroxyethyl)-1H-pyrazol-4-yl)-2-(4-methoxyphenylamino)pyrimidin-4-ylamino)piperidin-1-yl)-2,2,2-trifluoroethanone (Compound 78);

2-(4-(4-(piperidin-4-ylamino)-2-(1,2,3,4-tetrahydroiso-quinolin-7-ylamino)pyrimidin-5-yl)-1H-pyrazol-1-yl)ethanol (Compound 79);

2-(4-(2-(3-methyl-4-chlorophenylamino)-4-(piperidin-4-ylamino)pyrimidin-5-yl)-1H-pyrazol-1-yl)ethanol (Compound 80);

2-(4-(2-(4-methoxyphenylamino)-4-(piperidin-4-ylamino)pyrimidin-5-yl)-1H-pyrazol-1-yl)ethanol (Compound 81);

N-((1s,4s)-4-(2-(3,5-dichlorophenylamino)-5-(1-(2-hydroxyethyl)-1H-pyrazol-4-yl)pyrimidin-4-ylamino)cyclohexyl)-2,2,2-trifluoroacetamide (Compound 95);

N-((1s,4s)-4-(5-(1-(2-hydroxyethyl)-1H-pyrazol-4-yl)-2-(2-(2,2,2-trifluoroacetyl)-1,2,3,4-tetrahydroisoquinolin-7-ylamino)pyrimidin-4-ylamino)cyclohexyl)-2,2,2-trifluoroacetamide (Compound 96);

N-((1s,4s)-4-(2-(3-chlorophenylamino)-5-(1-(2-hydroxyethyl)-1H-pyrazol-4-yl)pyrimidin-4-ylamino)cyclohexyl)-2,2,2-trifluoroacetamide (Compound 100);

2-(4-(4-((1s,4s)-4-aminocyclohexylamino)-2-(3-chlorophenylamino)pyrimidin-5-yl)-1H-pyrazol-1-yl)ethanol (Compound 105);

N-((1s,4s)-4-((2-((4-chloro-3-methylphenyl)amino)-5-(1-(2-hydroxyethyl)-1H-pyrazol-4-yl)pyrimidin-4-yl)amino)cyclohexyl)-2,2,2-trifluoroacetamide (Compound 106);

2-(4-(4-((1s,4s)-4-aminocyclohexylamino)-2-(3-methyl-4-chlorophenylamino)pyrimidin-5-yl)-1H-pyrazol-1-yl)ethanol (Compound 107);

N-((1s,4s)-4-(2-(3,5-dichlorophenylamino)-5-(1-(1-(2,2,2-trifluoroacetyl)piperidin-4-yl)-1H-pyrazol-4-yl)pyrimidin-4-ylamino)cyclohexyl)-2,2,2-trifluoroacetamide (Compound 108);

N4-((1s,4s)-4-aminocyclohexyl)-N2-(3,5-dichlorophenyl)-5-(1-(piperidin-4-yl)-1H-pyrazol-4-yl)pyrimidine-2,4-diamine (Compound 111);

2-(4-(4-((1r,4r)-4-aminocyclohexylamino)-2-(3,5-dichlorophenylamino)pyrimidin-5-yl)-1H-pyrazol-1-yl)ethanol (Compound 113);

N-((1r,4r)-4-(2-(3,5-difluorophenylamino)-5-(1-(2-hydroxyethyl)-1H-pyrazol-4-yl)pyrimidin-4-ylamino)cyclohexyl)-2,2,2-trifluoroacetamide (Compound 115);

2-(4-(4-((1r,4r)-4-aminocyclohexylamino)-2-(3,5-difluorophenylamino)pyrimidin-5-yl)-1H-pyrazol-1-yl)ethan-1-ol (Compound 117);

N-((1r,4r)-4-(2-(3,5-bis(trifluoromethyl)phenylamino)-5-(1-(2-hydroxyethyl)-1H-pyrazol-4-yl)pyrimidin-4-ylamino)cyclohexyl)-2,2,2-trifluoroacetamide (Compound 119);

2-(4-(4-((1r,4r)-4-aminocyclohexylamino)-2-(3,5-bis(trifluoromethyl)phenylamino)pyrimidin-5-yl)-1H-pyrazol-1-yl)ethan-1-ol (Compound 121);

1-(4-(2-(3,5-dichlorophenylamino)-5-(1-(piperidin-4-yl)-1H-pyrazol-4-yl)pyrimidin-4-ylamino)cyclohexyl)-2,2,2-trifluoroacetamide (Compound 122);

2-(4-(2-(3,5-dichlorophenylamino)-4-(4-(piperidin-4-yl)phenylamino)pyrimidin-5-yl)-1H-pyrazol-1-yl)ethan-1-ol (Compound 201);

2-(4-(2-(3-chlorophenylamino)-4-(4-(piperidin-4-yl)phenyl amino)pyrimidin-5-yl)-1H-pyrazol-1-yl)ethan-1-ol (Compound 204); and 2-(4-(2-(3,5-difluorophenylamino)-4-(4-(piperidin-4-yl)phenylamino)pyrimidin-5-yl)-1H-pyrazol-1-yl)ethan-1-ol (Compound 205).

3. A pyrimidine derivative compound represented by Chemical Formula 3, an optical isomer thereof, or a pharmaceutically acceptable salt thereof:

[Chemical Formula 3]

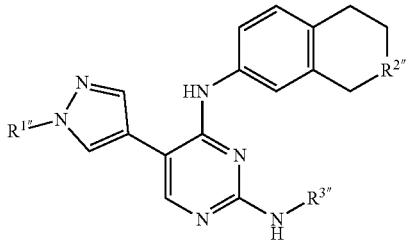

wherein:

$R^{1''}$ is hydrogen, substituted or unsubstituted $C_1$-$C_{10}$ alkyl, or substituted or unsubstituted piperidinyl, wherein the substituted alkyl or substituted piperidinyl is substituted with at least one substituent selected from the group consisting of halogen, $C_1$-$C_{10}$ haloalkyl, oxo (=O), hydroxy, cyano, nitro, amino, acetamino, trihalogen acetamino, trihalogen acetyl, $C_1$-$C_{10}$ alkyl, $C_1$-$C_{10}$ alkoxy, $C_4$-$C_{10}$ cycloalkyl, $C_4$-$C_{10}$ heterocycloalkyl, $C_4$-$C_{10}$ aryl, or $C_4$-$C_{10}$ heteroaryl;

$R^{2''}$ is amino, acetamino, or trihalogen acetamino; and $R^{3''}$ is substituted or unsubstituted $C_4$-$C_{10}$ cycloalkyl, substituted or unsubstituted $C_4$-$C_8$ heterocycloalkyl, substituted or unsubstituted $C_4$-$C_{10}$ aryl, substituted or unsubstituted $C_4$-$C_{10}$ heteroaryl, or substituted or unsubstituted fused ring in which $C_4$-$C_{10}$ aryl is fused with $C_4$-$C_8$ heterocycloalkyl, wherein the substituted cycloalkyl, substituted heterocycloalkyl, substituted aryl, substituted heteroaryl, or substituted fused ring is substituted with at least one substituent selected from the group consisting of halogen, $C_1$-$C_{10}$ haloalkyl, oxo (=O), hydroxy, cyano, nitro, amino, acetamino, trihalogen acetamino, trihalogen acetyl, $C_1$-$C_{10}$ alkyl, $C_1$-$C_{10}$ alkoxy, $C_4$-$C_{10}$ cycloalkyl, $C_4$-$C_8$ heterocycloalkyl, $C_4$-$C_{10}$ aryl, or $C_4$-$C_{10}$ heteroaryl.

4. The pyrimidine derivative compound, optical isomer thereof, or pharmaceutically acceptable salt thereof of claim 3, wherein, in Chemical Formula 3, $R^{1''}$ is hydrogen, substituted or unsubstituted $C_1$-$C_{10}$ alkyl, or substituted or unsubstituted piperidin-4-yl, wherein the substituted alkyl or substituted piperidin-4-yl is substituted with at least one substituent selected from the group consisting of halogen, $C_1$-$C_{10}$ haloalkyl, oxo (=O), hydroxy, cyano, nitro, amino, acetamino, trihalogen acetamino, trihalogen acetyl, $C_1$-$C_{10}$ alkyl, or $C_1$-$C_{10}$ alkoxy;

$R^{2''}$ is amino, acetamino, or trihalogen acetamino; and $R^{3''}$ is substituted or unsubstituted $C_4$-$C_{10}$ aryl, wherein the substituted aryl is substituted with at least one substituent selected from the group consisting of halogen, $C_1$-$C_{10}$ haloalkyl, hydroxy, cyano, nitro, amino, acetamino, trihalogen acetamino, trihalogen acetyl, $C_1$-$C_{10}$ alkyl, or $C_1$-$C_{10}$ alkoxy.

5. The pyrimidine derivative compound, optical isomer thereof, or pharmaceutically acceptable salt thereof of claim 3, wherein the compound of Chemical Formula 3 is at least one selected from the group consisting of:

1-(7-(2-(3,5-dichlorophenylamino)-5-(1-methyl-1H-pyrazol-4-yl)pyrimidin-4-ylamino)-3,4-dihydroisoquinolin-2(1H)-yl)-2,2,2-trifluoroethanone (Compound 82);

1-(7-(2-(3-methyl-4-chlorophenylamino)-5-(1-methyl-1H-pyrazol-4-yl)pyrimidin-4-ylamino)-3,4-dihydroisoquinolin-2(1H)-yl)-2,2,2-trifluoroethanone (Compound 83);

N2-(3,5-dichlorophenyl)-5-(1-methyl-1H-pyrazol-4-yl)-N4-(1,2,3,4-tetrahydroisoquinolin-7-yl)pyrimidine-2,4-diamine (Compound 84);

N2-(3-methyl-4-chlorophenyl)-5-(1-methyl-1H-pyrazol-4-yl)-N4-(1,2,3,4-tetrahydroisoquinolin-7-yl)pyrimidine-2,4-diamine (Compound 85);

1-(7-(2-(3,5-dichlorophenylamino)-5-(1-(2-hydroxyethyl)-1H-pyrazol-4-yl)pyrimidin-4-ylamino)-3,4-dihydroisoquinolin-2(1H)-yl)-2,2,2-trifluoroethanone (Compound 87);

2-(4-(2-(3,5-dichlorophenylamino)-4-(1,2,3,4-tetrahydroisoquinolin-7-ylamino)pyrimidin-5-yl)-1H-pyrazol-1-yl)ethanol (Compound 89);

1-(7-(2-(3-chlorophenylamino)-5-(1-(2-hydroxyethyl)-1H-pyrazol-4-yl)pyrimidin-4-ylamino)-3,4-dihydroisoquinolin-2(1H)-yl)-2,2,2-trifluoroethanone (Compound 93);

1-(7-(2-(3-fluorophenylamino)-5-(1-(2-hydroxyethyl)-1H-pyrazol-4-yl)pyrimidin-4-ylamino)-3,4-dihydroisoquinolin-2(1H)-yl)-2,2,2-trifluoroethanone (Compound 94);

2-(4-(2-(3-chlorophenylamino)-4-(1,2,3,4-tetrahydroisoquinolin-7-ylamino)pyrimidin-5-yl)-1H-pyrazol-1-yl)ethanol (Compound 101);

2-(4-(2-(3-fluorophenylamino)-4-(1,2,3,4-tetrahydroisoquinolin-7-ylamino)pyrimidin-5-yl)-1H-pyrazol-1-yl)ethanol (Compound 102);

1-(7-(2-(3,5-difluorophenylamino)-5-(1-(2-hydroxyethyl)-1H-pyrazol-4-yl)pyrimidin-4-ylamino)-3,4-dihydroisoquinolin-2(1H)-yl)-2,2,2-trifluoroethanone (Compound 123);

1-(7-(2-(3,5-bis(trifluoromethyl)phenylamino)-5-(1-(2-hydroxyethyl)-1H-pyrazol-4-yl)pyrimidin-4-ylamino)-3,4-dihydroisoquinolin-2(1H)-yl)-2,2,2-trifluoroethanone (Compound 124);

1-(7-(2-(2,3-dichlorophenylamino)-5-(1-(2-hydroxyethyl)-1H-pyrazol-4-yl)pyrimidin-4-ylamino)-3,4-dihydroisoquinolin-2(1H)-yl)-2,2,2-trifluoroethanone (Compound 125);

1-(7-(2-(2-methyl-3-chlorophenylamino)-5-(1-(2-hydroxyethyl)-1H-pyrazol-4-yl)pyrimidin-4-ylamino)-3,4-dihydroisoquinolin-2(1H)-yl)-2,2,2-trifluoroethanone (Compound 126);

2-(4-(2-(3,5-difluorophenylamino)-4-(1,2,3,4-tetrahydroisoquinolin-7-ylamino)pyrimidin-5-yl)-1H-pyrazol-1-yl)-ethan-1-ol (Compound 127);

2-(4-(2-(3,5-bis(trifluoromethyl)phenylamino)-4-((1,2,3,4-tetrahydroisoquinolin-7-ylamino)pyrimidin-5-yl)-1H-pyrazol-1-yl)-ethan-1-ol (Compound 128);

2-(4-(2-(2,3-dichlorophenylamino)-4-(1,2,3,4-tetrahydroisoquinolin-7-ylamino)pyrimidin-5-yl)-1H-pyrazol-1-yl)-ethan-1-ol (Compound 129);

2-(4-(2-(2-methyl-3-chlorophenylamino)-4-(1,2,3,4-tetrahydroisoquinolin-7-ylamino)pyrimidin-5-yl)-1H-pyrazol-1-yl)-ethan-1-ol (Compound 130);

N2-(3,5-difluorophenyl)-5-(1-(piperidin-4-yl)-1H-pyrazol-4-yl)-N4-(1,2,3,4-tetrahydroisoquinolin-7-yl)pyrimidine-2,4-diamine (Compound 131);

N2-(3,5-dichlorophenyl)-5-(1-(piperidin-4-yl)-1H-pyrazol-4-yl)-N4-(1,2,3,4-tetrahydroisoquinolin-7-yl)pyrimidine-2,4-diamine (Compound 132);

N2-(3,5-bis(trifluoromethyl)phenyl)-N4-(1,2,3,4-tetrahydroisoquinolin-7-yl)-5-(1-(piperidin-4-yl)-1H-pyrazol-4-yl)pyrimidine-2,4-diamine (Compound 133);

N2-(2,3-dichlorophenyl)-5-(1-(piperidin-4-yl)-1H-pyrazol-4-yl)-N4-(1,2,3,4-tetrahydroisoquinolin-7-yl)pyrimidine-2,4-diamine (Compound 134);

N2-(3,5-dimethoxyphenyl)-5-(1-methyl-1H-pyrazol-4-yl)-N4-(1,2,3,4-tetrahydroisoquinolin-7-yl)pyrimidine-2,4-diamine (Compound 135);

N2-(3,5-bis(trifluoromethyl)phenyl)-5-(1-methyl-1H-pyrazol-4-yl)-N4-(1,2,3,4-tetrahydroisoquinolin-7-yl)pyrimidine-2,4-diamine (Compound 136);

N2-(3,5-difluorophenyl)-5-(1-methyl-1H-pyrazol-4-yl)-N4-(1,2,3,4-tetrahydroisoquinolin-7-yl)pyrimidine-2,4-diamine (Compound 137);

1-(7-(2-(3,5-dimethoxyphenylamino)-5-(1-methyl-1H-pyrazol-4-yl)pyrimidin-4-ylamino)-3,4-dihydroisoquinolin-2(1H)-yl)-2,2,2-trifluoroethan-1-one (Compound 138);

1-(7-(2-(3,5-bis(trifluoromethyl)phenylamino)-5-(1-methyl-1H-pyrazol-4-yl)pyrimidin-4-ylamino)-3,4-dihydroisoquinolin-2(1H)-yl)-2,2,2-trifluoroethan-1-one (Compound 139);

1-(7-(2-(3,5-difluorophenylamino)-5-(1-methyl-1H-pyrazol-4-yl)pyrimidin-4-ylamino)-3,4-dihydroisoquinolin-2(1H)-yl)-2,2,2-trifluoroethan-1-one (Compound 140);

N2-(3,5-difluorophenyl)-N4-(2-(2,2,2-trifluoroacetyl)-1,2,3,4-tetrahydroisoquinolin-7-yl)-5-(1-(piperidin-4-yl)-1H-pyrazol-4-yl)pyrimidine-2,4-diamine (Compound 141);

N2-(3,5-dichlorophenyl)-N4-(2-(2,2,2-trifluoroacetyl)-1,2,3,4-tetrahydroisoquinolin-7-yl)-5-(1-(piperidin-4-yl)-1H-pyrazol-4-yl)pyrimidine-2,4-diamine (Compound 142);

N2-(3,5-bis(trifluoromethyl)phenyl)-N4-(2-(2,2,2-trifluoroacetyl)-1,2,3,4-tetrahydroisoquinolin-7-yl)-5-(1-(piperidin-4-yl)-1H-pyrazol-4-yl)pyrimidine-2,4-diamine (Compound 143);

N2-(2,3-dichlorophenyl)-N4-(2-(2,2,2-trifluoroacetyl)-1,2,3,4-tetrahydroisoquinolin-7-yl)-5-(1-(piperidin-4-yl)-1H-pyrazol-4-yl)pyrimidine-2,4-diamine (Compound 144);

N2-(3-chloro-5-fluorophenyl)-5-(1-methyl-1H-pyrazol-4-yl)-N4-(1,2,3,4-tetrahydroisoquinolin-7-yl)pyrimidine-2,4-diamine (Compound 145);

N2-(3-methoxy-5-(trifluoromethyl)phenyl)-5-(1-methyl-1H-pyrazol-4-yl)-N4-(1,2,3,4-tetrahydroisoquinolin-7-yl)pyrimidine-2,4-diamine (Compound 146);

2-(4-(2-(3-chloro-5-fluorophenylamino)-4-(1,2,3,4-tetrahydroisoquinolin-7-ylamino)pyrimidin-5-yl)-1H-pyrazol-1-yl)ethan-1-ol (Compound 147);

2-(4-(2-(3-methoxy-5-(trifluoromethyl)phenylamino)-4-(1,2,3,4-tetrahydroisoquinolin-7-ylamino)pyrimidin-5-yl)-1H-pyrazol-1-yl)ethan-1-ol (Compound 148);

N2-(3-chlorophenyl)-5-(1-methyl-1H-pyrazol-4-yl)-N4-(1,2,3,4-tetrahydroisoquinolin-7-yl)pyrimidine-2,4-diamine (Compound 149);

N2-(3-fluorophenyl)-5-(1-methyl-1H-pyrazol-4-yl)-N4-(1,2,3,4-tetrahydroisoquinolin-7-yl)pyrimidine-2,4-diamine (Compound 150);

5-(1-methyl-1H-pyrazol-4-yl)-N4-(1,2,3,4-tetrahydroisoquinolin-7-yl)-N2-(3-(trifluoromethyl)phenyl)pyrimidine-2,4-diamine (Compound 151);

N2-(3-methoxyphenyl)-5-(1-methyl-1H-pyrazol-4-yl)-N4-(1,2,3,4-tetrahydroisoquinolin-7-yl)pyrimidine-2,4-diamine (Compound 152);

5-(1-methyl-1H-pyrazol-4-yl)-N2-phenyl-N4-(1,2,3,4-tetrahydroisoquinolin-7-yl)pyrimidine-2,4-diamine (Compound 153);

N2-(2-isopropylphenyl)-5-(1-methyl-1H-pyrazol-4-yl)-N4-(1,2,3,4-tetrahydroisoquinolin-7-yl)pyrimidine-2,4-diamine (Compound 154);

5-(1-methyl-1H-pyrazol-4-yl)-N4-(1,2,3,4-tetrahydroisoquinolin-7-yl)-N2-(3-(trifluoromethyl)benzyl)pyrimidine-2,4-diamine (Compound 155);

5-(1-methyl-1H-pyrazol-4-yl)-N4-(1,2,3,4-tetrahydroisoquinolin-7-yl)-N2-(o-tolyl)pyrimidine-2,4-diamine (Compound 156);

N2-(2,6-difluorophenyl)-5-(1-methyl-1H-pyrazol-4-yl)-N4-(1,2,3,4-tetrahydroisoquinolin-7-yl)pyrimidine-2,4-diamine (Compound 157);

5-(1-methyl-1H-pyrazol-4-yl)-N4-(1,2,3,4-tetrahydroisoquinolin-7-yl)-N2-(m-tolyl)pyrimidine-2,4-diamine (Compound 158);

N2-(5-fluoro-2-methylphenyl)-5-(1-methyl-1H-pyrazol-4-yl)-N4-(1,2,3,4-tetrahydroisoquinolin-7-yl)pyrimidine-2,4-diamine (Compound 159);

N2-(3,5-dichlorophenyl)-5-(1-isopropyl-1H-pyrazol-4-yl)-N4-(1,2,3,4-tetrahydroisoquinolin-7-yl)pyrimidine-2,4-diamine (Compound 160);

N2-(3,5-bis(trifluoromethyl)phenyl)-5-(1-isopropyl-1H-pyrazol-4-yl)-N4-(1,2,3,4-tetrahydroisoquinolin-7-yl)pyrimidine-2,4-diamine (Compound 161);

N2-(3,5-difluorophenyl)-5-(1-isopropyl-1H-pyrazol-4-yl)-N4-(1,2,3,4-tetrahydroisoquinolin-7-yl)pyrimidine-2,4-diamine (Compound 162);

N2-(3-chloro-5-fluorophenyl)-5-(1-isopropyl-1H-pyrazol-4-yl)-N4-(1,2,3,4-tetrahydroisoquinolin-7-yl)pyrimidine-2,4-diamine (Compound 163);

5-(1-isopropyl-1H-pyrazol-4-yl)-N2-(3-methoxy-5-(trifluoromethyl)phenyl)-N4-(1,2,3,4-tetrahydroisoquinolin-7-yl)pyrimidine-2,4-diamine (Compound 164);

N2-(3,5-dimethoxyphenyl)-5-(1-isopropyl-1H-pyrazol-4-yl)-N4-(1,2,3,4-tetrahydroisoquinolin-7-yl)pyrimidine-2,4-diamine (Compound 165);

N2-(3,5-dimethylphenyl)-5-(1-isopropyl-1H-pyrazol-4-yl)-N4-(1,2,3,4-tetrahydroisoquinolin-7-yl)pyrimidine-2,4-diamine (Compound 166);

N2-(3-chlorophenyl)-5-(1-isopropyl-1H-pyrazol-4-yl)-N4-(1,2,3,4-tetrahydroisoquinolin-7-yl)pyrimidine-2,4-diamine (Compound 167);

5-(1-isopropyl-1H-pyrazol-4-yl)-N2-(3-methoxyphenyl)-N4-(1,2,3,4-tetrahydroisoquinolin-7-yl)pyrimidine-2,4-diamine (Compound 168);

5-(1-isopropyl-1H-pyrazol-4-yl)-N4-(1,2,3,4-tetrahydroisoquinolin-7-yl)-N2-(m-tolyl)pyrimidine-2,4-diamine (Compound 169);

5-(1-isopropyl-1H-pyrazol-4-yl)-N2-phenyl-N4-(1,2,3,4-tetrahydroisoquinolin-7-yl)pyrimidine-2,4-diamine (Compound 170);

N2-(3,5-dichlorophenyl)-5-(1-propyl-1H-pyrazol-4-yl)-N4-(1,2,3,4-tetrahydroisoquinolin-7-yl)pyrimidine-2,4-diamine (Compound 171);

N2-(3,5-bis(trifluoromethyl)phenyl)-5-(1-propyl-1H-pyrazol-4-yl)-N4-(1,2,3,4-tetrahydroisoquinolin-7-yl)pyrimidine-2,4-diamine (Compound 172);

N2-(3,5-difluorophenyl)-5-(1-propyl-1H-pyrazol-4-yl)-N4-(1,2,3,4-tetrahydroisoquinolin-7-yl)pyrimidine-2,4-diamine (Compound 173);

N2-(3-methoxy-5-(trifluoromethyl)phenyl)-5-(1-propyl-1H-pyrazol-4-yl)-N4-(1,2,3,4-tetrahydroisoquinolin-7-yl)pyrimidine-2,4-diamine (Compound 174);

N2-(3-chloro-5-fluorophenyl)-5-(1-propyl-1H-pyrazol-4-yl)-N4-(1,2,3,4-tetrahydroisoquinolin-7-yl)pyrimidine-2,4-diamine (Compound 175);

N2-(3,5-dimethoxyphenyl)-5-(1-propyl-1H-pyrazol-4-yl)-N4-(1,2,3,4-tetrahydroisoquinolin-7-yl)pyrimidine-2,4-diamine (Compound 176);

N2-(3,5-dimethylphenyl)-5-(1-propyl-1H-pyrazol-4-yl)-N4-(1,2,3,4-tetrahydroisoquinolin-7-yl)pyrimidine-2,4-diamine (Compound 177);

N2-(3-chlorophenyl)-5-(1-propyl-1H-pyrazol-4-yl)-N4-(1,2,3,4-tetrahydroisoquinolin-7-yl)pyrimidine-2,4-diamine (Compound 178);

N2-(3,5-dichlorophenyl)-5-(1-isobutyl-1H-pyrazol-4-yl)-N4-(1,2,3,4-tetrahydroisoquinolin-7-yl)pyrimidine-2,4-diamine (Compound 179);

N2-(3,5-bis(trifluoromethyl)phenyl)-5-(1-isobutyl-1H-pyrazol-4-yl)-N4-(1,2,3,4-tetrahydroisoquinolin-7-yl)pyrimidine-2,4-diamine (Compound 180);

N2-(3,5-difluorophenyl)-5-(1-isobutyl-1H-pyrazol-4-yl)-N4-(1,2,3,4-tetrahydroisoquinolin-7-yl)pyrimidine-2,4-diamine (Compound 181);

N2-(3-chloro-5-fluorophenyl)-5-(1-isobutyl-1H-pyrazol-4-yl)-N4-(1,2,3,4-tetrahydroisoquinolin-7-yl)pyrimidine-2,4-diamine (Compound 182);

5-(1-isobutyl-1H-pyrazol-4-yl)-N2-(3-methoxy-5-(trifluoromethyl)phenyl)-N4-(1,2,3,4-tetrahydroisoquinolin-7-yl)pyrimidine-2,4-diamine (Compound 183);

N2-(3,5-dimethoxyphenyl)-5-(1-isobutyl-1H-pyrazol-4-yl)-N4-(1,2,3,4-tetrahydroisoquinolin-7-yl)pyrimidine-2,4-diamine (Compound 184);

N2-(3,5-dimethylphenyl)-5-(1-isobutyl-1H-pyrazol-4-yl)-N4-(1,2,3,4-tetrahydroisoquinolin-7-yl)pyrimidine-2,4-diamine (Compound 185);

N2-(3-chlorophenyl)-5-(1-isobutyl-1H-pyrazol-4-yl)-N4-(1,2,3,4-tetrahydroisoquinolin-7-yl)pyrimidine-2,4-diamine (Compound 186);

5-(1-isobutyl-1H-pyrazol-4-yl)-N2-(3-methoxyphenyl)-N4-(1,2,3,4-tetrahydroisoquinolin-7-yl)pyrimidine-2,4-diamine (Compound 187);

5-(1-isobutyl-1H-pyrazol-4-yl)-N4-(1,2,3,4-tetrahydroisoquinolin-7-yl)-N2-(m-tolyl)pyrimidine-2,4-diamine (Compound 188);

5-(1-isobutyl-1H-pyrazol-4-yl)-N2-phenyl-N4-(1,2,3,4-tetrahydroisoquinolin-7-yl)pyrimidine-2,4-diamine (Compound 189);

N2-(2,3-dichlorophenyl)-5-(1-isobutyl-1H-pyrazol-4-yl)-N4-(1,2,3,4-tetrahydroisoquinolin-7-yl)pyrimidine-2,4-diamine (Compound 190);

N2-(2,5-difluorophenyl)-5-(1-isobutyl-1H-pyrazol-4-yl)-N4-(1,2,3,4-tetrahydroisoquinolin-7-yl)pyrimidine-2,4-diamine (Compound 191);

5-(1-isobutyl-1H-pyrazol-4-yl)-N2-(2-isopropylphenyl)-N4-(1,2,3,4-tetrahydroisoquinolin-7-yl)pyrimidine-2,4-diamine (Compound 192);

2-(4-(2-(3,5-dimethoxyphenylamino)-4-(1,2,3,4-tetrahydroisoquinolin-7-ylamino)pyrimidin-5-yl)-1H-pyrazol-1-yl)ethan-1-ol (Compound 193);

2-(4-(2-(3,5-dimethylphenylamino)-4-(1,2,3,4-tetrahydroisoquinolin-7-ylamino)pyrimidin-5-yl)-1H-pyrazol-1-yl)ethan-1-ol (Compound 194);

2-(4-(2-(2,3-dimethylphenylamino)-4-(1,2,3,4-tetrahydroisoquinolin-7-ylamino)pyrimidin-5-yl)-1H-pyrazol-1-yl)ethan-1-ol (Compound 195);

2-(4-(2-(3-chlorophenylamino)-4-(1,2,3,4-tetrahydroisoquinolin-7-ylamino)pyrimidin-5-yl)-1H-pyrazol-1-yl)ethan-1-ol (Compound 196); and 2-(4-(2-(2,3-dichlorophenylamino)-4-(1,2,3,4-tetrahydroisoquinolin-7-ylamino)pyrimidin-5-yl)-1H-pyrazol-1-yl)ethan-1-ol (Compound 197).

6. A pharmaceutical composition for prevention or treatment of a tyrosine-protein kinase receptor (Tyro 3)-related disease, the pharmaceutical composition containing, as an active ingredient, the pyrimidine derivative compound, optical isomer thereof, or pharmaceutically acceptable salt thereof of claim 1.

7. A pharmaceutical composition for prevention or treatment of a tyrosine-protein kinase receptor (Tyro 3)-related disease, the pharmaceutical composition containing, as an active ingredient, the pyrimidine derivative compound, optical isomer thereof, or pharmaceutically acceptable salt thereof of claim 2.

8. A pharmaceutical composition for prevention or treatment of a tyrosine-protein kinase receptor (Tyro 3)-related disease, the pharmaceutical composition containing, as an active ingredient, the pyrimidine derivative compound, optical isomer thereof, or pharmaceutically acceptable salt thereof of claim 3.

9. A pharmaceutical composition for prevention or treatment of a tyrosine-protein kinase receptor (Tyro 3)-related disease, the pharmaceutical composition containing, as an active ingredient, the pyrimidine derivative compound, optical isomer thereof, or pharmaceutically acceptable salt thereof of claim 4.

10. A pharmaceutical composition for prevention or treatment of a tyrosine-protein kinase receptor (Tyro 3)-related disease, the pharmaceutical composition containing, as an active ingredient, the pyrimidine derivative compound, optical isomer thereof, or pharmaceutically acceptable salt thereof of claim 5.

* * * * *